(12) United States Patent
Manoharan et al.

(10) Patent No.: US 8,013,136 B2
(45) Date of Patent: *Sep. 6, 2011

(54) OLIGONUCLEOTIDES COMPRISING A NON-PHOSPHATE BACKBONE LINKAGE

(75) Inventors: Muthiah Manoharan, Weston, MA (US); Kallanthottathil G. Rajeev, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 12/496,268

(22) Filed: Jul. 1, 2009

(65) Prior Publication Data
US 2009/0318676 A1  Dec. 24, 2009

Related U.S. Application Data

(63) Continuation of application No. 11/170,798, filed on Jun. 29, 2005, now Pat. No. 7,615,618.

(60) Provisional application No. 60/584,061, filed on Jun. 30, 2004, provisional application No. 60/614,528, filed on Sep. 30, 2004.

(51) Int. Cl.
*C07H 21/02* (2006.01)
*C07H 21/04* (2006.01)

(52) U.S. Cl. .............. 536/23.1; 536/22.1; 536/24.2; 536/24.3; 536/25.3

(58) Field of Classification Search .......... None
See application file for complete search history.

(56) References Cited

U.S. PATENT DOCUMENTS

| | | | |
|---|---|---|---|
| 5,606,049 A | 2/1997 | Vaghefi |
| 5,677,124 A | 10/1997 | DuBois et al. |
| 5,731,429 A | 3/1998 | Reddy et al. |
| 5,789,576 A | 8/1998 | Daily et al. |
| 5,919,625 A | 7/1999 | DuBois et al. |
| 5,939,262 A | 8/1999 | Pasloske et al. |
| 6,057,134 A | 5/2000 | Lader et al. |
| 6,232,103 B1 | 5/2001 | Short |
| 6,399,334 B1 | 6/2002 | Li et al. |
| 6,593,464 B1 | 7/2003 | Gebeyehu et al. |
| 6,610,490 B2 | 8/2003 | Schuster et al. |
| 6,620,926 B2 | 9/2003 | Sproat |
| 6,623,962 B1 | 9/2003 | Akhtar et al. |
| 6,649,751 B2 | 11/2003 | Usman et al. |
| 6,673,611 B2 | 1/2004 | Thompson et al. |
| 6,673,918 B2 | 1/2004 | Bellon et al. |
| 6,686,463 B2 | 2/2004 | Beigelman et al. |
| 6,797,815 B2 | 9/2004 | Matulic-Adamic et al. |
| 6,815,205 B2 | 11/2004 | Lin et al. |
| 6,818,447 B1 | 11/2004 | Pavco et al. |
| 6,818,759 B2 | 11/2004 | Beigelman et al. |
| 6,830,902 B1 | 12/2004 | Astatke et al. |
| 6,849,726 B2 | 2/2005 | Usman et al. |
| 6,933,121 B2 | 8/2005 | Schuster et al. |
| 6,972,330 B2 | 12/2005 | Beigelman et al. |
| 6,977,295 B2 | 12/2005 | Belotserkovskii et al. |
| 2002/0025526 A1 | 2/2002 | Schuster et al. |
| 2002/0034750 A1 | 3/2002 | Short |
| 2002/0086356 A1 | 7/2002 | Tuschl et al. |
| 2002/0132346 A1 | 9/2002 | Cibelli |
| 2002/0143166 A1 | 10/2002 | Pires et al. |
| 2002/0162126 A1 | 10/2002 | Beach et al. |
| 2002/0182590 A1 | 12/2002 | Strange et al. |
| 2003/0084471 A1 | 5/2003 | Beach et al. |
| 2003/0108923 A1 | 6/2003 | Tuschl et al. |
| 2003/0143732 A1 | 7/2003 | Fosnaugh et al. |
| 2003/0148507 A1 | 8/2003 | Fosnaugh et al. |
| 2003/0157030 A1 | 8/2003 | Davis et al. |
| 2003/0167490 A1 | 9/2003 | Hunter et al. |
| 2003/0170891 A1 | 9/2003 | McSwiggen |
| 2003/0175950 A1 | 9/2003 | McSwiggen |
| 2003/0190635 A1 | 10/2003 | McSwiggen |
| 2003/0190661 A1 | 10/2003 | Gruber et al. |
| 2003/0204077 A1 | 10/2003 | Simms |
| 2003/0206887 A1 | 11/2003 | Morrissey et al. |
| 2004/0009522 A1 | 1/2004 | Wu |

(Continued)

FOREIGN PATENT DOCUMENTS
DE  10200410 A1  7/2003
(Continued)

OTHER PUBLICATIONS

Kuhn et al. JACS (2002), vol. 124, pp. 1097-1103.

(Continued)

*Primary Examiner* — Patrick Lewis
(74) *Attorney, Agent, or Firm* — Jeffrey N. Townes; LeClairRyan

(57) ABSTRACT

One aspect of the present invention relates to a ribonucleoside substituted with a phosphonamidite group at the 3'-position. In certain embodiments, the phosphonamidite is an alkyl phosphonamidite. Another aspect of the present invention relates to a double-stranded oligonucleotide comprising at least one non-phosphate linkage. Representative non-phosphate linkages include phosphonate, hydroxylamine, hydroxylhydrazinyl, amide, and carbamate linkages. In certain embodiments, the non-phosphate linkage is a phosphonate linkage. In certain embodiments, a non-phosphate linkage occurs in only one strand. In certain embodiments, a non-phosphate linkage occurs in both strands. In certain embodiments, a ligand is bound to one of the oligonucleotide strands comprising the double-stranded oligonucleotide. In certain embodiments, a ligand is bound to both of the oligonucleotide strands comprising the double-stranded oligonucleotide. In certain embodiments, the oligonucleotide strands comprise at least one modified sugar moiety. Another aspect of the present invention relates to a single-stranded oligonucleotide comprising at least one non-phosphate linkage. Representative non-phosphate linkages include phosphonate, hydroxylamine, hydroxylhydrazinyl, amide, and carbamate linkages. In certain embodiments, the non-phosphate linkage is a phosphonate linkage. In certain embodiments, a ligand is bound to the oligonucleotide strand. In certain embodiments, the oligonucleotide comprises at least one modified sugar moiety.

35 Claims, 13 Drawing Sheets

U.S. PATENT DOCUMENTS

| | | |
|---|---|---|
| 2004/0009946 A1 | 1/2004 | Lewis et al. |
| 2004/0014113 A1 | 1/2004 | Yang et al. |
| 2004/0018181 A1 | 1/2004 | Kufe et al. |
| 2004/0018999 A1 | 1/2004 | Beach et al. |
| 2004/0019001 A1 | 1/2004 | McSwiggen |
| 2004/0044190 A1 | 3/2004 | Sproat |
| 2004/0058886 A1 | 3/2004 | Scaringe |
| 2004/0063654 A1 | 4/2004 | Davis et al. |
| 2004/0077574 A1 | 4/2004 | Klinghoffer et al. |
| 2004/0086884 A1 | 5/2004 | Beach et al. |
| 2004/0121353 A1 | 6/2004 | Lewis et al. |
| 2004/0138163 A1 | 7/2004 | McSwiggen et al. |
| 2004/0142895 A1 | 7/2004 | Lockridge et al. |
| 2004/0147735 A1 | 7/2004 | Laurent et al. |
| 2004/0161777 A1 | 8/2004 | Baker et al. |
| 2004/0191905 A1 | 9/2004 | Stevenson et al. |
| 2004/0192626 A1 | 9/2004 | McSwiggen et al. |
| 2004/0192629 A1 | 9/2004 | Xu et al. |
| 2004/0198640 A1 | 10/2004 | Leake et al. |
| 2004/0198682 A1 | 10/2004 | McSwiggen et al. |
| 2004/0203024 A1 | 10/2004 | Baker et al. |
| 2004/0203145 A1 | 10/2004 | Zamore et al. |
| 2004/0204420 A1 | 10/2004 | Rana |
| 2004/0209831 A1 | 10/2004 | McSwiggen et al. |
| 2004/0209832 A1 | 10/2004 | McSwiggen et al. |
| 2004/0214198 A1 | 10/2004 | Rana |
| 2004/0219671 A1 | 11/2004 | McSwiggen et al. |
| 2004/0220128 A1 | 11/2004 | Pavco et al. |
| 2004/0224405 A1 | 11/2004 | Leake et al. |
| 2004/0229266 A1 | 11/2004 | Tuschl et al. |
| 2004/0234504 A1 | 11/2004 | Verma et al. |
| 2004/0235775 A1 | 11/2004 | Kung et al. |
| 2004/0249178 A1 | 12/2004 | Vargeese et al. |
| 2004/0259247 A1 | 12/2004 | Tuschl et al. |
| 2004/0259248 A1 | 12/2004 | Tuschl et al. |
| 2004/0266707 A1 | 12/2004 | Leake et al. |
| 2005/0004063 A1 | 1/2005 | Kung et al. |
| 2005/0014172 A1 | 1/2005 | Richards et al. |
| 2005/0020525 A1 | 1/2005 | McSwiggen et al. |
| 2005/0026278 A1 | 2/2005 | Tuschl et al. |
| 2005/0032733 A1 | 2/2005 | McSwiggen et al. |
| 2005/0042646 A1 | 2/2005 | Davidson et al. |
| 2005/0048529 A1 | 3/2005 | McSwiggen |
| 2005/0054596 A1 | 3/2005 | McSwiggen et al. |
| 2005/0054598 A1 | 3/2005 | McSwiggen |
| 2005/0054847 A1 | 3/2005 | Madden et al. |
| 2005/0059817 A1 | 3/2005 | Beigelman et al. |
| 2005/0070497 A1 | 3/2005 | McSwiggen et al. |
| 2005/0075304 A1 | 4/2005 | McSwiggen et al. |
| 2005/0079610 A1 | 4/2005 | Polisky et al. |
| 2005/0096284 A1 | 5/2005 | McSwiggen |
| 2005/0106726 A1 | 5/2005 | McSwiggen et al. |
| 2005/0119211 A1 | 6/2005 | Chowrira et al. |
| 2005/0119212 A1 | 6/2005 | Haeberli et al. |
| 2005/0119214 A1 | 6/2005 | Manoharan et al. |
| 2005/0124566 A1 | 6/2005 | Robin et al. |
| 2005/0124567 A1 | 6/2005 | McSwiggen et al. |
| 2005/0124568 A1 | 6/2005 | Usman et al. |
| 2005/0124569 A1 | 6/2005 | Guerciolini et al. |
| 2005/0130181 A1 | 6/2005 | McSwiggen |
| 2005/0136436 A1 | 6/2005 | McSwiggen et al. |
| 2005/0137153 A1 | 6/2005 | McSwiggen et al. |
| 2005/0137155 A1 | 6/2005 | McSwiggen et al. |
| 2005/0142578 A1 | 6/2005 | Usman et al. |
| 2005/0143333 A1 | 6/2005 | Richards et al. |
| 2005/0148530 A1 | 7/2005 | McSwiggen et al. |
| 2005/0153914 A1 | 7/2005 | McSwiggen et al. |
| 2005/0153915 A1 | 7/2005 | Usman et al. |
| 2005/0153916 A1 | 7/2005 | McSwiggen et al. |
| 2005/0158735 A1 | 7/2005 | McSwiggen et al. |
| 2005/0159376 A1 | 7/2005 | McSwiggen et al. |
| 2005/0159378 A1 | 7/2005 | McSwiggen et al. |
| 2005/0159379 A1 | 7/2005 | McSwiggen et al. |
| 2005/0159380 A1 | 7/2005 | Guerciolini et al. |
| 2005/0159381 A1 | 7/2005 | McSwiggen et al. |
| 2005/0159382 A1 | 7/2005 | McSwiggen et al. |
| 2005/0164224 A1 | 7/2005 | McSwiggen et al. |
| 2005/0164966 A1 | 7/2005 | McSwiggen et al. |
| 2005/0164967 A1 | 7/2005 | McSwiggen et al. |
| 2005/0164968 A1 | 7/2005 | McSwiggen et al. |
| 2005/0170371 A1 | 8/2005 | McSwiggen et al. |
| 2005/0171039 A1 | 8/2005 | McSwiggen et al. |
| 2005/0171040 A1 | 8/2005 | Polisky et al. |
| 2005/0176018 A1 | 8/2005 | Thompson et al. |
| 2005/0176024 A1 | 8/2005 | McSwiggen et al. |
| 2005/0176025 A1 | 8/2005 | McSwiggen et al. |
| 2005/0176045 A1 | 8/2005 | Fedorov et al. |
| 2005/0176663 A1 | 8/2005 | McSwiggen et al. |
| 2005/0176664 A1 | 8/2005 | Richards et al. |
| 2005/0176665 A1 | 8/2005 | McSwiggen |
| 2005/0176666 A1 | 8/2005 | Richards et al. |
| 2005/0182006 A1 | 8/2005 | McSwiggen et al. |
| 2005/0182007 A1 | 8/2005 | McSwiggen et al. |
| 2005/0182008 A1 | 8/2005 | McSwiggen et al. |
| 2005/0182009 A1 | 8/2005 | McSwiggen et al. |
| 2005/0182010 A1 | 8/2005 | de Haan |
| 2005/0187174 A1 | 8/2005 | Richards et al. |
| 2005/0191618 A1 | 9/2005 | McSwiggen et al. |
| 2005/0191638 A1 | 9/2005 | McSwiggen |
| 2005/0196765 A1 | 9/2005 | McSwiggen et al. |
| 2005/0196767 A1 | 9/2005 | McSwiggen et al. |
| 2005/0196781 A1 | 9/2005 | Robin et al. |
| 2005/0197312 A1 | 9/2005 | Fitzgerald et al. |
| 2005/0202077 A1 | 9/2005 | Watson et al. |
| 2005/0203040 A1 | 9/2005 | Richards et al. |
| 2005/0203044 A1 | 9/2005 | Zinnen |
| 2005/0208658 A1 | 9/2005 | Castonguay |
| 2005/0209179 A1 | 9/2005 | McSwiggen et al. |
| 2005/0209180 A1 | 9/2005 | Jadhav et al. |
| 2005/0209182 A1 | 9/2005 | Morrissey et al. |
| 2005/0215777 A1 | 9/2005 | Vargeese et al. |
| 2005/0222064 A1 | 10/2005 | Vargeese et al. |
| 2005/0222066 A1 | 10/2005 | Richards et al. |
| 2005/0223427 A1 | 10/2005 | Leake et al. |
| 2005/0227935 A1 | 10/2005 | McSwiggen et al. |
| 2005/0227936 A1 | 10/2005 | McSwiggen et al. |
| 2005/0227937 A1 | 10/2005 | Pavco et al. |
| 2005/0233329 A1 | 10/2005 | McSwiggen et al. |
| 2005/0233344 A1 | 10/2005 | McSwiggen et al. |
| 2005/0233996 A1 | 10/2005 | McSwiggen |
| 2005/0233997 A1 | 10/2005 | Richards et al. |
| 2005/0233998 A1 | 10/2005 | Jadhav et al. |
| 2005/0234006 A1 | 10/2005 | Tuschl et al. |
| 2005/0234007 A1 | 10/2005 | Tuschl et al. |
| 2005/0234232 A1 | 10/2005 | Beigelman et al. |
| 2005/0239731 A1 | 10/2005 | McSwiggen et al. |
| 2005/0239739 A1 | 10/2005 | Matulic-Adamic et al. |
| 2005/0245475 A1 | 11/2005 | Khvorova et al. |
| 2005/0246794 A1 | 11/2005 | Khvorova et al. |
| 2005/0255120 A1 | 11/2005 | Simon |
| 2005/0255487 A1 | 11/2005 | Khvorova et al. |
| 2005/0256068 A1 | 11/2005 | McSwiggen et al. |
| 2005/0256076 A1 | 11/2005 | Bumcrot |
| 2005/0260214 A1 | 11/2005 | Simon |
| 2005/0260620 A1 | 11/2005 | Christiano et al. |
| 2005/0260652 A1 | 11/2005 | Ruvkun et al. |
| 2005/0261212 A1 | 11/2005 | McSwiggen |
| 2005/0261219 A1 | 11/2005 | Richards et al. |
| 2005/0261222 A1 | 11/2005 | Wolber et al. |
| 2005/0266422 A1 | 11/2005 | Vagle et al. |
| 2005/0267058 A1 | 12/2005 | McSwiggen et al. |
| 2005/0277133 A1 | 12/2005 | McSwiggen |
| 2005/0277608 A1 | 12/2005 | Guerciolini et al. |
| 2005/0282188 A1 | 12/2005 | Haeberli et al. |
| 2005/0287128 A1 | 12/2005 | Guerciolini et al. |
| 2005/0287668 A1 | 12/2005 | Finney |
| 2005/0288242 A1 | 12/2005 | McSwiggen |
| 2005/0288243 A1 | 12/2005 | Xu et al. |

FOREIGN PATENT DOCUMENTS

| | | |
|---|---|---|
| JP | 3504015 | 9/1991 |
| WO | 9003381 A1 | 4/1990 |
| WO | WO 00/28019 | 5/2000 |
| WO | WO 01/05963 A2 | 1/2001 |
| WO | WO 02/098443 A2 | 12/2002 |
| WO | WO 2004/024919 A1 | 3/2004 |

OTHER PUBLICATIONS

Goodchild, "Conjugates of Oligonucleotides and Modified Oligonucleotides: A Review of Their Synthesis and Properties", *Bioconjugate Chemistry*, 1(3):165-187 (ACS, Washington DC, May/Jun. 1990).

Manoharan, M., "Oligonucleotide Conjugates as Potential Antisense Drugs with Improved Uptake, Biodistribution, Targeted Delivery, and Mechanism of Action", *Antisense & Nucleic Acid Drug Development*, 12:103-128 (Mary Ann Lieber, Inc., NYC, NY 2002).

Manoharan, M. et al., Improving Antisense Oligonucleotide Binding to Human Serum Albumin: Dramatic Effect of Ibuprofen Conjugation, *Chembiochem*, 12:1257-1260 (Wiley—VCH Verlag GmbH & Co., KGoA, Weinheim, 2002).

Quartin, R. S. et al., "Number and distribution of methylphosphonate linkages in oligodeoxynucleotides affect exo- and endonuclease sensitivity and ability to form RNase H substrates", *Nucleic Acids Research*, 17(18):7253-7262 (Oxford Univ. Press, Surrey, UK, Sep. 25, 1989).

Uhlmann, E. et al., "Anitsense Oligonucleotides: A New Therapeutic Principle", *Chemical Reviews*, 90(4):543-584 (ACS, Washington, DC, Jun. 1990).

International Search Report dated Dec. 27, 2006.

Braasch et al., "RNA Interference in Mammalian Cells by Chemically-Modified RNA", *Biochemistry*, 42:7967-7975 (2003).

Amarzguioui et al., "Tolerance for mutations and Chemical Modifications in a siRNA", *Nucleic Acids Research*, 31(2):589-595 (2003).

Harborth et al., "Sequence, Chemical, and Structural Variation of Small Interfering RNAs and Short Hairpin RNAs and the Effect on Mammalian Gene Silencing", *Antisense and Nucleic Acid Drug Development*, 13:83-105 (2003).

Morteza M Vaghefi and Richard I Hogrefe, "A Convenient High Yield Synthesis of N4-lsobutyryl-2'-o-Methylcytidine and its Monomer Units for Incorporation into Oligonucleotides", Nucleosides & Nucleotides 12(10):1007-1013 (1993).

Daguang Wang and Paul O.P. Ts'o, "Syntheses of 2'-O-Methylisocytidine Phosphoramidite and Methylphosphonamidite Synthons", Nucleosides & Nucleotides 15(1-3):387-397 (1996).

Rudiger Welz and Sabine Muller, "5-(Benzylmercapto)-1H-tetrazole as activator for 2'-O-TBDMS phosphoramidite building blocks in RNA synthesis", Tetrahedron Letters 43:795-797 (2002).

Francine Wincott et al., "Synthesis, deprotection, analysis and purification of RNA and ribozymes", Nucleic Acids Research 23(14):2677-2684 (1995).

OLIGONUCLEOTIDES COMPRISING A NON-PHOSPHATE BACKBONE LINKAGE

RELATED APPLICATIONS

This application is a continuation application of U.S. application Ser. No. 11/170,798, filed Jun. 29, 2005, which claims the benefit of priority to U.S. Provisional Patent Application Ser. No. 60/584,061, filed Jun. 30, 2004; and U.S. Provisional Patent Application Ser. No. 60/614,528, filed Sep. 30, 2004; the contents of all of which are hereby incorporated by reference in their entirety.

BACKGROUND OF THE INVENTION

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.
siRNA RNA interference (RNAi) is an evolutionarily conserved gene silencing mechanism, originally discovered in studies of the nematode *Caenorhabditis elegans* (Lee et al, Cell 75:843 (1993); Reinhart et al., Nature 403:901 (2000)). It is triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, Ruvkun, Science 2294: 797 (2001)). This process is related to normal defense against viruses and the mobilization of transposons.

Double-stranded ribonucleic acids (dsRNAs) are naturally rare and have been found only in certain microorganisms, such as yeasts or viruses. Recent reports indicate that dsRNAs are involved in phenomena of regulation of expression, as well as in the initiation of the synthesis of interferon by cells (Declerq et al., Meth. Enzymol. 78:291 (1981); Wu-Li, Biol. Chem. 265:5470 (1990)). In addition, dsRNA has been reported to have anti-proliferative properties, which makes it possible also to envisage therapeutic applications (Aubel et al., Proc. Natl. Acad. Sci., USA 88:906 (1991)). For example, synthetic dsRNA has been shown to inhibit tumor growth in mice (Levy et al. Proc. Nat. Acad. Sci. USA, 62:357-361 (1969)), to be active in the treatment of leukemic mice (Zeleznick et al., Proc. Soc. Exp. Biol. Med. 130:126-128 (1969)); and to inhibit chemically-induced tumorigenesis in mouse skin (Gelboin et al., Science 167:205-207 (1970)).

Treatment with dsRNA has become an important method for analyzing gene functions in invertebrate organisms. For example, Dzitoveva et al. showed, that RNAi can be induced in adult fruit flies by injecting dsRNA into the abdomen of anesthetized *Drosophila*, and that this method can also target genes expressed in the central nervous system (Mol. Psychiatry. 6(6):665-670 (2001)). Both transgenes and endogenous genes were successfully silenced in adult *Drosophila* by intra-abdominal injection of their respective dsRNA. Moreover, Elbashir et al., provided evidence that the direction of dsRNA processing determines whether sense or antisense target RNA can be cleaved by a small interfering RNA (siRNA)-protein complex (Genes Dev. 15(2): 188-200 (2001)).

Two recent reports reveal that RNAi provides a rapid method to test the function of genes in the nematode *Caenorhabditis elegans*; and most of the genes on *C. elegans* chromosome I and III have now been tested for RNAi phenotypes (Barstead, Curr. Opin. Chem. Biol. 5(1):63-66 (2001); Tavernarakis, Nat. Genet. 24(2):180-183 (2000); Zamore, Nat. Struct. Biol. 8(9):746-750 (2001).). When used as a rapid approach to obtain loss-of-function information, RNAi was used to analyze a random set of ovarian transcripts and has identified 81 genes with essential roles in *C. elegans* embryogenesis (Piano et al., Curr. Biol. 10(24):1619-1622 (2000). RNAi has also been used to disrupt the pupal hemocyte protein of *Sarcophaga* (Nishikawa et al., Eur. J. Biochem. 268(20):5295-5299 (2001)).

Like RNAi in invertebrate animals, post-transcriptional gene silencing (PTGS) in plants is an RNA-degradation mechanism. In plants, this can occur at both the transcriptional and the post-transcriptional levels; however, in invertebrates only post-transcriptional RNAi has been reported to date (Bernstein et al., Nature 409(6818):295-296 (2001). Indeed, both involve double-stranded RNA (dsRNA), spread within the organism from a localized initiating area, to correlate with the accumulation of small interfering RNA (siRNA) and require putative RNA-dependent RNA polymerases, RNA helicases and proteins of unknown functions containing PAZ and Piwi domains.

Some differences are evident between RNAi and PTGS were reported by Vaucheret et al., J. Cell Sci. 114(Pt 17): 3083-3091 (2001). First, PTGS in plants requires at least two genes—SGS3 (which encodes a protein of unknown function containing a coil-coiled domain) and MET1 (which encodes a DNA-methyltransferase)—that are absent in *C. elegans*, and thus are not required for RNAi. Second, all of the *Arabidopsis* mutants that exhibit impaired PTGS are hyper-susceptible to infection by the cucumovirus CMV, indicating that PTGS participates in a mechanism for plant resistance to viruses. RNAi-mediated oncogene silencing has also been reported to confer resistance to crown gall tumorigenesis (Escobar et al., Proc. Natl. Acad. Sci. USA, 98(23):13437-13442 (2001)).

RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, but the protein components of this activity remained unknown. Hammond et al. (Science 293(5532):1146-1150 (August 2001)) reported biochemical purification of the RNAi effector nuclease from cultured *Drosophila* cells, and protein microsequencing of a ribonucleoprotein complex of the active fraction showed that one constituent of this complex is a member of the Argonaute family of proteins, which are essential for gene silencing in *Caenorhabditis elegans, Neurospora,* and *Arabidopsis*. This observation suggests links between the genetic analysis of RNAi from diverse organisms and the biochemical model of RNAi that is emerging from *Drosophila* in vitro systems.

Svoboda et al. reported in Development 127(19):4147-4156 (2000) that RNAi provides a suitable and robust approach to study the function of dormant maternal mRNAs in mouse oocytes. Mos (originally known as c-mos) and tissue plasminogen activator mRNAs are dormant maternal mRNAs are recruited during oocyte maturation, and translation of Mos mRNA results in the activation of MAP kinase. The dsRNA directed towards Mos or TPA mRNAs in mouse oocytes specifically reduced the targeted mRNA in both a time- and concentration-dependent manner, and inhibited the appearance of MAP kinase activity. See also, Svoboda et al. Biochem. Biophys. Res. Commun. 287(5):1099-1104 (2001).

Despite the advances in interference RNA technology, the need exists for siRNA conjugates having improved pharmacologic properties. In particular, the oligonucleotide sequences have poor serum solubility, poor cellular distribution and uptake, and are rapidly excreted through the kidneys. It is known that oligonucleotides bearing the native phosphodiester (P=O) backbone are susceptable to nuclease-mediated degradation. See L. L. Cummins et al. *Nucleic Acids Res.* 1995, 23, 2019. The stability of oligonucleotides has been increased by converting the P=O linkages to P=S linkages which are less susceptible to degradation by nucleases in vivo. Alternatively, the phosphate group can be converted to a phosphoramidate which is less prone to enzymatic degradation than the native phosphate. See Uhlmann, E.; Peyman, A. *Chem. Rev.* 1990, 90, 544. Modifications to the sugar groups of the oligonucleotide can confer stability to enzymatic degradation. For example, oligonucleotides comprising ribonucleic acids are less prone to nucleolytic degradation if the 2'-OH group of the sugar is converted to a methoxyethoxy group. See M. Manoharan *ChemBioChem.* 2002, 3, 1257 and references cited therein.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

Some progress has been made on increasing the cellular uptake of single-stranded oligonucleotides, including increasing the membrane permeability via conjugates and cellular delivery of oligonucleotides. In U.S. Pat. No. 6,656, 730, M. Manoharan describes compositions in which a ligand that binds serum, vascular, or cellular proteins may be attached via an optional linking moiety to one or more sites on an oligonucleotide. These sites include one or more of, but are not limited to, the 2'-position, 3'-position, 5'-position, the internucleotide linkage, and a nucleobase atom of any nucleotide residue.

Antisense RNA

Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that provide the disruption of the nucleic acid function, discussed by Cohen (*Oligonucleotides: Antisense Inhibitors of Gene Expression*, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller et al. (1987) *Anti-Cancer Drug Design*, 2:117-128), and α-anomer oligonucleotides are the two most extensively studied antisense agents which are thought to disrupt nucleic acid function by hybridization arrest.

Another means by which antisense oligonucleotides disrupt nucleic acid function is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research applications and potential therapeutic purposes. One of the major hurdles that has only partially been overcome in vivo is efficient cellular uptake which is severely hampered by the rapid degradation and excretion of oligonucleotides. The generally accepted process of cellular uptake is by receptor-mediated endocytosis which is dependent on the temperature and concentration of the oligonucleotides in serum and extra vascular fluids.

Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport. An alternative that is particularly attractive for transmembrane delivery of oligonucleotides is modification of the physicochemical properties of the oligonucleotide.

Micro-RNA

Micro-RNAs are a large group of small RNAs produced naturally in organisms, at least some of which regulate the expression of target genes. Micro-RNAs are formed from an approximately 70 nucleotide single-stranded hairpin precursor transcript by Dicer. V. Ambros et al. *Current Biology* 2003, 13, 807. In many instances, the micro-RNA is transcribed from a portion of the DNA sequence that previously had no known function. Micro-RNAs are not translated into proteins, but rather bind to specific messenger RNAs blocking translation. It is thought that micro-RNAs base-pair imprecisely with their targets to inhibit translation. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

The need exists for modified oligonucleotide compounds with improved serum solubility, cellular distribution and uptake, and stability in vivo. The oligonucleotide compounds of the invention comprising non-phosphate linkages fulfill this need and provide other related advantages.

SUMMARY OF THE INVENTION

One aspect of the present invention relates to a ribonucleoside substituted with a phosphonamidite group at the 3'-position. In certain embodiments, the phosphonamidite is an alkyl phosphonamidite. Another aspect of the present invention relates to a double-stranded oligonucleotide comprising at least one non-phosphate linkage. Representative non-phosphate linkages include phosphonate, hydroxylamine, hydroxylhydrazinyl, amide, and carbamate linkages. In certain embodiments, the non-phosphate linkage is a phosphonate linkage. In certain embodiments, a non-phosphate linkage occurs in only one strand. In certain embodiments, a non-phosphate linkage occurs in both strands. In certain embodiments, a ligand is bound to one of the oligonucleotide strands comprising the double-stranded oligonucleotide. In certain embodiments, a ligand is bound to both of the oligonucleotide strands comprising the double-stranded oligonucleotide. In certain embodiments, the oligonucleotide strands comprise at least one modified sugar moiety. Another aspect of the present invention relates to a single-stranded oligonucleotide comprising at least one non-phosphate linkage. Representative non-phosphate linkages include phosphonate, hydroxylamine, hydroxylhydrazinyl, amide, and carbamate linkages. In certain embodiments, the non-phosphate linkage is a phosphonate linkage. In certain embodiments, a ligand is bound to the oligonucleotide strand. In certain embodiments, the oligonucleotide comprises at least one modified sugar moiety.

DETAILED DESCRIPTION OF THE INVENTION

Figure 1:
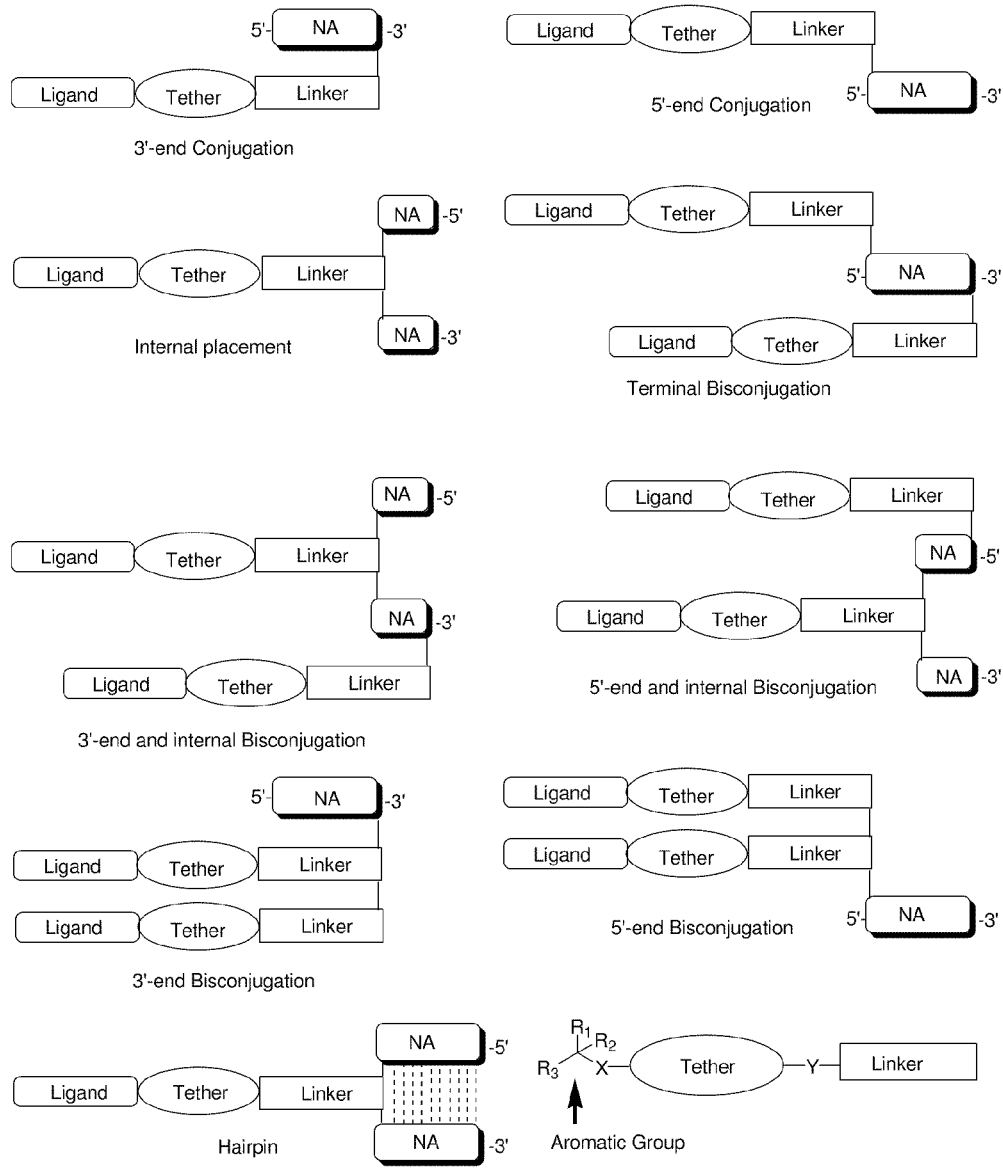
FIG. 1 depicts various oligonucleotides that are conjugated to a ligand. Note that NA is an oligonucleotide (or a nucleic acid) comprising of either RNA or DNA or chimeric RNA-DNA, DNA-RNA, RNA-DNA-RNA or DNA-RNA-DNA. In certain instances, at least one among $R_1$, $R_2$ and $R_3$ is aromatic or substituted aromatic, when $R_1$ is aromatic or substituted aromatic, $R_2$ is either H or any organic substituent, and $R_3$ is either H or any organic substituent.
Figure 2:
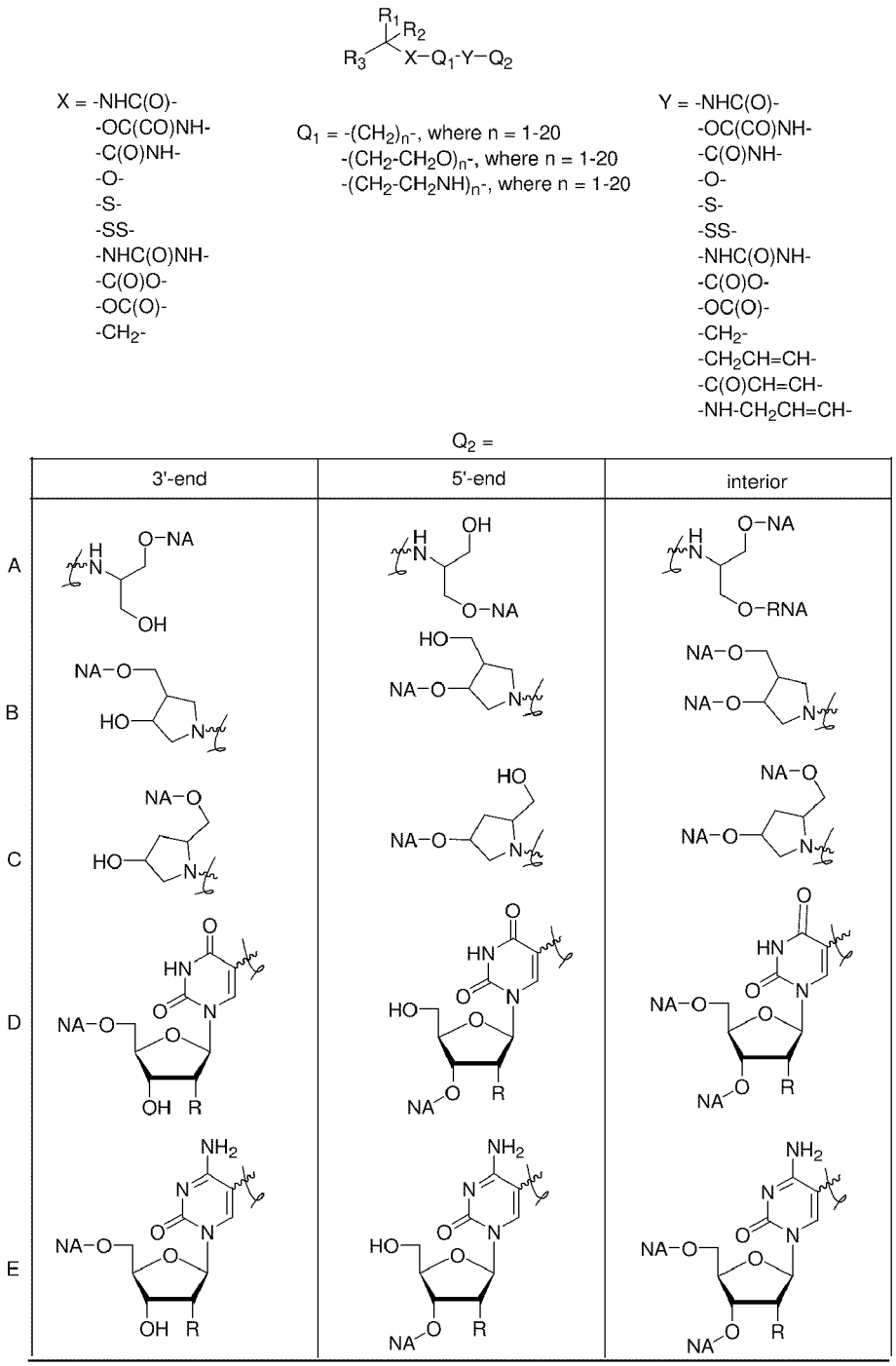
FIG. 2 depicts various oligonucleotides that are conjugated to a ligand. Note: In certain instances, at least one among $R_1$, $R_2$ and $R_3$ is aromatic or substituted aromatic. For rows A-E: NA=DNA or RNA. For row A: racemic and R and S isomers. For rows B and C: racemic and all four stereo isomers (RR, RS, SR and SS). For rows D and E: R=H or OH.
Figure 3:
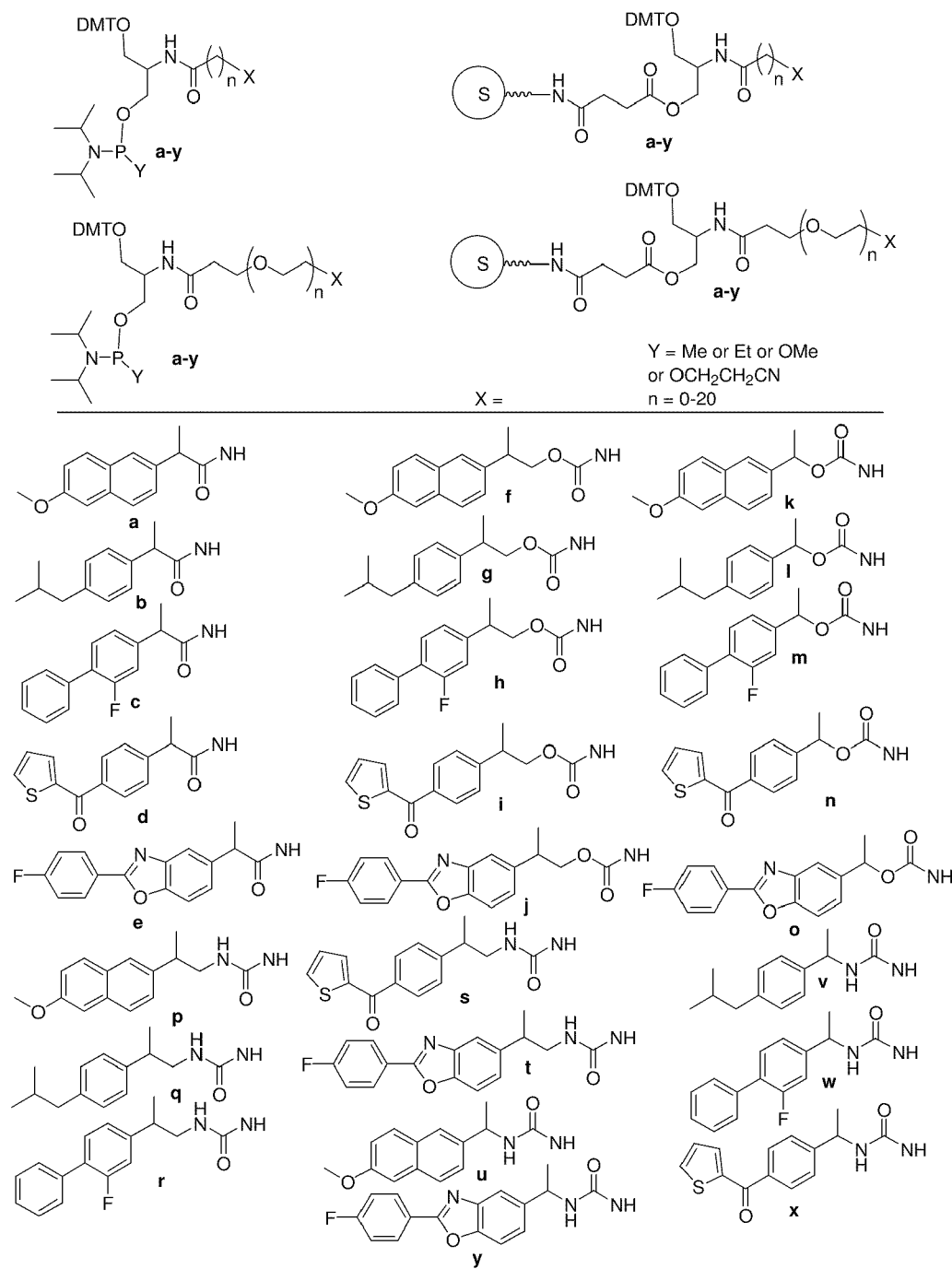
FIG. 3 depicts various NA building blocks with a serinol linker (see row A in FIG. 2) having aralkyl ligands linked through alkyl and PEG tethers. Each ligand shown is either racemic or optically enriched or pure R or S isomer.
Figure 4:
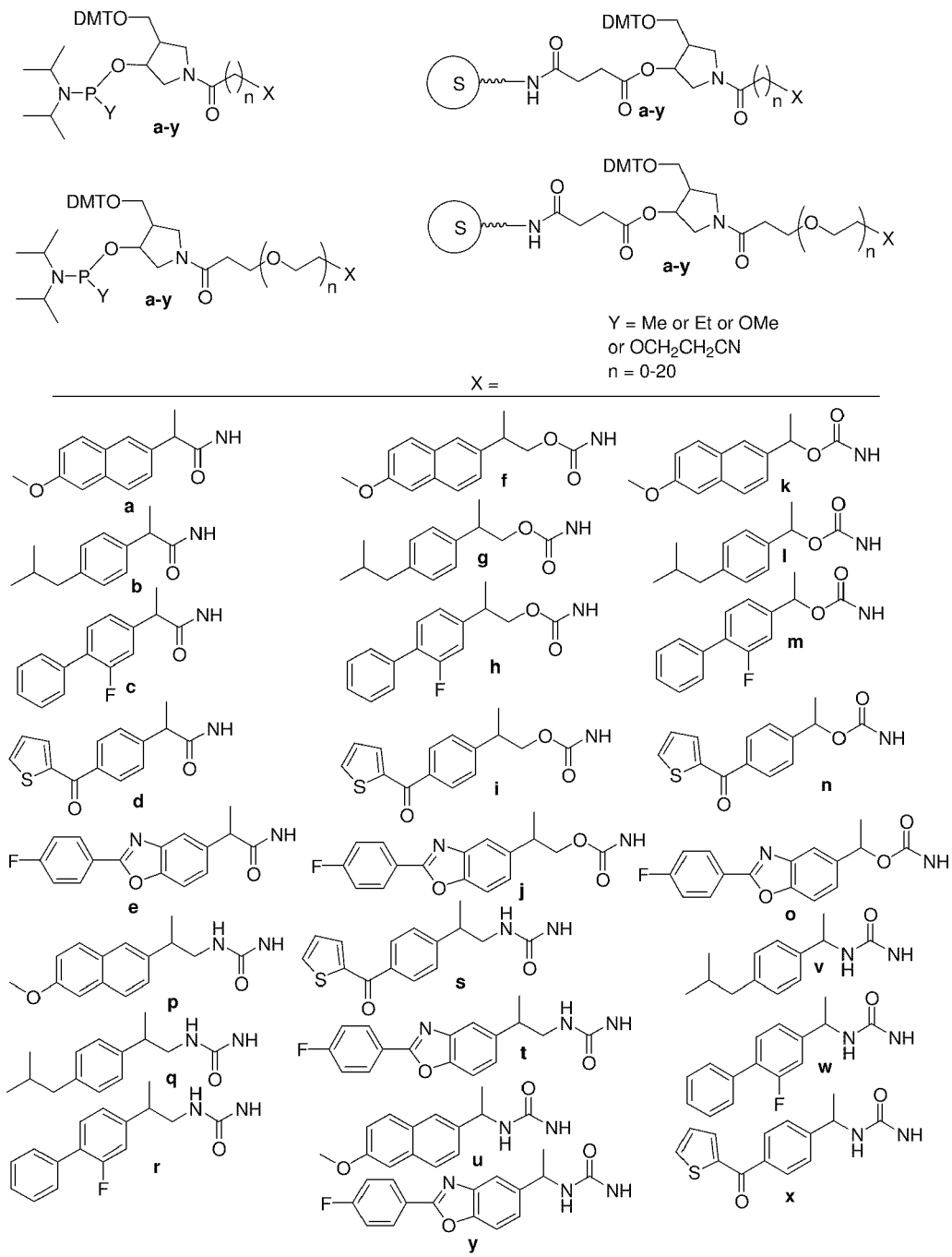
FIG. 4 depicts various NA building blocks with a pyrrolidine linker (see row B in FIG. 2) having aralkyl ligands linked through alkyl and PEG tethers. Each ligand shown is either racemic or optically enriched or pure R or S isomer.
Figure 5:
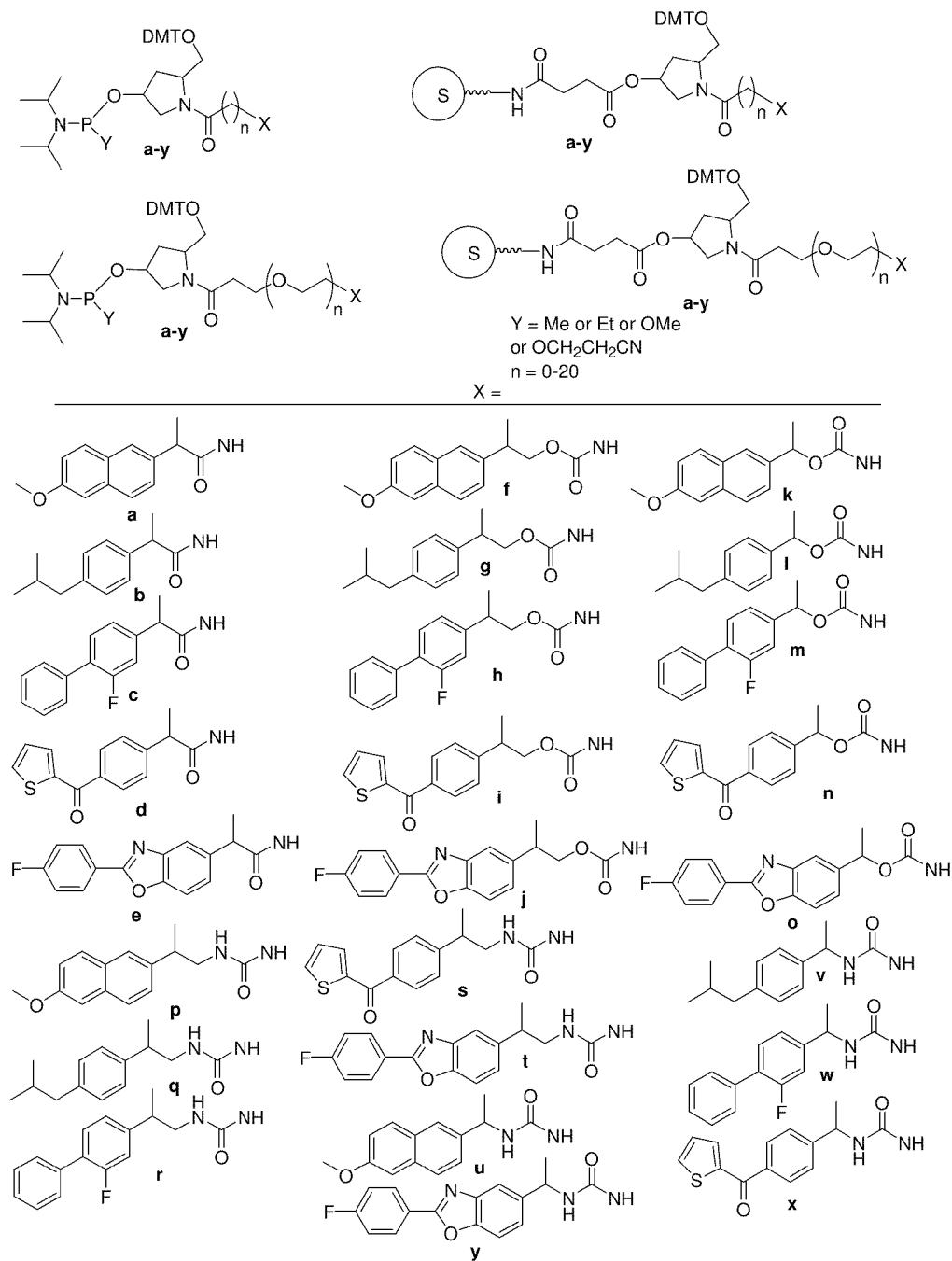
FIG. 5 depicts various NA building blocks with a hydroxyprolinol linker (see row C in FIG. 2) having aralkyl ligands linked through alkyl and PEG tethers. Each ligand shown is either racemic or optically enriched or pure R or S isomer.
Figure 6:
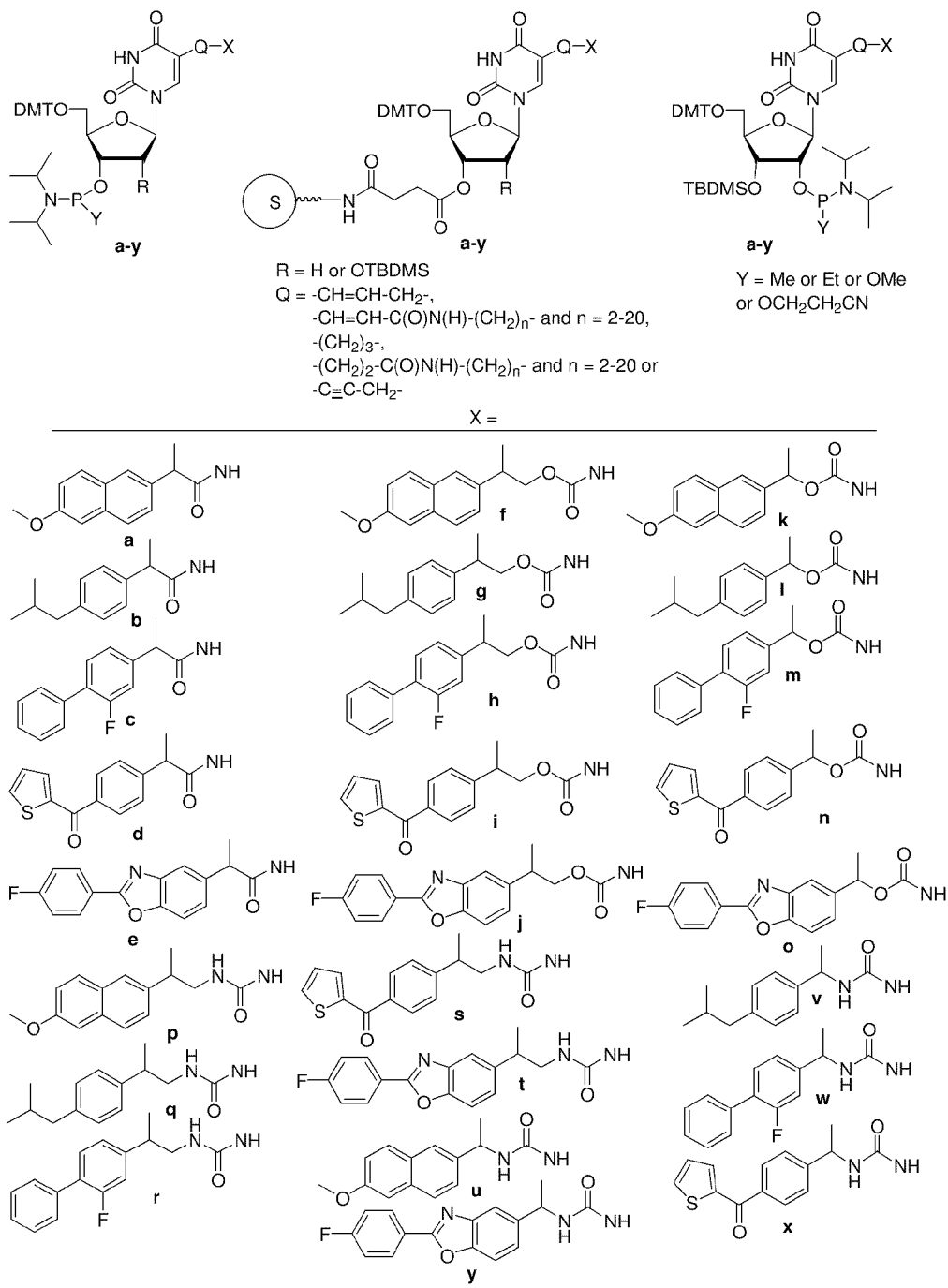
FIG. 6 depicts various NA building blocks with a nucleoside linker (see row D in FIG. 2) having aralkyl ligands linked through selected tethers. Each ligand shown is either racemic or optically enriched or pure R or S isomer.
Figure 7:
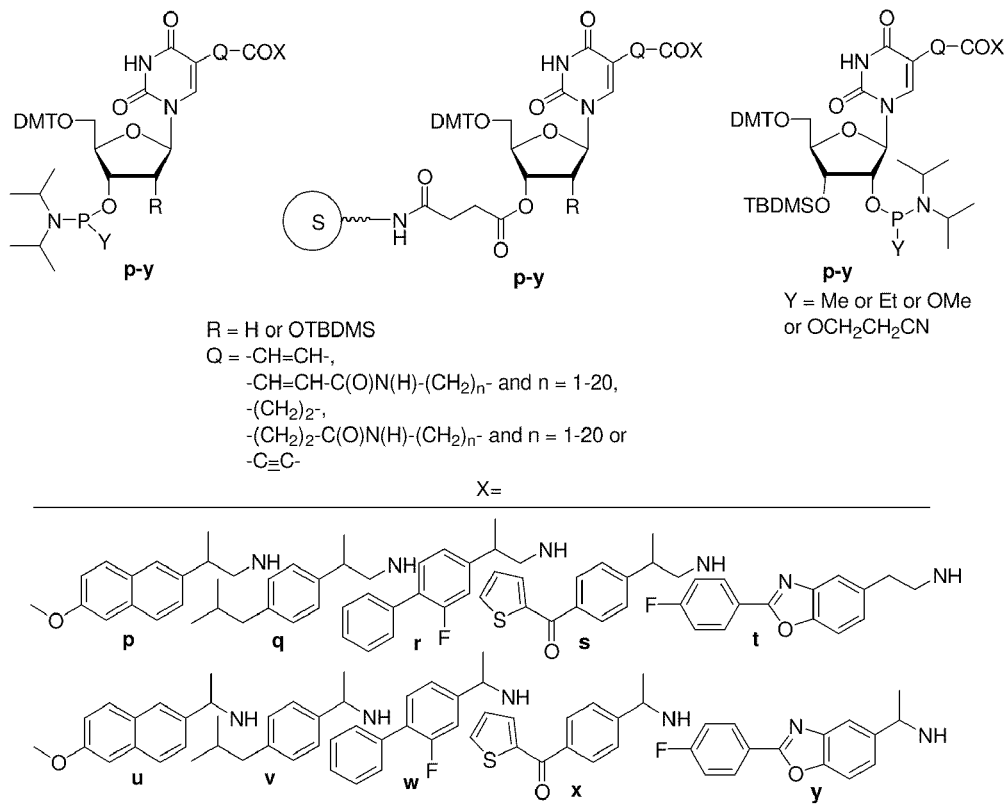
FIG. 7 depicts various NA building blocks with a nucleoside linker (see row D in FIG. 2) having aralkyl ligands linked through selected tethers. Each ligand shown is either racemic or optically enriched or pure R or S isomer.
Figure 8:
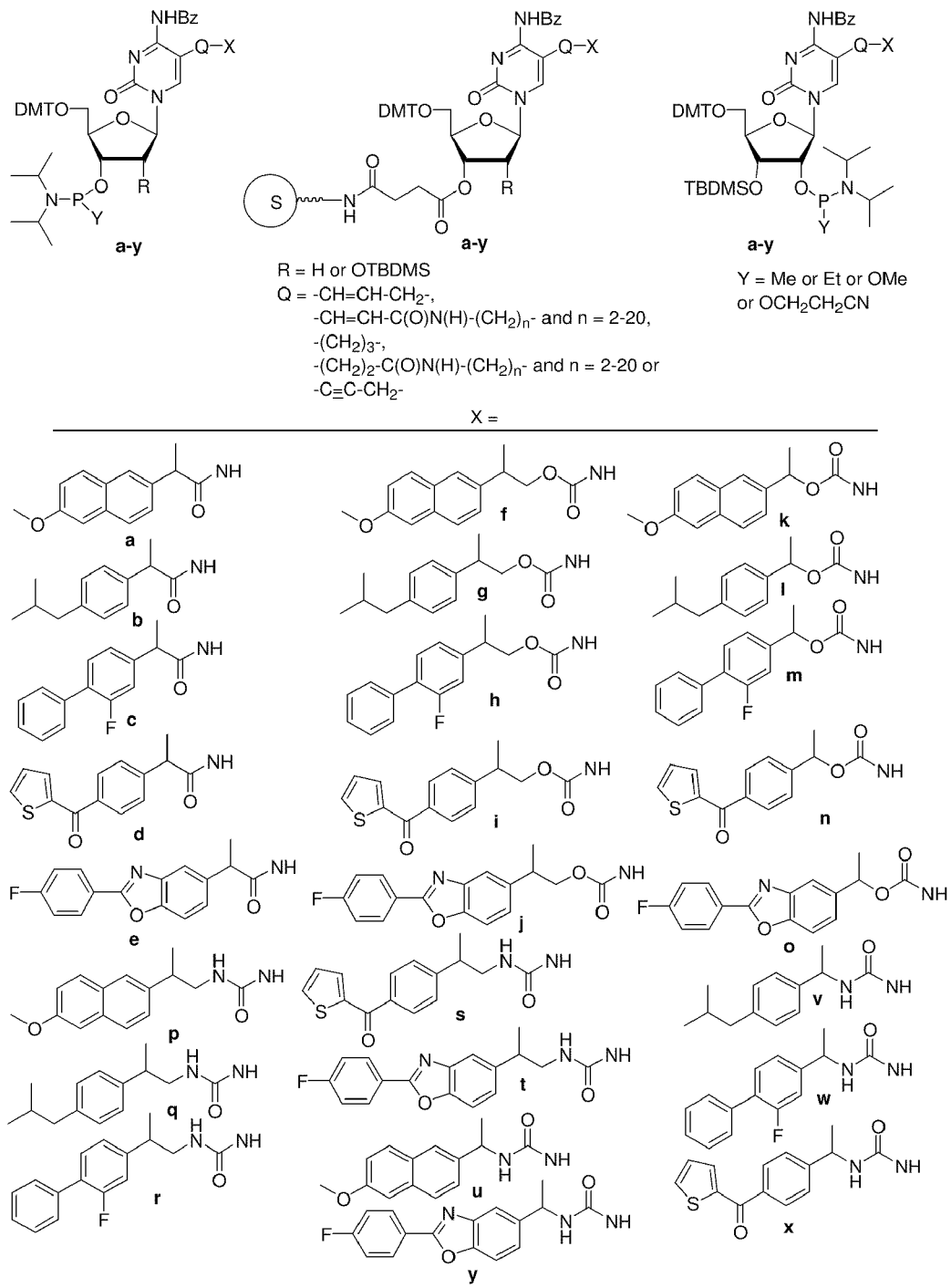
FIG. 8 depicts various NA building blocks with a nucleoside linker (see row E in FIG. 2) having aralkyl ligands linked through selected tethers. Each ligand shown is either racemic or optically enriched or pure R or S isomer.
Figure 9:
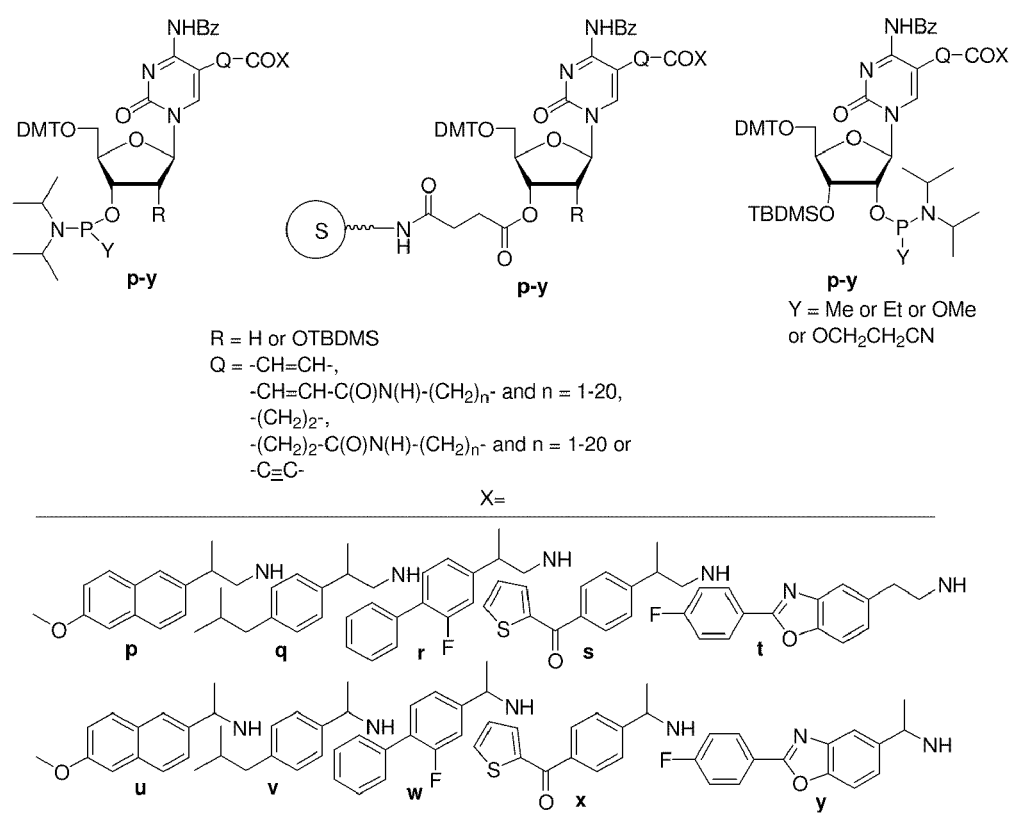
FIG. 9 depicts various NA building blocks with a nucleoside linker (see row E in FIG. 2) having aralkyl ligands linked through selected tethers. Each ligand shown is either racemic or optically enriched or pure R or S isomer.

One aspect of the present invention relates to a ribonucleoside substituted with a phosphonamidite group at the 3'-position. These compounds can be used to prepare oligonucleotides used in gene therapy. Oligonucleosides prepared from 3'-phosphonamidite substituted nucleosides have phosphonate linkages which are less prone to degradation in vivo. In certain instances, the phosphonamidite is an alkyl phosphonamidite. In addition, the 2'-position of the ribonucleoside can be protected with a protecting group that can be easily removed under mild conditions. One example of a protecting group that can be removed under mild conditions is a silyl protecting group. In a preferred embodiment, the protecting group is tert-butyldimethylsilyl.

Another aspect of the present invention relates to a double-stranded oligonucleotide comprising at least one non-phosphate linkage. The non-phosphate moiety renders the oligonucleotide less prone to degradation in vivo. A large number of non-phosphate functional groups are known in the art and are amenable to the present invention. The non-phosphate linkage can be a functional group that contains a phosphorous atom, or a functional group that does not contain a phosphorous atom. Representative non-phosphate linkages amenable to the present invention are phosphonate, hydroxylamine, hydroxylhydrazinyl, amide, and carbamate linkages. In certain embodiments, the non-phosphate linkage is a phosphonate linkage. The non-phosphate linkage can occur in only one strand or in both strands. In certain instances, there are about 1-5 non-phosphate linkages per double-stranded oligonucleotide. In certain instances, there are about 5-10 non-phosphate linkages per double-stranded oligonucleotide. In certain instances, there are about 10-20 non-phosphate linkages per double-stranded oligonucleotide. In certain instances, there are about 1-2 non-phosphate linkages per strand in the double-stranded oligonucleotide. In certain instances, there are about 3-5 non-phosphate linkages per strand in the double-stranded oligonucleotide. In certain instances, there are about 5-10 non-phosphate linkages per strand in the double-stranded oligonucleotide. In certain instances, there are about 10-15 non-phosphate linkages per strand in the double-stranded oligonucleotide. A non-phosphate linkage can be located near the terminus of the oligonucleotide strand or in the interior of the oligonucleotide strand. In certain instances, a non-phosphate linkage is located between the first and second nucleoside at the 3'-terminus of the oligonucleotide strand. In certain instances, a non-phosphate linkage is located between the first and second nucleoside at the 5'-terminus of the oligonucleotide strand. In certain instances, a non-phosphate linkage is located between the first and second nucleoside at the 3'-terminus of the oligonucleotide strand, and a non-phosphate linkage is located between the first and second nucleoside at the 5'-terminus of the oligonucleotide strand. In certain instances, there are two adjacent non-phosphate linkages.

Additional examples of non-phosphate linkages include, for example, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5', or 2' to 2' linkage. In certain instances, the oligonucleotides have inverted polarity comprising a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative examples of non-phosphate linkages that contain a phosphorus atom include phosphoramidate (—O—P(O)(NJ)-O—), phosphonate (—O—P(J)(O)—O—), thionophosphoramidate (—O—P(O)(NJ)-S—), thionoalkylphosphonate (—O—P(S)(J)-O—), thionoalkylphosphotriester (—O—P(O)(OJ)-S—), phosphoramidate (—N(J)-P(O)(O)—O—), and boranophosphate (—R—P(O)(O)-J—), wherein J denotes a substituent group which is commonly hydrogen or an alkyl group or a more complicated group (e.g., aryl, aralkyl, cycloalkyl, heterocycloalkyl, alkenyl, and the like) that varies from one type of linkage to another. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697; and 5,625,050; each of which is herein incorporated by reference.

Non-phosphate linkages that do not include a phosphorus atom include short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ components. For additional details, see Y. S. Sanghvi in Comprehensive Natural Products, Barton, B.; Nakanishi, K.; Meth-Coth, O.; and Kool, E. T. Eds.; Elsevier, New York, 1999, vol 7, 285 which is hereby incorporated by reference.

Representative non-phosphorus containing linkages include thiodiester (—O—C(O)—S—), thionocarbamate (—O—C(O)(NJ)-S—), siloxane (—O—Si(J)$_2$-O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—SO$_2$—NH—), sulfide (—CH$_2$—S—CH$_2$—), sulfonate (—O—SO$_2$—CH$_2$—), N,N'-dimethylhydrazine (—CH$_2$—N(CH$_3$)—N(CH$_3$)—), thioformacetal (—S—CH$_2$—O—), formacetal (—O—CH$_2$—O—), thioketal (—S—C(J)$_2$-O—), ketal (—O—C(J)$_2$-O—), amine (—NH—CH$_2$—CH$_2$—), hydroxylamine (—CH$_2$—N(J)-O—), hydroxyimine (—CH=N—O—), and hydrazinyl (—CH$_2$—N(H)—N(H)—); wherein J denotes a substituent group which is commonly hydrogen or an alkyl group or a more complicated group that varies from one type of linkage to another. Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269; and 5,677,439; each of which is herein incorporated by reference.

Particularly preferred embodiments of the invention are oligonucleotides with phosphorothioate backbones and phosphonate backbones. In addition, oligonucleotides with phosphorothioate backbones and heteroatom backbones are preferred, and in particular —CH$_2$—NH—O—CH$_2$—, —CH$_2$—N(CH$_3$)—O—CH$_2$—[known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— as described in U.S. Pat. No. 5,489,677, and the amide backbones described in U.S. Pat. No. 5,602,240. Also preferred are oligonucleotides having morpholino backbone structures as described in U.S. Pat. No. 5,034,506.

In a preferred embodiment, the oligonucleotide is a ribonucleotide comprising a non-phosphate linkage, and the non-phosphate linkage is a phosphorothioate, phosphorodithioate, boranophosphate, phosphorofluoridate, phosphoroselenoate, phosphoramidate, aminoalkylphosphonate, alkylphosphonate, phosphoramidate, phosphoramidimidate, phosphorotriester, phosphinate, amide, guanidine, urea, carbamate, thiocarbamate, amine, hydroxylamine, siloxane, sulfide, sulfone, sulfonate, sulfonamide, formacetal, thioformacetal, ether, alkyl, aryl, aralkyl, heteroalkyl, cycloalkyl, heterocycloalkyl, heteroaryl, heteroaralkyl, alkenyl, alkynyl, acrylyl, dimethylhydrazinyl, hydroxyhydrazinyl, ketal, thioketal, or formacetal.

Another aspect of the present invention relates to a single-stranded oligonucleotide comprising at least one non-phosphate linkage. Representative non-phosphate linkages include phosphonate, hydroxylamine, hydroxylhydrazinyl, amide, and carbamate linkages. A more thorough listing of contemplated non-phosphate linkages is described above. In certain embodiments, the non-phosphate linkage is a phosphonate linkage. In certain embodiments, a ligand is bound to the oligonucleotide strand. In certain embodiments, the oligonucleotide comprises at least one modified sugar moiety. In certain embodiments, the oligonucleotide is a ribonucleotide.

In a preferred embodiment, the single-stranded oligonucleotide is a ribonucleotide comprising a non-phosphate linkage, and the non-phosphate linkage is a phosphorothioate, phosphorodithioate, boranophosphate, phosphorofluoridate, phosphoroselenoate, phosphoramidate, aminoalkylphosphonate, alkylphosphonate, phosphoramidate, phosphoramidimidate, phosphorotriester, phosphinate, amide, guanidine, urea, carbamate, thiocarbamate, amine, hydroxylamine, siloxane, sulfide, sulfone, sulfonate, sulfonamide, formacetal, thioformacetal, ether, alkyl, aryl, aralkyl, heteroalkyl, cycloalkyl, heterocycloalkyl, heteroaryl, heteroaralkyl, alkenyl, alkynyl, acrylyl, dimethylhydrazinyl, hydroxyhydrazinyl, ketal, thioketal, or formacetal.

Representative examples of oligonucleotides amenable to both single-stranded and double-stranded oligonucleotides of the invention containing one or more of alkylphosphonate, alkylthiophosphonate, and alkylphosphonate/alkylthiophosphonate backbone modifications are shown in the tables below.

TABLE 1

Single incorporation of P-alkylphosphonate backbone at the 3'-end of oligonucleotide

I

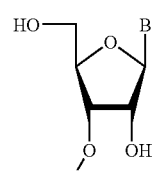

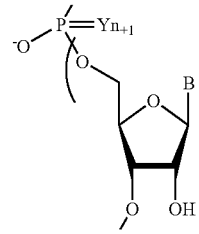

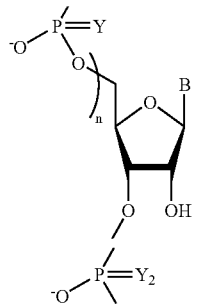

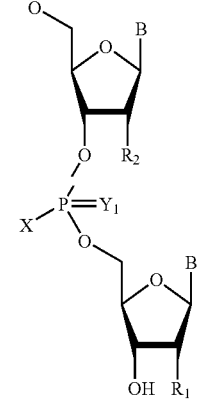

TABLE 1-continued

II

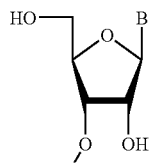

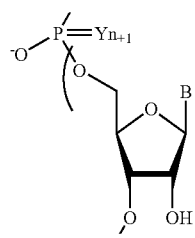

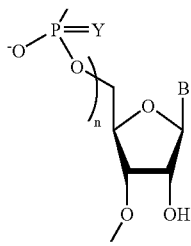

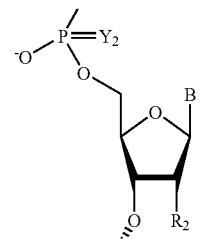

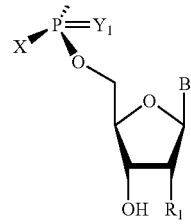

III

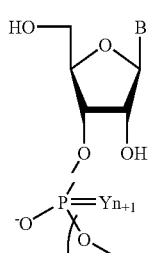

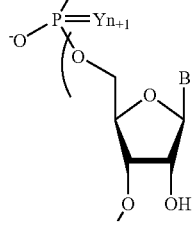

TABLE 1-continued

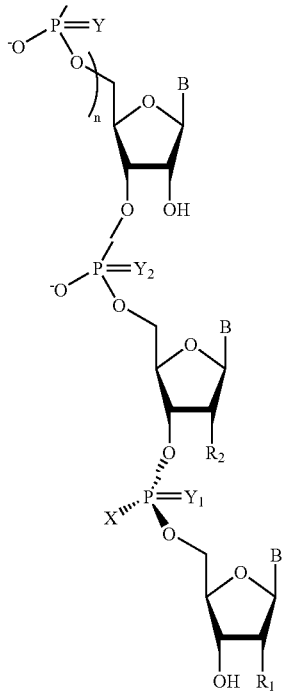

1. $R_1, R_2 = H$, $X = $ Me/isopropyl/tert-butyl, $Y_1—Y_{n+1} = O$
2. $R_1, R_2 = H$, $X = $ Me/isopropyl/tert-butyl, $Y_1—Y_{n+1} = S$
3. $R_1, R_2 = H$, $X = $ Me/isopropyl/tert-butyl,
   $Y_1 = S, Y_2—Y_n = O, Y_{n+1} = S$
4. $R_1, R_2 = H$, $X = $ Me/isopropyl/tert-butyl,
   $Y_1 = O, Y_2—Y_n = S, Y_{n+1} = O$
5. $R_1, R_2 = H$, $X = $ Me/isopropyl/tert-butyl,
   $Y_1 = S, Y_2—Y_{n+1} = O$
6. $R_1, R_2 = H$, $X = $ Me/isopropyl/tert-butyl,
   $Y_1 = O, Y_2—Y_{n+1} = S$
7. $R_1, R_2 = H$, $X = $ Me/isopropyl/tert-butyl,
   $Y_1, Y_2 = S, Y_3—Y_n = O, Y_{n+1} = S$
8. $R_1, R_2 = H$, $X = $ Me/isopropyl/tert-butyl,
   $Y_1, Y_3 \ldots Y_{n+1} = S, Y_2, Y_4, Y_6 \ldots Y_n = O$
9. $R_1, R_2 = H$, $X = $ Me/isopropyl/tert-butyl,
   $Y_1, Y_3 \ldots Y_{n+1} = O, Y_2, Y_4, Y_6 \ldots Y_n = S$
10. $R_1 = H, R_2 = OH$, $X = $ Me/isopropyl/tert-butyl, $Y_1—Y_{n+1} = O$
11. $R_1 = H, R_2 = OH$, $X = $ Me/isopropyl/tert-butyl, $Y_1—Y_{n+1} = S$
12. $R_1 = H, R_2 = OH$, $X = $ Me/isopropyl/tert-butyl,
    $Y_1 = S, Y_2—Y_n = O, Y_{n+1} = S$
13. $R_1 = H, R_2 = OH$, $X = $ Me/isopropyl/tert-butyl,
    $Y_1 = O, Y_2—Y_n = S, Y_{n+1} = O$
14. $R_1 = H, R_2 = OH$, $X = $ Me/isopropyl/tert-butyl,
    $Y_1 = S, Y_2—Y_{n+1} = O$
15. $R_1 = H, R_2 = OH$, $X = $ Me/isopropyl/tert-butyl,
    $Y_1 = O, Y_2—Y_{n+1} = S$
16. $R_1 = H, R_2 = OH$, $X = $ Me/isopropyl/tert-butyl,
    $Y_1, Y_2 = S, Y_3—Y_n = O, Y_{n+1} = S$
17. $R_1 = H, R_2 = OH$, $X = $ Me/isopropyl/tert-butyl,
    $Y_1, Y_3 \ldots Y_{n+1} = S, Y_2, Y_4, Y_6 \ldots Y_n = O$
18. $R_1 = H, R_2 = OH$, $X = $ Me/isopropyl/tert-butyl,
    $Y_1, Y_3 \ldots Y_{n+1} = O, Y_2, Y_4, Y_6 \ldots Y_n = S$
19. $R_1, R_2 = OH$, $X = $ Me/isopropyl/tert-butyl, $Y_1—Y_{n+1} = O$
20. $R_1, R_2 = OH$, $X = $ Me/isopropyl/tert-butyl, $Y_1—Y_{n+1} = S$
21. $R_1, R_2 = OH$, $X = $ Me/isopropyl/tert-butyl,
    $Y_1 = S, Y_2—Y_n = O, Y_{n+1} = S$
22. $R_1, R_2 = OH$, $X = $ Me/isopropyl/tert-butyl,
    $Y_1 = O, Y_2—Y_n = S, Y_{n+1} = O$
23. $R_1, R_2 = OH$, $X = $ Me/isopropyl/tert-butyl,
    $Y_1 = S, Y_2—Y_{n+1} = O$
24. $R_1, R_2 = OH$, $X = $ Me/isopropyl/tert-butyl,
    $Y_1 = O, Y_2—Y_{n+1} = S$
25. $R_1, R_2 = OH$, $X = $ Me/isopropyl/tert-butyl,
    $Y_1, Y_2 = S, Y_3—Y_n = O, Y_{n+1} = S$
26. $R_1, R_2 = OH$, $X = $ Me/isopropyl/tert-butyl,
    $Y_1, Y_3 \ldots Y_{n+1} = S, Y_2, Y_4, Y_6 \ldots Y_n = O$
27. $R_1, R_2 = OH$, $X = $ Me/isopropyl/tert-butyl,
    $Y_1, Y_3 \ldots Y_{n+1} = O, Y_2, Y_4, Y_6 \ldots Y_n = S$

TABLE 2

Single incorporation of P-alkylphosphonate backbone at the 5'-end of oligonucleotide

IV

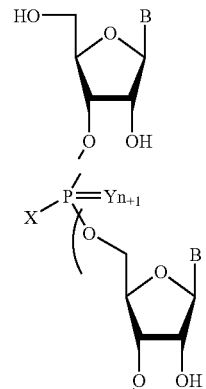
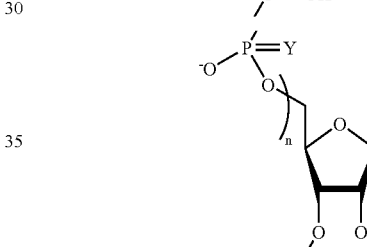
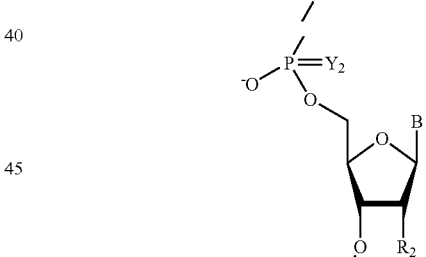
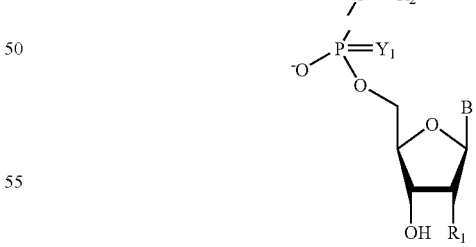

V

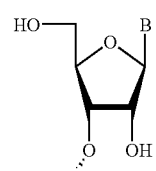

TABLE 2-continued

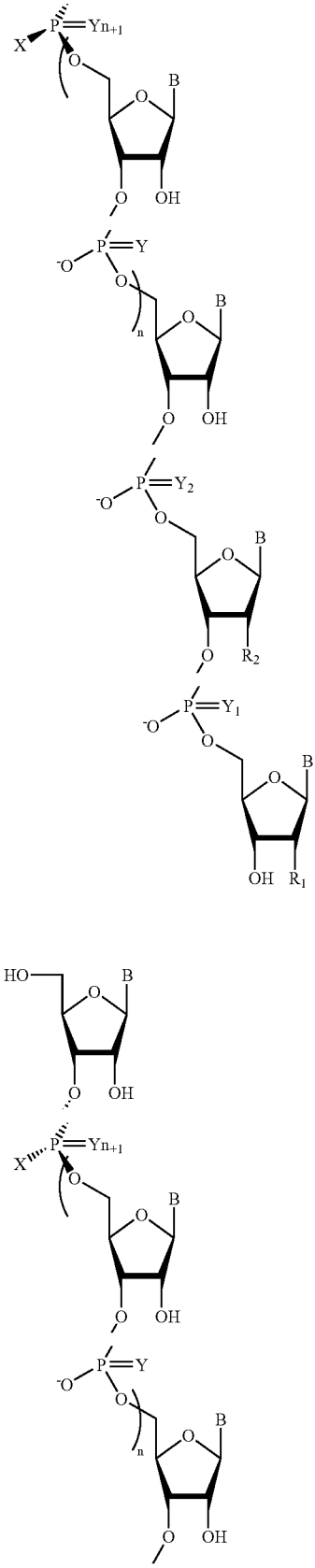

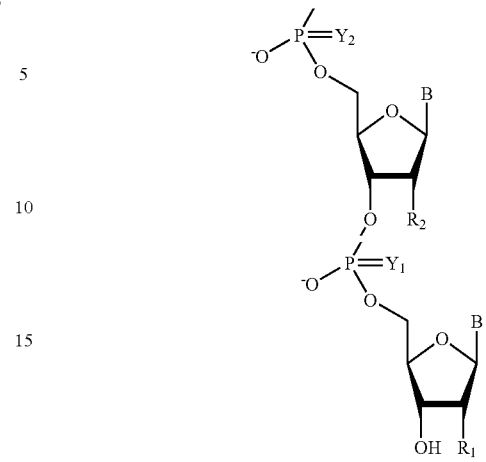

VI

1. $R_1, R_2 = H, X = Me/isopropyl/tert-butyl, Y_1—Y_{n+1} = O$
2. $R_1, R_2 = H, X = Me/isopropyl/tert-butyl, Y_1—Y_{n+1} = S$
3. $R_1, R_2 = H, X = Me/isopropyl/tert-butyl,$
   $Y_1 = S, Y_2—Y_n = O, Y_{n+1} = S$
4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$
16. $R_1 = H, R_2 = OH, X = Me/isopropyl/tert-butyl,$
    $Y_1, Y_2 = S, Y_3—Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl,$
    $Y_1 = S, Y_2—Y_n = O, Y_{n+1} = S$
22. $R_1, R_2 = OH, X = Me/isopropyl/tert-butyl,$
    $Y_1 = O, Y_2—Y_n = S, Y_{n+1} = O$
23. $R_1, R_2 = OH, X = Me/isopropyl/tert-butyl,$
    $Y_1 = S, Y_2—Y_{n+1} = O$
24. $R_1, R_2 = OH, X = Me/isopropyl/tert-butyl,$
    $Y_1 = O, Y_2—Y_{n+1} = S$
25. $R_1, R_2 = OH, X = Me/isopropyl/tert-butyl,$
    $Y_1, Y_2 = S, Y_3—Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$

TABLE 3
Double incorporation of P-alkylphosphonate backbone at the 3'-end of oligonucleotide
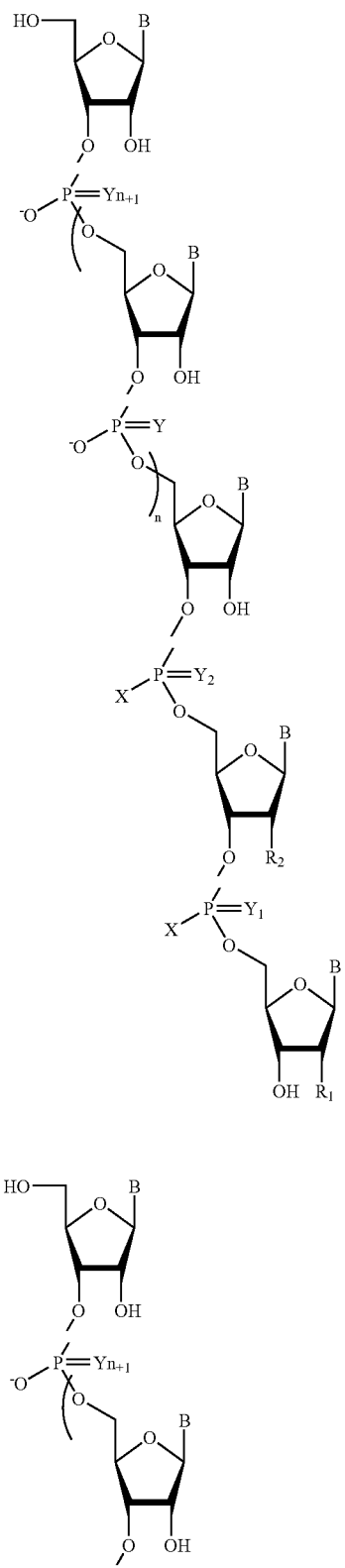
VII
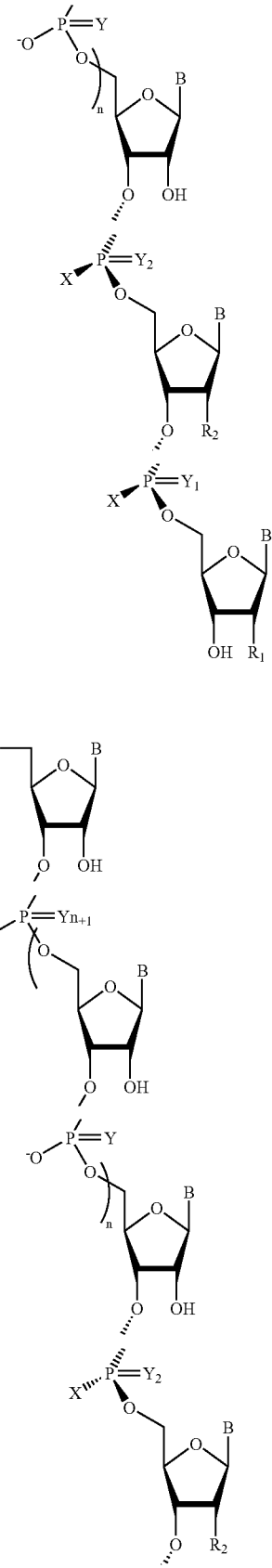
VIII
IX TABLE 3-continued

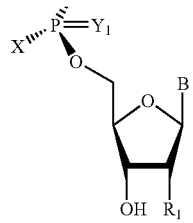

1. $R_1, R_2 = H, X = Me/isopropyl/tert-butyl, Y_1-Y_{n+1} = O$
2. $R_1, R_2 = H, X = Me/isopropyl/tert-butyl, Y_1-Y_{n+1} = S$
3. $R_1, R_2 = H, X = Me/isopropyl/tert-butyl,$
   $Y_1 = S, Y_2-Y_n = O, Y_{n+1} = S$
4. $R_1, R_2 = H, X = Me/isopropyl/tert-butyl,$
   $Y_1 = O, Y_2-Y_n = S, Y_{n+1} = O$
5. $R_1, R_2 = H, X = Me/isopropyl/tert-butyl,$
   $Y_1 = S, Y_2-Y_{n+1} = O$
6. $R_1, R_2 = H, X = Me/isopropyl/tert-butyl,$
   $Y_1 = O, Y_2-Y_{n+1} = S$
7. $R_1, R_2 = H, X = Me/isopropyl/tert-butyl,$
   $Y_1, Y_2 = S, Y_3-Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1-Y_{n+1} = O$
11. $R_1 = H, R_2 = OH, X = Me/isopropyl/tert-butyl, Y_1-Y_{n+1} = S$
12. $R_1 = H, R_2 = OH, X = Me/isopropyl/tert-butyl,$
    $Y_1 = S, Y_2-Y_n = O, Y_{n+1} = S$
13. $R_1 = H, R_2 = OH, X = Me/isopropyl/tert-butyl,$
    $Y_1 = O, Y_2-Y_n = S, Y_{n+1} = O$
14. $R_1 = H, R_2 = OH, X = Me/isopropyl/tert-butyl,$
    $Y_1 = S, Y_2-Y_{n+1} = O$
15. $R_1 = H, R_2 = OH, X = Me/isopropyl/tert-butyl,$
    $Y_1 = O, Y_2-Y_{n+1} = S$
16. $R_1 = H, R_2 = OH, X = Me/isopropyl/tert-butyl,$
    $Y_1, Y_2 = S, Y_3-Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1-Y_{n+1} = O$
20. $R_1, R_2 = OH, X = Me/isopropyl/tert-butyl, Y_1-Y_{n+1} = S$
21. $R_1, R_2 = OH, X = Me/isopropyl/tert-butyl,$
    $Y_1 = S, Y_2-Y_n = O, Y_{n+1} = S$
22. $R_1, R_2 = OH, X = Me/isopropyl/tert-butyl,$
    $Y_1 = O, Y_2-Y_n = S, Y_{n+1} = O$
23. $R_1, R_2 = OH, X = Me/isopropyl/tert-butyl,$
    $Y_1 = S, Y_2-Y_{n+1} = O$
24. $R_1, R_2 = OH, X = Me/isopropyl/tert-butyl,$
    $Y_1 = O, Y_2-Y_{n+1} = S$
25. $R_1, R_2 = OH, X = Me/isopropyl/tert-butyl,$
    $Y_1, Y_2 = S, Y_3-Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of isopropyl and tert-butyl

TABLE 5

Double incorporation of P-alkylphosphonate backbone at the 3'- and 5'-end of oligonucleotide

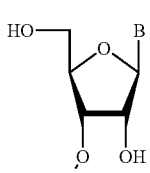

TABLE 5-continued

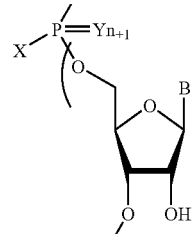

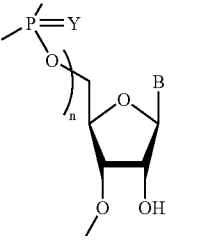

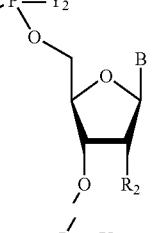

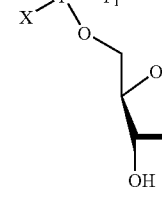

XI

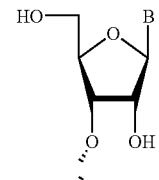

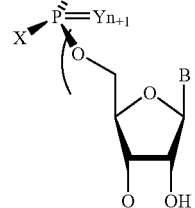

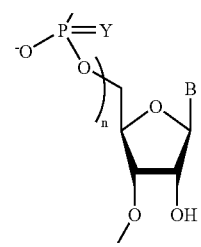

TABLE 5-continued

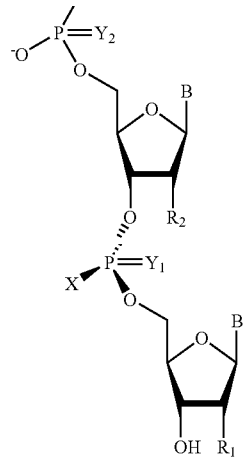

XII

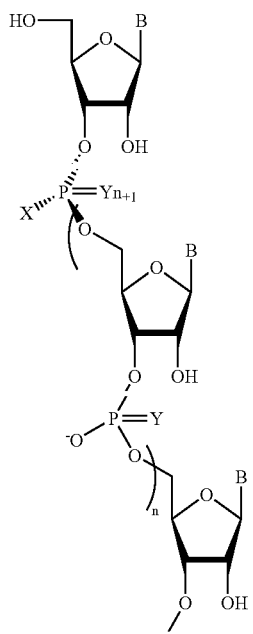

1. $R_1, R_2 = H, X = Me/isopropyl/tert-butyl, Y_1—Y_{n+1} = O$
2. $R_1, R_2 = H, X = Me/isopropyl/tert-butyl, Y_1—Y_{n+1} = S$
3. $R_1, R_2 = H, X = Me/isopropyl/tert-butyl,$
   $Y_1 = S, Y_2—Y_n = O, Y_{n+1} = S$ TABLE 5-continued 4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$
16. $R_1 = H, R_2 = OH, X = Me/isopropyl/tert-butyl,$
    $Y_1, Y_2 = S, Y_3—Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl,$
    $Y_1 = S, Y_2—Y_n = O, Y_{n+1} = S$
22. $R_1, R_2 = OH, X = Me/isopropyl/tert-butyl,$
    $Y_1 = O, Y_2—Y_n = S, Y_{n+1} = O$
23. $R_1, R_2 = OH, X = Me/isopropyl/tert-butyl,$
    $Y_1 = S, Y_2—Y_{n+1} = O$
24. $R_1, R_2 = OH, X = Me/isopropyl/tert-butyl,$
    $Y_1 = O, Y_2—Y_{n+1} = S$
25. $R_1, R_2 = OH, X = Me/isopropyl/tert-butyl,$
    $Y_1, Y_2 = S, Y_3—Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of isopropyl and tert-butyl

TABLE 5

Multiple Incorporation P-alkylphosphonate Backbone into Oligonucleotides.

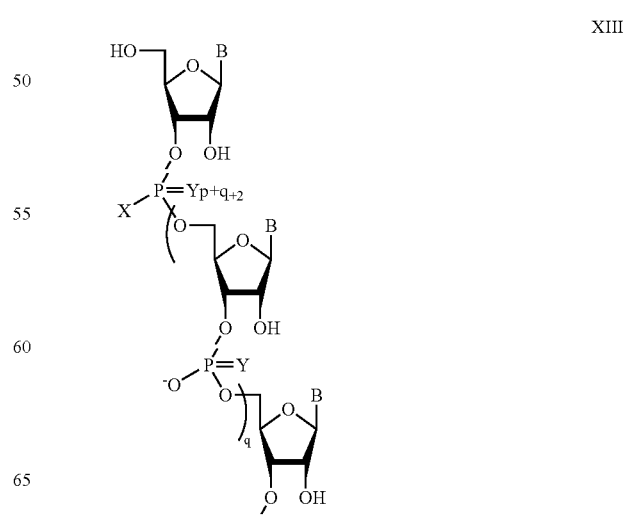

XIII

TABLE 5-continued
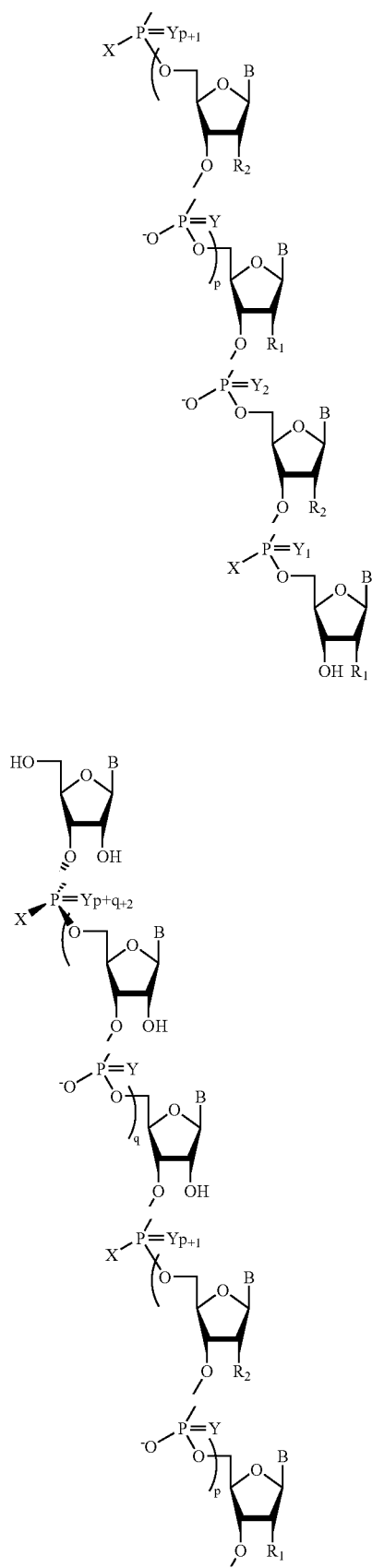
XIV
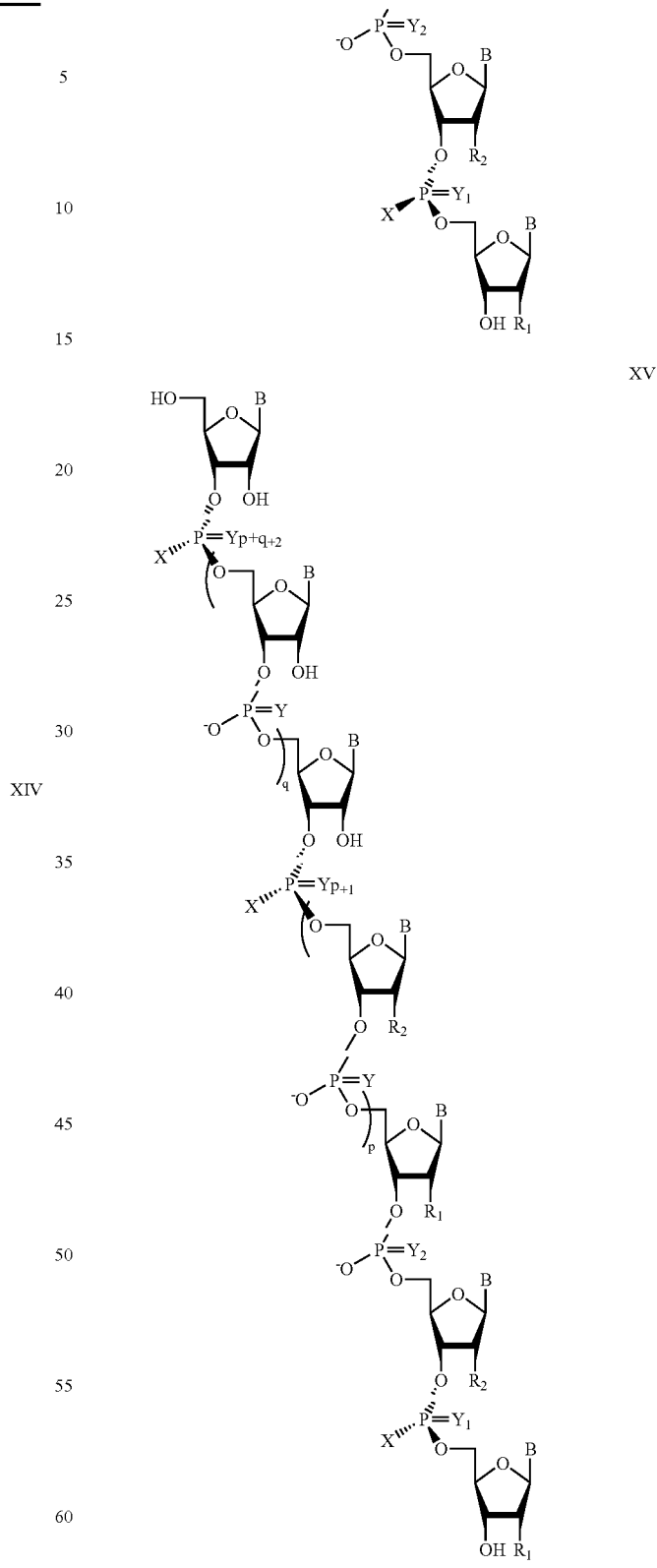
XV
1. $R_1, R_2 = H$, $X = Me/isopropyl/tert-butyl$, $Y_1—Y_{p+q+2} = O$
2. $R_1, R_2 = H$, $X = Me/isopropyl/tert-butyl$, $Y_1—Y_{p+q+2} = S$
3. $R_1, R_2 = H$, $X = Me/isopropyl/tert-butyl$,
   $Y_1 = S$, $Y_2—Y_{p+q+1} = O$, $Y_{p+q+2} = S$

TABLE 5-continued

4. $R_1, R_2 = H, X = \text{Me/isopropyl/tert-butyl},$
 $Y_1 = O, Y_2\text{—}Y_{p+q+1} = S, Y_{p+q+2} = O$
5. $R_1, R_2 = H, X = \text{Me/isopropyl/tert-butyl},$
 $Y_1 = S, Y_2\text{—}Y_{p+q+2} = O$
6. $R_1, R_2 = H, X = \text{Me/isopropyl/tert-butyl},$
 $Y_1 = O, Y_2\text{—}Y_{p+q+2} = S$
7. $R_1, R_2 = H, X = \text{Me/isopropyl/tert-butyl},$
 $Y_1, Y_{p+1}, Y_{p+q+2} = S, Y_2\text{—}Y_p, Y_q\text{—}Y_{p+q+1} = O$
8. $R_1, R_2 = H, X = \text{Me/isopropyl/tert-butyl},$
 $Y_1, Y_{p+1}, Y_{p+q+2} = O, Y_2\text{—}Y_p, Y_q\text{—}Y_{p+q+1} = S$
9. $R_1, R_2 = H, X = \text{Me/isopropyl/tert-butyl},$
 $Y_{p+1} = S, Y_1\text{—}Y_p, Y_q\text{—}Y_{p+q+1} = O$
10. $R_1, R_2 = H, X = \text{Me/isopropyl/tert-butyl},$
 $Y_{p+1} = O, Y_1\text{—}Y_p, Y_q\text{—}Y_{p+q+2} = S$
11. $R_1, R_2 = H, X = \text{Me/isopropyl/tert-butyl},$
 $Y_{p+q+2} = S, Y_1\text{—}Y_{p+q+1} = O$
12. $R_1, R_2 = H, X = \text{Me/isopropyl/tert-butyl},$
 $Y_{p+q+2} = P, Y_1\text{—}Y_{p+q+1} = S$
13. $R_1 = H, R_2 = OH, X = \text{Me/isopropyl/tert-butyl}, Y_1\text{—}Y_{p+q+2} = O$
14. $R_1 = H, R_2 = OH, X = \text{Me/isopropyl/tert-butyl}, Y_1\text{—}Y_{p+q+2} = S$
15. $R_1 = H, R_2 = OH, X = \text{Me/isopropyl/tert-butyl},$
 $Y_1 = S, Y_2\text{—}Y_{p+q+1} = O, Y_{p+q+2} = S$
16. $R_1 = H, R_2 = OH, X = \text{Me/isopropyl/tert-butyl},$
 $Y_1 = O, Y_2\text{—}Y_{p+q+1} = S, Y_{p+q+2} = O$
17. $R_1 = H, R_2 = OH, X = \text{Me/isopropyl/tert-butyl},$
 $Y_1 = S, Y_2\text{—}Y_{p+q+2} = O$
18. $R_1 = H, R_2 = OH, X = \text{Me/isopropyl/tert-butyl},$
 $Y_1 = O, Y_2\text{—}Y_{p+q+2} = S$
19. $R_1 = H, R_2 = OH, X = \text{Me/isopropyl/tert-butyl},$
 $Y_1, Y_{p+1}, Y_{p+q+2} = S, Y_2\text{—}Y_p, Y_q\text{—}Y_{p+q+1} = O$
20. $R_1 = H, R_2 = OH, X = \text{Me/isopropyl/tert-butyl},$
 $Y_1, Y_{p+1}, Y_{p+q+2} = O, Y_2\text{—}Y_p, Y_q\text{—}Y_{p+q+1} = S$
21. $R_1 = H, R_2 = OH, X = \text{Me/isopropyl/tert-butyl},$
 $Y_{p+1} = S, Y_1\text{—}Y_p, Y_q\text{—}Y_{p+q+2} = O$
22. $R_1 = H, R_2 = OH, X = \text{Me/isopropyl/tert-butyl},$
 $Y_{p+1} = O, Y_1\text{—}Y_p, Y_q\text{—}Y_{p+q+2} = S$
23. $R_1 = H, R_2 = OH, X = \text{Me/isopropyl/tert-butyl},$
 $Y_{p+q+2} = S, Y_1\text{—}Y_{p+q+1} = O$
24. $R_1 = H, R_2 = OH, X = \text{Me/isopropyl/tert-butyl},$
 $Y_{p+q+2} = P, Y_1\text{—}Y_{p+q+1} = S$
25. $R_1, R_2 = OH, X = \text{Me/isopropyl/tert-butyl}, Y_1\text{—}Y_{p+q+2} = O$
26. $R_1, R_2 = OH, X = \text{Me/isopropyl/tert-butyl}, Y_1\text{—}Y_{p+q+2} = S$
27. $R_1, R_2 = OH, X = \text{Me/isopropyl/tert-butyl},$
 $Y_1 = S, Y_2\text{—}Y_{p+q+1} = O, Y_{p+q+2} = S$
28. $R_1, R_2 = OH, X = \text{Me/isopropyl/tert-butyl},$
 $Y_1 = O, Y_2\text{—}Y_{p+q+1} = S, Y_{p+q+2} = O$
29. $R_1, R_2 = OH, X = \text{Me/isopropyl/tert-butyl},$
 $Y_1 = S, Y_2\text{—}Y_{p+q+2} = O$
30. $R_1, R_2 = OH, X = \text{Me/isopropyl/tert-butyl},$
 $Y_1 = O, Y_2\text{—}Y_{p+q+2} = S$
31. $R_1, R_2 = OH, X = \text{Me/isopropyl/tert-butyl},$
 $Y_1, Y_{p+1}, Y_{p+q+2} = S, Y_2\text{—}Y_p, Y_q\text{—}Y_{p+q+1} = O$
32. $R_1, R_2 = OH, X = \text{Me/isopropyl/tert-butyl},$
 $Y_1, Y_{p+1}, Y_{p+q+2} = O, Y_2\text{—}Y_p, Y_q\text{—}Y_{p+q+1} = S$
33. $R_1, R_2 = OH, X = \text{Me/isopropyl/tert-butyl},$
 $Y_{p+1} = S, Y_1\text{—}Y_p, Y_q\text{—}Y_{p+q+2} = O$
34. $R_1, R_2 = OH, X = \text{Me/isopropyl/tert-butyl},$
 $Y_{p+1} = O, Y_1\text{—}Y_p, Y_q\text{—}Y_{p+q+2} = S$
35. $R_1, R_2 = OH, X = \text{Me/isopropyl/tert-butyl},$
 $Y_{p+q+2} = S, Y_1\text{—}Y_{p+q+1} = O$
36. $R_1, R_2 = OH, X = \text{Me/isopropyl/tert-butyl},$
 $Y_{p+q+2} = P, Y_1\text{—}Y_{p+q+1} = S$
37. Xs can also be combinations of methyl and isopropyl or combinations of methyl and tert-butyl or combinations of methyl, isopropyl and tert-butyl or combinations of isopropyl and tert-butyl

TABLE 6

Multiple Incorporation P-alkylphosphonate Backbone into Oligonucleotides.

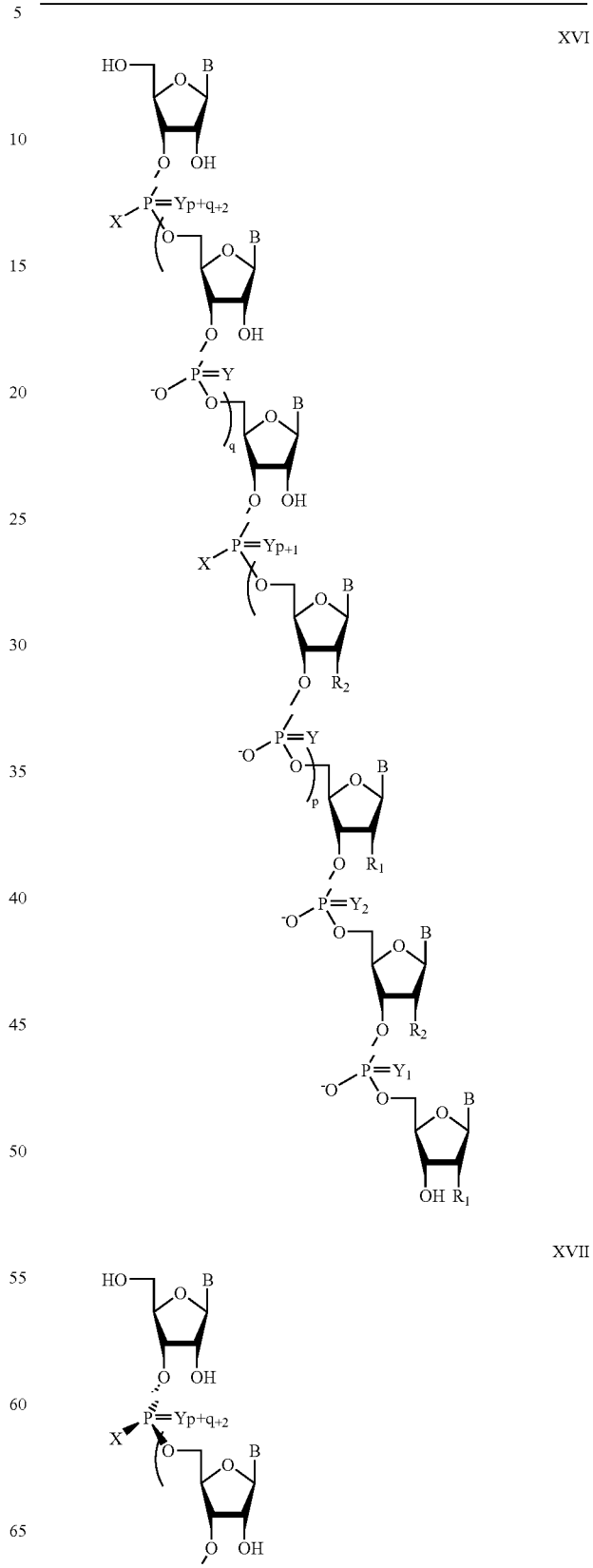

TABLE 6-continued

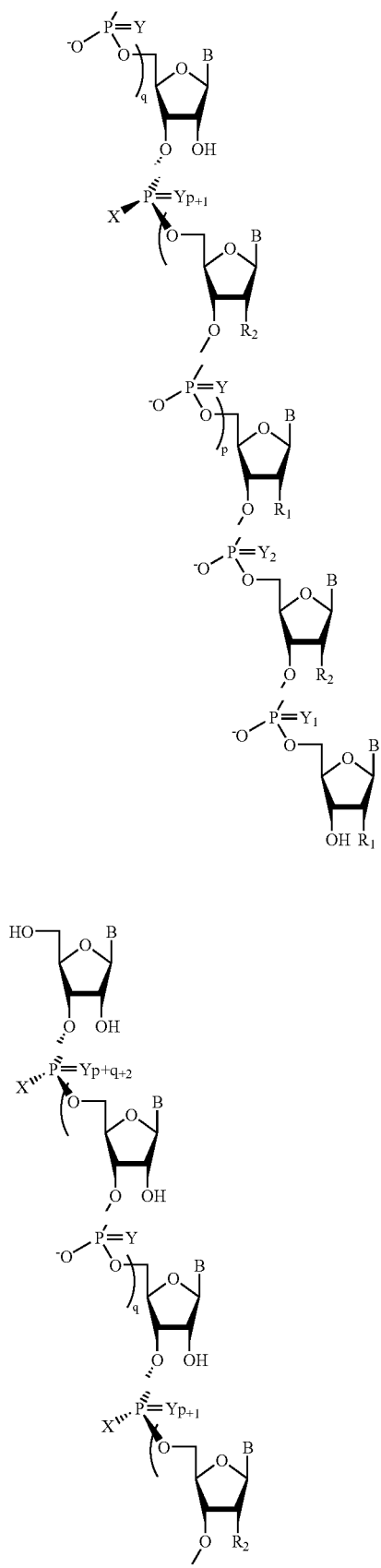

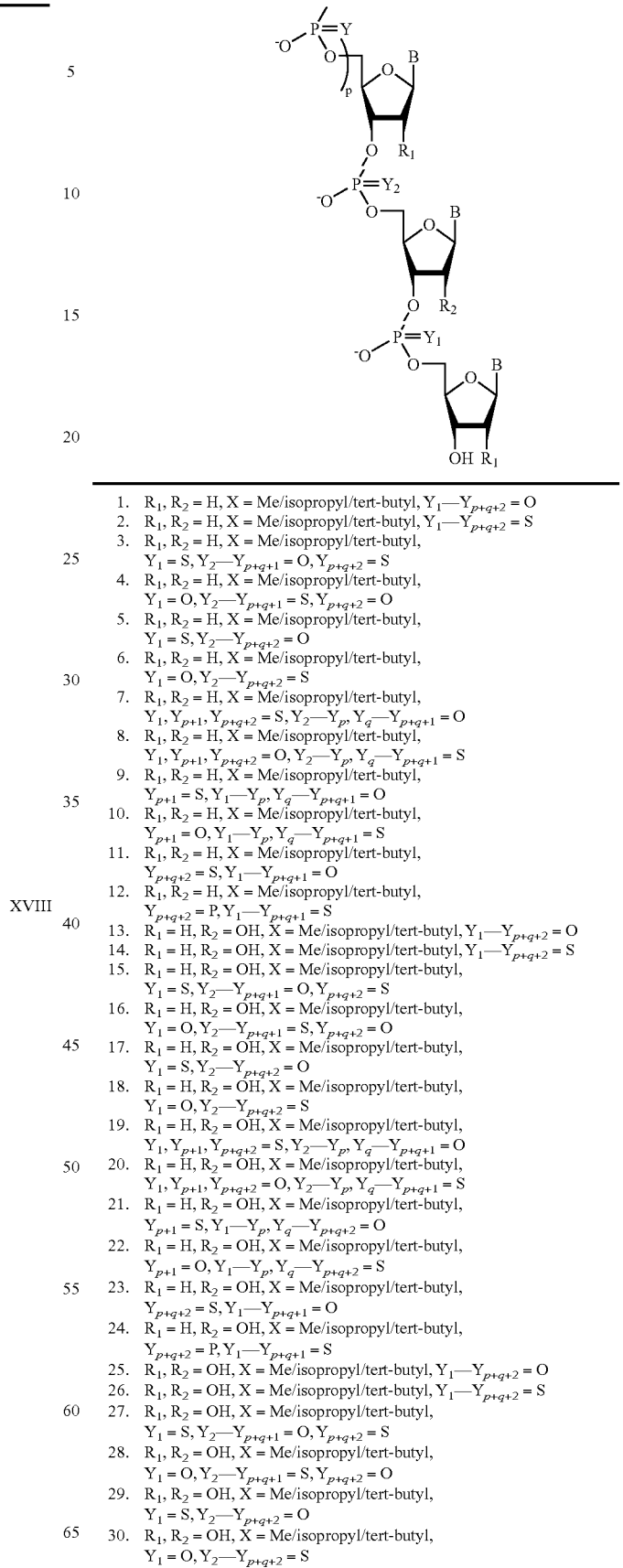

1. $R_1, R_2 = H, X = Me/isopropyl/tert-butyl, Y_1—Y_{p+q+2} = O$
2. $R_1, R_2 = H, X = Me/isopropyl/tert-butyl, Y_1—Y_{p+q+2} = S$
3. $R_1, R_2 = H, X = Me/isopropyl/tert-butyl,$
   $Y_1 = S, Y_2—Y_{p+q+1} = O, Y_{p+q+2} = S$
4. $R_1, R_2 = H, X = Me/isopropyl/tert-butyl,$
   $Y_1 = O, Y_2—Y_{p+q+1} = S, Y_{p+q+2} = O$
5. $R_1, R_2 = H, X = Me/isopropyl/tert-butyl,$
   $Y_1 = S, Y_2—Y_{p+q+2} = O$
6. $R_1, R_2 = H, X = Me/isopropyl/tert-butyl,$
   $Y_1 = O, Y_2—Y_{p+q+2} = S$
7. $R_1, R_2 = H, X = Me/isopropyl/tert-butyl,$
   $Y_1, Y_{p+1}, Y_{p+q+2} = S, Y_2—Y_p, Y_q—Y_{p+q+1} = O$
8. $R_1, R_2 = H, X = Me/isopropyl/tert-butyl,$
   $Y_1, Y_{p+1}, Y_{p+q+2} = O, Y_2—Y_p, Y_q—Y_{p+q+1} = S$
9. $R_1, R_2 = H, X = Me/isopropyl/tert-butyl,$
   $Y_{p+1} = S, Y_1—Y_p, Y_q—Y_{p+q+1} = O$
10. $R_1, R_2 = H, X = Me/isopropyl/tert-butyl,$
    $Y_{p+1} = O, Y_1—Y_p, Y_q—Y_{p+q+1} = S$
11. $R_1, R_2 = H, X = Me/isopropyl/tert-butyl,$
    $Y_{p+q+2} = S, Y_1—Y_{p+q+1} = O$
12. $R_1, R_2 = H, X = Me/isopropyl/tert-butyl,$
    $Y_{p+q+2} = P, Y_1—Y_{p+q+1} = S$
13. $R_1 = H, R_2 = OH, X = Me/isopropyl/tert-butyl, Y_1—Y_{p+q+2} = O$
14. $R_1 = H, R_2 = OH, X = Me/isopropyl/tert-butyl, Y_1—Y_{p+q+2} = S$
15. $R_1 = H, R_2 = OH, X = Me/isopropyl/tert-butyl,$
    $Y_1 = S, Y_2—Y_{p+q+1} = O, Y_{p+q+2} = S$
16. $R_1 = H, R_2 = OH, X = Me/isopropyl/tert-butyl,$
    $Y_1 = O, Y_2—Y_{p+q+1} = S, Y_{p+q+2} = O$
17. $R_1 = H, R_2 = OH, X = Me/isopropyl/tert-butyl,$
    $Y_1 = S, Y_2—Y_{p+q+2} = O$
18. $R_1 = H, R_2 = OH, X = Me/isopropyl/tert-butyl,$
    $Y_1 = O, Y_2—Y_{p+q+2} = S$
19. $R_1 = H, R_2 = OH, X = Me/isopropyl/tert-butyl,$
    $Y_1, Y_{p+1}, Y_{p+q+2} = S, Y_2—Y_p, Y_q—Y_{p+q+1} = O$
20. $R_1 = H, R_2 = OH, X = Me/isopropyl/tert-butyl,$
    $Y_1, Y_{p+1}, Y_{p+q+2} = O, Y_2—Y_p, Y_q—Y_{p+q+1} = S$
21. $R_1 = H, R_2 = OH, X = Me/isopropyl/tert-butyl,$
    $Y_{p+1} = S, Y_1—Y_p, Y_q—Y_{p+q+2} = O$
22. $R_1 = H, R_2 = OH, X = Me/isopropyl/tert-butyl,$
    $Y_{p+1} = O, Y_1—Y_p, Y_q—Y_{p+q+2} = S$
23. $R_1 = H, R_2 = OH, X = Me/isopropyl/tert-butyl,$
    $Y_{p+q+2} = S, Y_1—Y_{p+q+1} = O$
24. $R_1 = H, R_2 = OH, X = Me/isopropyl/tert-butyl,$
    $Y_{p+q+2} = P, Y_1—Y_{p+q+1} = S$
25. $R_1, R_2 = OH, X = Me/isopropyl/tert-butyl, Y_1—Y_{p+q+2} = O$
26. $R_1, R_2 = OH, X = Me/isopropyl/tert-butyl, Y_1—Y_{p+q+2} = S$
27. $R_1, R_2 = OH, X = Me/isopropyl/tert-butyl,$
    $Y_1 = S, Y_2—Y_{p+q+1} = O, Y_{p+q+2} = S$
28. $R_1, R_2 = OH, X = Me/isopropyl/tert-butyl,$
    $Y_1 = O, Y_2—Y_{p+q+1} = S, Y_{p+q+2} = O$
29. $R_1, R_2 = OH, X = Me/isopropyl/tert-butyl,$
    $Y_1 = S, Y_2—Y_{p+q+2} = O$
30. $R_1, R_2 = OH, X = Me/isopropyl/tert-butyl,$
    $Y_1 = O, Y_2—Y_{p+q+2} = S$

XVIII

TABLE 6-continued

31. $R_1, R_2 = OH, X = Me/isopropyl/tert-butyl,$
    $Y_1, Y_{p+1}, Y_{p+q+2} = S, Y_2$—$Y_p, Y_q$—$Y_{p+q+1} = O$
32. $R_1, R_2 = OH, X = Me/isopropyl/tert-butyl,$
    $Y_1, Y_{p+1}, Y_{p+q+2} = O, Y_2$—$Y_p, Y_q$—$Y_{p+q+1} = S$
33. $R_1, R_2 = OH, X = Me/isopropyl/tert-butyl,$
    $Y_{p+1} = S, Y_1$—$Y_p, Y_q$—$Y_{p+q+2} = O$
34. $R_1, R_2 = OH, X = Me/isopropyl/tert-butyl,$
    $Y_{p+1} = O, Y_1$—$Y_p, Y_q$—$Y_{p+q+2} = S$
35. $R_1, R_2 = OH, X = Me/isopropyl/tert-butyl,$
    $Y_{p+q+2} = S, Y_1$—$Y_{p+q+1} = O$
36. $R_1, R_2 = OH, X = Me/isopropyl/tert-butyl,$
    $Y_{p+q+2} = P, Y_1$—$Y_{p+q+1} = S$
37. Xs can also be combinations of methyl and isopropyl
    or combinations of methyl and tert-
    butyl or combinations of isopropyl
    and tert-butyl

TABLE 7

Multiple Incorporation P-alkylphosphonate Backbone into Oligonucleotides.

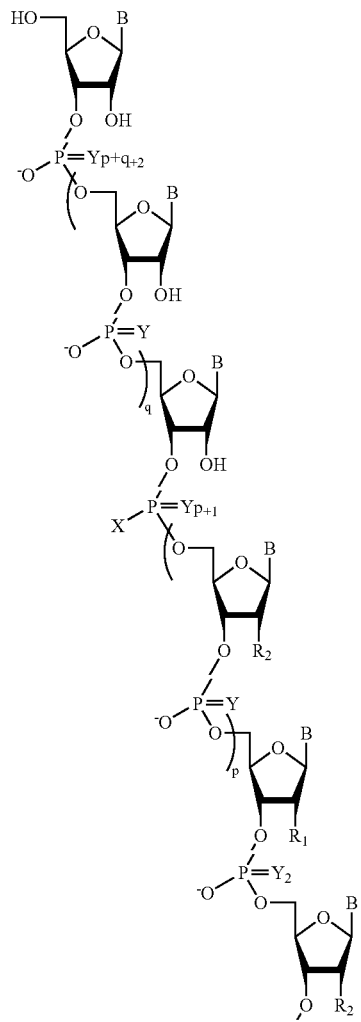

XIX

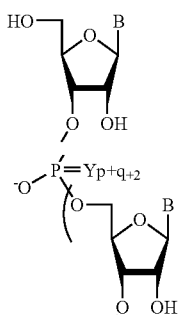

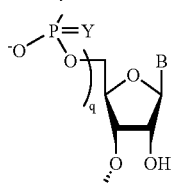

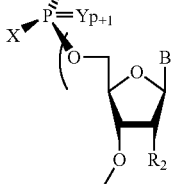

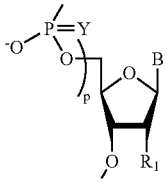

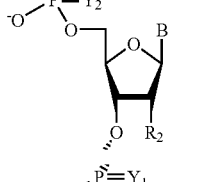

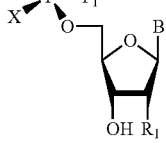

XX

XXI

TABLE 7-continued

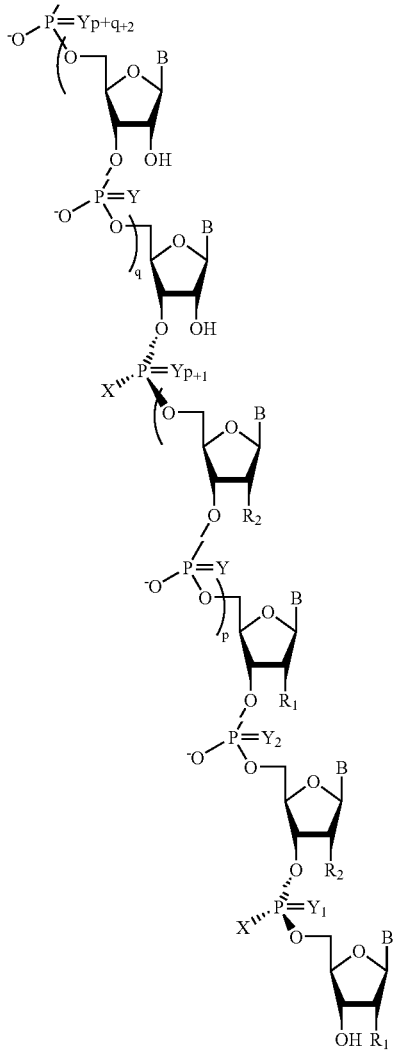

1. $R_1, R_2 = H, X = Me/isopropyl/tert-butyl, Y_1—Y_{p+q+2} = O$
2. $R_1, R_2 = H, X = Me/isopropyl/tert-butyl, Y_1—Y_{p+q+2} = S$
3. $R_1, R_2 = H, X = Me/isopropyl/tert-butyl,$
   $Y_1 = S, Y_2—Y_{p+q+1} = O, Y_{p+q+2} = S$
4. $R_1, R_2 = H, X = Me/isopropyl/tert-butyl,$
   $Y_1 = O, Y_2—Y_{p+q+1} = S, Y_{p+q+2} = O$
5. $R_1, R_2 = H, X = Me/isopropyl/tert-butyl,$
   $Y_1 = S, Y_2—Y_{p+q+2} = O$
6. $R_1, R_2 = H, X = Me/isopropyl/tert-butyl,$
   $Y_1 = O, Y_2—Y_{p+q+2} = S$
7. $R_1, R_2 = H, X = Me/isopropyl/tert-butyl,$
   $Y_1, Y_{p+1}, Y_{p+q+2} = S, Y_2—Y_p, Y_q—Y_{p+q+1} = O$
8. $R_1, R_2 = H, X = Me/isopropyl/tert-butyl,$
   $Y_1, Y_{p+1}, Y_{p+q+2} = O, Y_2—Y_p, Y_q—Y_{p+q+1} = S$
9. $R_1, R_2 = H, X = Me/isopropyl/tert-butyl,$
   $Y_{p+1} = S, Y_1—Y_p, Y_q—Y_{p+q+1} = O$
10. $R_1, R_2 = H, X = Me/isopropyl/tert-butyl,$
    $Y_{p+1} = O, Y_1—Y_p, Y_q—Y_{p+q+1} = S$
11. $R_1, R_2 = H, X = Me/isopropyl/tert-butyl,$
    $Y_{p+q+2} = S, Y_1—Y_{p+q+1} = O$
12. $R_1, R_2 = H, X = Me/isopropyl/tert-butyl,$
    $Y_{p+q+2} = P, Y_1—Y_{p+q+1} = S$
13. $R_1 = H, R_2 = OH, X = Me/isopropyl/tert-butyl, Y_1—Y_{p+q+2} = O$
14. $R_1 = H, R_2 = OH, X = Me/isopropyl/tert-butyl, Y_1—Y_{p+q+2} = S$
15. $R_1 = H, R_2 = OH, X = Me/isopropyl/tert-butyl,$
    $Y_1 = S, Y_2—Y_{p+q+1} = O, Y_{p+q+2} = S$
16. $R_1 = H, R_2 = OH, X = Me/isopropyl/tert-butyl,$
    $Y_1 = O, Y_2—Y_{p+q+1} = S, Y_{p+q+2} = O$
17. $R_1 = H, R_2 = OH, X = Me/isopropyl/tert-butyl,$
    $Y_1 = S, Y_2—Y_{p+q+2} = O$
18. $R_1 = H, R_2 = OH, X = Me/isopropyl/tert-butyl,$
    $Y_1 = O, Y_2—Y_{p+q+2} = S$
19. $R_1 = H, R_2 = OH, X = Me/isopropyl/tert-butyl,$
    $Y_1, Y_{p+1}, Y_{p+q+2} = S, Y_2—Y_p, Y_q—Y_{p+q+1} = O$
20. $R_1 = H, R_2 = OH, X = Me/isopropyl/tert-butyl,$
    $Y_1, Y_{p+1}, Y_{p+q+2} = O, Y_2—Y_p, Y_q—Y_{p+q+1} = S$
21. $R_1 = H, R_2 = OH, X = Me/isopropyl/tert-butyl,$
    $Y_{p+1} = S, Y_1—Y_p, Y_q—Y_{p+q+2} = O$
22. $R_1 = H, R_2 = OH, X = Me/isopropyl/tert-butyl,$
    $Y_{p+1} = O, Y_1—Y_p, Y_q—Y_{p+q+2} = S$
23. $R_1 = H, R_2 = OH, X = Me/isopropyl/tert-butyl,$
    $Y_{p+q+2} = S, Y_1—Y_{p+q+1} = O$
24. $R_1 = H, R_2 = OH, X = Me/isopropyl/tert-butyl,$
    $Y_{p+q+2} = P, Y_1—Y_{p+q+1} = S$
25. $R_1, R_2 = OH, X = Me/isopropyl/tert-butyl, Y_1—Y_{p+q+2} = O$
26. $R_1, R_2 = OH, X = Me/isopropyl/tert-butyl, Y_1—Y_{p+q+2} = S$
27. $R_1, R_2 = OH, X = Me/isopropyl/tert-butyl,$
    $Y_1 = S, Y_2—Y_{p+q+1} = O, Y_{p+q+2} = S$
28. $R_1, R_2 = OH, X = Me/isopropyl/tert-butyl,$
    $Y_1 = O, Y_2—Y_{p+q+1} = S, Y_{p+q+2} = O$
29. $R_1, R_2 = OH, X = Me/isopropyl/tert-butyl,$
    $Y_1 = S, Y_2—Y_{p+q+2} = O$
30. $R_1, R_2 = OH, X = Me/isopropyl/tert-butyl,$
    $Y_1 = O, Y_2—Y_{p+q+2} = S$
31. $R_1, R_2 = OH, X = Me/isopropyl/tert-butyl,$
    $Y_1, Y_{p+1}, Y_{p+q+2} = S, Y_2—Y_p, Y_q—Y_{p+q+1} = O$
32. $R_1, R_2 = OH, X = Me/isopropyl/tert-butyl,$
    $Y_1, Y_{p+1}, Y_{p+q+2} = O, Y_2—Y_p, Y_q—Y_{p+q+1} = S$
33. $R_1, R_2 = OH, X = Me/isopropyl/tert-butyl,$
    $Y_{p+1} = S, Y_1—Y_p, Y_q—Y_{p+q+1} = O$
34. $R_1, R_2 = OH, X = Me/isopropyl/tert-butyl,$
    $Y_{p+1} = O, Y_1—Y_p, Y_q—Y_{p+q+1} = S$
35. $R_1, R_2 = OH, X = Me/isopropyl/tert-butyl,$
    $Y_{p+q+2} = S, Y_1—Y_{p+q+1} = O$
36. $R_1, R_2 = OH, X = Me/isopropyl/tert-butyl,$
    $Y_{p+q+2} = P, Y_1—Y_{p+q+1} = S$
37. Xs can also be combinations of methyl and isopropyl or combinations of methyl and tert-butyl or combinations of isopropyl and tert-butyl

TABLE 8

Oligonucleotide with P-alkylphosphonate backbone

XXII

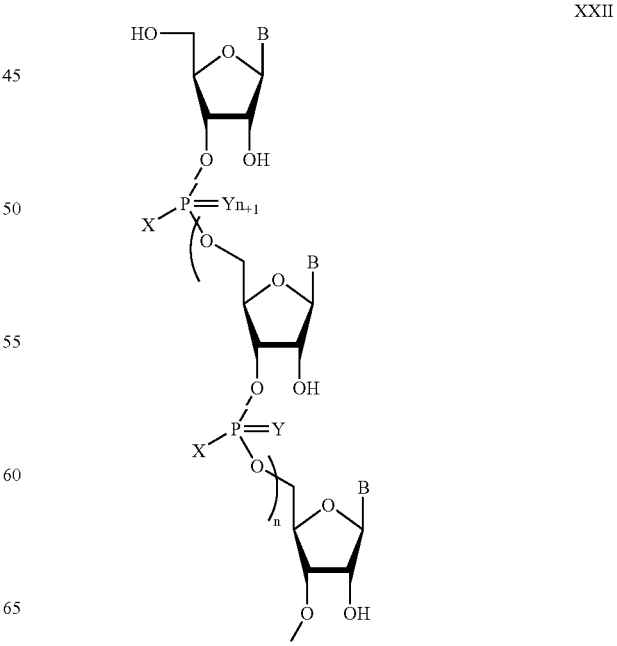

TABLE 8-continued

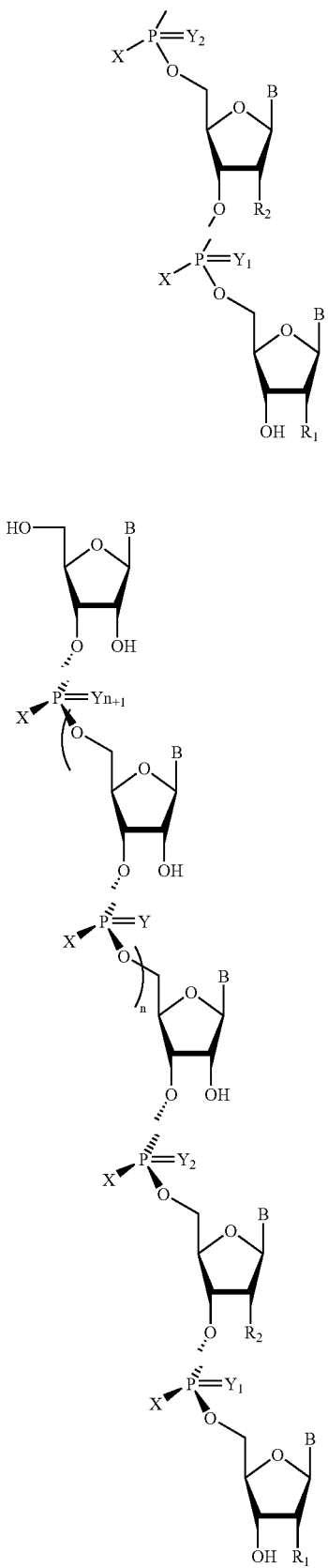

XXIII

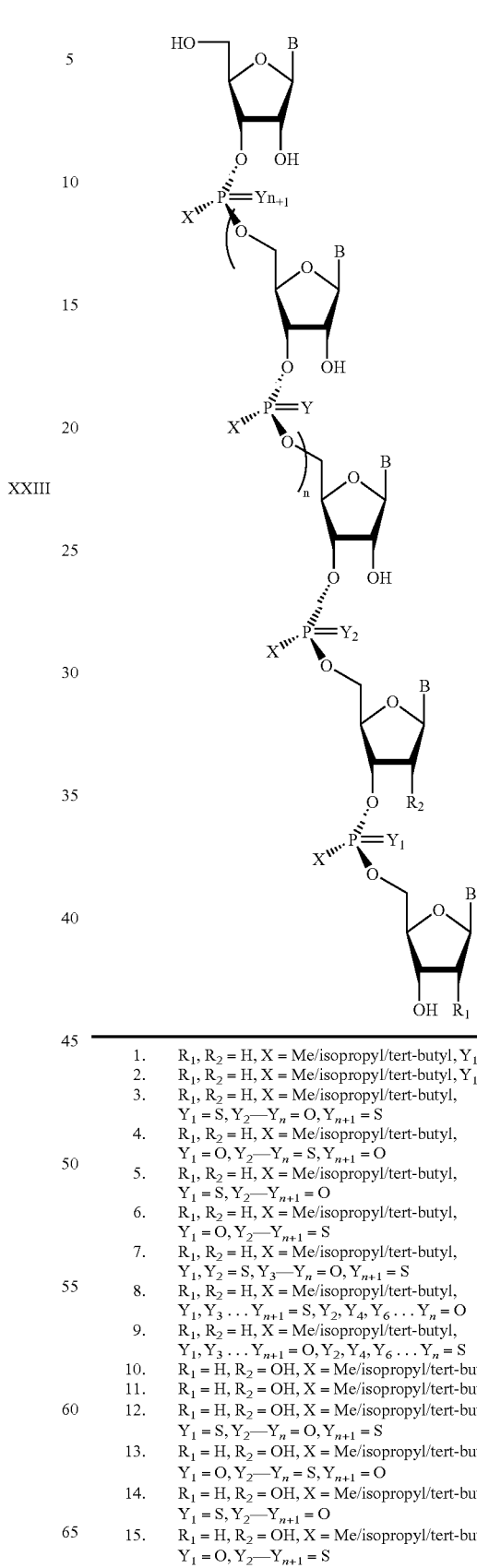

XXIV

1. $R_1, R_2 = H, X = Me/isopropyl/tert-butyl, Y_1—Y_{n+1} = O$
2. $R_1, R_2 = H, X = Me/isopropyl/tert-butyl, Y_1—Y_{n+1} = S$
3. $R_1, R_2 = H, X = Me/isopropyl/tert-butyl,$
   $Y_1 = S, Y_2—Y_n = O, Y_{n+1} = S$
4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$ TABLE 8-continued 16. $R_1 = H, R_2 = OH, X = Me/isopropyl/tert-butyl, Y_1, Y_2 = S, Y_3—Y_n = O, Y_{n+1} = S$
17. $R_1 = H, R_2 = OH, X = Me/isopropyl/tert-butyl, Y_1, Y_3 \ldots Y_{n+1} = S, Y_2, Y_4, Y_6 \ldots Y_n = O$
18. $R_1 = H, R_2 = OH, X = Me/isopropyl/tert-butyl, Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl, Y_1 = S, Y_2—Y_n = O, Y_{n+1} = S$
22. $R_1, R_2 = OH, X = Me/isopropyl/tert-butyl, Y_1 = O, Y_2—Y_n = O, Y_{n+1} = O$
23. $R_1, R_2 = OH, X = Me/isopropyl/tert-butyl, Y_1 = S, Y_2—Y_{n+1} = O$
24. $R_1, R_2 = OH, X = Me/isopropyl/tert-butyl, Y_1 = O, Y_2—Y_{n+1} = S$
25. $R_1, R_2 = OH, X = Me/isopropyl/tert-butyl, Y_1, Y_2 = S, Y_3—Y_n = O, Y_{n+1} = S$
26. $R_1, R_2 = OH, X = Me/isopropyl/tert-butyl, Y_1, Y_3 \ldots Y_{n+1} = S, Y_2, Y_4, Y_6 \ldots Y_n = O$
27. $R_1, R_2 = OH, X = Me/isopropyl/tert-butyl, Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of methyl, isopropyl and tert-butyl or combinations of isopropyl and tert-butyl

TABLE 9

Single incorporation of P-alkylphosphonate backbone with α-anomer at the 3'-end of oligonucleotide

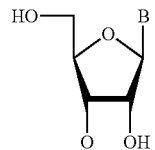

Ia

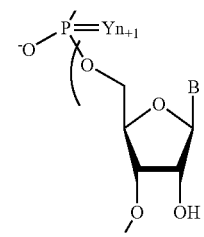

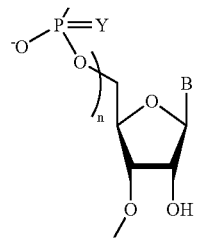

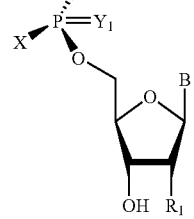

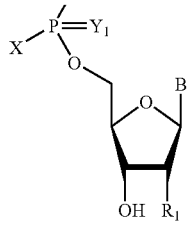

IIa

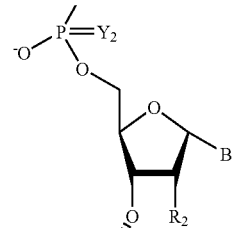

IIIa

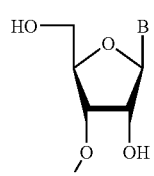

TABLE 9-continued

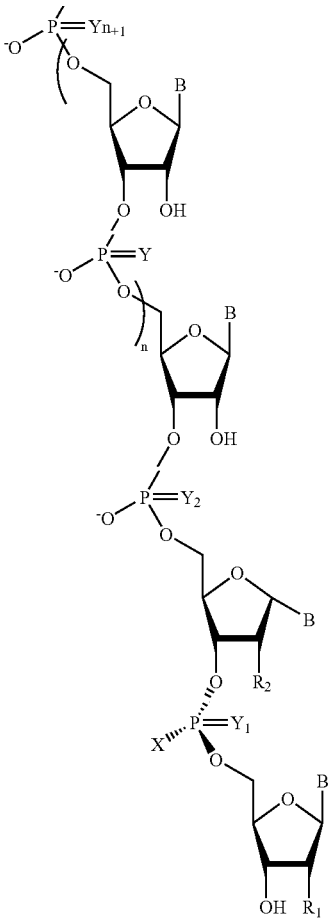

1. $R_1, R_2 = H$, $X = Me/isopropyl/tert-butyl$, $Y_1—Y_{n+1} = O$
2. $R_1, R_2 = H$, $X = Me/isopropyl/tert-butyl$, $Y_1—Y_{n+1} = S$
3. $R_1, R_2 = H$, $X = Me/isopropyl/tert-butyl$, $Y_1 = S, Y_2—Y_n = O, Y_{n+1} = S$
4. $R_1, R_2 = H$, $X = Me/isopropyl/tert-butyl$, $Y_1 = O, Y_2—Y_n = S, Y_{n+1} = O$
5. $R_1, R_2 = H$, $X = Me/isopropyl/tert-butyl$, $Y_1 = S, Y_2—Y_{n+1} = O$
6. $R_1, R_2 = H$, $X = Me/isopropyl/tert-butyl$, $Y_1 = O, Y_2—Y_{n+1} = S$
7. $R_1, R_2 = H$, $X = Me/isopropyl/tert-butyl$, $Y_1, Y_2 = S, Y_3—Y_n = O, Y_{n+1} = S$
8. $R_1, R_2 = H$, $X = Me/isopropyl/tert-butyl$, $Y_1, Y_3 \ldots Y_{n+1} = S, Y_2, Y_4, Y_6 \ldots Y_n = O$
9. $R_1, R_2 = H$, $X = Me/isopropyl/tert-butyl$, $Y_1, Y_3 \ldots Y_{n+1} = O, Y_2, Y_4, Y_6 \ldots Y_n = S$
10. $R_1 = H, R_2 = OH$, $X = Me/isopropyl/tert-butyl$, $Y_1—Y_{n+1} = O$
11. $R_1 = H, R_2 = OH$, $X = Me/isopropyl/tert-butyl$, $Y_1—Y_{n+1} = S$
12. $R_1 = H, R_2 = OH$, $X = Me/isopropyl/tert-butyl$, $Y_1 = S, Y_2—Y_n = O, Y_{n+1} = S$
13. $R_1 = H, R_2 = OH$, $X = Me/isopropyl/tert-butyl$, $Y_1 = O, Y_2—Y_n = S, Y_{n+1} = O$
14. $R_1 = H, R_2 = OH$, $X = Me/isopropyl/tert-butyl$, $Y_1 = S, Y_2—Y_{n+1} = O$
15. $R_1 = H, R_2 = OH$, $X = Me/isopropyl/tert-butyl$, $Y_1 = O, Y_2—Y_{n+1} = S$
16. $R_1 = H, R_2 = OH$, $X = Me/isopropyl/tert-butyl$, $Y_1, Y_2 = S, Y_3—Y_n = O, Y_{n+1} = S$
17. $R_1 = H, R_2 = OH$, $X = Me/isopropyl/tert-butyl$, $Y_1, Y_3 \ldots Y_{n+1} = S, Y_2, Y_4, Y_6 \ldots Y_n = O$
18. $R_1 = H, R_2 = OH$, $X = Me/isopropyl/tert-butyl$, $Y_1, Y_3 \ldots Y_{n+1} = O, Y_2, Y_4, Y_6 \ldots Y_n = S$
19. $R_1, R_2 = OH$, $X = Me/isopropyl/tert-butyl$, $Y_1—Y_{n+1} = O$
20. $R_1, R_2 = OH$, $X = Me/isopropyl/tert-butyl$, $Y_1—Y_{n+1} = S$
21. $R_1, R_2 = OH$, $X = Me/isopropyl/tert-butyl$, $Y_1 = S, Y_2—Y_n = O, Y_{n+1} = S$
22. $R_1, R_2 = OH$, $X = Me/isopropyl/tert-butyl$, $Y_1 = O, Y_2—Y_n = O, Y_{n+1} = O$
23. $R_1, R_2 = OH$, $X = Me/isopropyl/tert-butyl$, $Y_1 = S, Y_2—Y_{n+1} = O$
24. $R_1, R_2 = OH$, $X = Me/isopropyl/tert-butyl$, $Y_1 = O, Y_2—Y_{n+1} = S$
25. $R_1, R_2 = OH$, $X = Me/isopropyl/tert-butyl$, $Y_1, Y_2 = S, Y_3—Y_n = O, Y_{n+1} = S$
26. $R_1, R_2 = OH$, $X = Me/isopropyl/tert-butyl$, $Y_1, Y_3 \ldots Y_{n+1} = S, Y_2, Y_4, Y_6 \ldots Y_n = O$
27. $R_1, R_2 = OH$, $X = Me/isopropyl/tert-butyl$, $Y_1, Y_3 \ldots Y_{n+1} = O, Y_2, Y_4, Y_6 \ldots Y_n = S$

TABLE 10

Single incorporation of P-alkylphosphonate backbone with α-anomer at the 5'-end of oligonucleotide IVa

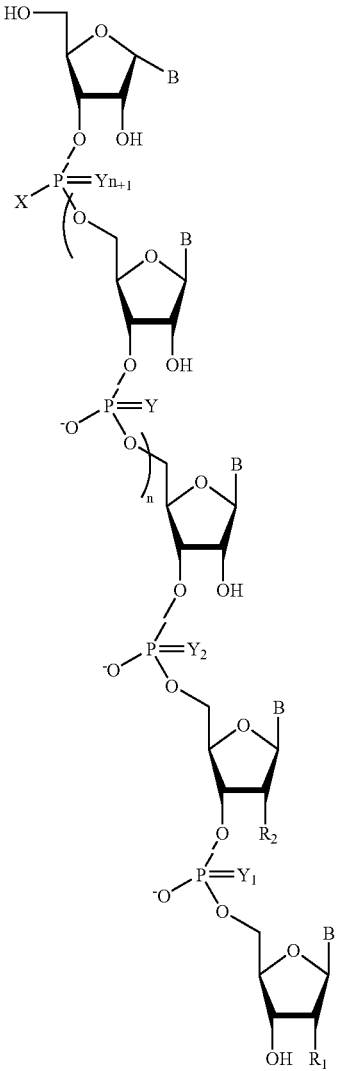

TABLE 10-continued

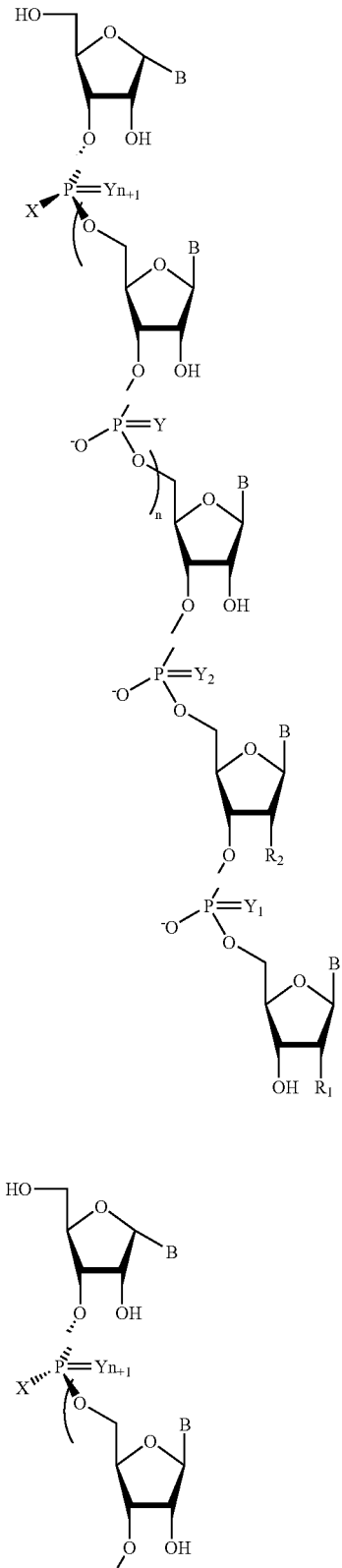

Va

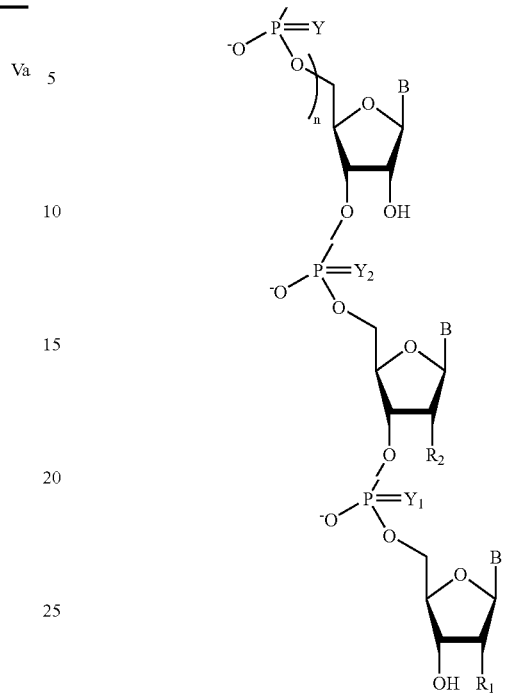

VIa

1. $R_1, R_2 = H, X = $ Me/isopropyl/tert-butyl, $Y_1—Y_{n+1} = O$
2. $R_1, R_2 = H, X = $ Me/isopropyl/tert-butyl, $Y_1—Y_{n+1} = S$
3. $R_1, R_2 = H, X = $ Me/isopropyl/tert-butyl,
   $Y_1 = S, Y_2—Y_n = O, Y_{n+1} = S$
4. $R_1, R_2 = H, X = $ Me/isopropyl/tert-butyl,
   $Y_1 = O, Y_2—Y_n = S, Y_{n+1} = O$
5. $R_1, R_2 = H, X = $ Me/isopropyl/tert-butyl,
   $Y_1 = S, Y_2—Y_{n+1} = O$
6. $R_1, R_2 = H, X = $ Me/isopropyl/tert-butyl,
   $Y_1 = O, Y_2—Y_{n+1} = S$
7. $R_1, R_2 = H, X = $ Me/isopropyl/tert-butyl,
   $Y_1, Y_2 = S, Y_3—Y_n = O, Y_{n+1} = S$
8. $R_1, R_2 = H, X = $ Me/isopropyl/tert-butyl,
   $Y_1, Y_3 \ldots Y_{n+1} = S, Y_2, Y_4, Y_6 \ldots Y_n = O$
9. $R_1, R_2 = H, X = $ Me/isopropyl/tert-butyl,
   $Y_1, Y_3 \ldots Y_{n+1} = O, Y_2, Y_4, Y_6 \ldots Y_n = S$
10. $R_1 = H, R_2 = OH, X = $ Me/isopropyl/tert-butyl, $Y_1—Y_{n+1} = O$
11. $R_1 = H, R_2 = OH, X = $ Me/isopropyl/tert-butyl, $Y_1—Y_{n+1} = S$
12. $R_1 = H, R_2 = OH, X = $ Me/isopropyl/tert-butyl,
    $Y_1 = S, Y_2—Y_n = O, Y_{n+1} = S$
13. $R_1 = H, R_2 = OH, X = $ Me/isopropyl/tert-butyl,
    $Y_1 = O, Y_2—Y_n = S, Y_{n+1} = O$
14. $R_1 = H, R_2 = OH, X = $ Me/isopropyl/tert-butyl,
    $Y_1 = S, Y_2—Y_{n+1} = O$
15. $R_1 = H, R_2 = OH, X = $ Me/isopropyl/tert-butyl,
    $Y_1 = O, Y_2—Y_{n+1} = S$
16. $R_1 = H, R_2 = OH, X = $ Me/isopropyl/tert-butyl,
    $Y_1, Y_2 = S, Y_3—Y_n = O, Y_{n+1} = S$
17. $R_1 = H, R_2 = OH, X = $ Me/isopropyl/tert-butyl,
    $Y_1, Y_3 \ldots Y_{n+1} = S, Y_2, Y_4, Y_6 \ldots Y_n = O$
18. $R_1 = H, R_2 = OH, X = $ Me/isopropyl/tert-butyl,
    $Y_1, Y_3 \ldots Y_{n+1} = O, Y_2, Y_4, Y_6 \ldots Y_n = S$
19. $R_1, R_2 = OH, X = $ Me/isopropyl/tert-butyl, $Y_1—Y_{n+1} = O$
20. $R_1, R_2 = OH, X = $ Me/isopropyl/tert-butyl, $Y_1—Y_{n+1} = S$
21. $R_1, R_2 = OH, X = $ Me/isopropyl/tert-butyl,
    $Y_1 = S, Y_2—Y_n = O, Y_{n+1} = S$
22. $R_1, R_2 = OH, X = $ Me/isopropyl/tert-butyl,
    $Y_1 = O, Y_2—Y_n = O, Y_{n+1} = O$
23. $R_1, R_2 = OH, X = $ Me/isopropyl/tert-butyl,
    $Y_1 = S, Y_2—Y_{n+1} = O$
24. $R_1, R_2 = OH, X = $ Me/isopropyl/tert-butyl,
    $Y_1 = O, Y_2—Y_{n+1} = S$
25. $R_1, R_2 = OH, X = $ Me/isopropyl/tert-butyl,
    $Y_1, Y_2 = S, Y_3—Y_n = O, Y_{n+1} = S$
26. $R_1, R_2 = OH, X = $ Me/isopropyl/tert-butyl,
    $Y_1, Y_3 \ldots Y_{n+1} = S, Y_2, Y_4, Y_6 \ldots Y_n = O$

TABLE 10-continued
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
TABLE 11
Double incorporation of P-alkylphosphonate backbone at the 3'-end of oligonucleotide
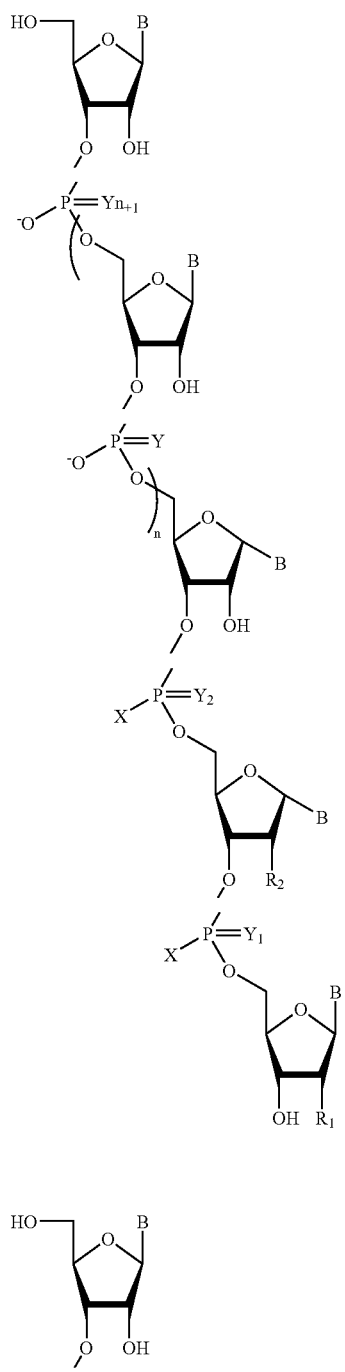
VIIa
VIIIa
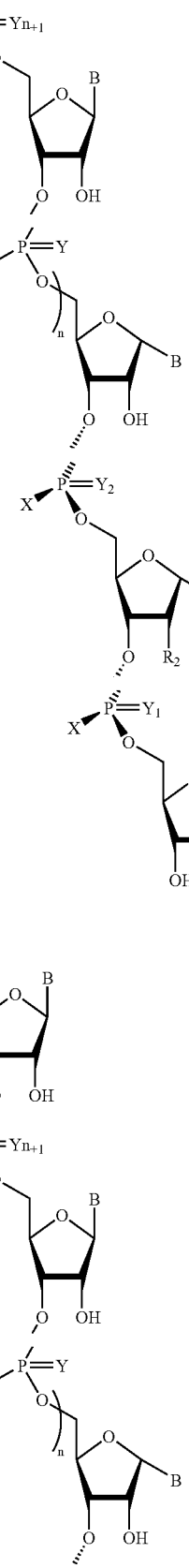
IXa

TABLE 11-continued

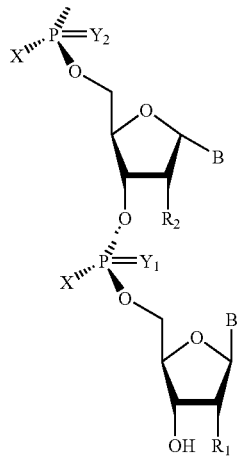

1. $R_1, R_2 = H, X = Me/isopropyl/tert-butyl, Y_1—Y_{n+1} = O$
2. $R_1, R_2 = H, X = Me/isopropyl/tert-butyl, Y_1—Y_{n+1} = S$
3. $R_1, R_2 = H, X = Me/isopropyl/tert-butyl,$
   $Y_1 = S, Y_2—Y_n = O, Y_{n+1} = S$
4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$
16. $R_1 = H, R_2 = OH, X = Me/isopropyl/tert-butyl,$
    $Y_1, Y_2 = S, Y_3—Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl,$
    $Y_1 = S, Y_2—Y_n = O, Y_{n+1} = S$
22. $R_1, R_2 = OH, X = Me/isopropyl/tert-butyl,$
    $Y_1 = O, Y_2—Y_n = O, Y_{n+1} = O$
23. $R_1, R_2 = OH, X = Me/isopropyl/tert-butyl,$
    $Y_1 = S, Y_2—Y_{n+1} = O$
24. $R_1, R_2 = OH, X = Me/isopropyl/tert-butyl,$
    $Y_1 = O, Y_2—Y_{n+1} = S$
25. $R_1, R_2 = OH, X = Me/isopropyl/tert-butyl,$
    $Y_1, Y_2 = S, Y_3—Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of isopropyl and tert-butyl

TABLE 12

Double incorporation of P-alkylphosphonate backbone with α-anomer at the 3'- and 5'-end of oligonucleotide

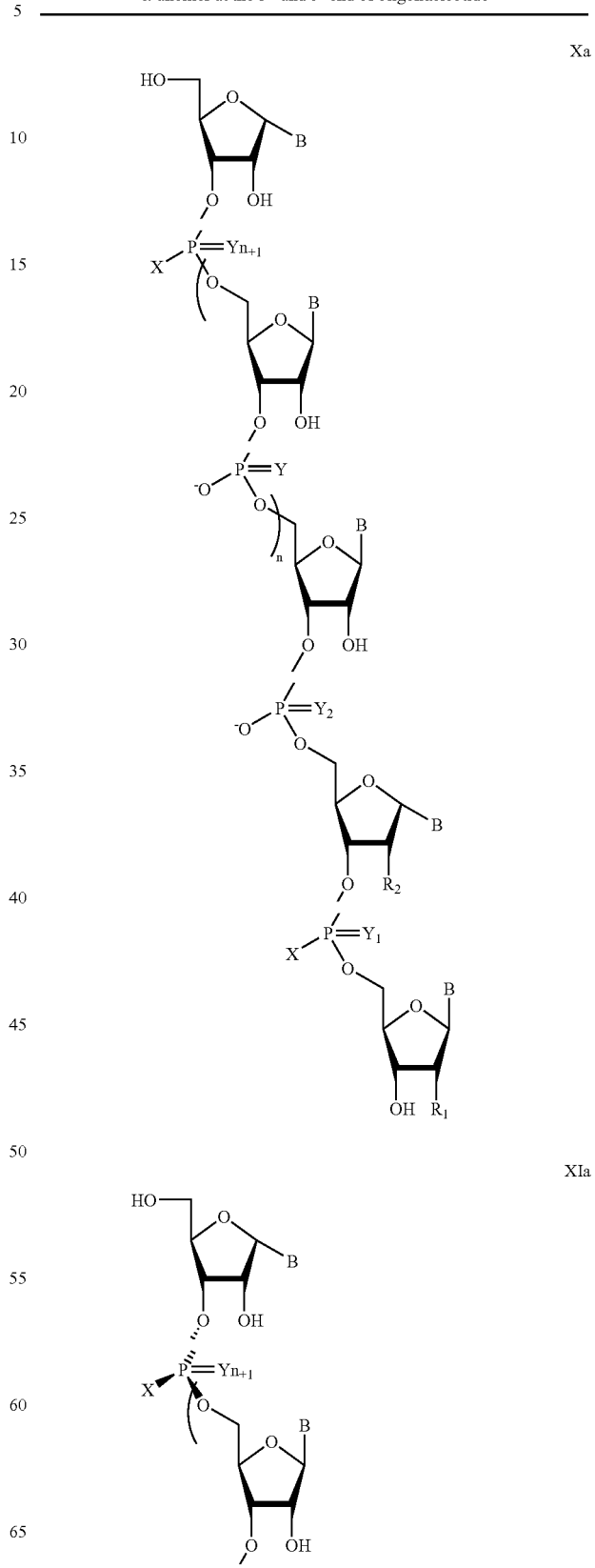

Xa

XIa

TABLE 12-continued

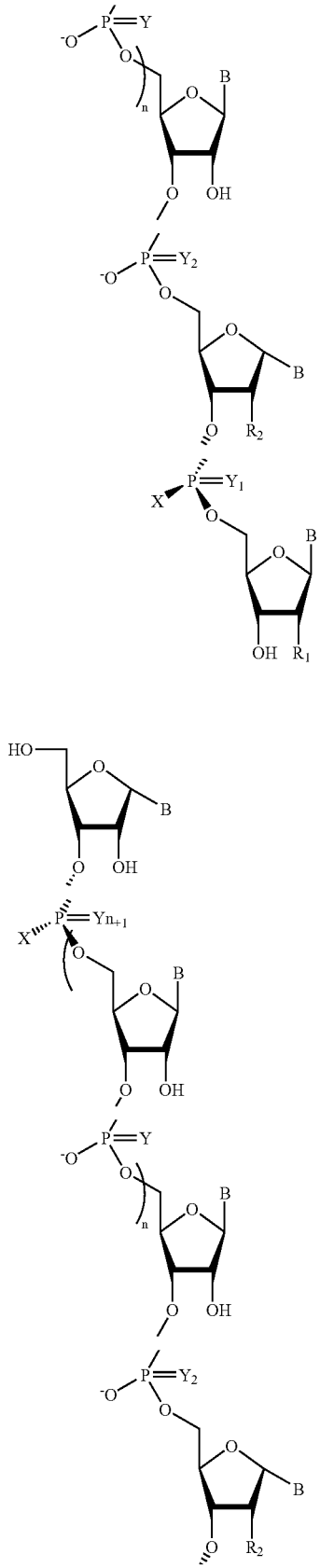

XIIa

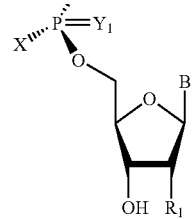

1. $R_1, R_2 = H, X = Me/isopropyl/tert-butyl, Y_1—Y_{n+1} = O$
2. $R_1, R_2 = H, X = Me/isopropyl/tert-butyl, Y_1—Y_{n+1} = S$
3. $R_1, R_2 = H, X = Me/isopropyl/tert-butyl,$
   $Y_1 = S, Y_2—Y_n = O, Y_{n+1} = S$
4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$
16. $R_1 = H, R_2 = OH, X = Me/isopropyl/tert-butyl,$
    $Y_1, Y_2 = S, Y_3—Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl,$
    $Y_1 = S, Y_2—Y_n = O, Y_{n+1} = S$
22. $R_1, R_2 = OH, X = Me/isopropyl/tert-butyl,$
    $Y_1 = O, Y_2—Y_n = O, Y_{n+1} = O$
23. $R_1, R_2 = OH, X = Me/isopropyl/tert-butyl,$
    $Y_1 = S, Y_2—Y_{n+1} = O$
24. $R_1, R_2 = OH, X = Me/isopropyl/tert-butyl,$
    $Y_1 = O, Y_2—Y_{n+1} = S$
25. $R_1, R_2 = OH, X = Me/isopropyl/tert-butyl,$
    $Y_1, Y_2 = S, Y_3—Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of isopropyl and tert-butyl

TABLE 13

Multiple Incorporation P-alkylphosphonate Backbone with α-Anomer into Oligonucleotides.

XIIIa

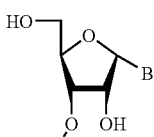

TABLE 13-continued
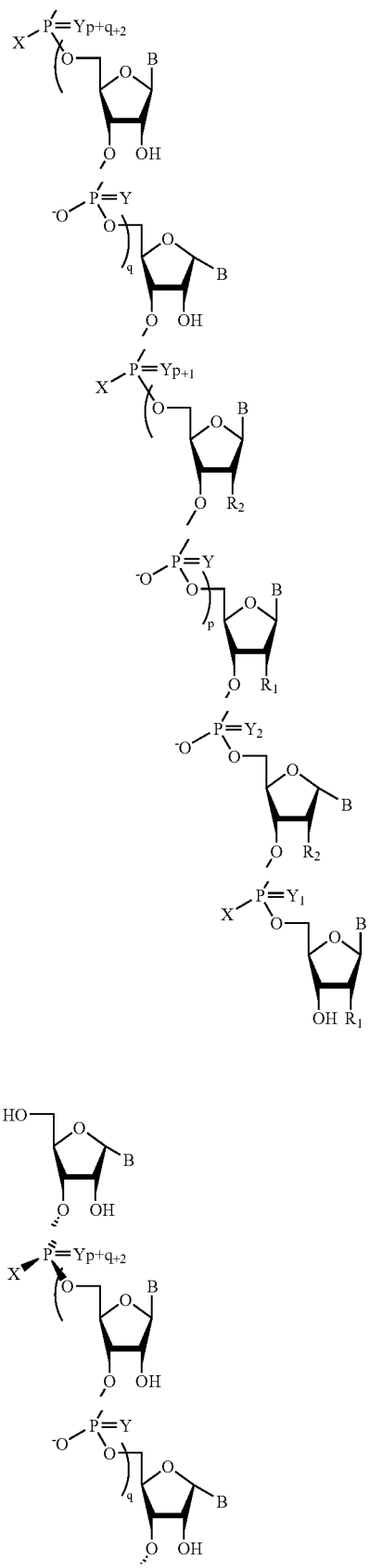
XIVa
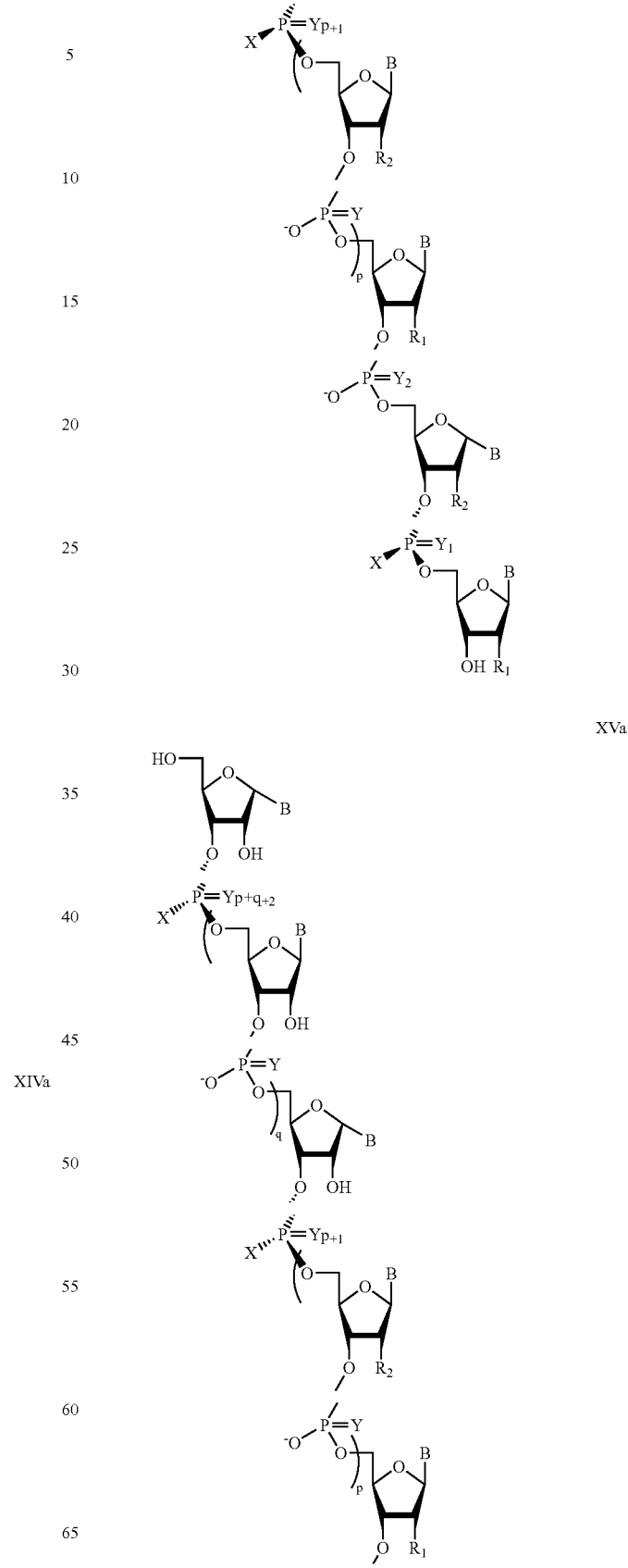
XVa

TABLE 13-continued

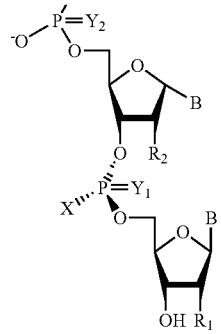

1. $R_1, R_2 = H, X = Me/isopropyl/tert-butyl, Y_1-Y_{p+q+2} = O$
2. $R_1, R_2 = H, X = Me/isopropyl/tert-butyl, Y_1-Y_{p+q+2} = S$
3. $R_1, R_2 = H, X = Me/isopropyl/tert-butyl,$
   $Y_1 = S, Y_2-Y_{p+q+1} = O, Y_{p+q+2} = S$
4. $R_1, R_2 = H, X = Me/isopropyl/tert-butyl,$
   $Y_1 = O, Y_2-Y_{p+q+1} = S, Y_{p+q+2} = O$
5. $R_1, R_2 = H, X = Me/isopropyl/tert-butyl,$
   $Y_1 = S, Y_2-Y_{p+q+2} = O$
6. $R_1, R_2 = H, X = Me/isopropyl/tert-butyl,$
   $Y_1 = O, Y_2-Y_{p+q+2} = S$
7. $R_1, R_2 = H, X = Me/isopropyl/tert-butyl,$
   $Y_1, Y_{p+1}, Y_{p+q+2} = S, Y_2-Y_p, Y_q-Y_{p+q+1} = O$
8. $R_1, R_2 = H, X = Me/isopropyl/tert-butyl,$
   $Y_1, Y_{p+1}, Y_{p+q+2} = O, Y_2-Y_p, Y_q-Y_{p+q+1} = S$
9. $R_1, R_2 = H, X = Me/isopropyl/tert-butyl,$
   $Y_{p+1} = S, Y_1-Y_p, Y_q-Y_{p+q+1} = O$
10. $R_1, R_2 = H, X = Me/isopropyl/tert-butyl,$
    $Y_{p+1} = O, Y_1-Y_p, Y_q-Y_{p+q+1} = S$
11. $R_1, R_2 = H, X = Me/isopropyl/tert-butyl,$
    $Y_{p+q+2} = S, Y_1-Y_{p+q+1} = O$
12. $R_1, R_2 = H, X = Me/isopropyl/tert-butyl,$
    $Y_{p+q+2} = P, Y_1-Y_{p+q+1} = S$
13. $R_1 = H, R_2 = OH, X = Me/isopropyl/tert-butyl, Y_1-Y_{p+q+2} = O$
14. $R_1 = H, R_2 = OH, X = Me/isopropyl/tert-butyl, Y_1-Y_{p+q+2} = S$
15. $R_1 = H, R_2 = OH, X = Me/isopropyl/tert-butyl,$
    $Y_1 = S, Y_2-Y_{p+q+1} = O, Y_{p+q+2} = S$
16. $R_1 = H, R_2 = OH, X = Me/isopropyl/tert-butyl,$
    $Y_1 = O, Y_2-Y_{p+q+1} = S, Y_{p+q+2} = O$
17. $R_1 = H, R_2 = OH, X = Me/isopropyl/tert-butyl,$
    $Y_1 = S, Y_2-Y_{p+q+2} = O$
18. $R_1 = H, R_2 = OH, X = Me/isopropyl/tert-butyl,$
    $Y_1 = O, Y_2-Y_{p+q+2} = S$
19. $R_1 = H, R_2 = OH, X = Me/isopropyl/tert-butyl,$
    $Y_1, Y_{p+1}, Y_{p+q+2} = S, Y_2-Y_p, Y_q-Y_{p+q+1} = O$
20. $R_1 = H, R_2 = OH, X = Me/isopropyl/tert-butyl,$
    $Y_1, Y_{p+1}, Y_{p+q+2} = O, Y_2-Y_p, Y_q-Y_{p+q+1} = S$
21. $R_1 = H, R_2 = OH, X = Me/isopropyl/tert-butyl,$
    $Y_{p+1} = S, Y_1-Y_p, Y_q-Y_{p+q+2} = O$
22. $R_1 = H, R_2 = OH, X = Me/isopropyl/tert-butyl,$
    $Y_{p+1} = O, Y_1-Y_p, Y_q-Y_{p+q+2} = S$
23. $R_1 = H, R_2 = OH, X = Me/isopropyl/tert-butyl,$
    $Y_{p+q+2} = S, Y_1-Y_{p+q+1} = O$
24. $R_1 = H, R_2 = OH, X = Me/isopropyl/tert-butyl,$
    $Y_{p+q+2} = P, Y_1-Y_{p+q+1} = S$
25. $R_1, R_2 = OH, X = Me/isopropyl/tert-butyl, Y_1-Y_{p+q+2} = O$
26. $R_1, R_2 = OH, X = Me/isopropyl/tert-butyl, Y_1-Y_{p+q+2} = S$
27. $R_1, R_2 = OH, X = Me/isopropyl/tert-butyl,$
    $Y_1 = S, Y_2-Y_{p+q+1} = O, Y_{p+q+2} = S$
28. $R_1, R_2 = OH, X = Me/isopropyl/tert-butyl,$
    $Y_1 = O, Y_2-Y_{p+q+1} = S, Y_{p+q+2} = O$
29. $R_1, R_2 = OH, X = Me/isopropyl/tert-butyl,$
    $Y_1 = S, Y_2-Y_{p+q+2} = O$
30. $R_1, R_2 = OH, X = Me/isopropyl/tert-butyl,$
    $Y_1 = O, Y_2-Y_{p+q+2} = S$
31. $R_1, R_2 = OH, X = Me/isopropyl/tert-butyl,$
    $Y_1, Y_{p+1}, Y_{p+q+2} = S, Y_2-Y_p, Y_q-Y_{p+q+1} = O$
32. $R_1, R_2 = OH, X = Me/isopropyl/tert-butyl,$
    $Y_1, Y_{p+1}, Y_{p+q+2} = O, Y_2-Y_p, Y_q-Y_{p+q+1} = S$
33. $R_1, R_2 = OH, X = Me/isopropyl/tert-butyl,$
    $Y_{p+1} = S, Y_1-Y_p, Y_q-Y_{p+q+2} = O$
34. $R_1, R_2 = OH, X = Me/isopropyl/tert-butyl,$
    $Y_{p+1} = O, Y_1-Y_p, Y_q-Y_{p+q+2} = S$
35. $R_1, R_2 = OH, X = Me/isopropyl/tert-butyl,$
    $Y_{p+q+2} = S, Y_1-Y_{p+q+1} = O$
36. $R_1, R_2 = OH, X = Me/isopropyl/tert-butyl,$
    $Y_{p+q+2} = P, Y_1-Y_{p+q+1} = S$
37. Xs can also be combinations of methyl and isopropyl or combinations of methyl and tert-butyl or combinations of methyl, isopropyl and tert-butyl or combinations of isopropyl and tert-butyl

TABLE 14

Multiple Incorporation P-alkylphosphonate Backbone with α-Anomer into Oligonucleotides.

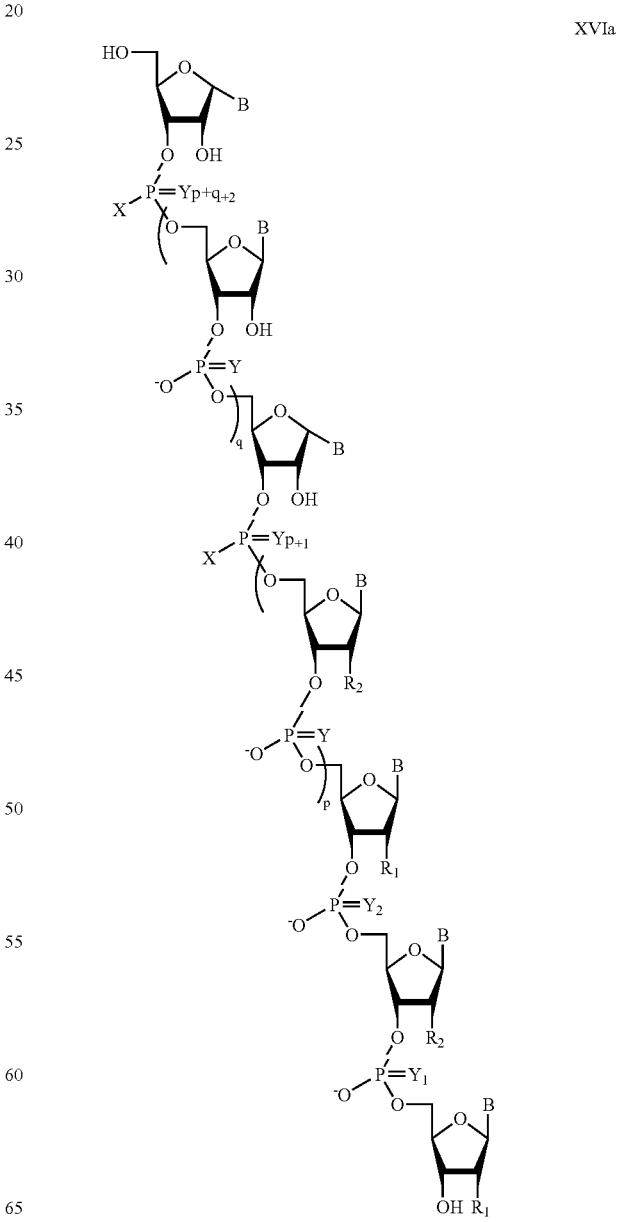

XVIa

TABLE 14-continued

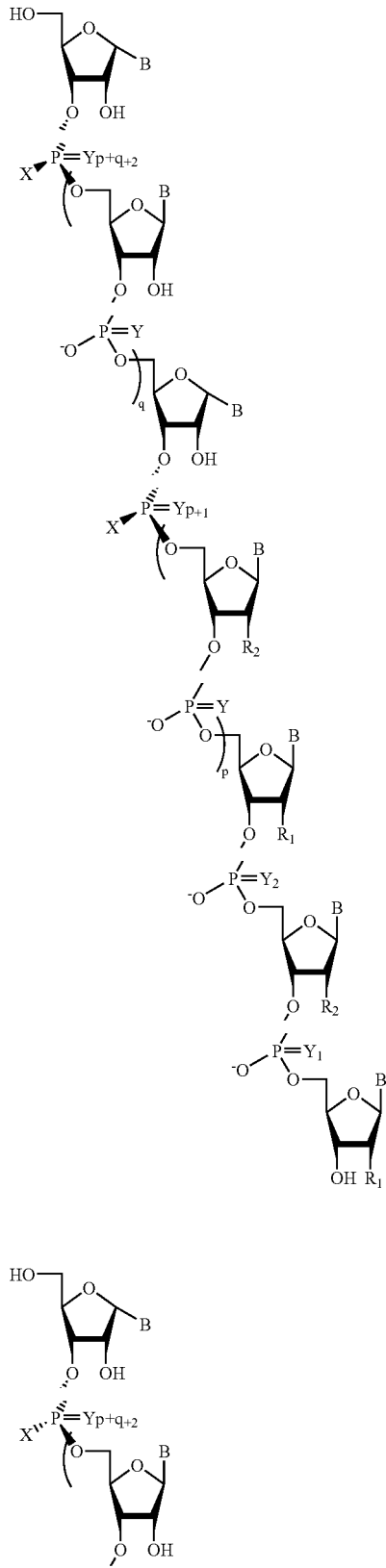

XVIIa

XVIIIa

TABLE 14-continued

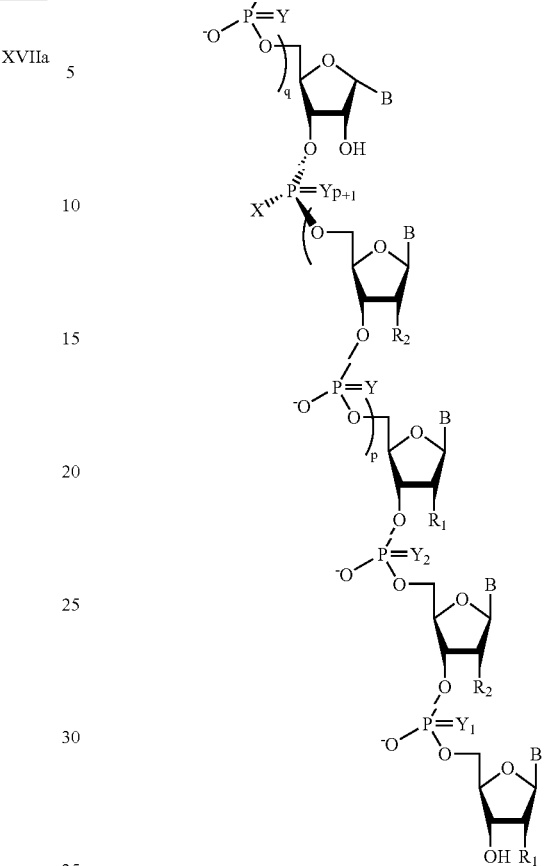

1. $R_1, R_2 = H, X = Me/isopropyl/tert-butyl, Y_1 - Y_{p+q+2} = O$
2. $R_1, R_2 = H, X = Me/isopropyl/tert-butyl, Y_1 - Y_{p+q+2} = S$
3. $R_1, R_2 = H, X = Me/isopropyl/tert-butyl,$
   $Y_1 = S, Y_2 - Y_{p+q+1} = O, Y_{p+q+2} = S$
4. $R_1, R_2 = H, X = Me/isopropyl/tert-butyl,$
   $Y_1 = O, Y_2 - Y_{p+q+1} = S, Y_{p+q+2} = O$
5. $R_1, R_2 = H, X = Me/isopropyl/tert-butyl,$
   $Y_1 = S, Y_2 - Y_{p+q+2} = O$
6. $R_1, R_2 = H, X = Me/isopropyl/tert-butyl,$
   $Y_1 = O, Y_2 - Y_{p+q+2} = S$
7. $R_1, R_2 = H, X = Me/isopropyl/tert-butyl,$
   $Y_1, Y_{p+1}, Y_{p+q+2} = S, Y_2 - Y_p, Y_q - Y_{p+q+1} = O$
8. $R_1, R_2 = H, X = Me/isopropyl/tert-butyl,$
   $Y_1, Y_{p+1}, Y_{p+q+2} = O, Y_2 - Y_p, Y_q - Y_{p+q+1} = S$
9. $R_1, R_2 = H, X = Me/isopropyl/tert-butyl,$
   $Y_{p+1} = S, Y_1 - Y_p, Y_q - Y_{p+q+1} = O$
10. $R_1, R_2 = H, X = Me/isopropyl/tert-butyl,$
    $Y_{p+1} = O, Y_1 - Y_p, Y_q - Y_{p+q+1} = S$
11. $R_1, R_2 = H, X = Me/isopropyl/tert-butyl,$
    $Y_{p+q+2} = S, Y_1 - Y_{p+q+1} = O$
12. $R_1, R_2 = H, X = Me/isopropyl/tert-butyl,$
    $Y_{p+q+2} = P, Y_1 - Y_{p+q+1} = S$
13. $R_1 = H, R_2 = OH, X = Me/isopropyl/tert-butyl, Y_1 - Y_{p+q+2} = O$
14. $R_1 = H, R_2 = OH, X = Me/isopropyl/tert-butyl, Y_1 - Y_{p+q+2} = S$
15. $R_1 = H, R_2 = OH, X = Me/isopropyl/tert-butyl,$
    $Y_1 = S, Y_2 - Y_{p+q+1} = O, Y_{p+q+2} = S$
16. $R_1 = H, R_2 = OH, X = Me/isopropyl/tert-butyl,$
    $Y_1 = O, Y_2 - Y_{p+q+1} = S, Y_{p+q+2} = O$
17. $R_1 = H, R_2 = OH, X = Me/isopropyl/tert-butyl,$
    $Y_1 = S, Y_2 - Y_{p+q+2} = O$
18. $R_1 = H, R_2 = OH, X = Me/isopropyl/tert-butyl,$
    $Y_1 = O, Y_2 - Y_{p+q+2} = S$
19. $R_1 = H, R_2 = OH, X = Me/isopropyl/tert-butyl,$
    $Y_1, Y_{p+1}, Y_{p+q+2} = S, Y_2 - Y_p, Y_q - Y_{p+q+1} = O$
20. $R_1 = H, R_2 = OH, X = Me/isopropyl/tert-butyl,$
    $Y_1, Y_{p+1}, Y_{p+q+2} = O, Y_2 - Y_p, Y_q - Y_{p+q+1} = S$
21. $R_1 = H, R_2 = OH, X = Me/isopropyl/tert-butyl,$
    $Y_{p+1} = S, Y_1 - Y_p, Y_q - Y_{p+q+2} = O$

TABLE 14-continued

22. $R_1 = H, R_2 = OH, X = Me/isopropyl/tert-butyl, Y_{p+1} = O, Y_1—Y_p, Y_q—Y_{p+q+2} = S$
23. $R_1 = H, R_2 = OH, X = Me/isopropyl/tert-butyl, Y_{p+q+2} = S, Y_1—Y_{p+q+1} = O$
24. $R_1 = H, R_2 = OH, X = Me/isopropyl/tert-butyl, Y_{p+q+2} = P, Y_1—Y_{p+q+1} = S$
25. $R_1, R_2 = OH, X = Me/isopropyl/tert-butyl, Y_1—Y_{p+q+2} = O$
26. $R_1, R_2 = OH, X = Me/isopropyl/tert-butyl, Y_1—Y_{p+q+2} = S$
27. $R_1, R_2 = OH, X = Me/isopropyl/tert-butyl, Y_1 = S, Y_2—Y_{p+q+1} = O, Y_{p+q+2} = S$
28. $R_1, R_2 = OH, X = Me/isopropyl/tert-butyl, Y_1 = O, Y_2—Y_{p+q+1} = S, Y_{p+q+2} = O$
29. $R_1, R_2 = OH, X = Me/isopropyl/tert-butyl, Y_1 = S, Y_2—Y_{p+q+2} = O$
30. $R_1, R_2 = OH, X = Me/isopropyl/tert-butyl, Y_1 = O, Y_2—Y_{p+q+2} = S$
31. $R_1, R_2 = OH, X = Me/isopropyl/tert-butyl, Y_1, Y_{p+1}, Y_{p+q+2} = S, Y_2—Y_p, Y_q—Y_{p+q+1} = O$
32. $R_1, R_2 = OH, X = Me/isopropyl/tert-butyl, Y_1, Y_{p+1}, Y_{p+q+2} = O, Y_2—Y_p, Y_q—Y_{p+q+1} = S$
33. $R_1, R_2 = OH, X = Me/isopropyl/tert-butyl, Y_{p+1} = S, Y_1—Y_p, Y_q—Y_{p+q+2} = O$
34. $R_1, R_2 = OH, X = Me/isopropyl/tert-butyl, Y_{p+1} = O, Y_1—Y_p, Y_q—Y_{p+q+2} = S$
35. $R_1, R_2 = OH, X = Me/isopropyl/tert-butyl, Y_{p+q+2} = S, Y_1—Y_{p+q+1} = O$
36. $R_1, R_2 = OH, X = Me/isopropyl/tert-butyl, Y_{p+q+2} = P, Y_1—Y_{p+q+1} = S$
37. Xs can also be combinations of methyl and isopropyl or combinations of methyl and tert-butyl or combinations of isopropyl and tert-butyl

TABLE 15

Multiple Incorporation P-alkylphosphonate Backbone with α-Anomer into Oligonucleotides.

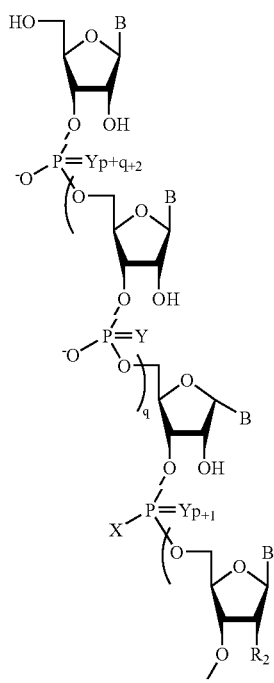

XIXa

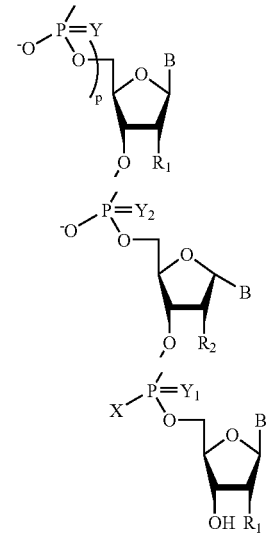

XXa

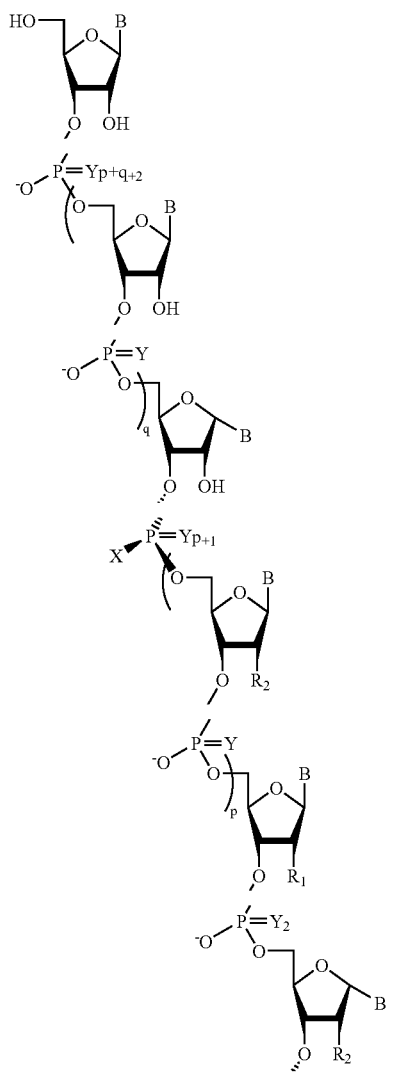

TABLE 15-continued

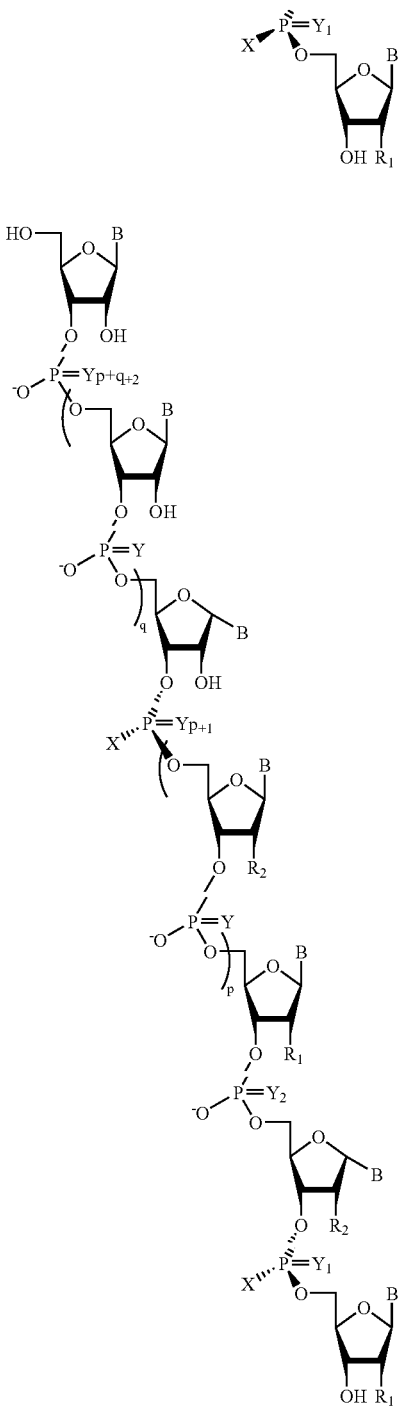

XXIa

1. $R_1, R_2 = H, X = Me/isopropyl/tert-butyl, Y_1—Y_{p+q+2} = O$
2. $R_1, R_2 = H, X = Me/isopropyl/tert-butyl, Y_1—Y_{p+q+2} = S$
3. $R_1, R_2 = H, X = Me/isopropyl/tert-butyl,$
   $Y_1 = S, Y_2—Y_{p+q+1} = O, Y_{p+q+2} = S$
4. $R_1, R_2 = H, X = Me/isopropyl/tert-butyl,$
   $Y_1 = O, Y_2—Y_{p+q+1} = S, Y_{p+q+2} = O$
5. $R_1, R_2 = H, X = Me/isopropyl/tert-butyl,$
   $Y_1 = S, Y_2—Y_{p+q+2} = O$
6. $R_1, R_2 = H, X = Me/isopropyl/tert-butyl,$
   $Y_1 = O, Y_2—Y_{p+q+2} = S$
7. $R_1, R_2 = H, X = Me/isopropyl/tert-butyl,$
   $Y_1, Y_{p+1}, Y_{p+q+2} = S, Y_2—Y_p, Y_q—Y_{p+q+1} = O$
8. $R_1, R_2 = H, X = Me/isopropyl/tert-butyl,$
   $Y_1, Y_{p+1}, Y_{p+q+2} = O, Y_2—Y_p, Y_q—Y_{p+q+1} = S$
9. $R_1, R_2 = H, X = Me/isopropyl/tert-butyl,$
   $Y_{p+1} = S, Y_1—Y_p, Y_q—Y_{p+q+1} = O$
10. $R_1, R_2 = H, X = Me/isopropyl/tert-butyl,$
    $Y_{p+1} = O, Y_1—Y_p, Y_q—Y_{p+q+1} = S$
11. $R_1, R_2 = H, X = Me/isopropyl/tert-butyl,$
    $Y_{p+q+2} = S, Y_1—Y_{p+q+1} = O$
12. $R_1, R_2 = H, X = Me/isopropyl/tert-butyl,$
    $Y_{p+q+2} = P, Y_1—Y_{p+q+1} = S$
13. $R_1 = H, R_2 = OH, X = Me/isopropyl/tert-butyl, Y_1—Y_{p+q+2} = O$
14. $R_1 = H, R_2 = OH, X = Me/isopropyl/tert-butyl, Y_1—Y_{p+q+2} = S$
15. $R_1 = H, R_2 = OH, X = Me/isopropyl/tert-butyl,$
    $Y_1 = S, Y_2—Y_{p+q+1} = O, Y_{p+q+2} = S$
16. $R_1 = H, R_2 = OH, X = Me/isopropyl/tert-butyl,$
    $Y_1 = O, Y_2—Y_{p+q+1} = S, Y_{p+q+2} = O$
17. $R_1 = H, R_2 = OH, X = Me/isopropyl/tert-butyl,$
    $Y_1 = S, Y_2—Y_{p+q+2} = O$
18. $R_1 = H, R_2 = OH, X = Me/isopropyl/tert-butyl,$
    $Y_1 = O, Y_2—Y_{p+q+2} = S$
19. $R_1 = H, R_2 = OH, X = Me/isopropyl/tert-butyl,$
    $Y_1, Y_{p+1}, Y_{p+q+2} = S, Y_2—Y_p, Y_q—Y_{p+q+1} = O$
20. $R_1 = H, R_2 = OH, X = Me/isopropyl/tert-butyl,$
    $Y_1, Y_{p+1}, Y_{p+q+2} = O, Y_2—Y_p, Y_q—Y_{p+q+1} = S$
21. $R_1 = H, R_2 = OH, X = Me/isopropyl/tert-butyl,$
    $Y_{p+1} = S, Y_1—Y_p, Y_q—Y_{p+q+2} = O$
22. $R_1 = H, R_2 = OH, X = Me/isopropyl/tert-butyl,$
    $Y_{p+1} = O, Y_1—Y_p, Y_q—Y_{p+q+2} = S$
23. $R_1 = H, R_2 = OH, X = Me/isopropyl/tert-butyl,$
    $Y_{p+q+2} = S, Y_1—Y_{p+q+1} = O$
24. $R_1 = H, R_2 = OH, X = Me/isopropyl/tert-butyl,$
    $Y_{p+q+2} = P, Y_1—Y_{p+q+1} = S$
25. $R_1, R_2 = OH, X = Me/isopropyl/tert-butyl, Y_1—Y_{p+q+2} = O$
26. $R_1, R_2 = OH, X = Me/isopropyl/tert-butyl, Y_1—Y_{p+q+2} = S$
27. $R_1, R_2 = OH, X = Me/isopropyl/tert-butyl,$
    $Y_1 = S, Y_2—Y_{p+q+1} = O, Y_{p+q+2} = S$
28. $R_1, R_2 = OH, X = Me/isopropyl/tert-butyl,$
    $Y_1 = O, Y_2—Y_{p+q+1} = S, Y_{p+q+2} = O$
29. $R_1, R_2 = OH, X = Me/isopropyl/tert-butyl,$
    $Y_1 = S, Y_2—Y_{p+q+2} = O$
30. $R_1, R_2 = OH, X = Me/isopropyl/tert-butyl,$
    $Y_1 = O, Y_2—Y_{p+q+2} = S$
31. $R_1, R_2 = OH, X = Me/isopropyl/tert-butyl,$
    $Y_1, Y_{p+1}, Y_{p+q+2} = S, Y_2—Y_p, Y_q—Y_{p+q+1} = O$
32. $R_1, R_2 = OH, X = Me/isopropyl/tert-butyl,$
    $Y_1, Y_{p+1}, Y_{p+q+2} = O, Y_2—Y_p, Y_q—Y_{p+q+1} = S$
33. $R_1, R_2 = OH, X = Me/isopropyl/tert-butyl,$
    $Y_{p+1} = S, Y_1—Y_p, Y_q—Y_{p+q+2} = O$
34. $R_1, R_2 = OH, X = Me/isopropyl/tert-butyl,$
    $Y_{p+1} = O, Y_1—Y_p, Y_q—Y_{p+q+2} = S$
35. $R_1, R_2 = OH, X = Me/isopropyl/tert-butyl,$
    $Y_{p+q+2} = S, Y_1—Y_{p+q+1} = O$
36. $R_1, R_2 = OH, X = Me/isopropyl/tert-butyl,$
    $Y_{p+q+2} = P, Y_1—Y_{p+q+1} = S$
37. Xs can also be combinations of methyl and isopropyl or combinations of methyl and tert-butyl or combinations of isopropyl and tert-butyl

TABLE 16

Oligonucleotide with P-alkylphosphonate backbone

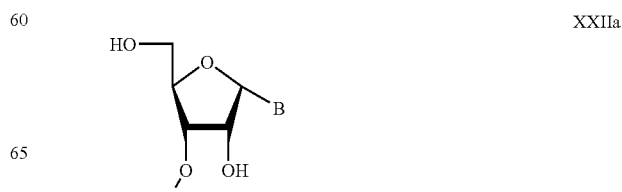

XXIIa

TABLE 16-continued
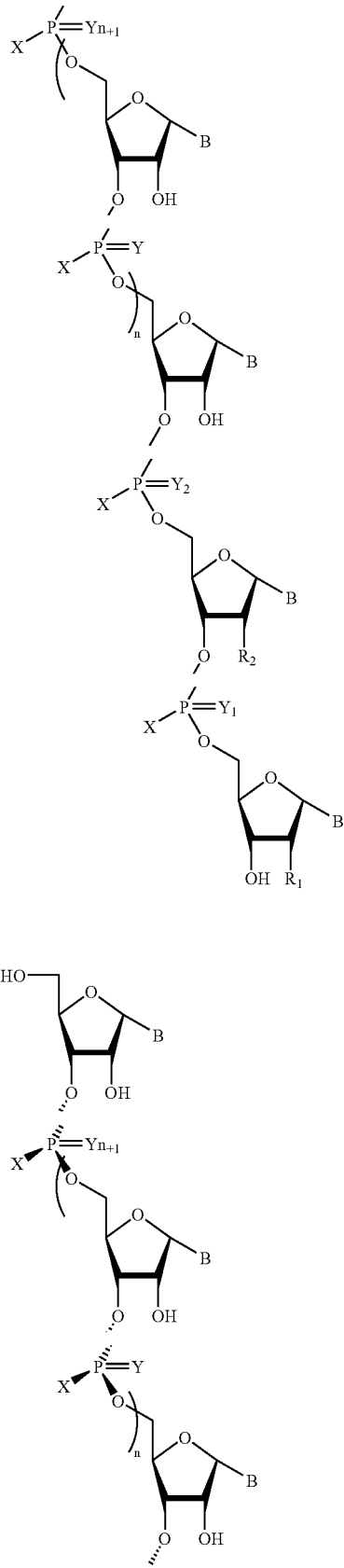
XXIIIa
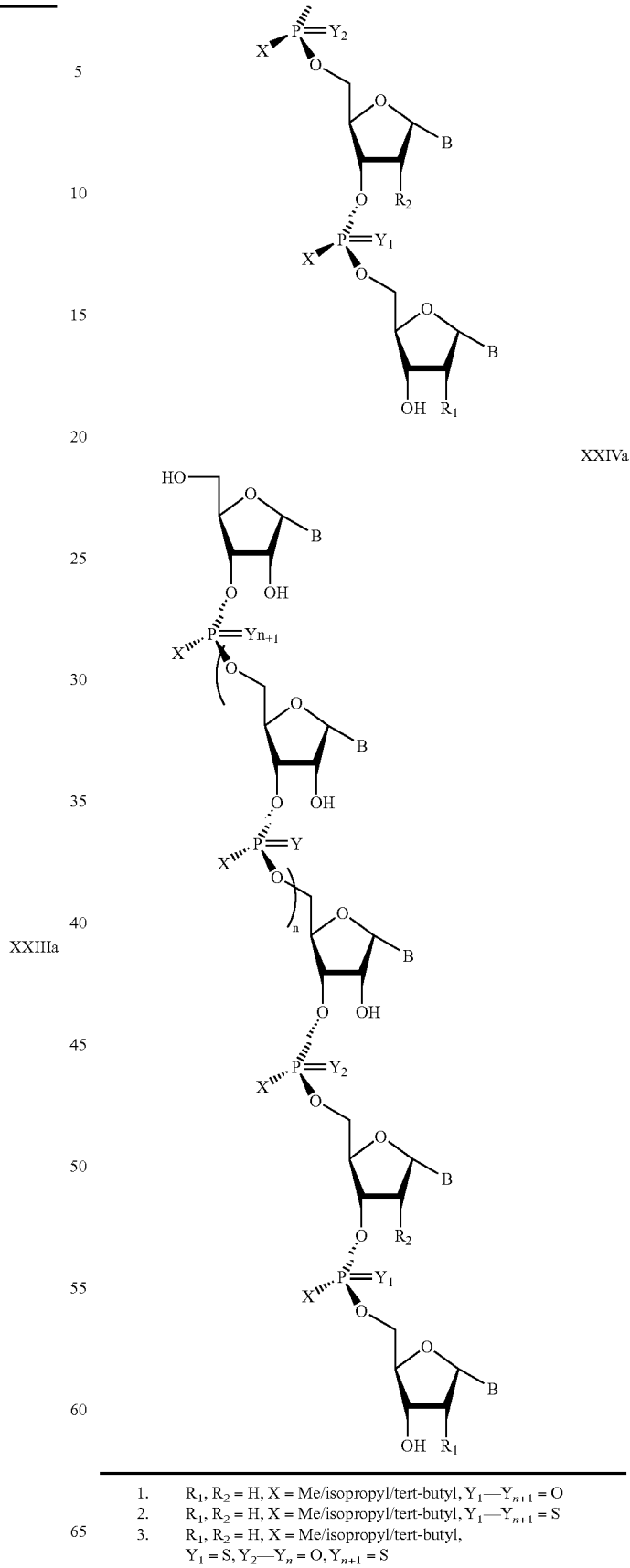
XXIVa
1. $R_1, R_2 = H, X = Me/isopropyl/tert-butyl, Y_1\text{—}Y_{n+1} = O$
2. $R_1, R_2 = H, X = Me/isopropyl/tert-butyl, Y_1\text{—}Y_{n+1} = S$
3. $R_1, R_2 = H, X = Me/isopropyl/tert-butyl,$
   $Y_1 = S, Y_2\text{—}Y_n = O, Y_{n+1} = S$ TABLE 16-continued 4. $R_1, R_2 = H, X = Me/isopropyl/tert-butyl,$
   $Y_1 = O, Y_2—Y_n = S, Y_{n+1} = O$
5. $R_1, R_2 = H, X = Me/isopropyl/tert-butyl,$
   $Y_1 = S, Y_2—Y_{n+1} = O$
6. $R_1, R_2 = H, X = Me/isopropyl/tert-butyl,$
   $Y_1 = O, Y_2—Y_{n+1} = S$
7. $R_1, R_2 = H, X = Me/isopropyl/tert-butyl,$
   $Y_1, Y_2 = S, Y_3—Y_n = O, Y_{n+1} = S$
8. $R_1, R_2 = H, X = Me/isopropyl/tert-butyl,$
   $Y_1, Y_3 \ldots Y_{n+1} = S, Y_2, Y_4, Y_6 \ldots Y_n = O$
9. $R_1, R_2 = H, X = Me/isopropyl/tert-butyl,$
   $Y_1, Y_3 \ldots Y_{n+1} = O, Y_2, Y_4, Y_6 \ldots Y_n = S$
10. $R_1 = H, R_2 = OH, X = Me/isopropyl/tert-butyl, Y_1—Y_{n+1} = O$
11. $R_1 = H, R_2 = OH, X = Me/isopropyl/tert-butyl, Y_1—Y_{n+1} = S$
12. $R_1 = H, R_2 = OH, X = Me/isopropyl/tert-butyl,$
    $Y_1 = S, Y_2—Y_n = O, Y_{n+1} = S$
13. $R_1 = H, R_2 = OH, X = Me/isopropyl/tert-butyl,$
    $Y_1 = O, Y_2—Y_n = S, Y_{n+1} = O$
14. $R_1 = H, R_2 = OH, X = Me/isopropyl/tert-butyl,$
    $Y_1 = S, Y_2—Y_{n+1} = O$
15. $R_1 = H, R_2 = OH, X = Me/isopropyl/tert-butyl,$
    $Y_1 = O, Y_2—Y_{n+1} = S$
16. $R_1 = H, R_2 = OH, X = Me/isopropyl/tert-butyl,$
    $Y_1, Y_2 = S, Y_3—Y_n = O, Y_{n+1} = S$
17. $R_1 = H, R_2 = OH, X = Me/isopropyl/tert-butyl,$
    $Y_1, Y_3 \ldots Y_{n+1} = S, Y_2, Y_4, Y_6 \ldots Y_n = O$
18. $R_1 = H, R_2 = OH, X = Me/isopropyl/tert-butyl,$
    $Y_1, Y_3 \ldots Y_{n+1} = O, Y_2, Y_4, Y_6 \ldots Y_n = S$
19. $R_1, R_2 = OH, X = Me/isopropyl/tert-butyl, Y_1—Y_{n+1} = O$
20. $R_1, R_2 = OH, X = Me/isopropyl/tert-butyl, Y_1—Y_{n+1} = S$
21. $R_1, R_2 = OH, X = Me/isopropyl/tert-butyl,$
    $Y_1 = S, Y_2—Y_n = O, Y_{n+1} = S$
22. $R_1, R_2 = OH, X = Me/isopropyl/tert-butyl,$
    $Y_1 = O, Y_2—Y_n = O, Y_{n+1} = O$
23. $R_1, R_2 = OH, X = Me/isopropyl/tert-butyl,$
    $Y_1 = S, Y_2—Y_{n+1} = O$
24. $R_1, R_2 = OH, X = Me/isopropyl/tert-butyl,$
    $Y_1 = O, Y_2—Y_{n+1} = S$
25. $R_1, R_2 = OH, X = Me/isopropyl/tert-butyl,$
    $Y_1, Y_2 = S, Y_3—Y_n = O, Y_{n+1} = S$
26. $R_1, R_2 = OH, X = Me/isopropyl/tert-butyl,$
    $Y_1, Y_3 \ldots Y_{n+1} = S, Y_2, Y_4, Y_6 \ldots Y_n = O$
27. $R_1, R_2 = OH, X = Me/isopropyl/tert-butyl,$
    $Y_1, Y_3 \ldots Y_{n+1} = O, Y_2, Y_4, Y_6 \ldots Y_n = S$
28. Xs can also be combinations of methyl and isopropyl or combinations of methyl and tert-butyl or combinations of methyl, isopropyl and tert-butyl or combinations of isopropyl and tert-butyl In certain instances, a ligand is bound to the oligonucleotide. The ligand improves the pharmacokinetic properties of the oligonucleotide. For double-stranded oligonucleotides, a ligand is bound to one of the oligonucleotide strands comprising the double-stranded oligonucleotide in certain instances. For double-stranded oligonucleotides, a ligand is bound to both of the oligonucleotide strands comprising the double-stranded oligonucleotide in certain instances. The ligand is an aromatic group, aralkyl group, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring. In certain embodiments, the ligand is an aralkyl group. In addition, the oligonucleotide may comprise a modified sugar moiety in certain instances. The sugar can be modified by replacing the 2'-hydroxyl group with a fluorine atom or an —O-allyl group. This modification renders the oligonucleotide less prone to nucleolytic degration.

For example, the present invention provides aralkyl-ligand-conjugated siRNA compounds that will impart improved pharmacokinetic properties to the siRNA agent. Such compounds are prepared by covalently attaching an aralkyl ligand to siRNA. The aralkyl ligand, e.g., naproxen, improves the pharmacologic properties of the siRNA because the ligand binds reversibly to one or more serum, vascular or cellular proteins. This reversible binding is expected to decrease urinary excretion, increase serum half-life, and greatly increase the distribution of oligomeric compounds thus conjugated. In addition, the backbone of the oligonucleotide is modified to improve the stability of the siRNA compound.

Conjugating a ligand to a siRNA can enhance its cellular absorption. In certain instances, a hydrophobic ligand is conjugated to the siRNA to facilitate direct permeation of the cellular membrane. Alternatively, the ligand conjugated to the siRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. siRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The therapeutic effect of an oligonucleotide is realized when it interacts with a specific cellular nucleic acid and effectively negates its function. A preferred target is DNA or mRNA encoding a protein that is responsible for a disease state. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression. Nevertheless, the ultimate goal is to regulate the amount of such a protein.

To reach a target nucleic acid after administration, an oligonucleotide should be able to overcome inherent factors such as rapid degradation in serum, short half-life in serum and rapid filtration by the kidneys with subsequent excretion in the urine. Oligonucleotides that overcome these inherent factors have increased serum half-life, distribution, cellular uptake and hence improved efficacy.

These enhanced pharmacokinetic parameters have been shown for selected drug molecules that bind plasma proteins (Olson and Christ, *Annual Reports in Medicinal Chemistry*, 1996, 31:327). Two proteins that have been studied more than most are human serum albumin (HSA) and α-1-acid glycoprotein. HSA binds a variety of endogenous and exogenous ligands with association constants typically in the range of $10^4$ to $10^6$ M$^{-1}$. Association constants for ligands with α-1-acid glycoprotein are similar to those for HSA.

In a preferred embodiment of the invention, the protein targeted by the oligonucleotide is a serum protein. It is preferred that the serum protein targeted by a conjugated oligomeric compound is an immunoglobulin (an antibody). Preferred immunoglobulins are immunoglobulin G and immunoglobulin M. Immunoglobulins are known to appear in blood serum and tissues of vertebrate animals.

In another embodiment of the invention, the serum protein targeted by the oligonucleotide is a lipoprotein. Lipoproteins are blood proteins having molecular weights generally above 20,000 that carry lipids and are recognized by specific cell-surface receptors. The association with lipoproteins in the serum will initially increase pharmacokinetic parameters such as half-life and distribution. A secondary consideration is the ability of lipoproteins to enhance cellular uptake via receptor-mediated endocytosis.

In yet another embodiment, the serum protein targeted by the oligonucleotide compound is α-2-macroglobulin. In yet a further embodiment the serum protein targeted by the oligonucleotide is α-1-glycoprotein.

At least for therapeutic purposes, oligonucleotides should have a degree of stability in serum to allow distribution and cellular uptake. The prolonged maintenance of therapeutic levels of antisense agents in serum will have a significant effect on the distribution and cellular uptake and unlike conjugate groups that target specific cellular receptors, the increased serum stability will effect all cells.

In the context of this invention, the siRNA comprises double-stranded oligonucleotides, wherein the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases. The oligonucleotides of the present invention preferably comprise from about 5 to about 50 nucleosides. It is more preferred that such oligonucleotides comprise from about 8 to about 30 nucleosides, with 15 to 25 nucleosides being particularly preferred.

An oligonucleotide is a polymer of repeating units generically known as nucleotides or nucleosides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the C5 (5') position of the sugar of a first nucleotide and the C3 (3') position of a second, adjacent nucleotide. A "nucleoside" is the combination of (1) a nucleobase and (2) a sugar in the absence of a phosphate moiety (Kornberg, DNA Replication, W. H. Freeman & Co., San Francisco, 1980, pages 4-7). The backbone of an oligonucleotide positions a series of bases in a specific order; the written representation of this series of bases, which is conventionally written in 5' to 3' order, is known as a nucleotide sequence.

Oligonucleotides may comprise nucleoside or nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleosides or nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The ligand-conjugated oligonucleotides of the invention can be prepared by attaching the ligand to the oligonucleotide through a monomer, e.g., a chemically modified monomer that is integrated into the oligonucleotide agent. In a preferred embodiment, the coupling is by a tether or a linker (or both) as described below, and the complex has the formula represented by:

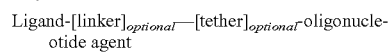
Ligand-[linker]$_{optional}$—[tether]$_{optional}$-oligonucleotide agent While, in most cases, embodiments are described with respect to an oligonucleotide agent including a number of nucleotides, the invention also includes monomeric subunits having the structure:

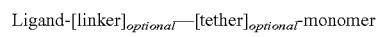
Ligand-[linker]$_{optional}$—[tether]$_{optional}$-monomer

Methods of making and incorporating the monomers into the oligonucleotide agents and methods of using those agents are included in the invention. In preferred embodiments, the sugar, e.g., the ribose sugar of one or more of the nucleotides, (e.g., ribonucleotide, deoxynucleotide, or modified nucleotide) subunits of an oligonucleotide agent can be replaced with another moiety, e.g., a non-carbohydrate carrier. In certain instances, the non-carbohydrate is cyclic. A nucleotide subunit in which the sugar of the subunit has been so replaced is referred to herein as a sugar replacement modification subunit (SRMS). This is often referred to as a tether. A cyclic carrier may be a carbocyclic ring system, i.e., all ring atoms are carbon atoms or a heterocyclic ring system, i.e., one or more ring atoms may be a heteroatom, e.g., nitrogen, oxygen, or sulfur. The cyclic carrier may be a monocyclic ring system, or may contain two or more rings, e.g. fused rings. The cyclic carrier may be a fully saturated ring system, or it may contain one or more double bonds.

The oligonucleotide agents of the invention include nucleic acid targeting (NAT) oligonucleotide agents and protein-targeting (PT) oligonucleotide agents. NAT and PT oligonucleotide agents refer to single-stranded oligomers or polymers of ribonucleic acid (RNA) or deoxyribonucleic acid (DNA) or combined (chimeric) modifications of DNA and RNA. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as enhanced cellular uptake, enhanced affinity for nucleic acid target, and/or increased stability in the presence of nucleases. NATs designed to bind to specific RNA or DNA targets have substantial complementarity, e.g., at least 70, 80, 90, or 100% complementary, with at least 10, 20, or 30 or more bases of a target nucleic acid, and include antisense RNAs, miRNAs, and other non-duplex structures which can modulate expression. Other NAT oligonucleotide agents include external guide sequence (EGS) oligonucleotides (oligozymes), DNAzymes, and ribozymes. These NATs may or may not bind via Watson-Crick complementarity to their targets. PT oligonucleotide agents bind to protein targets, preferably by virtue of three-dimensional interactions, and modulate protein activity. They include decoy RNAs, aptamers, and the like.

The single-stranded oligonucleotide compounds of the invention preferably comprise from about 8 to about 50 nucleobases (i.e. from about 8 to about 50 linked nucleosides). NAT oligonucleotide agents are preferably about 15 nucleotides long, or more preferably about 30 nucleotides long. PT oligonucleotide agents are preferably about 18 nucleotides long, or more preferably about 23 nucleotides long. Particularly preferred compounds are miRNAs and antisense oligonucleotides, even more preferably those comprising from about 12 to about 30 nucleobases.

While not wishing to be bound by theory, an oligonucleotide agent may act by one or more of a number of mechanisms, including a cleavage-dependent or cleavage-independent mechanism. A cleavage-based mechanism can be RNAse H dependent and/or can include RISC complex function. Cleavage-independent mechanisms include occupancy-based translational arrest, such as is mediated by miRNAs, or binding of the oligonucleotide agent to a protein, as do aptamers. Oligonucleotide agents may also be used to alter the expression of genes by changing the choice of the splice site in a pre-mRNA. Inhibition of splicing can also result in degradation of the improperly processed message, thus downregulating gene expression. Kole and colleagues (Sierakowska, et al. *Proc. Natl. Acad. Sci. USA*, 1996, 93:12840-12844) showed that 2'-O-Me phosphorothioate oligonucleotides could correct aberrant beta-globin splicing in a cellular system. Fully modified 2'-methoxyethyl oligonucleotides and peptide nucleic acids (PNAs) were able to redirect splicing of IL-5 receptor-α pre-mRNA (Karras et al., *Mol. Pharmacol.* 2000, 58:380-387; Karras, et al., *Biochemistry* 2001, 40:7853-7859).

MicroRNAs

The oligonucleotide agents include microRNAs (miRNAs). MicroRNAs are small noncoding RNA molecules that are capable of causing post-transcriptional silencing of specific genes in cells such as by the inhibition of translation or through degradation of the targeted mRNA. A miRNA can be completely complementary or can have a region of non-complementarity with a target nucleic acid, consequently resulting in a "bulge" at the region of non-complementarity. The region of non-complementarity (the bulge) can be flanked by regions of sufficient complementarity, preferably complete complementarity to allow duplex formation. Preferably, the regions of complementarity are at least 8 to 10 nucleotides long (e.g., 8, 9, or 10 nucleotides long). A miRNA can inhibit gene expression by repressing translation, such as when the microRNA is not completely complementary to the target nucleic acid, or by causing target RNA degradation, which is believed to occur only when the miRNA binds its target with perfect complementarity. The invention also includes double-stranded precursors of miRNAs that may or may not form a bulge when bound to their targets.

A miRNA or pre-miRNA can be about 18-100 nucleotides in length, and more preferably from about 18-80 nucleotides in length. Mature miRNAs can have a length of about 19-30 nucleotides, preferably about 21-25 nucleotides, particularly 21, 22, 23, 24, or 25 nucleotides. MicroRNA precursors can have a length of about 70-100 nucleotides and have a hairpin conformation. MicroRNAs can be generated in vivo from pre-miRNAs by enzymes called Dicer and Drosha that specifically process long pre-miRNA into functional miRNA. The microRNAs or precursor miRNAs featured in the invention can be synthesized in vivo by a cell-based system or can be chemically synthesized. MicroRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

In particular, an miRNA or a pre-miRNA featured in the invention can have a chemical modification on a nucleotide in an internal (i.e., non-terminal) region having noncomplementarity with the target nucleic acid. For example, a modified nucleotide can be incorporated into the region of a miRNA that forms a bulge. The modification can include a ligand attached to the miRNA, e.g., by a linker. The modification can, for example, improve pharmacokinetics or stability of a therapeutic miRNA, or improve hybridization properties (e.g., hybridization thermodynamics) of the miRNA to a target nucleic acid. In some embodiments, it is preferred that the orientation of a modification or ligand incorporated into or tethered to the bulge region of a miRNA is oriented to occupy the space in the bulge region. This orientation facilitates the improved hybridization properties or an otherwise desired characteristic of the miRNA. For example, the modification can include a modified base or sugar on the nucleic acid strand or a ligand that functions as an intercalator. These are preferably located in the bulge. The intercalator can be an aromatic, e.g., a polycyclic aromatic or heterocyclic aromatic compound. A polycyclic intercalator can have stacking capabilities, and can include systems with 2, 3, or 4 fused rings. Universal bases can also be incorporated into the miRNAs.

In one embodiment, an miRNA or a pre-miRNA can include an aminoglycoside ligand, which can cause the miRNA to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity.

Neo-S-acridine, an acridine analog, has an increased affinity for the HIV Rev-response element (RRE). In some embodiments, the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

In one embodiment, the ligand can include a cleaving group that contributes to target gene inhibition by cleavage of the target nucleic acid. Preferably, the cleaving group is tethered to the miRNA in a manner such that it is positioned in the bulge region, where it can access and cleave the target RNA. The cleaving group can be, for example, a bleomycin (e.g., bleomycin-$A_5$, bleomycin-$A_2$, or bleomycin-$B_2$), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miRNA or a pre-miRNA to promote cleavage of the target RNA, such as at the bulge region. For example, 1,8-dimethyl-1,3,6,8,10,13-hexaazacyclotetradecane (cyclam) can be conjugated to a peptide (e.g., by an amino acid derivative) to promote target RNA cleavage. The methods and compositions featured in the invention include miRNAs that inhibit target gene expression by a cleavage or non-cleavage dependent mechanism.

A miRNA or a pre-miRNA can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long). For increased nuclease resistance and/or binding affinity to the target, the miRNA sequences can include 2'-O-methyl, 2'-fluorine, 2'-O-methoxyethyl, 2'-O-aminopropyl, 2'-amino, and/or phosphorothioate linkages. The inclusion of furanose sugars in the oligonucleotide backbone can also decrease endonucleolytic cleavage. An miRNA or a pre-miRNA can be further modified by including a 3'-cationic group, or by inverting the nucleoside at the 3'-terminus with a 3'-3' linkage. In another alternative, the 3'-terminus can be blocked with an aminoalkyl group, e.g., a 3'-C5-aminoalkyl dT. Other 3'-conjugates can inhibit 3'-5' exonucleolytic cleavage. While not being bound by theory, a 3'-conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

In one embodiment, a miRNA or a pre-miRNA includes a modification that improves targeting, e.g. a targeting modification described above. Examples of modifications that target miRNA molecules to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

A miRNA or a pre-miRNA can be constructed using chemical synthesis and/or enzymatic ligation reactions using procedures known in the art. For example, a miRNA or a pre-miRNA can be chemically synthesized using naturally occurring nucleotides or variously modified nucleotides designed to increase the biological stability of the molecules or to increase the physical stability of the duplex formed between the miRNA or a pre-miRNA and target nucleic acids, e.g., phosphorothioate derivatives and acridine substituted nucleotides can be used. Other appropriate nucleic acid modifications are described herein. Alternatively, the miRNA or pre-miRNA nucleic acid can be produced biologically using an expression vector into which a nucleic acid has been subcloned in an antisense orientation, i.e., RNA transcribed from the inserted nucleic acid will be of an antisense orientation to a target nucleic acid of interest.

Antisense Nucleic Acid Sequences

The single-stranded oligonucleotide agents featured in the invention include antisense nucleic acids. An "antisense" nucleic acid includes a nucleotide sequence that is complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. Accordingly, an antisense nucleic acid can form hydrogen bonds with a sense nucleic acid target.

Given a coding strand sequence such as the sequence of a sense strand of a cDNA molecule, antisense nucleic acids can be designed according to the rules of Watson and Crick base pairing. The antisense nucleic acid molecule can be complementary to a portion of the coding or noncoding region of an RNA, e.g., a pre-mRNA or mRNA. For example, the antisense oligonucleotide can be complementary to the region surrounding the translation start site of a pre-mRNA or mRNA, e.g., the 5' UTR. An antisense oligonucleotide can be about 10 to 25 nucleotides in length (e.g., 11, 12, 13, 14, 15, 16, 18, 19, 20, 21, 22, 23, or 24 nucleotides in length). An antisense oligonucleotide can also be complementary to a miRNA or pre-miRNA.

An antisense nucleic acid can be constructed using chemical synthesis and/or enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and target nucleic acids, e.g., phosphorothioate derivatives and acridine substituted nucleotides can be used. Other appropriate nucleic acid modifications are described herein. Alternatively, the antisense nucleic acid can be produced biologically using an expression vector into which a nucleic acid has been subcloned in an antisense orientation, i.e., RNA transcribed from the inserted nucleic acid will be of an antisense orientation to a target nucleic acid of interest.

An antisense agent can include ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme such as RNAse H. Degradation of the target RNA prevents translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAse H activity is desired.

For increased nuclease resistance, an antisense agent can be further modified by inverting the nucleoside at the 3'-terminus with a 3'-3' linkage. In another alternative, the 3'-terminus can be blocked with an aminoalkyl group. In certain instances, the antisense oligonucleotide agent includes a modification that improves targeting, e.g. a targeting modification.

Decoy Nucleic Acids

An oligonucleotide agent featured in the invention can be a decoy nucleic acid such as decoy RNA. A decoy nucleic acid resembles a natural nucleic acid, but is modified to inhibit or interrupt the activity of the natural nucleic acid. For example, a decoy RNA can mimic the natural binding domain for a ligand, and compete with natural binding target for the binding of a specific ligand. It has been shown that over-expression of HIV trans-activation response (TAR) RNA can act as a "decoy" and efficiently bind HIV tat protein, thereby preventing it from binding to TAR sequences encoded in the HIV RNA. In one embodiment, a decoy RNA includes a modification that improves targeting. The chemical modifications described above for miRNAs and antisense RNAs, and described elsewhere herein, are also appropriate for use in decoy nucleic acids.

Aptamers

Oligonucleotide agents of the invention also include aptamers. An aptamer binds to a non-nucleic acid ligand, such as a small organic molecule or protein, e.g., a transcription or translation factor, and subsequently modifies its activity. An aptamer can fold into a specific structure that directs the recognition of the targeted binding site on the non-nucleic acid ligand. An aptamer can contain any of the modifications described herein. In certain instances, the aptamer includes a modification that improves targeting, e.g., a targeting modification. The chemical modifications described above for miRNAs and antisense RNAs, and described elsewhere herein, are also appropriate for use in decoy nucleic acids.

Additional Features of the Oligonucleotides of the Invention

An oligonucleotide agent that is NAT ("nucleic acid targeting") includes a region of sufficient complementarity to the target gene, and is of sufficient length in terms of nucleotides, such that the oligonucleotide agent forms a duplex with the target nucleic acid. The oligonucleotide agent can modulate the function of the targeted molecule. For example, when the targeted molecule is an mRNA or pre-mRNA, the NAT can inhibit gene expression; when the target is an miRNA, the NAT will inhibit the miRNA function and will thus up-regulate expression of the mRNAs targeted by the particular miRNA. Alternatively, when the target is a region of a pre-mRNA that affects splicing, the NAT can alter the choice of splice site and thus the mRNA sequence; when the NAT functions as an miRNA, expression of the targeted mRNA is inhibited. For ease of exposition the term nucleotide or ribonucleotide is sometimes used herein in reference to one or more monomeric subunits of an oligonucleotide agent. It will be understood that the term "ribonucleotide" or "nucleotide" can, in the case of a modified RNA or nucleotide surrogate, also refer to a modified nucleotide, or surrogate replacement moiety at one or more positions.

A NAT oligonucleotide agent is, or includes, a region that is at least partially, and in some embodiments fully, complementary to the target RNA. It is not necessary that there be perfect complementarity between the oligonucleotide agent and the target, but the correspondence must be sufficient to enable the oligonucleotide agent, or a cleavage product thereof, to modulate (e.g., inhibit) target gene expression.

The oligonucleotide agent will preferably have one or more of the following properties: (1) it will have a 5' modification that includes one or more phosphate groups or one or more analogs of a phosphate group; (2) it will, despite modifications even to a very large number of bases, specifically base pair and form a duplex structure with a homologous target RNA of sufficient thermodynamic stability to allow modulation of the activity of the targeted RNA; and (3) it will, despite modifications even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain a 2'-fluoro group in place of 2'-hydroxyl group. This deoxyribonucleotide-containing agent can still be expected to exhibit RNA-like properties. While not wishing to be bound by theory, the electronegative fluorine prefers an axial orientation when attached to the C2'-position of ribose. This spatial preference of fluorine can force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2'-sugar position will be able to enter into hydrogen-bonding which is more characteristic of the 2'-OH moiety of a ribonucleotide than the 2'-H moiety of a deoxyribonucleotide. A preferred oligonucleotide agent will: exhibit a $C_{3'}$-endo pucker in all, or at least about 50, 75, 80, 85, 90, or 95% of its sugars; exhibit a $C_{3'}$-endo pucker in a sufficient amount of its sugars that it can give rise to the RNA-characteristic A-family-type helix; will generally have no more than about 20, 10, 5, 4, 3, 2, or 1 sugar which is not a $C_{3'}$-endo pucker structure. In certain instances, oligonucleotide will exhibit $C_{3'}$-endo suger pucker and be modified at the 2'-position. Exemplary modifications include 2'-OH, 2'-O—Me, 2'-O-methoxyethyl, 2'-O-aminopropyl, 2'-F, 2'-O—$CH_2$—CO—NHMe, 2'-O—$CH_2$—$CH_2$—O—$CH_2$—$CH_2$—N(Me)$_2$, and LNA. In certain instances, regardless of the nature of the modification, and even though the oligonucleotide agent can contain deoxynucleotides or modified deoxynucleotides, it is preferred that DNA molecules, or any molecule in which more than 50, 60, or 70% of the nucleotides in the molecule are deoxyribonucleotides, or modified deoxyribonucleotides which are deoxy at the 2' position, are excluded from the definition of oligonucleotide agent. Some preferred 2'-modifications with sugar moieties exhibiting C2'-endo sugar pucker include 2'-H, 2'-Me, 2'-S—Me, 2'-Ethynyl, and 2'-ara-F. Additional sugar modifications include L-sugars and 2'-5'-linked sugars.

As used herein, "specifically hybridizable" and "complementary" are terms that are used to indicate a sufficient degree of complementarity such that stable and specific binding occurs between a compound of the invention and a target RNA molecule. This nomenclature also applies to instances when NAT oligonucleotides agents bind to target RNAs. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed. It has been shown that a single mismatch between targeted and non-targeted sequences are sufficient to provide discrimination for siRNA targeting of an mRNA (Brummelkamp et al., *Cancer Cell*, 2002, 2:243).

In certain instances, a NAT oligonucleotide agent is "sufficiently complementary" to a target RNA, such that the oligonucleotide agent inhibits production of protein encoded by the target mRNA. The target RNA can be a pre-mRNA, mRNA, or miRNA endogenous to the subject. In another embodiment, the oligonucleotide agent is "exactly complementary" (excluding the SRMS containing subunit(s)) to a target RNA, e.g., the target RNA and the oligonucleotide agent can anneal to form a hybrid made exclusively of Watson-Crick base pairs in the region of exact complementarity. A "sufficiently complementary" target RNA can include a region (e.g., of at least about 7 nucleotides) that is exactly complementary to a target RNA. Moreover, in some embodiments, the oligonucleotide agent specifically discriminates a single-nucleotide difference. In this case, the oligonucleotide agent only down-regulates gene expression if exact complementary is found in the region the single-nucleotide difference.

Oligonucleotide agents discussed include otherwise unmodified RNA and DNA as well as RNA and DNA that have been modified. Examples of modified RNA and DNA include modifications to improve efficacy and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The literature has referred to rare or unusual, but naturally occurring, RNAs as modified RNAs. See Limbach et al. *Nucleic Acids Res.* 1994, 22, 2183-2196. Such rare or unusual RNAs, often termed modified RNAs, are typically the result of a post-transcriptional modification and are within the scope of the term unmodified RNA as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

Sugar Replacement Monomer Subunits (SRMS)

A nucleotide subunit in which the sugar of the subunit has been so replaced is referred to herein as a sugar replacement modification subunit (SRMS). The SRMS includes two "backbone attachment points" (hydroxyl groups), a "tethering attachment point," and a ligand, which is connected indirectly to the SRMS via an intervening tether. The SRMS may be the 5'- or 3'-terminal subunit of the oligonucleotide agent and located adjacent to two or more unmodified or modified ribonucleotides. Alternatively, the SRMS may occupy an internal position located adjacent to one or more unmodified or modified ribonucleotides. More than one SRMS may be present in an oligonucleotide agent. Preferred positions for inclusion of a SRMS tethered to a moiety (e.g., a lipophilic moiety such as cholesterol) are at the 3'-terminus, the 5'-terminus, or at an internal position.

Ligands

A wide variety of entities can be tethered to the oligonucleotide agent. A ligand tethered to an oligonucleotide agent can have a favorable effect on the agent. For example, the ligand can improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of a miRNA/target duplex. The intercalator can be an aromatic group including polycyclic aromatics or heterocyclic aromatic groups. A polycyclic intercalator can have stacking capabilities, and can include systems with 2, 3, or 4 fused rings. Universal bases can be included on a ligand.

In one embodiment, the ligand includes a cleaving group that contributes to target gene inhibition by cleavage of the target nucleic acid. The cleaving group can be a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal-ion chelating group. The metal-ion chelating group can be an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions such as Lu(III). In some instances, a peptide ligand can be tethered to a miRNA to promote cleavage of the target RNA. In certain instances, the cleavage may occur at the bulge region. For example, 1,8-dimethyl-1,3,6,8,10,13-hexaazacyclotetradecane (cyclam) can be conjugated to a peptide, such as via an amino acid derivative, to promote target RNA cleavage.

A tethered ligand can be an aminoglycoside ligand which can cause an oligonucleotide agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent. A tethered ligand can be a poly-arginine peptide, peptoid or peptidomimetic, which can enhance the cellular uptake of an oligonucleotide agent.

Preferred moieties are ligands, which are coupled, preferably covalently, either directly or indirectly via an intervening tether, to the SRMS carrier. In preferred embodiments, the ligand is attached to the carrier via an intervening tether. As discussed above, the ligand or tethered ligand may be present on the SRMS monomer when the SRMS monomer is incorporated into the growing strand. In some embodiments, the ligand may be incorporated into a "precursor" SRMS after a "precursor" SRMS monomer has been incorporated into the growing strand. For example, an SRMS monomer having an amino-terminated tether (i.e., having no associated ligand), or TAP-$(CH_2)_n NH_2$ may be incorporated into a growing oligonucleotide strand. In a subsequent operation, a ligand having an electrophilic group can subsequently be attached to the precursor SRMS by coupling the electrophilic group of the ligand with a terminal nucleophilic group of the precursor SRMS tether. Representative electrophilic groups include pentafluorophenyl esters or an aldehyde. Other electrophilic groups amenable to the present invention can be readily determined by one of ordinary skill in the art.

Induction of DNA Methylation by siRNA

In addition to the well characterized mechanisms of siRNA-induced gene silencing in the cytoplasm, recent studies indicate that siRNA also acts in the nucleus to cause alterations in patterns of DNA methylation, heterochromatin formation, and programmed DNA elimination thus resulting in gene silencing. For reviews, see N. Agrawal et al. *Microbiol. Mol. Biol. Rev.* 2003, 67, 657-685; Kent, O. A.; MacMillan, A. M. *Org. Biomol. Chem.* 2004, 2, 1957-1961; Lippman, Z.; Martienssen, R. *Nature* 2004, 43/, 364-370; M. Matzke et al. *Biochim. Biophys. Acta.* 2004, 1677, 129-141; and Schramke, V.; Allshire, R. *Curr. Opin. Genet. Dev.* 2004, 14, 174-180. This silencing requires components of the RNAi machinery, but the mechanism is not well understood.

Unlike the rest of the nuclear DNA, heterochromatin remains condensed throughout the cell cycle. Heterochromatin is of interest because of its ability to influence the regulation of nearby genes. Heterochromatic repeats are not similar in sequence between species, but in all species, heterochromatic DNA is not transcribed, but instead is silenced by conserved epigenetic modifications of histones and DNA itself. This silencing is believed to prevent illegitimate recombination. The role of DNA methylation in silencing has long been recognized. As almost all DNA methylation is confined to transposons and repeat elements, these regions must somehow be distinguished from genes. RNAi appears to be one mechanism that allows sequence-specific targeting of methylation.

The first indication that there is a link between the RNAi machinery and heterochromatin formation came from a study in yeast that showed that deletion of RNAi associated proteins relieved silencing of genes inserted into centromeric heterochromatin. See T. A. Volpe et al. *Science.* 2002, 297, 1833-1837. Subsequently, Schramke and Allshire demonstrated in fission yeast that expression of a synthetic short hairpin RNA could silence expression of a euchromatic gene. See Schramke, V.; Allshire, R. *Science* 2003, 301, 1069-1074. Silencing was coupled to chromatin modification and recruitment of heterochromatin proteins and cohesin to the target locus. Silencing via this mechanism requires Argonaute, Dicer, and RNA-directed RNA polymerase, the known components of the RNAi machinery. See Volpe et al. cited above.

Biochemical purification of chromodomain complexes in fission yeast has yielded the RITS (RNAi-induced transcriptional gene silencing) complex. See A. Verdel et al. *Science* 2004, 303, 672-676. RITS recognizes and binds to specific chromosome regions to initiate heterochromatic gene silencing. Specific sequence recognition is directed by siRNA. RITS contains Ago1, the *S. pombe* homolog of the Argonaute family of proteins. At least two subunits of the RITS complex, Chp1 and Tas3, specifically associate with the heterochromatic DNA regions, which suggests that the complex localizes directly to its target DNA. RITS also contains a chromodomain protein, Chp1, which is localized throughout heterochromatic DNA regions and requires the methyltransferase Clr4 and histone H3-K9 methylation for localization to chromatin. Thus, RITS contains both a subunit (Ago 1) that binds to siRNAs and can function in RNA or DNA targeting by sequence-specific pairing interaction and a subunit (Chp1) that associates with specifically modified histones and may be involved in further stabilizing its association with chromatin.

Two groups have recently demonstrated that siRNAs can induce DNA methylation and histone H3 methylation in human cells. See Kawasaki, H.; Taira, K. *Nature* 2004, 431, 211-217 and Morris et al. *Science* 2004, 305, 1289-1292. It has also been shown that Dicer, the nuclease that processes siRNA from precursor, is required for heterochromatin formation in chicken cells. Fukagawa et al. *Nat. Cell Biol.* 2004, 6, 784-791.

Synthesis of Oligonucleotides of the Invention siRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

Ligand-conjugated oligonucleotides of the invention may be synthesized by the use of an oligonucleotide that bears a pendant reactive functionality, such as that derived from the attachment of a linking molecule onto the oligonucleotide. This reactive oligonucleotide may be reacted directly with commercially-available ligands, ligands that are synthesized bearing any of a variety of protecting groups, or ligands that have a linking moiety attached thereto. The methods of the present invention facilitate the synthesis of ligand-conjugated oligonucleotides by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the present invention via reaction of a selected serum-binding ligand with a linking moiety located on the 5' position of a nucleoside or oligonucleotide. In certain instances, an oligonucleotide bearing an aralkyl ligand attached to the 3'-terminus of the oligonucleotide is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No.

5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl, or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the present invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis,* 3rd *International Symposium,* 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. J. *Am. Chem. Soc.* 2003,125, 2380.

In certain instances, the ribose sugar moiety that naturally occurs in nucleosides is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. In a preferred embodiment, the hexose is a D-hexose. In a preferred embodiment, the hexose sugar is glucose or mannose. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane. In certain instances, the sugar moiety is represented by A' or A", and the definition of $A^2$, Y, $R^5$, and x is consistent with that described below for the oligonucleotide of formula II.

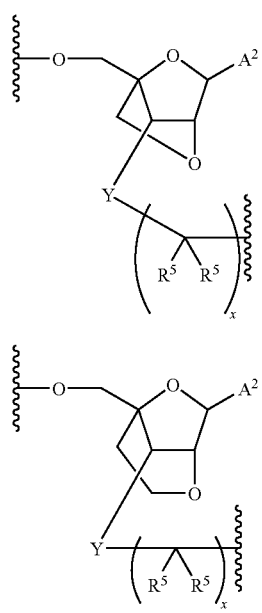

In certain instances, the sugar moiety is replaced with a non-natural sugar selected from the group consisting of

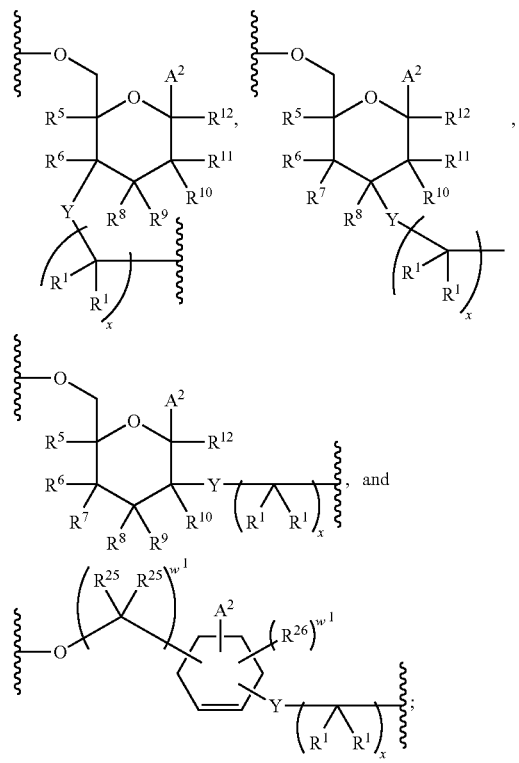

wherein $R^1$ represents independently for each occurrence H, alkyl, or halogen;

$R^5$ represents independently for each occurrence H, or an instance of $R^5$ and $R^{12}$ taken together form a 4-, 5-, 6-, 7-, or 8-membered ring; or an instance of $R^5$ and $R^6$ taken together form a bond;

$R^6$ represents independently for each occurrence H, OH, F, —Oalkyl, —Oallyl, or —Oalkylamine; or an instance of $R^5$ and $R^6$ taken together form a bond; or an instance of $R^6$ and $R^8$ taken together form a bond;

$R^7$, $R^9$, and $R^{11}$ represent independently for each occurrence H, F, —Oalkyl, —Oallyl, or —Oalkylamine;

$R^8$ represents independently for each occurrence H, OH, F, —Oalkyl, —Oallyl, or —Oalkylamine; or an instance of $R^6$ and $R^8$ taken together form a bond; or an instance of $R^8$ and $R^{10}$ taken together form a bond;

$R^{10}$ represents independently for each occurrence H, OH, F, —Oalkyl, —Oallyl, or —Oalkylamine; or an instance of $R^8$ and $R^{10}$ taken together form a bond; or an instance of $R^{10}$ and $R^{12}$ taken together form a bond;

$R^{12}$ represents independently for each occurrence for each occurrence H, or an instance of $R^5$ and $R^{12}$ taken together form a 4-, 5-, 6-, 7-, or 8-membered ring; or an instance of $R^{10}$ and $R^{12}$ taken together form a bond;

$R^{25}$ represents independently for each occurrence H, halogen, alkoxyl, alkyl, aryl, or aralkyl;

$R^{26}$ represents independently for each occurrence H, halogen, amino, hydroxyl, alkoxyl, alkyl, alkylamino, aryl, aralkyl, —C(O)$R^{27}$, —CO$_2R^{27}$, —OC(O)$R^{27}$, —N($R^{27}$)CO$R^{27}$, or —N($R^{27}$)CO$_2R^{27}$;

$R^{27}$ represents independently for each occurrence H, alkyl, aryl, or aralkyl;

$w^1$ represents independently for each occurrence 0, 1, 2, 3, 4, 5, or 6;

x represents independently for each occurrence 0, 1, 2, or 3; and the definition Y and $A^2$ is the same as presented below for oligonucleotide of formula II.

Therapeutic Uses for Compounds of the Invention

In a preferred embodiment of the present invention, the non-phosphate linkage enhances the pharmacokinetic properties of the oligonucleotide therapeutic or diagnostic agent. Such improved pharmacokinetic properties include increased binding of the antisense compound to serum proteins, increased plasma concentration of the antisense compound, increased tissue distribution, increased capacity of binding of the antisense compound to serum proteins, and increased half-lives.

The present invention provides a method for increasing the concentration of an oligonucleotide in serum. According to such methods, an oligonucleotide comprising a non-phosphate linkage is synthesized and then added to the serum.

The present invention further provides methods for increasing the capacity of serum for an oligonucleotide. According to such methods, an oligonucleotide comprising a non-phosphate linkage is synthesized and then added to the serum.

The present invention also provides methods for increasing the binding of an oligonucleotide to a portion of the vascular system. According to such methods, a vascular protein is selected which resides, in part, in the circulating serum and, in part, in the non-circulating portion of the vascular system. Then, an oligonucleotide comprising a non-phosphate linkage is synthesized, which is then added to the vascular system. In certain instances, the oligonucleotide may be conjugated to a ligand to increase the binding of the oligonucleotide to a portion of the vascular system.

The present invention further provides methods for promoting the cellular uptake of an oligonucleotide in a cell. According to such methods, a cellular protein is selected. This cellular protein is a protein that resides on the cellular membrane and extends, in part, extracellularly so that part of this cellular protein extends onto the external side of the cellular membrane. Next, an oligonucleotide comprising a non-phosphate linkage is synthesized and is then brought into contact with cells in which cellular uptake of the oligonucleotide is to be promoted.

The present invention also provides methods of increasing cellular uptake of an oligonucleotide comprising contacting an organism with an oligonucleotide of the invention, said oligonucleotide comprising a non-phosphate linkage.

In one preferred embodiment of the invention the protein targeted by the oligonucleotide is a serum protein. It is preferred that the serum protein targeted by the oligonucleotide compound is an immunoglobulin (an antibody). Preferred immunoglobulins are immunoglobulin G and immunoglobulin M. Immunoglobulins are known to appear in blood serum and tissues of vertebrate animals.

In another embodiment of the invention the serum protein targeted by the oligonucleotide is a lipoprotein. Lipoproteins are blood proteins having molecular weights generally above 20,000 that carry lipids and are recognized by specific cell-surface receptors. The association with lipoproteins in the serum will initially increase pharmacokinetic parameters such as half-life and distribution. A secondary consideration is the ability of lipoproteins to enhance cellular uptake via receptor-mediated endocytosis.

In yet another embodiment the serum protein targeted by the oligonucleotide compound is α-2-macroglobulin. In yet a further embodiment the serum protein targeted by an oligonucleotide compound is α-1-glycoprotein.

Genes and Diseases

One aspect of the invention relates to a method of treating a subject at risk for or afflicted with unwanted cell proliferation, e.g., malignant or nonmalignant cell proliferation. The method comprises providing an oligonucleotide agent comprising a non-phosphate linkage, wherein the oligonucleotide is homologous to and can silence, e.g., by cleavage, a gene which promotes unwanted cell proliferation; and administering a therapeutically effective dose of the oligonucleotide agent to a subject, preferably a human subject.

In a preferred embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In a preferred embodiment the oligonucleotide agent silences the PDGF beta gene, and thus can be used to treat a subject having or at risk for a disorder characterized by unwanted PDGF beta expression, e.g., testicular and lung cancers.

In another preferred embodiment the oligonucleotide agent silences the Erb-B gene, and thus can be used to treat a subject having or at risk for a disorder characterized by unwanted Erb-B expression, e.g., breast cancer.

In a preferred embodiment the oligonucleotide agent silences the Src gene, and thus can be used to treat a subject having or at risk for a disorder characterized by unwanted Src expression, e.g., colon cancers.

In a preferred embodiment the oligonucleotide agent silences the CRK gene, and thus can be used to treat a subject having or at risk for a disorder characterized by unwanted CRK expression, e.g., colon and lung cancers.

In a preferred embodiment the oligonucleotide agent silences the GRB2 gene, and thus can be used to treat a subject having or at risk for a disorder characterized by unwanted GRB2 expression, e.g., squamous cell carcinoma.

In another preferred embodiment the oligonucleotide agent silences the RAS gene, and thus can be used to treat a subject having or at risk for a disorder characterized by unwanted RAS expression, e.g., pancreatic, colon and lung cancers, and chronic leukemia.

In another preferred embodiment the oligonucleotide agent silences the MEKK gene, and thus can be used to treat a subject having or at risk for a disorder characterized by unwanted MEKK expression, e.g., squamous cell carcinoma, melanoma or leukemia.

In another preferred embodiment the oligonucleotide agent silences the JNK gene, and thus can be used to treat a subject having or at risk for a disorder characterized by unwanted JNK expression, e.g., pancreatic or breast cancers.

In a preferred embodiment the oligonucleotide agent silences the RAF gene, and thus can be used to treat a subject having or at risk for a disorder characterized by unwanted RAF expression, e.g., lung cancer or leukemia.

In a preferred embodiment the oligonucleotide agent silences the Erk1/2 gene, and thus can be used to treat a subject having or at risk for a disorder characterized by unwanted Erk1/2 expression, e.g., lung cancer.

In another preferred embodiment the oligonucleotide agent silences the PCNA(p21) gene, and thus can be used to treat a subject having or at risk for a disorder characterized by unwanted PCNA expression, e.g., lung cancer.

In a preferred embodiment the oligonucleotide agent silences the MYB gene, and thus can be used to treat a subject having or at risk for a disorder characterized by unwanted MYB expression, e.g., colon cancer or chronic myelogenous leukemia.

In a preferred embodiment the oligonucleotide agent silences the c-MYC gene, and thus can be used to treat a subject having or at risk for a disorder characterized by unwanted c-MYC expression, e.g., Burkitt's lymphoma or neuroblastoma.

In another preferred embodiment the oligonucleotide agent silences the JUN gene, and thus can be used to treat a subject having or at risk for a disorder characterized by unwanted JUN expression, e.g., ovarian, prostate or breast cancers.

In another preferred embodiment the oligonucleotide agent silences the FOS gene, and thus can be used to treat a subject having or at risk for a disorder characterized by unwanted FOS expression, e.g., skin or prostate cancers.

In a preferred embodiment the oligonucleotide agent silences the BCL-2 gene, and thus can be used to treat a subject having or at risk for a disorder characterized by unwanted BCL-2 expression, e.g., lung or prostate cancers or Non-Hodgkin lymphoma.

In a preferred embodiment the oligonucleotide agent silences the Cyclin D gene, and thus can be used to treat a subject having or at risk for a disorder characterized by unwanted Cyclin D expression, e.g., esophageal and colon cancers.

In a preferred embodiment the oligonucleotide agent silences the VEGF gene, and thus can be used to treat a subject having or at risk for a disorder characterized by unwanted VEGF expression, e.g., esophageal and colon cancers.

In a preferred embodiment the oligonucleotide agent silences the EGFR gene, and thus can be used to treat a subject having or at risk for a disorder characterized by unwanted EGFR expression, e.g., breast cancer.

In another preferred embodiment the oligonucleotide agent silences the Cyclin A gene, and thus can be used to treat a subject having or at risk for a disorder characterized by unwanted Cyclin A expression, e.g., lung and cervical cancers.

In another preferred embodiment the oligonucleotide agent silences the Cyclin E gene, and thus can be used to treat a subject having or at risk for a disorder characterized by unwanted Cyclin E expression, e.g., lung and breast cancers.

In another preferred embodiment the oligonucleotide agent silences the WNT-1 gene, and thus can be used to treat a subject having or at risk for a disorder characterized by unwanted WNT-1 expression, e.g., basal cell carcinoma.

In another preferred embodiment the oligonucleotide agent silences the beta-catenin gene, and thus can be used to treat a subject having or at risk for a disorder characterized by unwanted beta-catenin expression, e.g., adenocarcinoma or hepatocellular carcinoma.

In another preferred embodiment the oligonucleotide agent silences the c-MET gene, and thus can be used to treat a subject having or at risk for a disorder characterized by unwanted c-MET expression, e.g., hepatocellular carcinoma.

In another preferred embodiment the oligonucleotide agent silences the PKC gene, and thus can be used to treat a subject having or at risk for a disorder characterized by unwanted PKC expression, e.g., breast cancer.

In a preferred embodiment the oligonucleotide agent silences the NFKB gene, and thus can be used to treat a subject having or at risk for a disorder characterized by unwanted NFKB expression, e.g., breast cancer.

In a preferred embodiment the oligonucleotide agent silences the STAT3 gene, and thus can be used to treat a subject having or at risk for a disorder characterized by unwanted STAT3 expression, e.g., prostate cancer.

In another preferred embodiment the oligonucleotide agent silences the survivin gene, and thus can be used to treat a subject having or at risk for a disorder characterized by unwanted survivin expression, e.g., cervical or pancreatic cancers.

In another preferred embodiment the oligonucleotide agent silences the Her2/Neu gene, and thus can be used to treat a subject having or at risk for a disorder characterized by unwanted Her2/Neu expression, e.g., breast cancer.

In another preferred embodiment the oligonucleotide agent silences the topoisomerase I gene, and thus can be used to treat a subject having or at risk for a disorder characterized by unwanted topoisomerase I expression, e.g., ovarian and colon cancers.

In a preferred embodiment the oligonucleotide agent silences the topoisomerase II alpha gene, and thus can be used to treat a subject having or at risk for a disorder characterized by unwanted topoisomerase II expression, e.g., breast and colon cancers.

In a preferred embodiment the oligonucleotide agent silences mutations in the p73 gene, and thus can be used to treat a subject having or at risk for a disorder characterized by unwanted p73 expression, e.g., colorectal adenocarcinoma.

In a preferred embodiment the oligonucleotide agent silences mutations in the p21(WAF1/CIP1) gene, and thus can be used to treat a subject having or at risk for a disorder characterized by unwanted p21(WAF1/CIP1) expression, e.g., liver cancer.

In a preferred embodiment the oligonucleotide agent silences mutations in the p27(KIP1) gene, and thus can be used to treat a subject having or at risk for a disorder characterized by unwanted p27(KIP1) expression, e.g., liver cancer.

In a preferred embodiment the oligonucleotide agent silences mutations in the PPM1D gene, and thus can be used to treat a subject having or at risk for a disorder characterized by unwanted PPM1D expression, e.g., breast cancer.

In a preferred embodiment the oligonucleotide agent silences mutations in the RAS gene, and thus can be used to treat a subject having or at risk for a disorder characterized by unwanted RAS expression, e.g., breast cancer.

In another preferred embodiment the oligonucleotide agent silences mutations in the caveolin I gene, and thus can be used to treat a subject having or at risk for a disorder characterized by unwanted caveolin I expression, e.g., esophageal squamous cell carcinoma.

In another preferred embodiment the oligonucleotide agent silences mutations in the MIB I gene, and thus can be used to treat a subject having or at risk for a disorder characterized by unwanted MIB I expression, e.g., male breast carcinoma (MBC).

In another preferred embodiment the oligonucleotide agent silences mutations in the MTAI gene, and thus can be used to treat a subject having or at risk for a disorder characterized by unwanted MTAI expression, e.g., ovarian carcinoma.

In another preferred embodiment the oligonucleotide agent silences mutations in the M68 gene, and thus can be used to treat a subject having or at risk for a disorder characterized by unwanted M68 expression, e.g., human adenocarcinomas of the esophagus, stomach, colon, and rectum.

In preferred embodiments the oligonucleotide agent silences mutations in tumor suppressor genes, and thus can be used as a method to promote apoptotic activity in combination with chemotherapeutics.

In a preferred embodiment the oligonucleotide agent silences mutations in the p53 tumor suppressor gene, and thus can be used to treat a subject having or at risk for a disorder characterized by unwanted p53 expression, e.g., gall bladder, pancreatic and lung cancers.

In a preferred embodiment the oligonucleotide agent silences mutations in the p53 family member DN-p63, and thus can be used to treat a subject having or at risk for a disorder characterized by unwanted DN-p63 expression, e.g., squamous cell carcinoma In a preferred embodiment the oligonucleotide agent silences mutations in the pRb tumor suppressor gene, and thus can be used to treat a subject having or at risk for a disorder characterized by unwanted pRb expression, e.g., oral squamous cell carcinoma In a preferred embodiment the oligonucleotide agent silences mutations in the APC1 tumor suppressor gene, and thus can be used to treat a subject having or at risk for a disorder characterized by unwanted APC1 expression, e.g., colon cancer.

In a preferred embodiment the oligonucleotide agent silences mutations in the BRCA1 tumor suppressor gene, and thus can be used to treat a subject having or at risk for a disorder characterized by unwanted BRCA1 expression, e.g., breast cancer.

In a preferred embodiment the oligonucleotide agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In a preferred embodiment the oligonucleotide agent silences mLL fusion genes, e.g., mLL-AF9, and thus can be used to treat a subject having or at risk for a disorder characterized by unwanted mLL fusion gene expression, e.g., acute leukemias.

In another preferred embodiment the oligonucleotide agent silences the BCR/ABL fusion gene, and thus can be used to treat a subject having or at risk for a disorder characterized by unwanted BCR/ABL fusion gene expression, e.g., acute and chronic leukemias.

In another preferred embodiment the oligonucleotide agent silences the TEL/AML1 fusion gene, and thus can be used to treat a subject having or at risk for a disorder characterized by unwanted TEL/AML1 fusion gene expression, e.g., childhood acute leukemia.

In another preferred embodiment the oligonucleotide agent silences the EWS/FLI1 fusion gene, and thus can be used to treat a subject having or at risk for a disorder characterized by unwanted EWS/FLI1 fusion gene expression, e.g., Ewing Sarcoma.

In another preferred embodiment the oligonucleotide agent silences the TLS/FUS1 fusion gene, and thus can be used to treat a subject having or at risk for a disorder characterized by unwanted TLS/FUS1 fusion gene expression, e.g., Myxoid liposarcoma.

In another preferred embodiment the oligonucleotide agent silences the PAX3/FKHR fusion gene, and thus can be used to treat a subject having or at risk for a disorder characterized by unwanted PAX3/FKHR fusion gene expression, e.g., Myxoid liposarcoma.

In another preferred embodiment the oligonucleotide agent silences the AML1/ETO fusion gene, and thus can be used to treat a subject having or at risk for a disorder characterized by unwanted AML1/ETO fusion gene expression, e.g., acute leukemia.

Another aspect of the invention relates to a method of treating a subject, e.g., a human, at risk for or afflicted with a disease or disorder that may benefit by angiogenesis inhibition e.g., cancer. The method comprises providing an oligonucleotide agent comprising a non-phosphate linkage, wherein said oligonucleotide agent is homologous to and can silence, e.g., by cleavage, a gene which mediates angiogenesis; and administering a therapeutically effective dosage of said oligonucleotide agent to a subject, preferrably a human.

In a preferred embodiment the oligonucleotide agent silences the alpha v-integrin gene, and thus can be used to treat a subject having or at risk for a disorder characterized by unwanted alpha V integrin, e.g., brain tumors or tumors of epithelial origin.

In a preferred embodiment the oligonucleotide agent silences the Flt-1 receptor gene, and thus can be used to treat a subject having or at risk for a disorder characterized by unwanted Flt-1 receptors, eg. cancer and rheumatoid arthritis.

In a preferred embodiment the oligonucleotide agent silences the tubulin gene, and thus can be used to treat a subject having or at risk for a disorder characterized by unwanted tubulin, eg. cancer and retinal neovascularization.

In a preferred embodiment the oligonucleotide agent silences the tubulin gene, and thus can be used to treat a subject having or at risk for a disorder characterized by unwanted tubulin, eg. cancer and retinal neovascularization.

Another aspect of the invention relates to a method of treating a subject infected with a virus or at risk for or afflicted with a disorder or disease associated with a viral infection. The method comprises providing an oligonucleotide agent comprising a non-phosphate linkage, wherein said oligonucleotide agent is homologous to and can silence, e.g., by cleavage, a viral gene of a cellular gene which mediates viral function, e.g., entry or growth; and administering a therapeutically effective dose of said oligonucleotide agent to a subject, preferably a human subject.

Thus, the invention provides for a method of treating patients infected by the Human Papilloma Virus (HPV) or at risk for or afflicted with a disorder mediated by HPV, e.g, cervical cancer. HPV is linked to 95% of cervical carcinomas and thus an antiviral therapy is an attractive method to treat these cancers and other symptoms of viral infection.

In a preferred embodiment, the expression of a HPV gene is reduced. In another preferred embodiment, the HPV gene is one of the group of E2, E6, or E7.

In a preferred embodiment the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In a preferred embodiment, the expression of a HIV gene is reduced. In another preferred embodiment, the HIV gene is CCR5, Gag, or Rev. In a preferred embodiment the expression of a human gene that is required for HIV replication is reduced. In another preferred embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In a preferred embodiment, the expression of a HBV gene is reduced. In another preferred embodiment, the targeted HBV gene encodes one of the group of the tail region of the HBV core protein, the pre-cregious (pre-c) region, or the cregious (c) region. In another preferred embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV. In a preferred embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In a preferred embodiment, the expression of a HCV gene is reduced. In another preferred embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In a preferred embodiment, the expression of a Hepatitis, D, E, F, G, or H gene is reduced. In another preferred embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In a preferred embodiment, the expression of a RSV gene is reduced. In another preferred embodiment, the targeted HBV gene encodes one of the group of genes N, L, or P. In a preferred embodiment the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In a preferred embodiment, the expression of a HSV gene is reduced. In another preferred embodiment, the targeted HSV gene encodes DNA polymerase or the helicase-primase. In a preferred embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In a preferred embodiment, the expression of a CMV gene is reduced. In a preferred embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In a preferred embodiment, the expression of a EBV gene is reduced. In a preferred embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In a preferred embodiment, the expression of a KSHV gene is reduced. In a preferred embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In a preferred embodiment, the expression of a JCV gene is reduced. In preferred embodiment the expression of a human gene that is required for JCV replication is reduced.

Methods of the invention also provide for treating patients infected by the myxovirus or at risk for or afflicted with a disorder mediated by myxovirus, e.g., influenza. In a preferred embodiment, the expression of a myxovirus gene is reduced. In a preferred embodiment the expression of a human gene that is required for myxovirus replication is reduced.

Methods of the invention also provide for treating patients infected by the rhinovirus or at risk for of afflicted with a disorder mediated by rhinovirus, e.g., the common cold. In a preferred embodiment, the expression of a rhinovirus gene is reduced. In preferred embodiment the expression of a human gene that is required for rhinovirus replication is reduced.

Methods of the invention also provide for treating patients infected by the coronavirus or at risk for of afflicted with a disorder mediated by coronavirus, e.g., the common cold. In a preferred embodiment, the expression of a coronavirus gene is reduced. In preferred embodiment the expression of a human gene that is required for coronavirus replication is reduced.

Methods of the invention also provide for treating patients infected by the flavivirus West Nile or at risk for or afflicted with a disorder mediated by West Nile Virus. In a preferred embodiment, the expression of a West Nile Virus gene is reduced. In another preferred embodiment, the West Nile Virus gene is one of the group comprising E, NS3, or NS5. In a preferred embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In a preferred embodiment, the expression of a St. Louis Encephalitis gene is reduced. In a preferred embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In a preferred embodiment, the expression of a Tick-borne encephalitis virus gene is reduced. In a preferred embodiment the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In a preferred embodiment, the expression of a Murray Valley encephalitis virus gene is reduced. In a preferred embodiment the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In a preferred embodiment, the expression of a dengue virus gene is reduced. In a preferred embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In a preferred embodiment, the expression of a SV40 gene is reduced. In a preferred embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In a preferred embodiment, the expression of a HTLV gene is reduced. In another preferred embodiment the HTLV1 gene is the Tax transcriptional activator. In a preferred embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In a preferred embodiment, the expression of a Mo-MuLV gene is reduced. In a preferred embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g. myocarditis. EMCV leads to myocarditis in mice and pigs and is capable of infecting human myocardial cells. This virus is therefore a concern for patients undergoing xenotransplantation. In a preferred embodiment, the expression of a EMCV gene is reduced. In a preferred embodiment the expression of a human gene that is required for EMCV replication is reduced.

The invention also includes a method for treating patients infected by the measles virus (MV) or at risk for or afflicted with a disorder mediated by MV, e.g. measles. In a preferred embodiment, the expression of a MV gene is reduced. In a preferred embodiment the expression of a human gene that is required for MV replication is reduced.

The invention also includes a method for treating patients infected by the Vericella zoster virus (VZV) or at risk for or afflicted with a disorder mediated by VZV, e.g. chicken pox or shingles (also called zoster). In a preferred embodiment, the expression of a VZV gene is reduced. In a preferred embodiment the expression of a human gene that is required for VZV replication is reduced.

The invention also includes a method for treating patients infected by an adenovirus or at risk for or afflicted with a disorder mediated by an adenovirus, e.g. respiratory tract infection. In a preferred embodiment, the expression of an adenovirus gene is reduced. In a preferred embodiment the expression of a human gene that is required for adenovirus replication is reduced.

The invention includes a method for treating patients infected by a yellow fever virus (YFV) or at risk for or afflicted with a disorder mediated by a YFV, e.g. respiratory tract infection. In a preferred embodiment, the expression of a YFV gene is reduced. In another preferred embodiment, the preferred gene is one of a group that includes the E, NS2A, or NS3 genes. In a preferred embodiment the expression of a human gene that is required for YFV replication is reduced.

Methods of the invention also provide for treating patients infected by the poliovirus or at risk for or afflicted with a disorder mediated by poliovirus, e.g., polio. In a preferred embodiment, the expression of a poliovirus gene is reduced. In a preferred embodiment the expression of a human gene that is required for poliovirus replication is reduced.

Methods of the invention also provide for treating patients infected by a poxvirus or at risk for or afflicted with a disorder mediated by a poxvirus, e.g., smallpox. In a preferred embodiment, the expression of a poxvirus gene is reduced. In a preferred embodiment the expression of a human gene that is required for poxvirus replication is reduced.

In another, aspect the invention features methods of treating a subject infected with a pathogen, e.g., a bacterial, amoebic, parasitic, or fungal pathogen. The method comprises providing an oligonucleotide agent comprising a non-phosphate linkage, wherein said oligonucleotide is homologous to and can silence, e.g., by cleavage of a pathogen gene; and administering a therapeutically effective dose of said oligonucleotide agent to a subject, preferably a human subject.

The target gene can be one involved in growth, cell wall synthesis, protein synthesis, transcription, energy metabolism, e.g., the Krebs cycle, or toxin production. Thus, the present invention provides for a method of treating patients infected by a *plasmodium* that causes malaria. In a preferred embodiment, the expression of a *plasmodium* gene is reduced. In another preferred embodiment, the gene is apical membrane antigen 1 (AMA1). In a preferred embodiment the expression of a human gene that is required for *plasmodium* replication is reduced.

The invention also includes methods for treating patients infected by the *Mycobacterium ulcerans*, or a disease or disorder associated with this pathogen, e.g., Buruli ulcers. In a preferred embodiment, the expression of a *Mycobacterium ulcerans* gene is reduced. In a preferred embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g., tuberculosis. In a preferred embodiment, the expression of a *Mycobacterium tuberculosis* gene is reduced. In a preferred embodiment the expression of a human gene that is required for *Mycobacterium tuberculosis* replication is reduced.

The invention also includes methods for treating patients infected by the *Mycobacterium leprae*, or a disease or disorder associated with this pathogen, e.g. leprosy. In a preferred embodiment, the expression of a *Mycobacterium leprae* gene is reduced. In a preferred embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g. infections of the skin and muscous membranes. In a preferred embodiment, the expression of a *Staphylococcus aureus* gene is reduced. In a preferred embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g. pneumonia or childhood lower respiratory tract infection. In a preferred embodiment, the expression of a *Streptococcus pneumoniae* gene is reduced. In a preferred embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g. Strep throat or Scarlet fever. In a preferred embodiment, the expression of a *Streptococcus pyogenes* gene is reduced. In a preferred embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g. pneumonia or childhood lower respiratory tract infection. In a preferred embodiment, the expression of a *Chlamydia pneumoniae* gene is reduced. In a preferred embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g. pneumonia or childhood lower respiratory tract infection. In a preferred embodiment, the expression of a *Mycoplasma pneumoniae* gene is reduced. In a preferred embodiment the expression of a human gene that is required for *Mycoplasma pneumoniae* replication is reduced.

Another aspect of the invention relates to a method of treating a subject, e.g., a human, at risk for or afflicted with a disease or disorder characterized by an unwanted immune response, e.g., an inflammatory disease or disorder, or an autoimmune disease or disorder. The method comprises providing an oligonucleotide agent comprising an a non-phosphate linkage, wherein said oligonucleotide agent is homologous to and can silence, e.g., by cleavage, a gene which mediates an unwanted immune response; and administering said oligonucleotide agent to a subject, preferably a human subject. In a preferred embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplantated organ or tissue, e.g., transplanted cardiac or vascular tissue; or thrombolysis. In a preferred embodiment the disease or disorder is restenosis, e.g., restenosis associated with surgical intervention e.g., angioplasty, e.g., percutaneous transluminal coronary angioplasty. In a preferred embodiment the disease or disorder is Inflammatory Bowel Disease, e.g., Crohn Disease or Ulcerative Colitis. In a preferred embodiment the disease or disorder is inflammation associated with an infection or injury. In a preferred embodiment the disease or disorder is asthma, lupus, multiple sclerosis, diabetes, e.g., type II diabetes, arthritis, e.g., rheumatoid or psoriatic. In particularly preferred embodiments the oligonucleotide agent silences an integrin or co-ligand thereof, e.g., VLA4, VCAM, ICAM. In particularly preferred embodiments the oligonucleotide agent silences a selectin or co-ligand thereof, e.g., P-selectin, E-selectin (ELAM), I-selectin, P-selectin glycoprotein-1 (PSGL-1). In particularly preferred embodiments the oligonucleotide agent silences a component of the complement system, e.g., C3, C5, C3aR, C5aR, C3 convertase, and C5 convertase.

In particularly preferred embodiments the oligonucleotide agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, and CCR3.

In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

Another aspect of the invention features, a method of treating a subject, e.g., a human, at risk for or afflicted with acute pain or chronic pain. The method comprises providing an oligonucleotide agent comprising a non-phosphate linkage, wherein said oligonucleotide is homologous to and can silence, e.g., by cleavage, a gene which mediates the processing of pain; and administering a therapeutically effective dose of said oligonucleotide agent to a subject, preferably a human subject. In particularly preferred embodiments the oligonucleotide agent silences a component of an ion channel. In particularly preferred embodiments the oligonucleotide agent silences a neurotransmitter receptor or ligand.

Another aspect of the invention relates to a method of treating a subject, e.g., a human, at risk for or afflicted with a neurological disease or disorder. The method comprises providing a oligonucleotide agent comprising a non-phosphate linkage, wherein said oligonucleotide is homologous to and can silence, e.g., by cleavage, a gene which mediates a neurological disease or disorder; and administering a therapeutically effective dose of said oligonucleotide agent the to a subject, preferably a human. In a preferred embodiment the disease or disorder is Alzheimer Disease or Parkinson Disease. In particularly preferred embodiments the oligonucleotide agent silences an amyloid-family gene, e.g., APP; a presenilin gene, e.g., PSEN1 and PSEN2, or 1-synuclein. In a preferred embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the oligonucleotide agent silences HD, DRPLA, SCA1, SCA2, MJD1, CACNL1A4, SCA7, or SCA8.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with an oligonucleotide agent of the invention. The oligonucleotide agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH. E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-I subunit, and transferrin receptor.

Accordingly, another aspect of the invention relates to a method of treating a disorder characterized by LOH, e.g., cancer. The method comprises optionally, determining the genotype of the allele of a gene in the region of LOH and preferably determining the genotype of both alleles of the gene in a normal cell; providing an oligonucleotide agent comprising a non-phosphate linkage which preferentially cleaves or silences the allele found in the LOH cells; and administerning a therapeutically effective dose of said oligonucleotide agent to the subject, preferably a human.

The invention also includes an oligonucleotide agent comprising a non-phosphate linkage disclosed herein, e.g, an oligonucleotide agent which can preferentially silence, e.g., cleave, one allele of a polymorphic gene.

In another aspect, the invention provides a method of cleaving or silencing more than one gene with an oligonucleotide agent comprising a non-phosphate linkage. In these embodiments the oligonucleotide agent is selected so that it has sufficient homology to a sequence found in more than one gene. For example, the sequence AAGCTGGCCCTGGACATGGAGAT (SEQ ID NO: 1) is conserved between mouse lamin B1, lamin B2, keratin complex 2-gene 1 and lamin A/C. Thus an oligonucleotide agent targeted to this sequence would effectively silence the entire collection of genes.

The invention also includes an oligonucleotide agent comprising a non-phosphate linkage disclosed herein, which can silence more than one gene.

Compounds of the Invention

One aspect of the present invention relates to 3'-phosphonamidite substituted nucleosides represented by formula I:

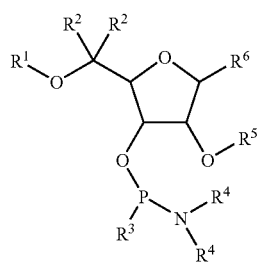

wherein $R^1$ is optionally substituted aralkyl, $-Si(R^7)_3$, $-C(O)R^4$, $-CO_2R^4$, or $-C(O)(NR^8)R^4$;

$R^2$ represents independently for each occurrence H, alkyl, or halogen;

$R^3$, $R^4$, and $R^7$ each represent independently for each occurrence alkyl, aryl, or aralkyl;

$R^5$ is $-Si(R^7)_3$, $-C(O)R^4$, $-CO_2R^4$, or $-C(O)(NR^8)R^4$;

$R^6$ is

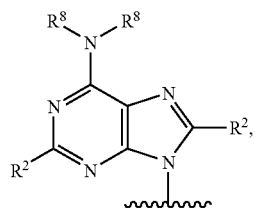

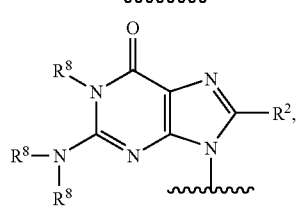

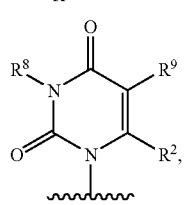 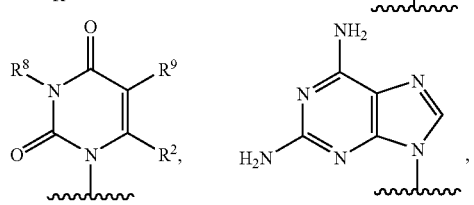

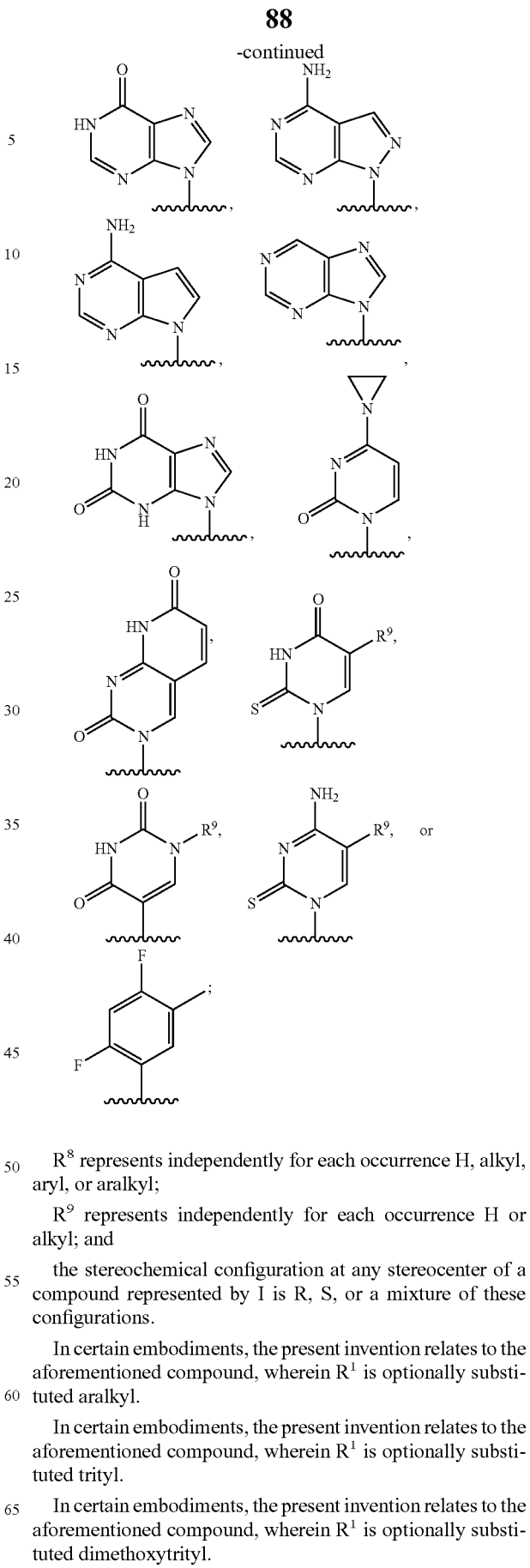

$R^8$ represents independently for each occurrence H, alkyl, aryl, or aralkyl;

$R^9$ represents independently for each occurrence H or alkyl; and the stereochemical configuration at any stereocenter of a compound represented by I is R, S, or a mixture of these configurations.

In certain embodiments, the present invention relates to the aforementioned compound, wherein $R^1$ is optionally substituted aralkyl.

In certain embodiments, the present invention relates to the aforementioned compound, wherein $R^1$ is optionally substituted trityl.

In certain embodiments, the present invention relates to the aforementioned compound, wherein $R^1$ is optionally substituted dimethoxytrityl.

In certain embodiments, the present invention relates to the aforementioned compound, wherein $R^1$ is

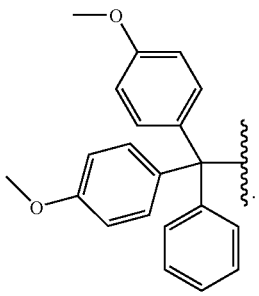

In certain embodiments, the present invention relates to the aforementioned compound, wherein $R^2$ is H.

In certain embodiments, the present invention relates to the aforementioned compound, wherein $R^3$ is alkyl.

In certain embodiments, the present invention relates to the aforementioned compound, wherein $R^3$ is methyl, ethyl, propyl, isopropyl, butyl, sec-butyl, isobutyl, tert-butyl, or pentyl.

In certain embodiments, the present invention relates to the aforementioned compound, wherein $R^3$ is methyl.

In certain embodiments, the present invention relates to the aforementioned compound, wherein $R^4$ is alkyl.

In certain embodiments, the present invention relates to the aforementioned compound, wherein $R^4$ represents independently for each occurrence methyl, ethyl, propyl, isopropyl, butyl, sec-butyl, isobutyl, tert-butyl, or pentyl.

In certain embodiments, the present invention relates to the aforementioned compound, wherein $R^4$ is isopropyl.

In certain embodiments, the present invention relates to the aforementioned compound, wherein $R^5$ is $Si(R^7)_3$.

In certain embodiments, the present invention relates to the aforementioned compound, wherein $R^5$ is $Si(R^7)_3$, and $R^7$ is alkyl.

In certain embodiments, the present invention relates to the aforementioned compound, wherein $R^5$ is $Si(CH_3)_2$-tert-butyl.

In certain embodiments, the present invention relates to the aforementioned compound, wherein $R^6$ is

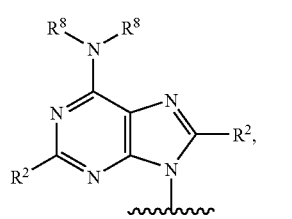

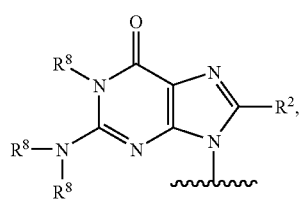

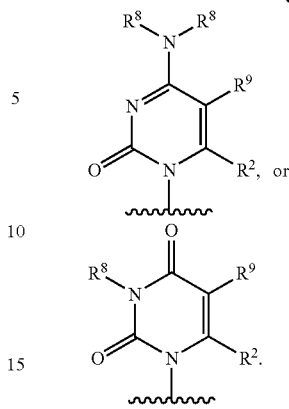

In certain embodiments, the present invention relates to the aforementioned compound, wherein $R^6$ is

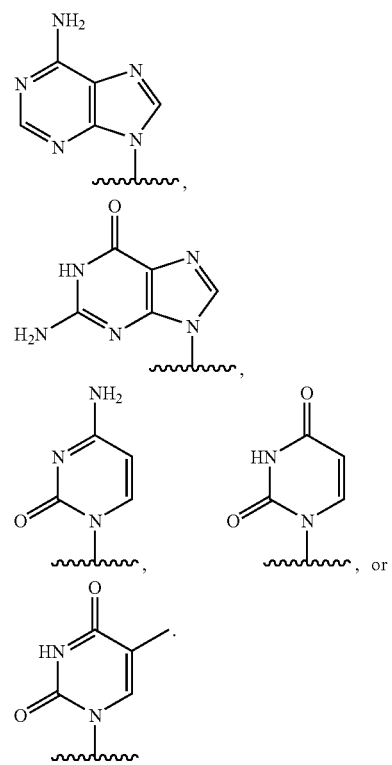

In certain embodiments, the present invention relates to the aforementioned compound, wherein $R^5$ is $Si(R^7)_3$, and $R^3$, $R^4$, and $R^7$ are alkyl.

In certain embodiments, the present invention relates to the aforementioned compound, wherein $R^5$ is $Si(R^7)_3$, and $R^3$, $R^4$, and $R^7$ are alkyl; $R^1$ is optionally substituted dimethoxytrityl; and $R^6$ is

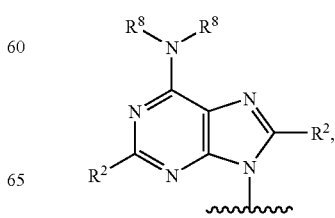

-continued

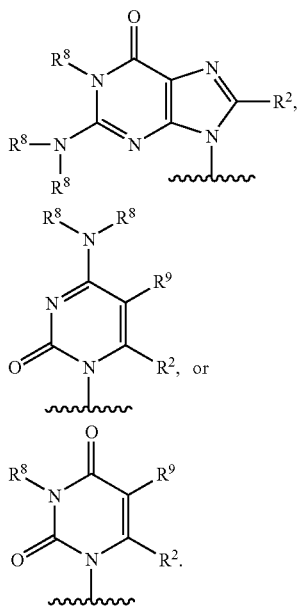

In certain embodiments, the present invention relates to the aforementioned compound, wherein $R^2$ is H, $R^3$ is methyl, $R^4$ is isopropyl, $R^5$ is $Si(CH_3)_2$-tert-butyl, $R^1$ is optionally substituted dimethoxytrityl, and $R^6$ is

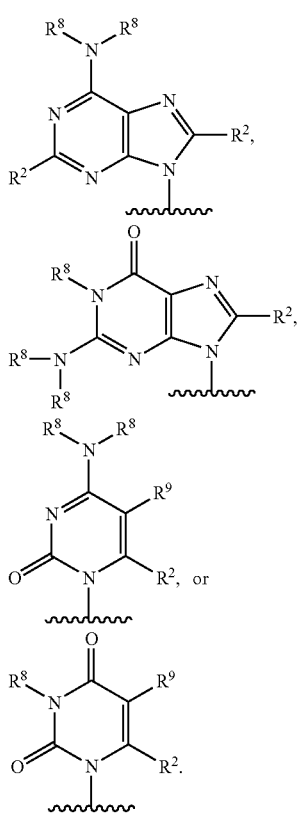

In certain embodiments, the present invention relates to the aforementioned compound, wherein $R^2$ is H, $R^3$ is methyl, $R^4$ is isopropyl, $R^5$ is $Si(CH_3)_2$-tert-butyl, $R^1$ is

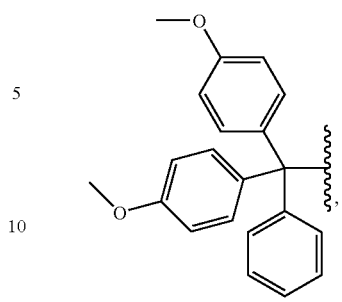

and $R^6$ is

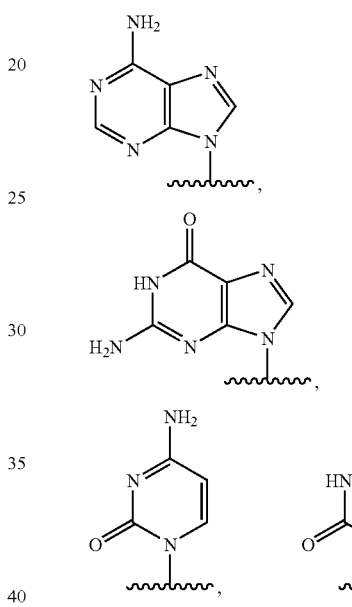

In certain embodiments, the present invention relates to the aforementioned compound, wherein said compound is represented by formula Ia:

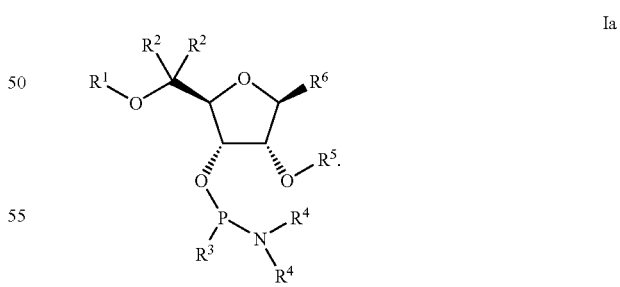

Ia

In certain embodiments, the present invention relates to the aforementioned compound, wherein $R^5$ is $Si(R^7)_3$, and $R^3$, $R^4$, and $R^7$ are alkyl.

In certain embodiments, the present invention relates to the aforementioned compound, wherein $R^5$ is $Si(R^7)_3$, and $R^3$, $R^4$, and $R^7$ are alkyl; $R^1$ is optionally substituted dimethoxytrityl; and $R^6$ is

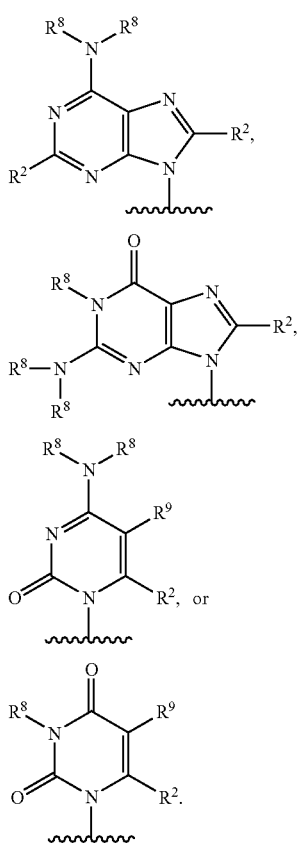

In certain embodiments, the present invention relates to the aforementioned compound, wherein $R^2$ is H, $R^3$ is methyl, $R^4$ is isopropyl, $R^5$ is Si(CH$_3$)$_2$-tert-butyl, $R^1$ is optionally substituted dimethoxytrityl, and $R^6$ is

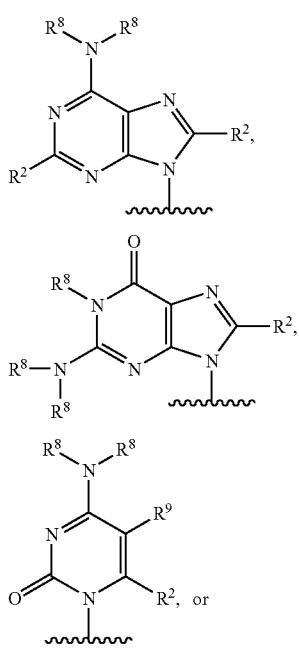

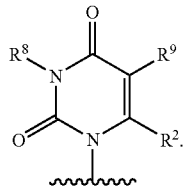

In certain embodiments, the present invention relates to the aforementioned compound, wherein $R^2$ is H, $R^3$ is methyl, $R^4$ is isopropyl, $R^5$ is Si(CH$_3$)$_2$-tert-butyl, $R^1$ is

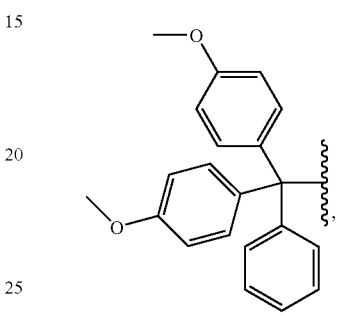

and $R^6$ is

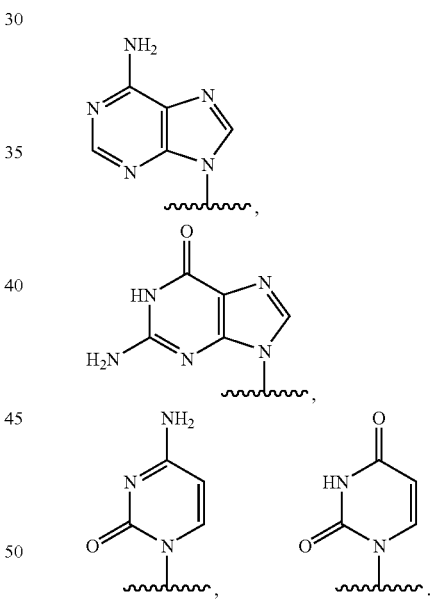

Another aspect of the present invention relates to an oligonucleotide bearing at least one non-phosphate linkage. In certain embodiments, the non-phosphate linkage is a phosphonate. In a preferred embodiment, the phosphonate linkage is an alkyl phosphonate. The phosphonate linkage renders the oligonucleotide less prone to degradation in vivo. In certain instances, the oligonucleotide is substituted with a ligand. In certain instances, the ligand is an aralkyl group. The aralkyl ligand renders the oligonucleotide compound less prone to degradation by nucleases present in the serum, liver, brain, and eye. In certain embodiments, the compounds of the invention relate to a double-stranded oligonucleotide sequence, wherein the aralkyl ligand is bound to only one of the two strands. In certain embodiments, the compounds of the invention relate to a double-stranded oligonucleotide sequence, wherein at least one aralkyl ligand is bound to both of the strands. In certain embodiments, the backbone of the oligonucleotide has been modified to improve the therapeutic or diagnostic properties of the oligonucleotide. In certain embodiments, at least one of the bases or at least one of the sugars of the oligonucleotide has been modified to improve the therapeutic or diagnostic properties of the oligonucleotide. The two strands of the oligonucleotide are complementary or partially complementary. Either strand or both strands may comprise a chimeric oligonucleotide. In certain instances, the oligonucleotide is an siRNA agent.

The siRNA agent includes a region of sufficient homology to the target gene, and is of sufficient length in terms of nucleotides, such that the siRNA agent, or a fragment thereof, can mediate down-regulation of the target gene. It will be understood that the term "ribonucleotide" or "nucleotide" can, in the case of a modified RNA or nucleotide surrogate, also refer to a modified nucleotide, or surrogate replacement moiety at one or more positions. Thus, the siRNA agent is or includes a region which is at least partially complementary to the target RNA. In certain embodiments, the siRNA agent is fully complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In addition, a siRNA agent will often be modified or include nucleoside surrogates. Single stranded regions of an siRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents include: molecules that are long enough to trigger the interferon response (which can be cleaved by Dicer (Bernstein et al., 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter siRNA agent" as used refers to an siRNA agent that is sufficiently short that it does not induce a deleterious interferon response in a human cell, e.g., it has a duplexed region of less than 60 but preferably less than 50, 40, or 30 nucleotide pairs. The siRNA agent, or a cleavage product thereof, can down regulate a target gene, e.g., by inducing RNAi with respect to a target RNA, preferably an endogenous or pathogen target RNA.

Each strand of a siRNA agent can be equal to or less than 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA agent will preferably have one or more of the following properties:

(1) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(2) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide. A preferred siRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. A single strand iRNA agent should be sufficiently long that it can enter the RISC and participate in RISC mediated cleavage of a target mRNA. A single strand iRNA agent is at least 14, and more preferably at least 15, 20, 25, 29, 35, 40, or 50 nucleotides in length. It is preferably less than 200, 100, or 60 nucleotides in length.

Hairpin iRNA agents will have a duplex region equal to or at least 17, 18, 19, 29, 21, 22, 23, 24, or 25 nucleotide pairs. The duplex region will preferably be equal to or less than 200, 100, or 50, in length. Preferred ranges for the duplex region are 15-30, 17 to 23, 19 to 23, and 19 to 21 nucleotides pairs in length. The hairpin will preferably have a single strand overhang or terminal unpaired region, preferably the 3', and preferably of the antisense side of the hairpin. Preferred overhangs are 2-3 nucleotides in length.

Chimeric oligonucleotides, or "chimeras," are oligonucleotides which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used. Chimeric oligonucleotides of the invention may be formed as composite structures of two or more oligonucleotides, modified oligonucleotides, oligonucleosides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

For the purposes of illustration, a nucleotide bearing an ligand can be divided into four regions: ligand, tether, linker, and oligonucleotide. The ligand is bound to the oligonucleotide via a tether and linker. The purpose of the tether is to covalently attach the ligand, or a structural derivative to the linker. The structure of the tether is dictated by the functional group used to bind the ligand. On the other hand, the linker serves to bond covalently the oligonucleotide to the tether. In a preferred embodiment, the linker is amenable to solid-phase synthesis techniques. A more detailed discussion of each of the variable regions presented below.

Ligand

In the present invention, the ligand is an aromatic group, aralkyl group, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring. In certain instances, the ligand is an aralkyl group, e.g., a 2-arylpropanoyl moiety. The structural features of the ligand are selected so that the ligand will bind to at least one protein in vivo. In certain embodiments, the structural features of the ligand are selected so that ligand binds to serum, vascular, or cellular proteins. In certain embodiments, the structural features of the ligand promote binding to albumin, an immunoglobulin, a lipoprotein, α-2-macroglubulin, or α-1-glycoprotein.

A large number of steroids are known in the art and are amenable to the present invention. Representative examples of steroids include cholesterol, 5β-cholanic acid, progesterone, aldosterone, dehydroaldosterone, isoandrosterone, esterone, estradiol, ergosterol, dehydroergosterol, lanosterol, 4-cholesten-3-one, guggulsterone, testosterone, nortestosterone, formestane, hydroxyecdysone, ketoestriol, corticosterone, dienestrol, dihydroxypregnanone, pregnanone, copornmon, equilenin, equilin, estriol, ethinylestradiol, mestranol, moxestrol, mytatrienediol, quinestradiol, quinestrol, helvolic acid, protostadiene, fusidic acid, cycloartenol, tricallol, cucurbitanin cedrelone, euphol, dammerenediol, parkeol, dexametasone, methylprednisolone, prednisolone, hydrocortisone, parametasone, betametasone, cortisone, fluocinonide, fluorometholone, halcinonide, and budesonide, or any one of them further substituted with one or more of hydroxyl, halogen, amino, alkylamino, alkyl, carboxylic acid, ester, amide, carbonyl, alkoxyl, or cyano.

A large number of bile acids are known in the art and are amenable to the present invention. Bile acids occur in conjugation with glycine or taurine in bile of most vertebrates and some of them find use in medicine. Thus, some bile acids—due to their inherent pharmacological properties—are used as cholerectics (see, for example, James E. F. Reynolds (editor) Martindale The Extra Pharmacopoeia, 30$^{th}$ Edition, The Pharmaceutical Press, London (1993), page 1341). Representative examples of bile acids include cholic acid, deoxycholic acid, taurocholic acid, glycocholic acid, glycodeoxycholic acid, taurodeoxycholic acid, ursodeoxycholic acid, and chenodeoxycholic acid. Additional bile acids amenable to the present invention include those described in U.S. Pat. Nos. 5,641,767; 5,656,277; 5,610,151; 5,428,182; and 3,910,888.

A large number of lipids are known in the art and are amenable to the present invention. Representative examples of lipids include lauric acid, myristic acid, palmitic acid, stearic acid, arachidic acid, palmitoleic acid, oleic acid, linoleic acid, linolenic acid, arachidonic acid, triacylglycerols, phosphoacylglycerols, sphingolipids, monoterpenes, sesquiterpenes, diterpenes, sesterterpenes, triterpenes, and tetraterpenes.

A large number of aromatic compounds are known in the art and are amenable to the present invention. Representative examples of aromatic compounds include optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, tetrazolyl, and furanyl.

A large number of carbohydrates are known in the art and are amenable to the present invention. Representative examples of carbohydrates include erythrose, threose, ribose, arabinose, xylose, lyxose, allose, altrose, glucose, mannose, gulose, idose, galactose, and talose; or a disaccharide or trisaccharide formed via a 1,4 glycoside linkage between any of them. In certain instances, the carbohydrate is a hexose or pentose.

A large number of polycyclic compounds are known in the art and are amenable to the present invention. Representative classes of polycyclic compounds include bicyclic compounds wherein, the first and second ring are independently a 3, 4, 5, or 6-member saturated or unsaturated carbon ring containing 0, 1, 2, or 3 hetereoatoms selected from the group consisting of O, N, or S. In certain instances, the first ring is an aromatic ring. In certain instances, the second ring is an aromatic ring. In certain instances, both rings are saturated. In certain instances, the first ring contains no heteroatoms. In certain instances, the second ring contains to heteroatoms. In certain instances, the first ring contains a nitrogen atom. In certain instances, the second ring contains a nitrogen atom. In certain instances, the polycyclic compound is a tricyclic compound, wherein the first, second, and third ring are independently a 3, 4, 5, or 6-member saturated or unsaturated carbon ring containing 0, 1, 2, or 3 hetereoatoms selected from the group consisting of O, N, or S. In certain instances, the first ring is an aromatic ring. In certain instances, the second ring is an aromatic ring. In certain instances, the third ring is an aromatic ring. In certain instances, all three rings are saturated. In certain instances, the first ring contains no heteroatoms. In certain instances, the second ring contains to heteroatoms. In certain instances, the third ring contains to heteroatoms. In certain instances, the first ring contains a nitrogen atom. In certain instances, the second ring contains a nitrogen atom. In certain instances, the third ring contains a nitrogen atom. In certain instances, the polycyclic compound is a bridged polycyclic compound. In certain instances, the polycyclic compound is a bicyclo[2.2.1]heptane, bicyclo[2.2.2]octane, bicyclo[3.2.1]octane, bicyclo[3.2.2]nonane, or bicyclo[3.3.1]nonane.

A large number of crown ethers are known in the art and are amenable to the present invention. Crown ethers are macrocyclic, polyether, neutral compounds containing 4-20 oxygen atoms each separated from the next by two or more carbon atoms. Macrocyclic polyethers have been found to form stable complexes with salts of alkali metals and other metals and ammonium salts; "Macrocyclic polyethers and their complexes", C. J. Pederson et al, Angew. Chem. Intern. Ed., Vol. 11, page 16, (1972) and U.S. Pat. Nos. 3,562,295 and 3,687,978. Since the stereo models of macrocyclic polyethers give a crown-like appearance, they are commonly designated as N-crown-M polyethers, wherein N is the total number of atoms in the polyether ring and M is the number of oxygen atoms in the polyether ring. Crown polyethers ranging in size from cyclic tetramers of ethylene oxide ([1,2]-crown-4) and propylene oxide ([1,6]-crown-4) to 60-membered polyether rings (dibenzo[60]-crown-20) have been reported. Preferred crown ethers include 12-crown-4, 15-crown-5, and 18-crown-6.

A large number of oligonucleotide intercalators are known in the art and are amenable to the present invention. One class of intercalators are DNA intercalators which bind noncovalently to duplex DNA and are characterized by a flat molecule which inserts between base pairs of the double helix of DNA. Representative examples of intercalators include p-carboxy methidium, p-carboxy ethidium, acridine and ellipticine.

A large number of oligonucleotide cleaver molecules are known in the art and are amenable to the present invention. A cleaver molecule is a compound that can sever an oligonucleotide strand. Bleomycin, a glycopeptide antibiotic, is known to bind to and cleave DNA in a reaction that depends on the presence of ferrous ion and molecular oxygen, "Bleomycin: Chemical, Biochemical and Biological Aspects"; Hecht, S. M., Ed.; Springer Verlag: New York, 1979; Sausville, E. A.; Peisach, J.; Horwitz, S. B. "Biochemistry" 1978, 17, 2740. Burger, R. M.; Peisach, J; Horwitz, S. B. "Life Sciences" 1981, 28, 715; and Lown, J. W.; Sim, S. F. "Biochem. Biophys. Res. Comm." 1977, 77, 1150. The antitumor agent streptonigrin is also capable of causing single strand breaks in DNA using oxygen and cuprous ion, Cone, R; Hasan, S. K.; Lown, J. W.; Morgan, A. R. "Can. J. Biochem." 1976, 54, 219. Recently, the 1-10 phenanthroline-cuprous complex has been shown to cleave DNA in the presence of oxygen, Sigman, D. S.; Graham, D. R.; D'Aurora, V.; Stern, A. M. "J. Biol. Chem." 1979, 254, 12269; Graham, D. R.; Marshall, L. E.; Reich, K. A.; Sigman, D. S. "J. Amer. Chem. Soc." 1980, 102, 5419; Marshall, L. E.; Graham, D. R.; Reich, K. A.; Sigman, D. S. "Biochemistry" 1981, 20, 244; and Que, B. G.; Downey, K. M.; So., A. G. "Biochemistry" 1980, 19, 5987. In addition, methidium, ethidium, and cisplatin are known to cleave oligonucleotide sequences.

A large number of saturated 5-membered rings are known in the art and are amenable to the present invention. Preferred saturated 5-membered rings are optionally substituted cyclopentane, pyrrolidine, tetrahydrofuran, tetrahydrothiophene, and 1,1-difluorocyclopentane.

Figure 10:
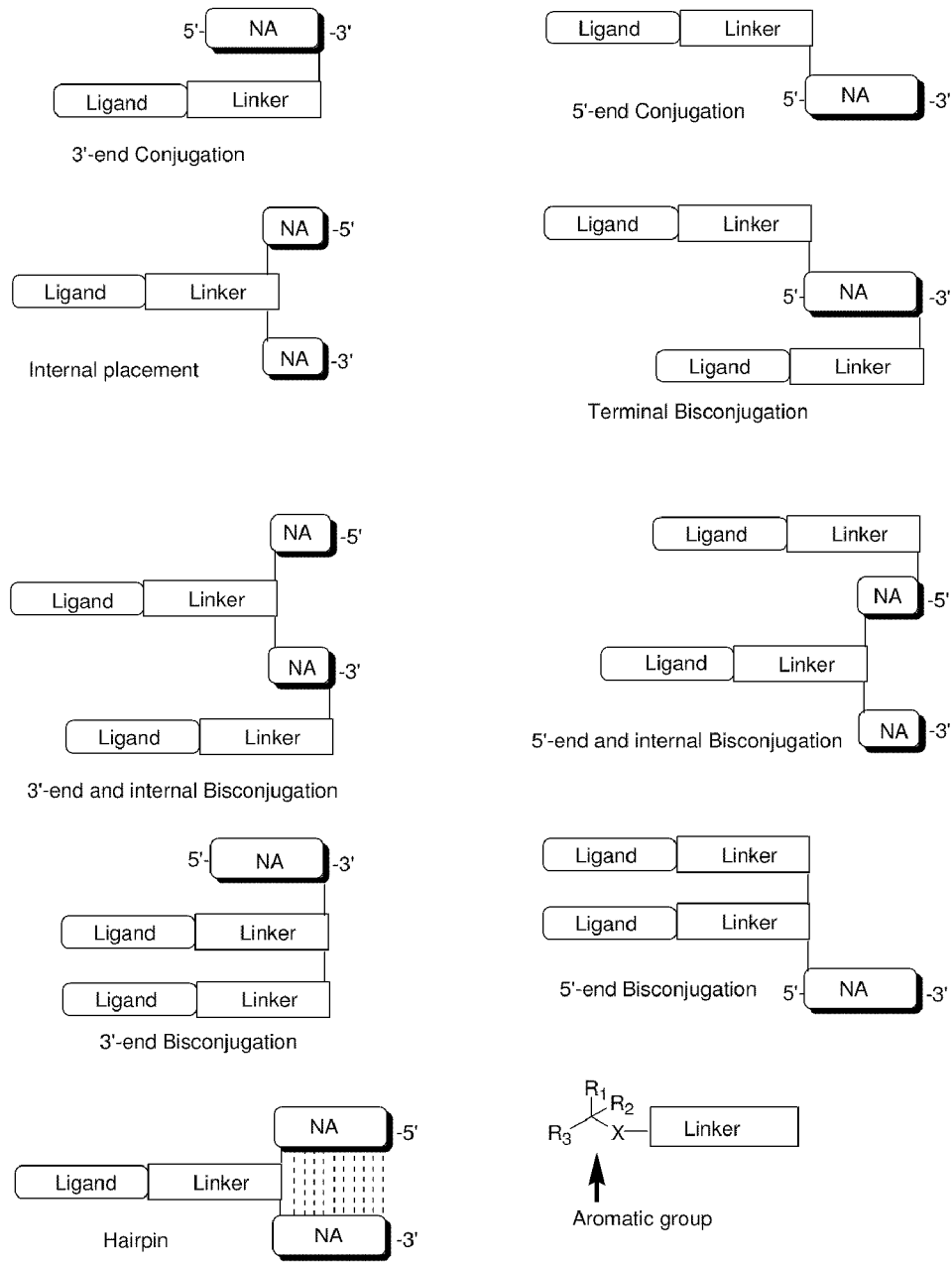
FIG. 10 depicts various oligonucleotides that are conjugated to a ligand. NA is an oligonucleotide (or a nucleic acid) comprising of RNA or DNA or chimeric RNA-DNA, DNA-RNA, RNA-DNA-RNA or DNA-RNA-DNA. In certain instances, at least one among $R_1$, $R_2$ and $R_3$ is aromatic or substituted aromatic, when $R_1$ is aromatic or substituted aromatic, $R_2$ is either H or any organic substituent and $R_3$ is either H or any organic substituent.
Figure 11:
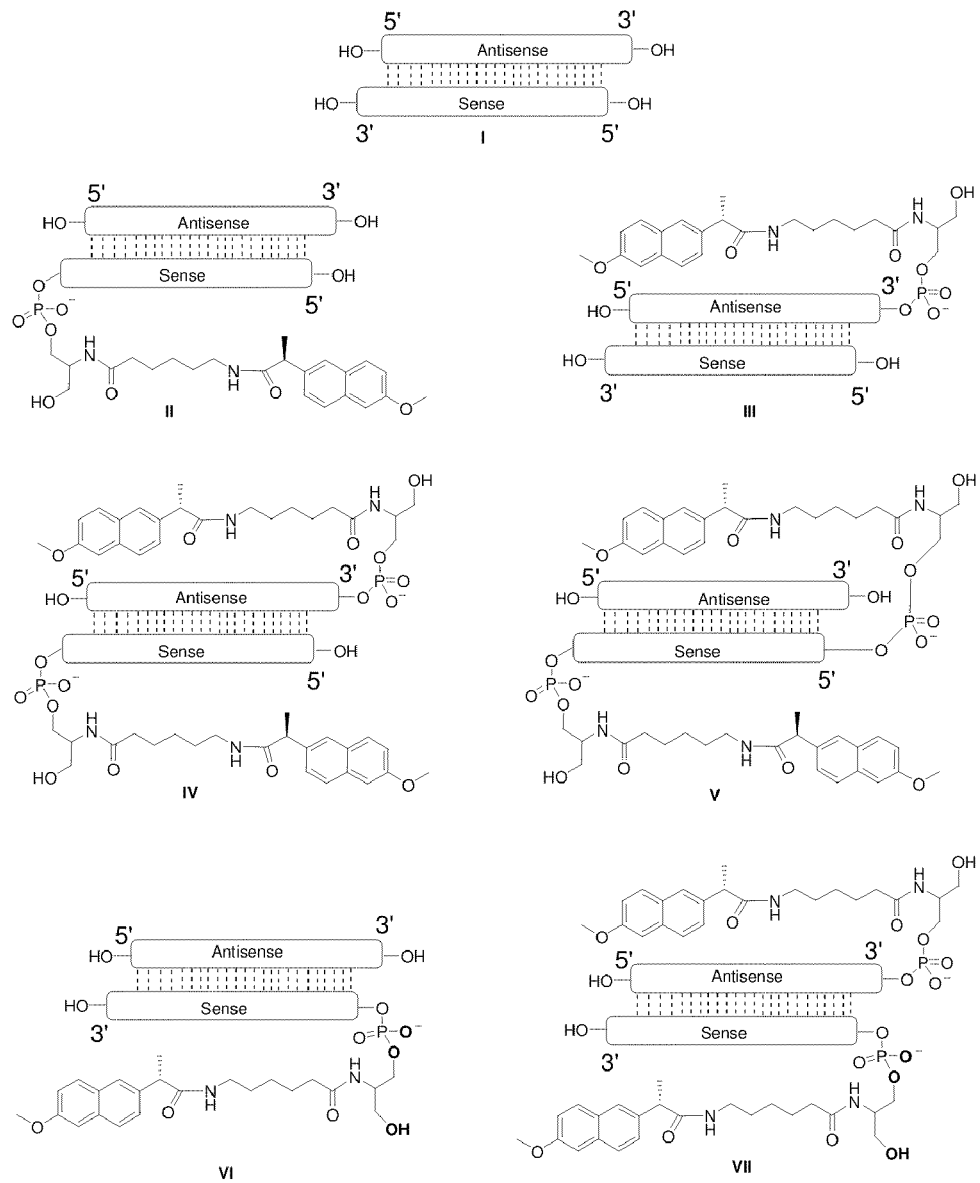
FIG. 11 depicts various siRNA duplexes conjugated with naproxen. I: Unmodified siRNA with overhang at the 3'-end of each strand. II: siRNA duplex with naproxen conjugation at the 3'-end of sense strand. III: siRNA duplex with naproxen conjugation at the 3'-end of antisense strand. IV: siRNA duplex with naproxen conjugation at the 3'-end of sense and antisense strands. V: siRNA with naproxen conjugation at the 3' and 5'-ends of sense strand. VI: siRNA duplex with naproxen conjugation at the 5'-end of sense strand. VII: siRNA duplex with naproxen conjugation at the 5'-end of sense and 3'-end antisense strands.
Figure 12:
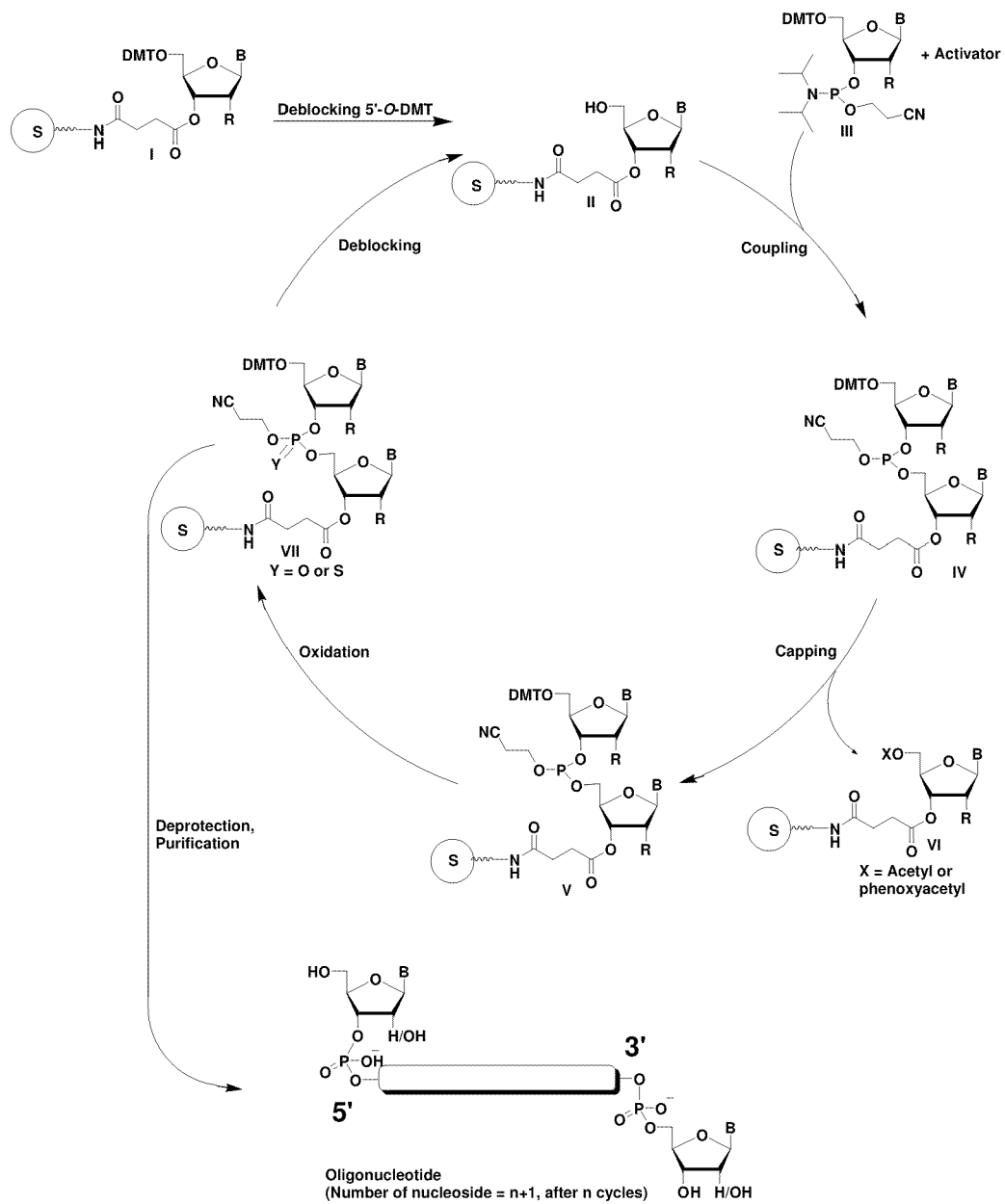
FIG. 12 depicts a procedure for solid-phase oligonucleotide synthesis.

In certain instances, the oligonucleotides of the invention contain at least one nucleoside that is bound to a ligand. In certain instances, there are 3, 4, 5, 10, or 15 nucleotides that are individually covalently bonded to separate ligands. In certain instances, the ligand is bonded to the 5'-position or the 3'-position of the terminal nucleoside. In certain instances, an aralkyl ligand is bonded to both the 5'-position and the 3'-position of the terminal nucleoside. In certain instances, a ligand is bonded to both the 3'-position of the nucleoside located at the 3'-terminus of the oligonucleotide. In certain instances, the linker forms a covalent linkage between two nucleosides and the linker is also bonded to the ligand via a tether. In certain instances, a hairpin structure is formed when the linker forms a covalent linkage between two nucleosides and the linker is also bonded to the ligand via a tether. In certain instances, more than one ligand is bonded to the tether. FIGS. 1 and 10 illustrate several ways in which the ligand is attached to the oligonucleotide.

In certain embodiments, the ligand is naproxen or a structural derivative of naproxen. Procedures for the synthesis of naproxen can be found in U.S. Pat. No. 3,904,682 and U.S. Pat. No. 4,009,197. Naproxen has the chemical name (S)-6-Methoxy-α-methyl-2-naphthaleneacetic acid and the structure is shown below.

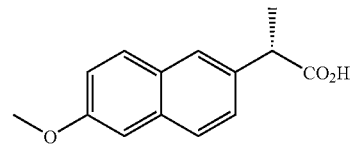

In certain embodiments, the ligand is ibuprofen or a structural derivative of ibuprofen. Procedures for the synthesis of ibuprofen can be found in U.S. Pat. No. 3,228,831. The structure of ibuprofen is shown below.

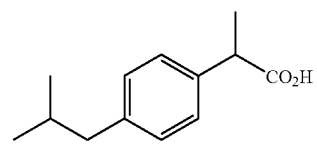

Various additional ligands are presented in FIGS. 3-9.

Oligonucleotide & Linker

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced siRNA activity when compared to like siRNA compounds that are not conjugated.

The ligand-conjugated oligonucleotides of the present invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

The oligonucleotides of the present invention have been chemically modified. A variety of specific oligonucleotide chemical modifications are described below. Importantly, it is not necessary for all positions in a given compound to be uniformly modified. Conversely, more than one modifications may be incorporated in a single siRNA compound or even in a single nucleotide thereof.

In certain instances, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

The oligonucleotides of the present invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027; all of which are hereby incorporated by reference.

In certain embodiments, the oligonucleotides of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. a further preferred modification includes 2'-dimethylaminooxyethoxy, i.e., a $O(CH_2)_2ON(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-Cancer Drug Design*, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the present invention include those having one of formula I or II:

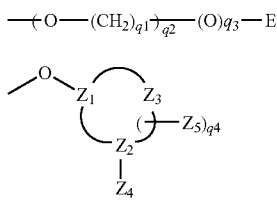

wherein,

E is $C_1$-$C_{10}$ alkyl, $N(Q_3)(Q_4)$ or $N\!=\!C\,(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;
$q_2$ is an integer from 1 to 10;
$q_3$ is 0 or 1;
$q_4$ is 0, 1 or 2;

each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, $C(\!=\!NH)N(H)M_2$, $C(\!=\!O)N(H)M_2$ or $OC(\!=\!O)N(H)M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, $CH_2$, CHF, and $CF_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-5-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

The present invention further encompasses oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.,* 1986, 83, 8859; Forster et al., *Cell,* 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-5-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nuc. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

Tether

In a preferred embodiment of the invention, the ligand is attached to an oligonucleotide via a tether and linking group, to form a ligand-conjugated oligonucleotide. Preferred tethers of the invention include, but are not limited to, 6-aminoalkoxy linkers, 6-aminoalkylamino linkers, cysteamine, heterobifunctional linkers, homobifunctional linkers, and a universal tether (derived from 3-dimethoxytrityloxy-2-aminopropanol). A particularly preferred tether for the synthesis of ligand conjugated oligonucleotides of the invention is a 6-aminohexyloxy group. A variety of heterobifunctional and homobifunctional tethers are available from Pierce Co. (Rockford, Ill.). Such heterobifunctional and homobifunctional tethers are particularly useful in conjunction with the 6-aminoalkoxy and 6-aminoalkylamino moieties to form extended tethers useful for linking ligands to a nucleoside. Further useful tethers that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a tether pre-attached to the nucleoside is commercially available from Glen Research Corporation under the tradename "Amino-Modifier-dT." This nucleoside-tether reagent, a uridine derivative having an [N(7-trifluoroacetylamino-heptyl)-3-acrylamido] substituent group at the 5 position of the pyrimidine ring, is synthesized as per the procedure of Jablonski et al. (*Nucleic Acid Research,* 1986, 14:6115).

In certain instances, conjugation of ligand molecules is achieved by conjugation of the ligand to an amino tether on the nucleoside. This can be effected in several ways. For example, a ligand-nucleoside conjugate of the invention can be prepared by conjugation of the ligand molecule to the nucleoside using EDC/sulfo-NHS (i.e., 1-ethyl-3(3-dimethylaminopropylcarbodiimide/N-hydroxysulfosuccinimide) to conjugate the carboxylate function of the ligand with the amino function of the linking group on the nucleoside.

The ligand-conjugated oligonucleotides of the present invention may be prepared by conjugation of the ligand (e.g., naproxen) molecule to the nucleoside sequence via a heterobifunctional tether such as m-maleimidobenzoyl-N-hydroxysulfosuccinimide ester (MBS) or succinimidyl 4-(N-maleimidomethyl)cyclohexane-1-carboxylate (SMCC), to link a nucleophilic position on the ligand molecule to the amino function of the tether group on nucleoside sequence. By this mechanism, an oligonucleoside-maleimide conjugate is formed by reaction of the amino group of the tether on the linked nucleosides with the MBS or SMCC maleimide linker. The conjugate is then reacted with the ligand.

Alternatively, a ligand conjugated-oligonucleotide can be prepared by conjugation of the ligand molecule to the oligonucleotide or nucleoside via a homobifunctional tether such as disuccinimidyl suberate (DSS), to link an amino function on the ligand to the amino group of a tether on the oligonucleotide sequence. By this mechanism, an oligonucleoside-succinimidyl conjugate is formed by reaction of the amino group of the tether on the nucleoside sequence with a disuccinimidyl suberate tether. The disuccinimidyl suberate tether couples with the amine tether on the nucleoside to extend the size of the tether. The extended tether is then reacted with an amino group of the ligand molecule.

Certain compounds of the invention are described below in greater detail. Importantly, the embodiments described below are included merely for purposes of illustration of certain aspects and embodiments of the present invention, and are not intended to limit the invention.

One aspect of the present invention relates to a double-stranded oligonucleotide comprising a first strand and a second strand, wherein said first strand and said second strand are represented independently by formula II:

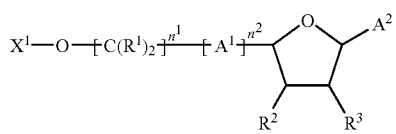

II wherein $X^1$ is H, —P(O)(OM)$_2$, —P(O)(OM)-O—P(O)(OM)$_2$, —P(O)(Oalkyl)$_2$, —P(O)(Oalkyl)-O—P(O)(Oalkyl)$_2$, or -A$^6$-[A$^7$-(A$^5$)$_w$]$_y$;

M represents independently for each occurrence an alkali metal or a transition metal with an overall charge of +1;

$R^1$ and $R^5$ represent independently for each occurrence H, alkyl, or halogen;

$R^2$ and $R^3$ represent independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, —S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, —O(C(R$^{19}$)$_2$)$_k$ON((C$_1$-C$_6$)alkyl)$_2$, or —O-A$^6$-[A$^7$-(A$^5$)$_w$]$_y$;

$R^4$ represents independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, —S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, or —O(C(R$^{19}$)$_2$)$_k$ON((C$_1$-C$_6$)alkyl)$_2$;

$R^6$, $R^7$, and $R^9$ represent independently for each occurrence H, alkyl, aryl, or aralkyl;

$R^8$ represents independently for each occurrence alkyl, aryl, or aralkyl;

k represents independently for each occurrence 1, 2, 3, or 4;

$n^1$ is 1, 2, or 3;

$n^2$ is an integer in the range of about 15-28, inclusive;

w represents independently for each occurrence 1, 2, or 3 in accord with the rules of valence;

x represents independently for each occurrence 0, 1, 2, or 3;

y represents independently for each occurrence 1, 2, 3, 4, or 5 in accord with the rules of valence;

$A^1$ represents independently for each occurrence:

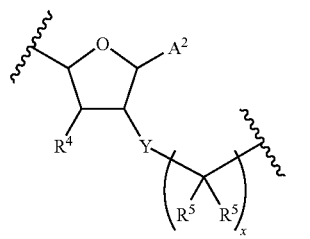

or

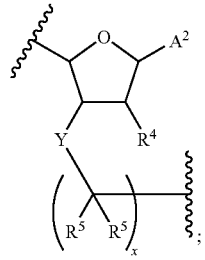

$A^2$ represents independently for each occurrence:

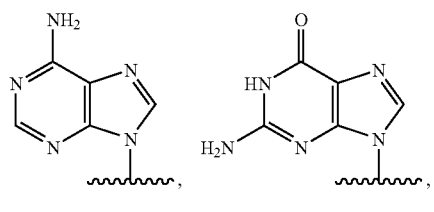

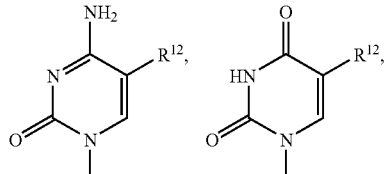

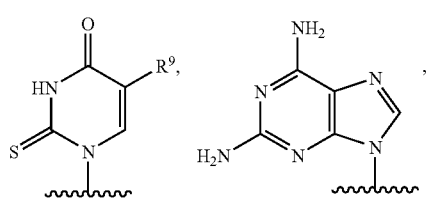

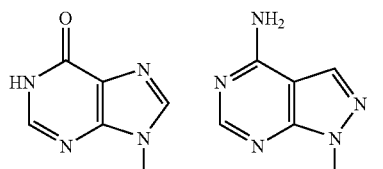

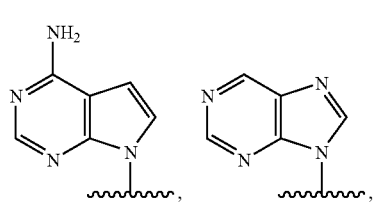

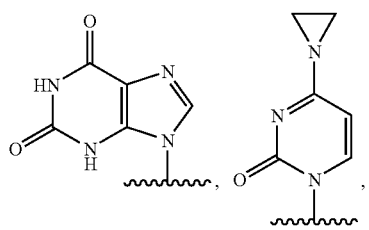

-continued

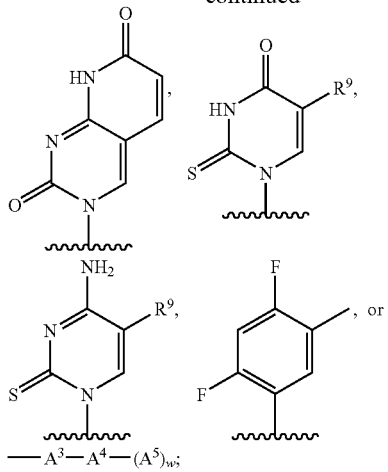

—A³—A⁴—(A⁵)_w;

A³ represents independently for each occurrence

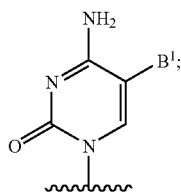

A⁴ represents independently for each occurrence a bond, alkyl diradical, heteroalkyl diradical, alkenyl diradical, alkynyl diradical, alkylalkynyl diradical, aminoalkyl diradical, thioether, —C(O)—, —S(O)—, —S(O)₂—, B¹C(R)₂B², B¹C(R)(B²)₂, B¹C(B²)₃, B¹N(R)(B²), B¹N(B²)₂, or has the formula:

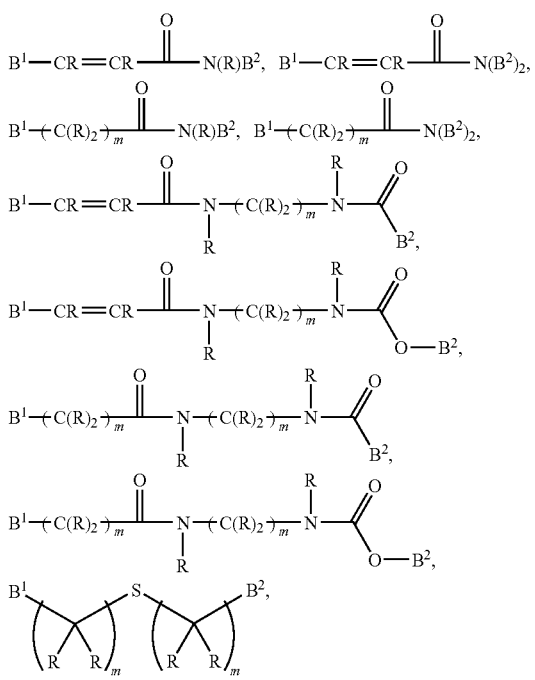

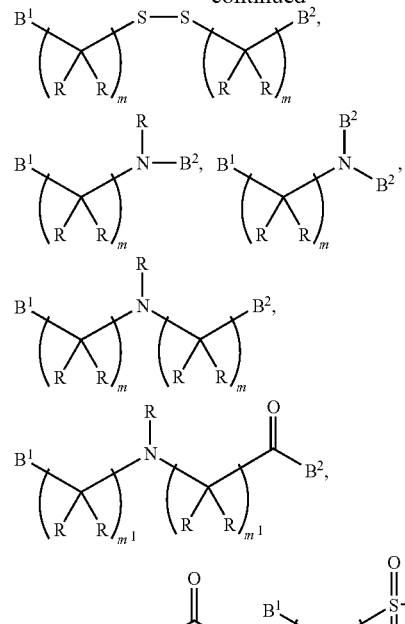

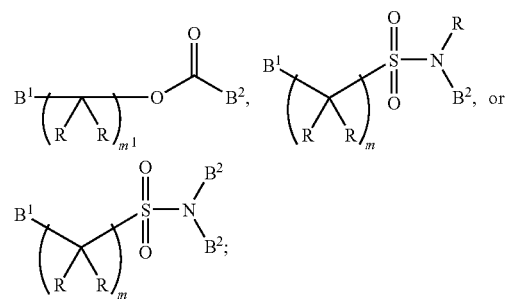

B¹ is a bond between A³ and A⁴;
B² is a bond between A⁴ and A⁵;
R represents independently for each occurrence hydrogen or alkyl;
m represents independently for each occurrence 1, 2, 3, 4, 5, 6, 7, or 8;
m¹ represents independently for each occurrence 0, 1, 2, 3, 4, 5, 6, 7, or 8;
Y represents independently for each occurrence an alkyl diradical, cycloalkyl diradical, heteroalkyl diradical, heterocycloalkyl diradical, alkenyl diradical, alkynyl diradical, aryl diradical, heteroaryl diradical, aralkyl diradical, heteroaralkyl diradical, —X²C(O)X² [C(R⁵)₂]_vX²—, —X²C(NR⁶)X²[C(R⁵)₂]_vX²—, —X²C(S)X² [C(R⁵)₂]_vX²—, —X²C(O)X²[C(R⁵)₂]_vX²C(O)X²—,

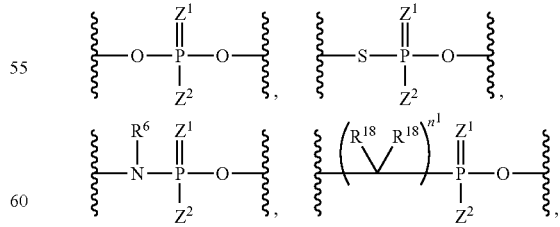

—[C(R⁵)₂]_tN(R⁶)O[C(R⁵)₂]_t—, —[C(R⁵)₂]_tN(R⁶)N(R⁶)O[C(R⁵)₂]_t—, —[C(R⁵)₂]_tN(R⁷)C(O)[C(R⁵)₂]_t—, —[C(R⁵)₂]_tN(R)CO₂[C(R⁵)₂]_t—, —[C(R⁵)₂]_tN(R⁷)C(S)[C(R⁵)₂]_t—, —[C(R⁵)₂]_tN(R⁷)C(S)o[C(R⁵)₂]_t—, —[C(R⁵)₂]_tOC(O)S[C(R⁵)₂]_t—, —[C(R⁵)₂]_tSN(R⁷)CO₂[C(R⁵)₂]_t—, —[C(R⁵)₂]_t $OSi(R^8)_2O[C(R^5)_2]_t$—, $[C(R^5)_2]_tOSO_2N(R^7)$ $[C(R^5)_2]_t$—, —$[C(R^5)_2]_tN(R^7)SO_2N(R^7)$ $[C(R^5)_2]_t$—, —$[C(R^5)_2]_tSO_2N$ (morpholino)-$[C(R^5)_2]_t$—, —$[C(R^5)_2]_tSO_2N(R^7)$ $[C(R^5)_2]_t$—, —$[C(R^5)_2]_tS[C(R^5)_2]_t$—, $[C(R^5)_2]_tOSO_2[C(R^5)_2]_t$—, —$[C(R^5)_2]_tS[C(R^5)_2]_vO[C(R^5)_2]_t$—, —$[C(R^5)_2]_tO[C(R^5)_2]_vO[C(R^5)_2]_t$—, —$[C(R^5)_2]_tO[C(R^5)_2]_t$—, —$[C(R^5)_2]_tN(R^7)[C(R^5)_2]_t$—, —$[C(R^5)_2]_tC=NO[C(R^5)_2]_t$—, —$[C(R^5)_2]_tC(O)C(R^5)=C(R^5)[C(R^5)_2]_t$—, —$[C(R^5)_2]_tC(R^5)=C(R^5)[C(R^5)_2]_t$—, or —$[C(R^5)_2]_tX^2C(O)X^2[C(R^5)_2]_t$—;

$X^2$ represents independently for each occurrence a bond, O, or $N(R^6)$;

$Z^1$ represents independently for each occurrence O, S, or $N(R^8)$;

$Z^2$ represents independently for each occurrence alkyl, aryl, aralkyl, $B(R^9)_3$, —OM, —Oalkyl, —Oaryl, —Oaralkyl, —SM, —Salkyl, —Saryl, —Saralkyl, —$[C(R^5)_2]_mN(R^6)_2$, —$N(R^{10})R^{11}$, —$N(R^{19})(C(R^{19})_2)_mN(R^{19})_2$, —$N(R^7)C(O)R^8$, H, —$OC(O)R^8$, —$CO_2R^8$, F, Se, —$SeR^8$, —$(C(R^{19})_2)_mOR^{19}$, —$(C(R^{19})_2)_mSR^{19}$, —$N(R^{19})(C(R^{19})_2)_mOR^{19}$, —$N(R^{19})(C(R^{19})_2)_mSR^{19}$, —$N(R^{19})(C(R^{19})_2)_mN(R^{19})C(O)$alkyl, —$(C(R^{19})_2)_mN(R^{19})C(O)$alkyl, or -$A^8$-$[A^9$-$(A^5)_w]_y$;

$R^{10}$ and $R^{11}$ are independently H, alkyl, or aryl; or $R^{10}$ and $R^{11}$ taken together form a 3-, 4-, 5-, 6-, or 7-member ring;

$R^{12}$ represents independently for each occurrence H, alkyl, or —$NHCH_2CH=CH_2$;

t represents independently for each occurrence 0, 1, 2, 3, or 4;

v represents independently for each occurrence 0, 1, 2, 3, 4, 5, 6, 7, or 8;

$A^5$ represents independently for each occurrence aryl, aralkyl, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring;

$A^6$ represents independently for each occurrence a bond, alkyl diradical, heteroalkyl diradical, alkenyl diradical, aminoalkyl, —C(O)—, —S(O)—, —$S(O)_2$—, or is represented by formula:

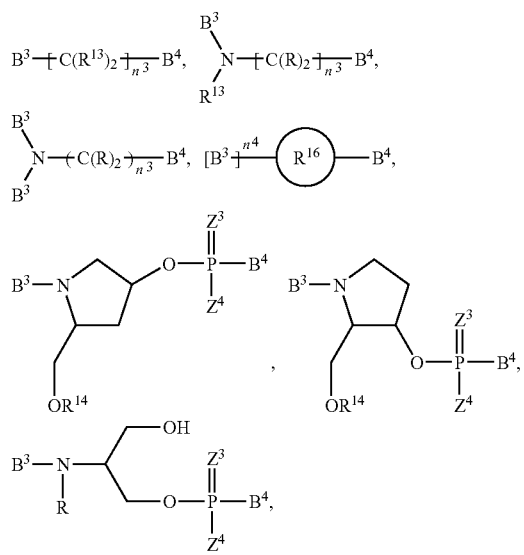

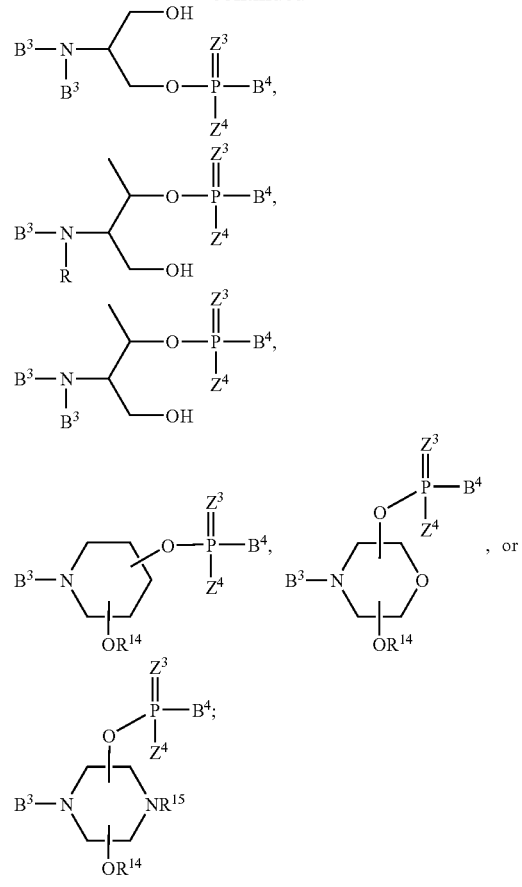

$Z^3$ represents independently for each occurrence O or S;

$Z^4$ represents independently for each occurrence —OM, —Oalkyl, —Oaryl, —Oaralkyl, —SM, —Salkyl, —Saryl, —Saralkyl, —$N(R^{10})R^{11}$, —$[C(R^5)_2]_mN(R^6)_2$, —$N(R^{19})(C(R^{19})_2)_mN(R^{19})_2$, —$(C(R^{19})_2)_mOR^{19}$, —$(C(R^{19})_2)_mSR^{19}$, —$N(R^{19})(C(R^{19})_2)OR^{19}$, —$N(R^{19})(C(R^{19})_2)SR^{19}$, —$N(R^{19})(C(R^{19})_2)_mN(R^{19})C(O)$alkyl, —$(C(R^{19})_2)_mN(R^{19})C(O)$alkyl, aryl, or alkyl;

$R^{13}$ represent independently for each occurrence H, alkyl, cycloalkyl, heteroalkyl, aryl, aralkyl, acyl, silyl, or $B^3$;

$R^{14}$ represents independently for each occurrence alkyl, aryl, aralkyl, acyl, or silyl;

$R^{15}$ represents independently for each occurrence hydrogen, alkyl, aryl, aralkyl, acyl, alkylsulfonyl, alkylsulfoxide, arylsulfonyl, arylsulfoxide, or silyl;

$R^{16}$ represents independently for each occurrence cycloalkyl, heterocycloalkyl, aryl, or heteroaryl;

$B^3$ is a bond between $A^6$ and $A^7$;

$B^4$ is a bond between $A^6$ and O;

$n^3$ represents independently for each occurrence an integer in the range of 1-15, inclusive;

$n^4$ represents independently for each occurrence 1, 2, 3, 4, or 5 in accord with the rules of valence;

$A^7$ represents independently for each occurrence a bond, alkyl diradical, heteroalkyl diradical, —C(O)—, —S(O)—, —$S(O)_2$—, $B^3C(R)_2B^5$, $B^3C(R)(B^5)_2$, $B^3C(B^5)_3$, $B^3N(R)(B^5)$, $B^3N(B^5)_2$, or has the formula:

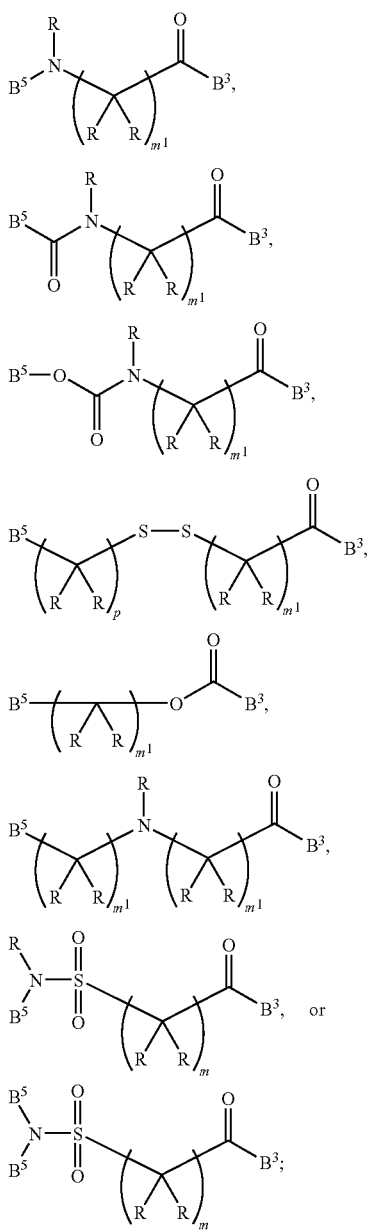

p represents independently for each occurrence 1, 2, 3, or 4;

$B^5$ is a bond between $A^5$ and $A^7$;

$A^8$ is a bond, alkyl diradical, heteroalkyl diradical, alkenyl diradical, aminoalkyl, or is represented by formula:

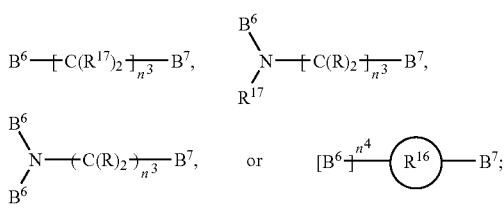

$R^{17}$ represent independently for each occurrence H, alkyl, cycloalkyl, heteroalkyl, aryl, aralkyl, acyl, silyl, or $B^6$;

$R^{18}$ represents independently for each occurrence H, halogen, alkyl, alkoxyl, —N(R^6)_2, —CN, —[C(R^5)_2]_vC(R^5)=C(R^5)_2;

$R^{19}$ represents independently for each occurrence H or alkyl;

$B^6$ is a bond between $A^8$ and $A^9$;

$B^7$ is a bond between $A^8$ and P;

$A^9$ is a bond, alkyl diradical, heteroalkyl diradical, —C(O)—, —S(O)—, —S(O)_2—, $B^6C(R)_2B^8$, $B^6C(R)(B^8)_2$, $B^6C(B^8)_3$, $B^6N(R)(B^8)$, $B^6N(B^8)_2$, or has the formula:

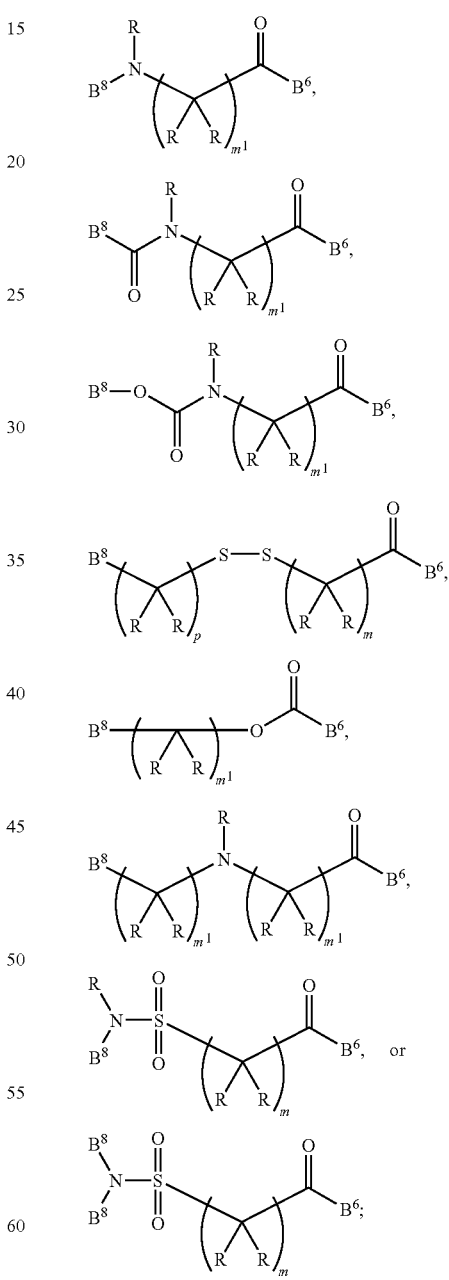

$B^8$ is a bond between $A^5$ and $A^9$; and provided that at least one instance of Y is not

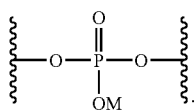

In certain embodiments, the present invention relates to the aforementioned compound, wherein $A^1$ represents independently for each occurrence:

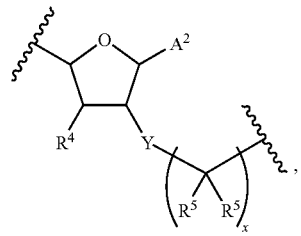

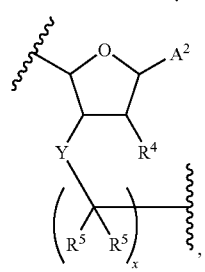

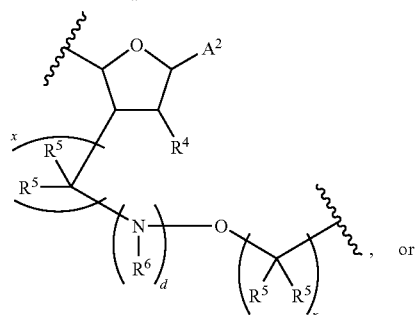, or

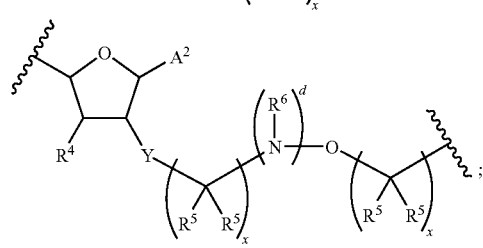;

and d is 1 or 2.

In certain embodiments, the present invention relates to the aforementioned compound, wherein Y is

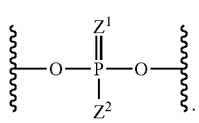.

In certain embodiments, the present invention relates to the aforementioned compound, wherein Y is

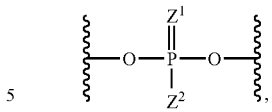

and $Z^2$ represents independently for each occurrence alkyl, aryl, aralkyl, $B(R^9)_3$, —OM, —Oalkyl, —Oaryl, or —Oaralkyl.

In certain embodiments, the present invention relates to the aforementioned compound, wherein Y is

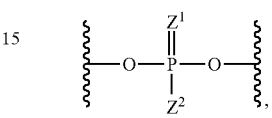

and $Z^2$ represents independently for each occurrence alkyl or —OM.

In certain embodiments, the present invention relates to the aforementioned compound, wherein Y is

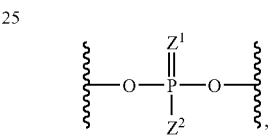

and $Z^2$ represents independently for each occurrence methyl, ethyl, propyl, isopropyl, or —OM.

In certain embodiments, the present invention relates to the aforementioned compound, wherein Y is

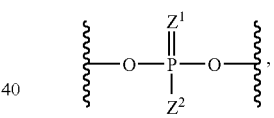

and $Z^2$ represents independently for each occurrence methyl or —OM.

In certain embodiments, the present invention relates to the aforementioned compound, wherein Y is

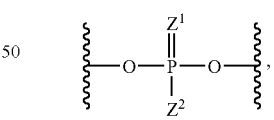

and there are at least two instances when $Z^2$ is alkyl.

In certain embodiments, the present invention relates to the aforementioned compound, wherein Y is

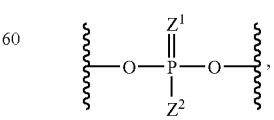

and there are at least five instances when $Z^2$ is alkyl.

In certain embodiments, the present invention relates to the aforementioned compound, wherein Y is

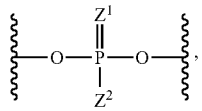

and there are at least seven instances when $Z^2$ is alkyl.

In certain embodiments, the present invention relates to the aforementioned compound, wherein Y is

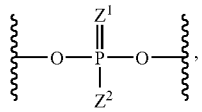

and there are at least ten instances when $Z^2$ is alkyl.

In certain embodiments, the present invention relates to the aforementioned compound, wherein in the linkage between the first nucleoside and second nucleoside at the terminus of said first strand, Y is

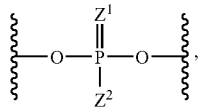

and $Z^2$ is alkyl.

In certain embodiments, the present invention relates to the aforementioned compound, wherein in the linkage between the first and second nucleoside at the 3'-terminus of said first strand, Y is

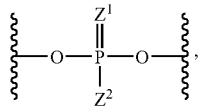

and $Z^2$ is alkyl.

In certain embodiments, the present invention relates to the aforementioned compound, wherein in the linkage between the first and second nucleoside at the 3'-terminus of said first strand and said second strand, Y is

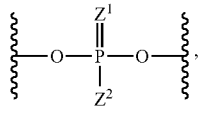

and $Z^2$ is alkyl.

In certain embodiments, the present invention relates to the aforementioned compound, wherein $n^1$ is 1.

In certain embodiments, the present invention relates to the aforementioned compound, wherein t is 0 or 1.

In certain embodiments, the present invention relates to the aforementioned compound, wherein x is 1.

In certain embodiments, the present invention relates to the aforementioned compound, wherein the $n^2$ is 17, 18, 19, 20, 21, 22, or 23.

In certain embodiments, the present invention relates to the aforementioned compound, wherein $n^2$ is 19, 20, or 21.

In certain embodiments, the present invention relates to the aforementioned compound, wherein $n^2$ is 20.

In certain embodiments, the present invention relates to the aforementioned compound, wherein $n^2$ is 20, and said first strand and said second strand are hybridized so that there is one unhybridized nucleoside on said first strand and said second strand.

In certain embodiments, the present invention relates to the aforementioned compound, wherein $n^2$ is 20, and said first strand and said second strand are hybridized so that there are two unhybridized nucleosides on said first strand and said second strand.

In certain embodiments, the present invention relates to the aforementioned compound, wherein $n^2$ is 20 for said first strand, and $n^2$ is 22 for said second strand.

In certain embodiments, the present invention relates to the aforementioned compound, wherein $R^1$ is H.

In certain embodiments, the present invention relates to the aforementioned compound, wherein $R^2$ and $R^3$ represent independently for each occurrence OH, F, —Oalkyl, —Oallyl, —Oalkylamine, or —O-$A^6$-[$A^7$-$(A^5)_w]_y$.

In certain embodiments, the present invention relates to the aforementioned compound, wherein $R^2$ and $R^3$ represent independently for each occurrence OH, F, —Oalkyl, —Oallyl, or —Oalkylamine.

In certain embodiments, the present invention relates to the aforementioned compound, wherein $R^2$ and $R^3$ represent independently for each occurrence OH, F, —Oalkyl, —N$(R^{19})_2$, or —O-$A^6$-[$A^7$-$(A^5)_w]_y$.

In certain embodiments, the present invention relates to the aforementioned compound, wherein $R^3$ represents independently for each occurrence H, OH, F, —OCH$_3$, —O(CH$_2$)$_2$OR$^{19}$, —O(CH$_2$)$_2$SR$^{19}$, —O(CH$_2$)$_2$N$(R^{19})_2$, —OCH$_2$C(O)N(H)CH$_3$, —NH$_2$, —N(CH$_3$)$_2$, —N(H)CH$_3$, —SCH$_3$, —O(CH$_2$)$_2$OCH$_3$, —O(CH$_2$)$_2$SCH$_3$, —O(CH$_2$)$_2$—O—(CH$_2$)$_2$N(CH$_3$)$_2$, or —O(CH$_2$)$_2$ON(CH$_3$)$_2$.

In certain embodiments, the present invention relates to the aforementioned compound, wherein $R^3$ represents independently for each occurrence —NH$_2$, —N(CH$_3$)$_2$, or —N(H)CH$_3$.

In certain embodiments, the present invention relates to the aforementioned compound, wherein $R^4$ represents independently for each occurrence H, OH, F, —OCH$_3$, —O(CH$_2$)$_2$OR$^{19}$, —O(CH$_2$)$_2$SR$^{19}$, —O(CH$_2$)$_2$N$(R^{19})_2$, —OCH$_2$C(O)N(H)CH$_3$, —NH$_2$, —N(CH$_3$)$_2$, —N(H)CH$_3$, —SCH$_3$, —O(CH$_2$)$_2$OCH$_3$, —O(CH$_2$)$_2$SCH$_3$, —O(CH$_2$)$_2$—O—(CH$_2$)$_2$N(CH$_3$)$_2$, or —O(CH$_2$)$_2$ON(CH$_3$)$_2$.

In certain embodiments, the present invention relates to the aforementioned compound, wherein $R^4$ represent independently for each occurrence OH, F, —Oalkyl, —Oallyl, or —Oalkylamine.

In certain embodiments, the present invention relates to the aforementioned compound, wherein $R^4$ represents independently for each occurrence —NH$_2$, —N(CH$_3$)$_2$, or —N(H)CH$_3$.

In certain embodiments, the present invention relates to the aforementioned compound, wherein $R^3$ and $R^4$ represent independently for each occurrence —NH$_2$, —N(CH$_3$)$_2$, or —N(H)CH$_3$.

In certain embodiments, the present invention relates to the aforementioned compound, wherein $R^5$ is H.

In certain embodiments, the present invention relates to the aforementioned compound, wherein $Z^2$ represents independently for each occurrence methyl, —OM, —Oalkyl, —Oaryl, —Oaralkyl, —SM, —Salkyl, —Saryl, —Saralkyl, —[C$(R^5)_2]_m$N$(R^6)_2$, —N$(R^{10})R^{11}$, or —N$(R^{19})$(C$(R^{19})_2)_m$N$(R^{19})_2$.

In certain embodiments, the present invention relates to the aforementioned compound, wherein $Z^3$ is O.

In certain embodiments, the present invention relates to the aforementioned compound, wherein $Z^4$ represents independently for each occurrence —OM, —Oalkyl, —Oaryl, or —Oaralkyl.

In certain embodiments, the present invention relates to the aforementioned compound, wherein $Z^4$ represents independently for each occurrence methyl, —OM, —Oalkyl, —Oaryl, —Oaralkyl, —SM, —Salkyl, —Saryl, —Saralkyl, —$[C(R^5)_2]_m N(R^6)_2$, —$N(R^{10})R^{11}$, or —$N(R^{19})C(R^{19})_2)_m N(R^{19})_2$.

In certain embodiments, the present invention relates to the aforementioned oligonucleotide, wherein $A^2$ represents independently for each occurrence:

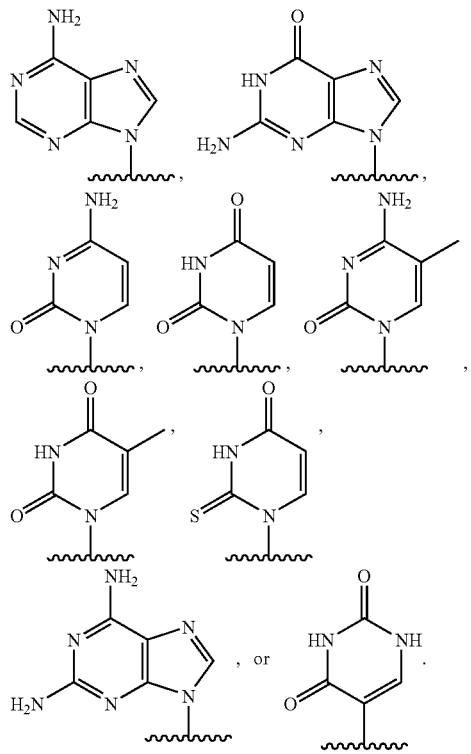

In certain embodiments, the present invention relates to the aforementioned compound, wherein $A^4$ represents independently for each occurrence

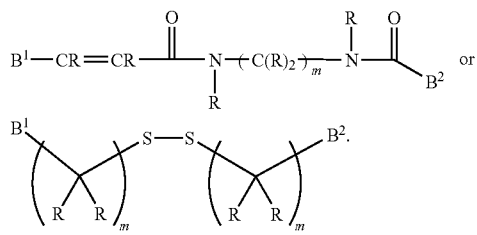

In certain embodiments, the present invention relates to the aforementioned compound, wherein $A^4$ represents independently for each occurrence

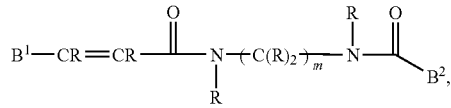

and $A^5$ represents independently for each occurrence

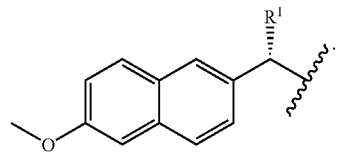

In certain embodiments, the present invention relates to the aforementioned compound, wherein $A^4$ represents independently for each occurrence

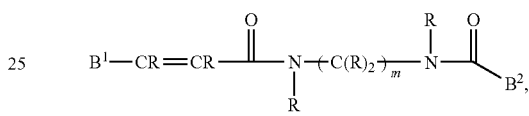

and $A^5$ represents independently for each occurrence

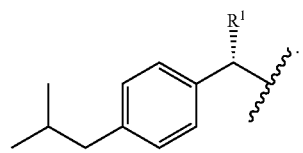

In certain embodiments, the present invention relates to the aforementioned compound, wherein $A^5$ occurs at least once.

In certain embodiments, the present invention relates to the aforementioned compound, wherein $A^5$ occurs at least five times.

In certain embodiments, the present invention relates to the aforementioned compound, wherein $A^5$ occurs at least ten times.

In certain embodiments, the present invention relates to the aforementioned compound, wherein $A^5$ occurs only in said first strand.

In certain embodiments, the present invention relates to the aforementioned compound, wherein said first strand and said second strand each contain at least one occurrence of $A^5$.

In certain embodiments, the present invention relates to the aforementioned compound, wherein $A^5$ is —$(C(R)_2)_m$-$A^{99}$, wherein $A^{99}$ is optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, or tetrazolyl.

In certain embodiments, the present invention relates to the aforementioned compound, wherein $A^5$ is represented by formula III:

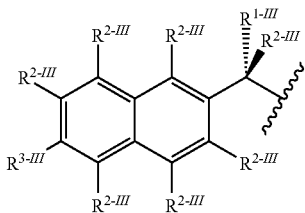

III wherein
$R^{1\text{-}III}$, $R^{2\text{-}III}$, and $R^{3\text{-}III}$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

In certain embodiments, the present invention relates to the aforementioned compound, wherein A is represented by formula III, and $R^{1\text{-}III}$ is alkyl.

In certain embodiments, the present invention relates to the aforementioned compound, wherein $A^5$ is represented by formula III, and $R^{1\text{-}III}$ is methyl, ethyl, propyl, isopropyl, butyl, sec-butyl, isobutyl, or tert-butyl.

In certain embodiments, the present invention relates to the aforementioned compound, wherein $A^5$ is represented by formula III, and $R^{1\text{-}III}$ is methyl.

In certain embodiments, the present invention relates to the aforementioned compound, wherein A is represented by formula III, and $R^{2\text{-}III}$ is H.

In certain embodiments, the present invention relates to the aforementioned compound, wherein $A^5$ is represented by formula III, and $R^{3\text{-}III}$ is alkoxyl.

In certain embodiments, the present invention relates to the aforementioned compound, wherein $A^5$ is represented by formula III, and $R^{3\text{-}III}$ is methoxy, ethoxy, propoxy, isopropoxy, butoxy, sec-butoxy, isobutoxy, or tert-butoxy.

In certain embodiments, the present invention relates to the aforementioned compound, wherein $A^5$ is represented by formula III, and $R^{3\text{-}III}$ is methoxy.

In certain embodiments, the present invention relates to the aforementioned compound, wherein A is represented by formula III, $R^{1\text{-}III}$ is methyl, $R^{2\text{-}III}$ is H, and $R^{3\text{-}III}$ is methoxy.

In certain embodiments, the present invention relates to the aforementioned compound, wherein $A^5$ is represented by formula IV:

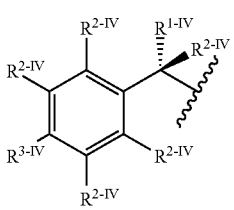

IV wherein
$R^{1\text{-}IV}$, $R^{2\text{-}IV}$, and $R^{3\text{-}IV}$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

In certain embodiments, the present invention relates to the aforementioned compound, wherein $A^5$ is represented by formula IV, and $R^{1\text{-}IV}$ is alkyl.

In certain embodiments, the present invention relates to the aforementioned compound, wherein $A^5$ is represented by formula IV, and $R^{1\text{-}IV}$ is methyl, ethyl, propyl, isopropyl, butyl, sec-butyl, isobutyl, or tert-butyl.

In certain embodiments, the present invention relates to the aforementioned compound, wherein $A^5$ is represented by formula IV, and $R^{1\text{-}IV}$ is methyl.

In certain embodiments, the present invention relates to the aforementioned compound, wherein $A^5$ is represented by formula IV, and $R^{2\text{-}IV}$ is H.

In certain embodiments, the present invention relates to the aforementioned compound, wherein $A^5$ is represented by formula IV, and $R^{3\text{-}IV}$ is alkyl.

In certain embodiments, the present invention relates to the aforementioned compound, wherein $A^5$ is represented by formula IV, and $R^{3\text{-}IV}$ is methyl, ethyl, propyl, isopropyl, butyl, sec-butyl, isobutyl, tert-butyl, pentyl, hexyl, or heptyl.

In certain embodiments, the present invention relates to the aforementioned compound, wherein $A^5$ is represented by formula IV, and $R^{3\text{-}IV}$ is isobutyl.

In certain embodiments, the present invention relates to the aforementioned compound, wherein $A^5$ is represented by formula IV, $R^{1\text{-}IV}$ is methyl, $R^{2\text{-}IV}$ is H, and $R^{3\text{-}IV}$ is isobutyl.

In certain embodiments, the present invention relates to the aforementioned compound, wherein $A^5$ is represented by formula IV, and $R^2$ represents independently for each occurrence H, OH, F, or —Oalkyl.

In certain embodiments, the present invention relates to the aforementioned compound, wherein $A^5$ is represented by formula IV, and $R^3$ and $R^4$ represent independently for each occurrence —NH$_2$, —N(H)CH$_3$, or —N(CH$_3$)$_2$.

In certain embodiments, the present invention relates to the aforementioned compound, further provided that at least ten instances of Y are not

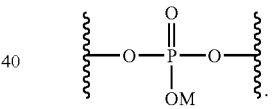

In certain embodiments, the present invention relates to the aforementioned compound, further provided that at least one instance of Y is not

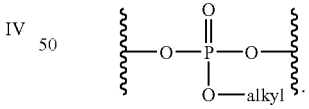

In certain embodiments, the present invention relates to the aforementioned compound, further provided that at least ten instances of Y are not

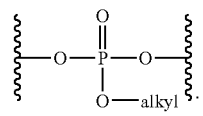

In certain embodiments, the present invention relates to the aforementioned compound, further provided that at least one instance of Y is not

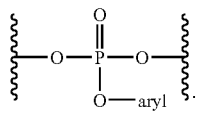

In certain embodiments, the present invention relates to the aforementioned compound, further provided that at least ten instances of Y are not

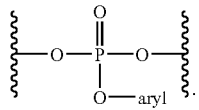

In certain embodiments, the present invention relates to the aforementioned compound, further provided that at least one instance of Y is not

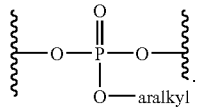

In certain embodiments, the present invention relates to the aforementioned compound, further provided that at least ten instances of Y are not

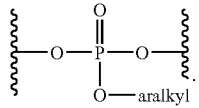

Another aspect of the present invention relates to a single-stranded oligonucleotide represented by formula V:

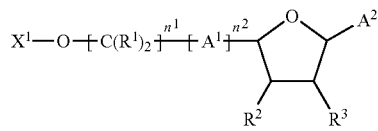

wherein $X^1$ is H, —P(O)(OM)$_2$, —P(O)(OM)-O—P(O)(OM)$_2$, —P(O)(Oalkyl)$_2$, —P(O)(Oalkyl)-O—P(O)(Oalkyl)$_2$, or -A$^6$-[A$^7$-(A$^5$)$_w$]$_y$;

M represents independently for each occurrence an alkali metal or a transition metal with an overall charge of +1;

$R^1$ and $R^5$ represent independently for each occurrence H, alkyl, or halogen;

$R^2$ and $R^3$ represent independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, —S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, —O(C(R$^{19}$)$_2$)$_k$ON((C$_1$-C$_6$)alkyl)$_2$, or —O-A$^6$-[A$^7$-(A$^5$)$_w$]$_y$;

$R^4$ represents independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, or —O(C(R$^{19}$)$_2$)$_k$ON((C$_1$-C$_6$)alkyl)$_2$;

$R^6$, $R^7$, and $R^9$ represent independently for each occurrence H, alkyl, aryl, or aralkyl;

$R^8$ represents independently for each occurrence alkyl, aryl, or aralkyl;

k represents independently for each occurrence 1, 2, 3, or 4;

$n^1$ is 1, 2, or 3;

$n^2$ is an integer in the range of about 15-28, inclusive;

w represents independently for each occurrence 1, 2, or 3 in accord with the rules of valence;

x represents independently for each occurrence 0, 1, 2, or 3;

y represents independently for each occurrence 1, 2, 3, 4, or 5 in accord with the rules of valence;

$A^1$ represents independently for each occurrence:

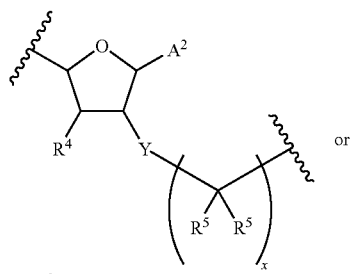

$A^2$ represents independently for each occurrence:

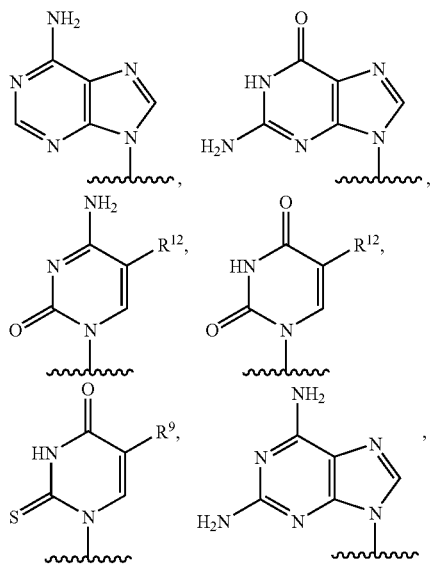

125

-continued

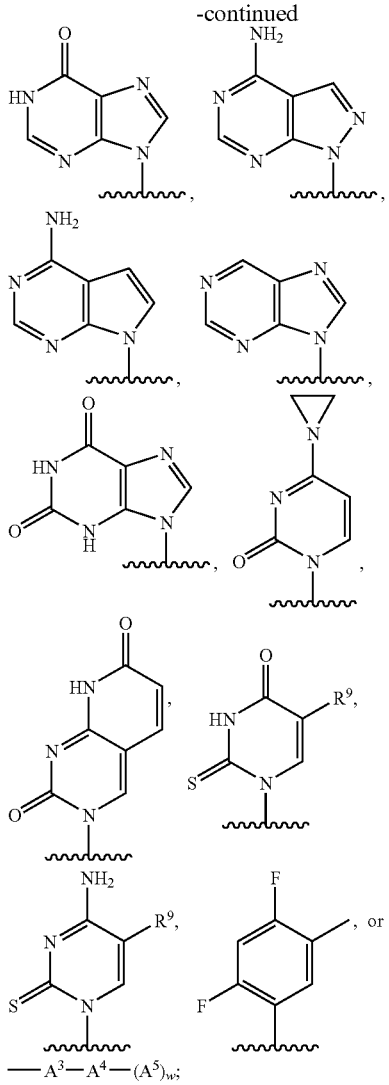

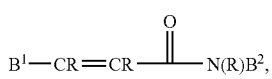

A³ represents independently for each occurrence

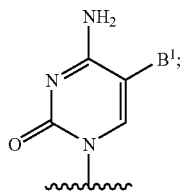

A⁴ represents independently for each occurrence a bond, alkyl diradical, heteroalkyl diradical, alkenyl diradical, alkynyl diradical, alkylalkynyl diradical, aminoalkyl diradical, thioether, —C(O)—, —S(O)—, —S(O)₂—, $B^1C(R)_2B^2$, $B^1C(R)(B^2)_2$, $B^1C(B^2)_3$, $B^1N(R)(B^2)$, $B^1N(B^2)_2$, or has the formula:

126

-continued

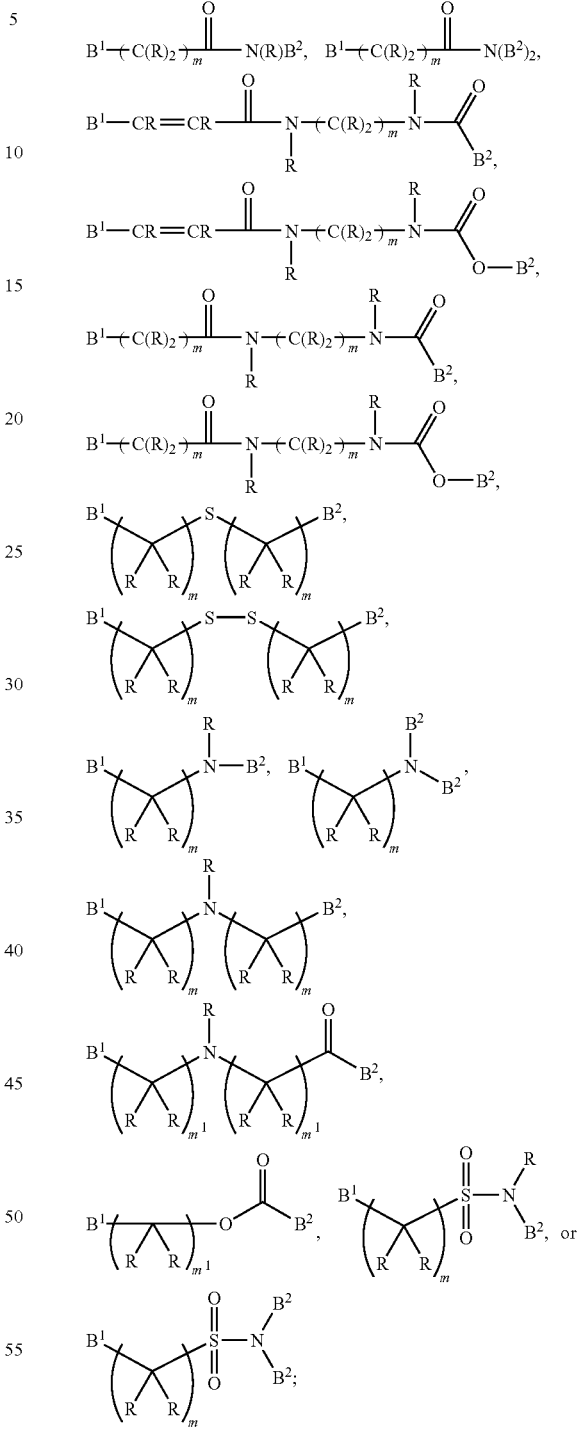

$B^1$ is a bond between $A^3$ and $A^4$;
$B^2$ is a bond between $A^4$ and $A^5$;
R represents independently for each occurrence hydrogen or alkyl;
m represents independently for each occurrence 1, 2, 3, 4, 5, 6, 7, or 8;
m¹ represents independently for each occurrence 0, 1, 2, 3, 4, 5, 6, 7, or 8;

Y represents independently for each occurrence an alkyl diradical, cycloalkyl diradical, heteroalkyl diradical, heterocycloalkyl diradical, alkenyl diradical, alkynyl diradical, aryl diradical, heteroaryl diradical, aralkyl diradical, heteroaralkyl diradical, $-X^2C(O)X^2$ $[C(R^5)_2]_vX^2-$, $-X^2C(NR^6)X^2$ $[C(R^5)_2]_vX^2-$, $-X^2C(S)X^2$ $[C(R^5)_2]_vX^2-$, $-X^2C(O)X^2$ $[C(R^5)_2]_vX^2C(O)X^2-$,

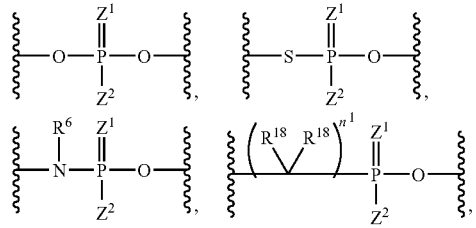

$-[C(R^5)_2]_tN(R^6)O[C(R^5)_2]_t-$, $-[C(R^5)_2]_tN(R^6)N(R^6)[C(R^5)_2]_t-$, $-[C(R^5)_2]_tN(R^7)C(O)$ $[C(R^5)_2]_t-$, $-[C(R^5)_2]_tN(R)CO_2[C(R^5)_2]_t-$, $-[C(R^5)_2]_tN(R^7)C(S)$ $[C(R^5)_2]_t-$, $-[C(R^5)_2]_tN(R^7)C(S)O[C(R^5)_2]_t-$, $-[C(R^5)_2]_tOC(O)S[C(R^5)_2]_t-$, $-[C(R^5)_2]_tSN(R^7)CO_2[C(R^5)_2]_t-$, $-[C(R^5)_2]_tOSi(R^8)_2O[C(R^5)_2]_t-$, $-[C(R^5)_2]_tOSO_2N(R^7)[C(R^5)_2]_t-$, $-[C(R^5)_2]_tN(R^7)SO_2N(R^7)[C(R^5)_2]_t-$, $-[C(R^5)_2]_tSO_2N(morpholino)-[C(R^5)_2]_t-$, $-[C(R^5)_2]_tSO_2N(R^7)[C(R^5)_2]_t-$, $-[C(R^5)_2]_tS[C(R^5)_2]_t-$, $-[C(R^5)_2]_tOSO_2[C(R^5)_2]_t-$, $-[C(R^5)_2]_tS[C(R^5)_2]_yO[C(R^5)_2]_t-$, $-[C(R^5)_2]_tO[C(R^5)_2]_yO[C(R^5)_2]_t-$, $-[C(R^5)_2]_tO[C(R^5)_2]_t-$, $-[C(R^5)_2]_tN(R^7)[C(R^5)_2]_t-$, $-[C(R^5)_2]_tC=NO[C(R^5)_2]_t-$, $-[C(R^5)_2]_tC(O)C(R^5)=C(R^5)[C(R^5)_2]_t-$, $-[C(R^5)_2]_tC(R^5)=C(R^5)[C(R^5)_2]_t-$, or $-[C(R^5)_2]_tX^2C(O)X^2[C(R^5)_2]_t-$;

$X^2$ represents independently for each occurrence a bond, O, or $N(R^6)$;

$Z^1$ represents independently for each occurrence O, S, or $N(R^8)$;

$Z^2$ represents independently for each occurrence alkyl, aryl, aralkyl, $B(R^9)_3$, $-OM$, $-Oalkyl$, $-Oaryl$, $-Oaralkyl$, $-SM$, $-Salkyl$, $-Saryl$, $-Saralkyl$, $-[C(R^5)_2]_mN(R^6)_2$, $-N(R^{10})R^{11}$, $-N(R^{19})(C(R^{19})_2)_mN(R^{19})_2$, $-N(R^7)C(O)R^8$, H, $-OC(O)R^8$, $-CO_2R^8$, F, Se, $-SeR^8$, $-(C(R^{19})_2)_mOR^{19}$, $-(C(R^{19})_2)_mSR^{19}$, $-N(R^{19})(C(R^{19})_2)_mOR^{19}$, $-N(R^{19})(C(R^{19})_2)_mSR^{19}$, $-N(R^{19})(C(R^{19})_2)_mN(R^{19})C(O)$alkyl, $-(C(R^{19})_2)_mN(R^{19})C(O)$alkyl, or $-A^8-[A^9-(A^5)_w]_y$;

$R^{10}$ and $R^{11}$ are independently H, alkyl, or aryl; or $R^{10}$ and $R^{11}$ taken together form a 3-, 4-, 5-, 6-, or 7-member ring;

$R^{12}$ represents independently for each occurrence H, alkyl, or $-NHCH_2CH=CH_2$;

t represents independently for each occurrence 0, 1, 2, 3, or 4;

v represents independently for each occurrence 0, 1, 2, 3, 4, 5, 6, 7, or 8;

$A^5$ represents independently for each occurrence aryl, aralkyl, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring;

$A^6$ represents independently for each occurrence a bond, alkyl diradical, heteroalkyl diradical, alkenyl diradical, aminoalkyl, $-C(O)-$, $-S(O)-$, $-S(O)_2-$, or is represented by formula:

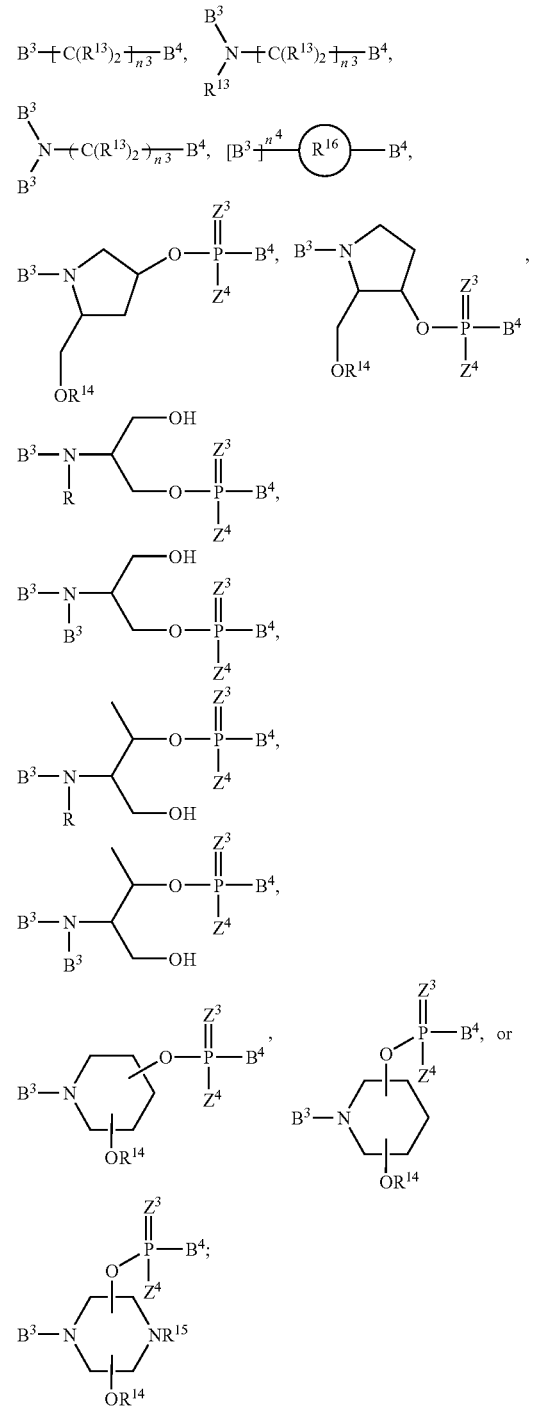

$Z^3$ represents independently for each occurrence O or S;

$Z^4$ represents independently for each occurrence $-OM$, $-Oalkyl$, $-Oaryl$, $-Oaralkyl$, $-SM$, $-Salkyl$, $-Saryl$, $-Saralkyl$, $-N(R^{10})R^{11}$, $-[C(R^5)_2]_mN(R^6)_2$, $-N(R^{19})(C(R^{19})_2)_mN(R^{19})_2$, $(C(R^{19})_2)_mOR^{19}$, $-(C(R^{19})_2)_mSR^{19}$, $-N(R^{19})(C(R^{19})_2)_mOR^{19}$, $N(R^{19})(C(R^{19})_2)_mSR^{19}$, $N(R^{19})(C(R^{19})_2)_mN(R^{19})C(O)$alkyl, $-(C(R^{19})_2)_mN(R^{19})C(O)$alkyl, aryl, or alkyl;

$R^{13}$ represent independently for each occurrence H, alkyl, cycloalkyl, heteroalkyl, aryl, aralkyl, acyl, silyl, or $B^3$;

$R^{14}$ represents independently for each occurrence alkyl, aryl, aralkyl, acyl, or silyl;

$R^{15}$ represents independently for each occurrence hydrogen, alkyl, aryl, aralkyl, acyl, alkylsulfonyl, alkylsulfoxide, arylsulfonyl, arylsulfoxide, or silyl;

$R^{16}$ represents independently for each occurrence cycloalkyl, heterocycloalkyl, aryl, or heteroaryl;

$B^3$ is a bond between $A^6$ and $A^7$;

$B^4$ is a bond between $A^6$ and O;

$n^3$ represents independently for each occurrence an integer in the range of 1-15, inclusive;

$n^4$ represents independently for each occurrence 1, 2, 3, 4, or 5 in accord with the rules of valence;

$A^7$ represents independently for each occurrence a bond, alkyl diradical, heteroalkyl diradical, —C(O)—, —S(O)—, —S(O)$_2$—, $B^3C(R)_2B^5$, $B^3C(R)(B^5)_2$, $B^3C(B^5)_3$, $B^3N(R)(B^5)$, $B^3N(B^5)_2$, or has the formula:

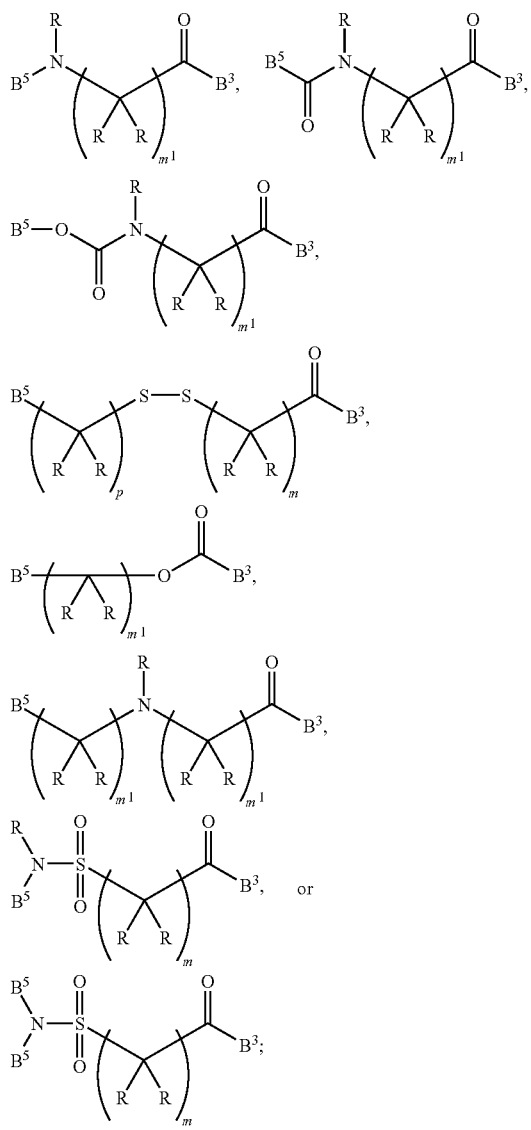

p represents independently for each occurrence 1, 2, 3, or 4;

$B^5$ is a bond between $A^5$ and $A^7$;

$A^8$ is a bond, alkyl diradical, heteroalkyl diradical, alkenyl diradical, aminoalkyl, or is represented by formula:

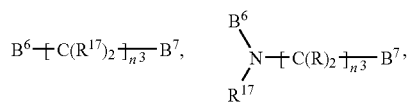

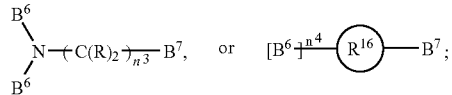

$R^{17}$ represent independently for each occurrence H, alkyl, cycloalkyl, heteroalkyl, aryl, aralkyl, acyl, silyl, or $B^6$;

$R^{18}$ represents independently for each occurrence H, halogen, alkyl, alkoxyl, —N($R^6$)$_2$, —CN, —[C($R^5$)$_2$]$_v$C($R^5$)=C($R^5$)$_2$;

$R^{19}$ represents independently for each occurrence H or alkyl;

$B^6$ is a bond between $A^8$ and $A^9$;

$B^7$ is a bond between $A^8$ and P;

$A^9$ is a bond, alkyl diradical, heteroalkyl diradical, —C(O)—, —S(O)—, —S(O)$_2$—, $B^6C(R)_2B^8$, $B^6C(R)(B^8)_2$, $B^6C(B^8)_3$, $B^6N(R)(B^8)$, $B^6N(B^8)_2$, or has the formula:

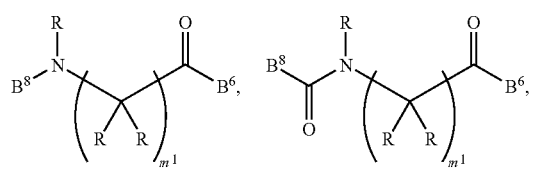

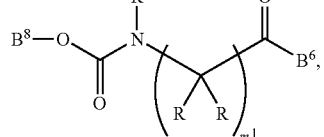

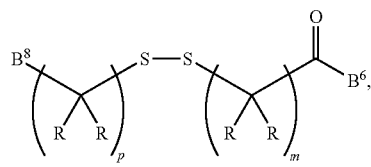

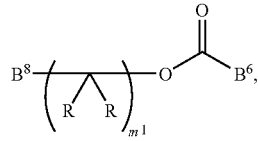

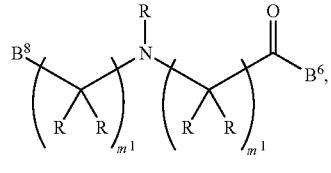

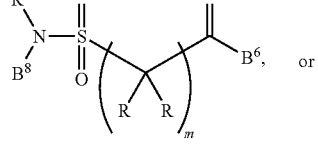

-continued

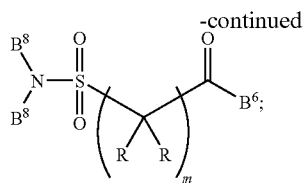

$B^8$ is a bond between $A^5$ and $A^9$; and
provided that at least one instance of Y is not

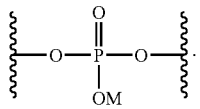

In certain embodiments, the present invention relates to the aforementioned compound, wherein $A^1$ represents independently for each occurrence:

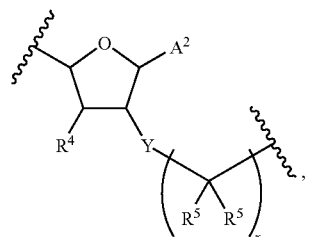

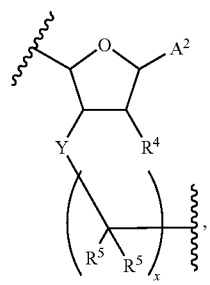

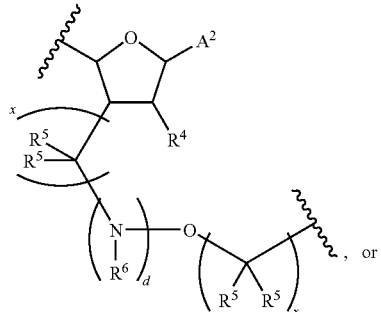

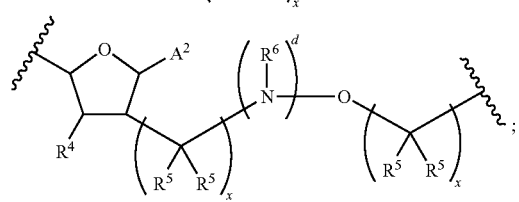

and d is 1 or 2.

In certain embodiments, the present invention relates to the aforementioned compound, wherein Y is

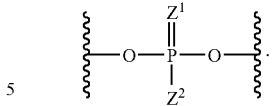

In certain embodiments, the present invention relates to the aforementioned compound, wherein Y is

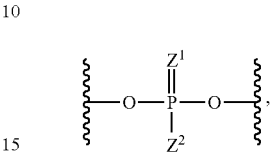

and $Z^2$ represents independently for each occurrence alkyl, aryl, aralkyl, $B(R^9)_3$, —OM, —Oalkyl, —Oaryl, or —Oaralkyl.

In certain embodiments, the present invention relates to the aforementioned compound, wherein Y is

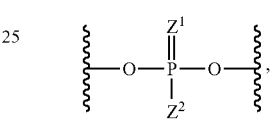

and $Z^2$ represents independently for each occurrence alkyl or —OM.

In certain embodiments, the present invention relates to the aforementioned compound, wherein Y is

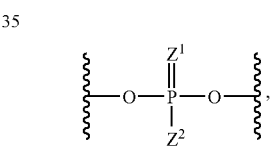

and $Z^2$ represents independently for each occurrence methyl, ethyl, propyl, isopropyl, or —OM.

In certain embodiments, the present invention relates to the aforementioned compound, wherein Y is

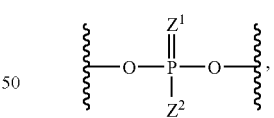

and $Z^2$ represents independently for each occurrence methyl or —OM.

In certain embodiments, the present invention relates to the aforementioned compound, wherein Y is

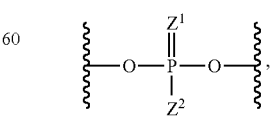

and there are at least two instances when $Z^2$ is alkyl.

In certain embodiments, the present invention relates to the aforementioned compound, wherein Y is

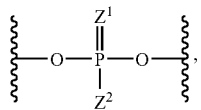

and there are at least five instances when $Z^2$ is alkyl.

In certain embodiments, the present invention relates to the aforementioned compound, wherein Y is

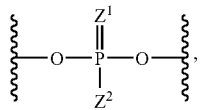

and there are at least seven instances when $Z^2$ is alkyl.

In certain embodiments, the present invention relates to the aforementioned compound, wherein Y is

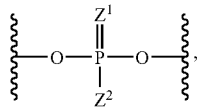

and there are at least ten instances when $Z^2$ is alkyl.

In certain embodiments, the present invention relates to the aforementioned compound, wherein in the linkage between the first nucleoside and second nucleoside at the terminus of said first strand, Y is

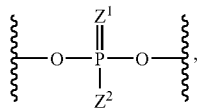

and $Z^2$ is alkyl.

In certain embodiments, the present invention relates to the aforementioned compound, wherein in the linkage between the first and second nucleoside at the 3'-terminus of said first strand, Y is

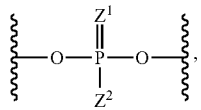

and $Z^2$ is alkyl.

In certain embodiments, the present invention relates to the aforementioned compound, wherein in the linkage between the first and second nucleoside at the 3'-terminus of said first strand and said second strand, Y is

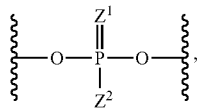

and $Z^2$ is alkyl.

In certain embodiments, the present invention relates to the aforementioned compound, wherein $n^1$ is 1.

In certain embodiments, the present invention relates to the aforementioned compound, wherein t is 0 or 1.

In certain embodiments, the present invention relates to the aforementioned compound, wherein x is 1.

In certain embodiments, the present invention relates to the aforementioned compound, wherein the $n^2$ is 17, 18, 19, 20, 21, 22, or 23.

In certain embodiments, the present invention relates to the aforementioned compound, wherein $n^2$ is 19, 20, or 21.

In certain embodiments, the present invention relates to the aforementioned compound, wherein $n^2$ is 20.

In certain embodiments, the present invention relates to the aforementioned compound, wherein $R^1$ is H.

In certain embodiments, the present invention relates to the aforementioned compound, wherein $R^2$ and $R^3$ represent independently for each occurrence OH, F, —Oalkyl, —Oallyl, —Oalkylamine, or —O-$A^6$-[$A^7$-($A^5$)$_w$]$_y$.

In certain embodiments, the present invention relates to the aforementioned compound, wherein $R^2$ and $R^3$ represent independently for each occurrence OH, F, —Oalkyl, —Oallyl, or —Oalkylamine.

In certain embodiments, the present invention relates to the aforementioned compound, wherein $R^2$ and $R^3$ represent independently for each occurrence OH, F, —Oalkyl, —Oallyl, —Oalkylamine, —N($R^{19}$)$_2$, or —O-$A^6$-[$A^7$-($A^5$)$_w$]$_y$.

In certain embodiments, the present invention relates to the aforementioned compound, wherein $R^2$ and $R^3$ represent independently for each occurrence OH, F, —Oalkyl, —Oallyl, —Oalkylamine, or —N($R^{19}$)$_2$.

In certain embodiments, the present invention relates to the aforementioned compound, wherein $R^3$ represents independently for each occurrence H, OH, F, —OCH$_3$, —O(CH$_2$)$_2$O$R^{19}$, —O(CH$_2$)$_2$S$R^{19}$, —O(CH$_2$)$_2$N($R^{19}$)$_2$, —OCH$_2$C(O)N(H)CH$_3$, —NH$_2$, —N(CH$_3$)$_2$, —N(H)CH$_3$, —SCH$_3$, —O(CH$_2$)$_2$OCH$_3$, —O(CH$_2$)$_2$SCH$_3$, —O(CH$_2$)$_2$—O—(CH$_2$)$_2$N(CH$_3$)$_2$, or —O(CH$_2$)$_2$ON(CH$_3$)$_2$.

In certain embodiments, the present invention relates to the aforementioned compound, wherein $R^3$ represents independently for each occurrence —NH$_2$, —N(CH$_3$)$_2$, or —N(H)CH$_3$.

In certain embodiments, the present invention relates to the aforementioned compound, wherein $R^4$ represents independently for each occurrence H, OH, F, —OCH$_3$, —O(CH$_2$)$_2$O$R^{19}$, —O(CH$_2$)$_2$S$R^{19}$, —O(CH$_2$)$_2$N($R^{19}$)$_2$, —OCH$_2$C(O)N(H)CH$_3$, —NH$_2$, —N(CH$_3$)$_2$, —N(H)CH$_3$, —SCH$_3$, —O(CH$_2$)$_2$OCH$_3$, —O(CH$_2$)$_2$SCH$_3$, —O(CH$_2$)$_2$—O—(CH$_2$)$_2$N(CH$_3$)$_2$, or —O(CH$_2$)$_2$ON(CH$_3$)$_2$.

In certain embodiments, the present invention relates to the aforementioned compound, wherein $R^4$ represents independently for each occurrence OH, F, —Oalkyl, —Oallyl, or —Oalkylamine.

In certain embodiments, the present invention relates to the aforementioned compound, wherein $R^4$ represents independently for each occurrence —NH$_2$, —N(H)CH$_3$, or —N(CH$_3$)$_2$.

In certain embodiments, the present invention relates to the aforementioned compound, wherein $R^3$ and $R^4$ represent independently OH, —Oalkyl, or —Oallyl.

In certain embodiments, the present invention relates to the aforementioned compound, wherein $R^3$ and $R^4$ represent independently —NH$_2$, —N(H)CH$_3$, or —N(CH$_3$)$_2$.

In certain embodiments, the present invention relates to the aforementioned compound, wherein at least two instances of $R^4$ are OH.

In certain embodiments, the present invention relates to the aforementioned compound, wherein at least five instances of $R^4$ are OH.

In certain embodiments, the present invention relates to the aforementioned compound, wherein at least ten instances of $R^4$ are OH.

In certain embodiments, the present invention relates to the aforementioned compound, wherein at least fifteen instances of $R^4$ are OH.

In certain embodiments, the present invention relates to the aforementioned compound, wherein $R^5$ is H.

In certain embodiments, the present invention relates to the aforementioned compound, wherein $Z^2$ represents independently for each occurrence methyl, —OM, —Oalkyl, —Oaryl, —Oaralkyl, —SM, —Salkyl, —Saryl, —Saralkyl, —[C($R^5$)$_2$]$_m$N($R^6$)$_2$, —N($R^{10}$)$R^{11}$, or —N($R^{19}$)(C($R^{19}$)$_2$)$_m$N($R^{19}$)$_2$.

In certain embodiments, the present invention relates to the aforementioned compound, wherein $Z^3$ is O.

In certain embodiments, the present invention relates to the aforementioned compound, wherein $Z^4$ represents independently for each occurrence —OM, —Oalkyl, —Oaryl, or —Oaralkyl.

In certain embodiments, the present invention relates to the aforementioned compound, wherein $Z^4$ represents independently for each occurrence methyl, —OM, —Oalkyl, —Oaryl, —Oaralkyl, —SM, —Salkyl, —Saryl, —Saralkyl, —[C($R^5$)$_2$]$_m$N($R^6$)$_2$, —N($R^{10}$)$R^{11}$, or —N($R^{19}$)(C($R^{19}$)$_2$)$_m$N($R^{19}$)$_2$.

In certain embodiments, the present invention relates to the aforementioned oligonucleotide, wherein $A^2$ represents independently for each occurrence:

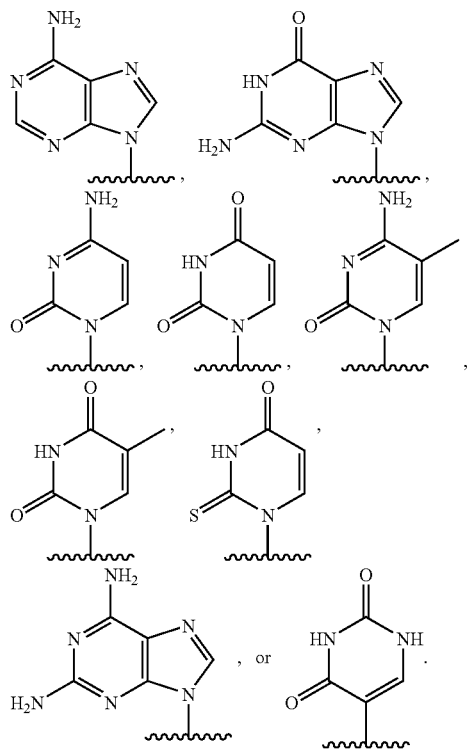

In certain embodiments, the present invention relates to the aforementioned compound, wherein $A^4$ represents independently for each occurrence

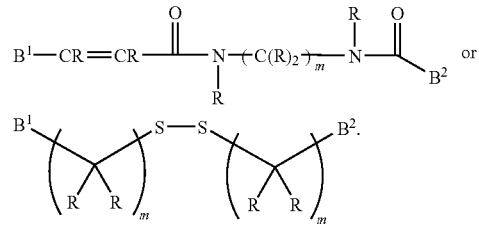

In certain embodiments, the present invention relates to the aforementioned compound, wherein $A^4$ represents independently for each occurrence

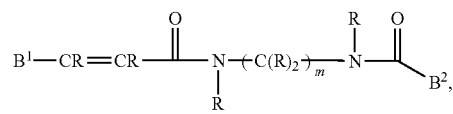

and $A^5$ represents independently for each occurrence

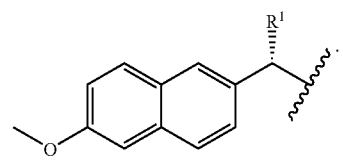

In certain embodiments, the present invention relates to the aforementioned compound, wherein $A^4$ represents independently for each occurrence

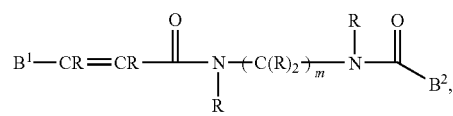

and $A^5$ represents independently for each occurrence

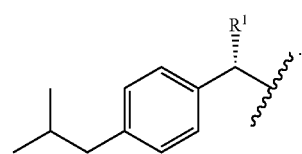

In certain embodiments, the present invention relates to the aforementioned compound, wherein $A^5$ occurs at least once.

In certain embodiments, the present invention relates to the aforementioned compound, wherein $A^5$ occurs at least five times.

In certain embodiments, the present invention relates to the aforementioned compound, wherein $A^5$ is —(C(R)$_2$)$_m$-$A^{99}$, wherein $A^{99}$ is optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, or tetrazolyl.

In certain embodiments, the present invention relates to the aforementioned compound, wherein $A^5$ is represented by formula VI:

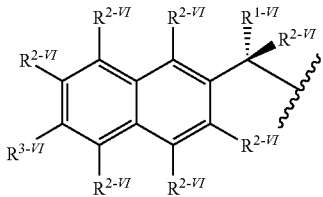

wherein
$R^{1-VI}$, $R^{2-VI}$, and $R^{3-VI}$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —$CO_2R$.

In certain embodiments, the present invention relates to the aforementioned compound, wherein $A^5$ is represented by formula VI, and $R^{1-VI}$ is alkyl.

In certain embodiments, the present invention relates to the aforementioned compound, wherein $A^5$ is represented by formula VI, and $R^{1-VI}$ is methyl, ethyl, propyl, isopropyl, butyl, sec-butyl, isobutyl, or tert-butyl.

In certain embodiments, the present invention relates to the aforementioned compound, wherein $A^5$ is represented by formula VI, and $R^{1-VI}$ is methyl.

In certain embodiments, the present invention relates to the aforementioned compound, wherein $A^5$ is represented by formula VI, and $R^{2-VI}$ is H.

In certain embodiments, the present invention relates to the aforementioned compound, wherein $A^5$ is represented by formula VI, and $R^{3-VI}$ is alkoxyl.

In certain embodiments, the present invention relates to the aforementioned compound, wherein $A^5$ is represented by formula VI, and $R^{3-VI}$ is methoxy, ethoxy, propoxy, isopropoxy, butoxy, sec-butoxy, isobutoxy, or tert-butoxy.

In certain embodiments, the present invention relates to the aforementioned compound, wherein $A^5$ is represented by formula VI, and $R^{3-VI}$ is methoxy.

In certain embodiments, the present invention relates to the aforementioned compound, wherein $A^5$ is represented by formula VI, $R^{1-VI}$ is methyl, $R^{2-VI}$ is H, and $R^{3-VI}$ is methoxy.

In certain embodiments, the present invention relates to the aforementioned compound, wherein $A^5$ is represented by formula VII:

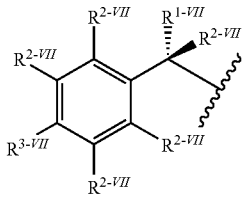

wherein
$R^{1-VII}$, $R^{2-VII}$, and $R^{3-VII}$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —$CO_2R$.

In certain embodiments, the present invention relates to the aforementioned compound, wherein $A^5$ is represented by formula VII, and $R^{1-VII}$ is alkyl.

In certain embodiments, the present invention relates to the aforementioned compound, wherein $A^5$ is represented by formula VII, and $R^{1-VII}$ is methyl, ethyl, propyl, isopropyl, butyl, sec-butyl, isobutyl, or tert-butyl.

In certain embodiments, the present invention relates to the aforementioned compound, wherein $A^5$ is represented by formula VII, and $R^{1-VII}$ is methyl.

In certain embodiments, the present invention relates to the aforementioned compound, wherein A is represented by formula VII, and $R^{2-VII}$ is H.

In certain embodiments, the present invention relates to the aforementioned compound, wherein $A^5$ is represented by formula VII, and $R^{3-VII}$ is alkyl.

In certain embodiments, the present invention relates to the aforementioned compound, wherein $A^5$ is represented by formula VII, and $R^{3-VII}$ is methyl, ethyl, propyl, isopropyl, butyl, sec-butyl, isobutyl, tert-butyl, pentyl, hexyl, or heptyl.

In certain embodiments, the present invention relates to the aforementioned compound, wherein $A^5$ is represented by formula VII, and $R^{3-VII}$ is isobutyl.

In certain embodiments, the present invention relates to the aforementioned compound, wherein $A^5$ is represented by formula VII, $R^{1-VII}$ is methyl, $R^{2-VII}$ is H, and $R^{3-VII}$ is isobutyl.

In certain embodiments, the present invention relates to the aforementioned compound, wherein $A^5$ is represented by formula VII, and $R^2$ represents independently for each occurrence H, OH, F, or —Oalkyl.

In certain embodiments, the present invention relates to the aforementioned compound, wherein $R^3$ and $R^4$ represent independently for each occurrence —$NH_2$, —$N(H)CH_3$, or —$N(CH_3)_2$.

In certain embodiments, the present invention relates to the aforementioned compound, further provided that at least ten instances of Y are not

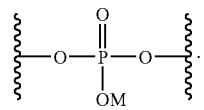

In certain embodiments, the present invention relates to the aforementioned compound, further provided that at least one instance of Y is not

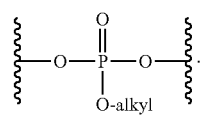

In certain embodiments, the present invention relates to the aforementioned compound, further provided that at least ten instances of Y are not

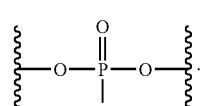

In certain embodiments, the present invention relates to the aforementioned compound, further provided that at least one instance of Y is not

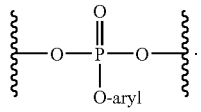

In certain embodiments, the present invention relates to the aforementioned compound, further provided that at least ten instances of Y are not

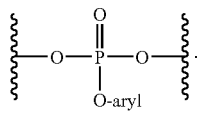

In certain embodiments, the present invention relates to the aforementioned compound, further provided that at least one instance of Y is not

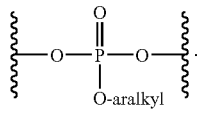

In certain embodiments, the present invention relates to the aforementioned compound, further provided that at least ten instances of Y are not

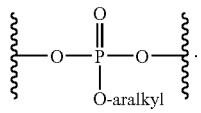

Methods of the Invention

One aspect of the present invention relates to a method of treating a patient suffering from a malady selected from the group consisting of unwanted cell proliferation, arthritis, retinal neovascularization, viral infection, bacterial infection, amoebic infection, parasitic infection, fungal infection, unwanted immune response, asthma, lupus, multiple sclerosis, diabetes, acute pain, chronic pain, neurological disease, and a disorder characterized by loss of heterozygosity; comprising the step of:

administering to a patient in need thereof a therapeutically effective amount of an oligonucleotide, wherein said oligonucleotide is a single-stranded oligonucleotide represented by formula V as described above, or said oligonucleotide is a double-stranded oligonucleotide comprising a first strand and a second strand, wherein said first strand and said second are represented independently by formula II as described above.

In certain embodiments, the present invention relates to the aforementioned method, wherein said malady is unwanted cell proliferation.

In certain embodiments, the present invention relates to the aforementioned method, wherein said malady is testicular cancer, lung cancer, breast cancer, colon cancer, squamous cell carcinoma, pancreatic cancer, leukemia, melanoma, Burkitt's lymphoma, neuroblastoma, ovarian cancer, prostate cancer, skin cancer, non-Hodgkin lymphoma, esophageal cancer, cervical cancer, basal cell carcinoma, adenocarcinoma, hepatocellular carcinoma, colorectal adenocarcinoma, liver cancer, male breast carcinoma, adenocarcinomas of the esophagus, adenocarcinomas of the stomach, adenocarcinomas of the colon, adenocarcinomas of the rectum, gall bladder cancer, hamartomas, gliomas, endometrial cancer, acute leukemia, chronic leukemia, childhood acute leukemia, Ewing Sarcoma, Myxoid liposarcoma, brain cancer, or tumors of epithelial origin.

In certain embodiments, the present invention relates to the aforementioned method, wherein said malady is rheumatoid arthritis or retinal neovascularization.

In certain embodiments, the present invention relates to the aforementioned method, wherein said malady is a viral infection.

In certain embodiments, the present invention relates to the aforementioned method, wherein said malady is a disorder mediated by Human Papilloma Virus, Human Immunodeficiency Virus, Hepatitis A Virus, Hepatitis B Virus, Hepatitis C Virus, Hepatitis D Virus, Hepatitis E Virus, Hepatitis F Virus, Hepatitis G Virus, Hepatitis H Virus, Respiratory Syncytial Virus, Herpes Simplex Virus, herpes Cytomegalovirus, herpes Epstein Barr Virus, a Kaposi's Sarcoma-associated Herpes Virus, JC Virus, myxovirus, rhinovirus, coronavirus, West Nile Virus, St. Louis Encephalitis, Tick-borne encephalitis virus gene, Murray Valley encephalitis virus gene, dengue virus gene, Simian Virus 40, Human T Cell Lymphotropic Virus, a Moloney-Murine Leukemia Virus, encephalomyocarditis virus, measles virus, Vericella zoster virus, adenovirus, yellow fever virus, poliovirus, or poxvirus.

In certain embodiments, the present invention relates to the aforementioned method, wherein said malady is a bacterial infection, amoebic infection, parasitic infection, or fungal infection.

In certain embodiments, the present invention relates to the aforementioned method, wherein said malady is a disorder mediated by *plasmodium, Mycobacterium ulcerans, Mycobacterium tuberculosis, Mycobacterium leprae, Staphylococcus aureus, Streptococcus pneumoniae, Streptococcus pyogenes, Chlamydia pneumoniae*, or *Mycoplasma pneumoniae*.

In certain embodiments, the present invention relates to the aforementioned method, wherein said malady is an unwanted immune response, asthma, lupus, multiple sclerosis, or diabetes.

In certain embodiments, the present invention relates to the aforementioned method, wherein said malady is an ischemia, reperfusion injury, response to a transplantated organ or tissue, restenosis, or Inflammatory Bowel Disease.

In certain embodiments, the present invention relates to the aforementioned method, wherein said malady is acute pain or chronic pain.

In certain embodiments, the present invention relates to the aforementioned method, wherein said malady is a neurological disease.

In certain embodiments, the present invention relates to the aforementioned method, wherein said malady is Alzheimer Disease, Parkinson Disease, or a neurodegenerative trinucleotide repeat disorder.

In certain embodiments, the present invention relates to the aforementioned method, wherein said malady is a disorder characterized by loss of heterozygosity.

In certain embodiments, the present invention relates to the aforementioned method, wherein said oligonucleotide is a double-stranded oligonucleotide comprising a first strand and a second strand, wherein said first strand and said second are represented independently by formula II as described above.

Another aspect of the present invention relates to a method of gene-silencing, comprising the steps of:

administering a therapeutically effective amount of an oligonucleotide to a mammalian cell to silence a gene promoting unwanted cell proliferation, growth factor gene, growth factor receptor gene, a kinase gene, a gene encoding a G protein superfamily molecule, a gene encoding a transcription factor, a gene which mediates angiogenesis, a viral gene of a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene; wherein said oligonucleotide is a single-stranded oligonucleotide represented by formula V as described above, or said oligonucleotide is a double-stranded oligonucleotide comprising a first strand and a second strand represented by formula II as described above.

In certain embodiments, the present invention relates to the aforementioned method, wherein said oligonucleotide is a double-stranded oligonucleotide comprising a first strand and a second strand, wherein said first strand and said second are represented independently by formula II as described above.

Another aspect of the present invention relates to a method of gene-silencing, comprising the steps of:

administering a therapeutically effective amount of an oligonucleotide to a mammalian cell to silence a PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium* ulcerans gene, a gene that is required for *Mycobacterium* ulcerans replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene; wherein said oligonucleotide is a single-stranded oligonucleotide represented by formula V as described above, or said oligonucleotide is a double-stranded oligonucleotide comprising a first strand and a second strand represented by formula II as described above.

In certain embodiments, the present invention relates to the aforementioned method, wherein said oligonucleotide is a double-stranded oligonucleotide comprising a first strand and a second strand, wherein said first strand and said second are represented independently by formula II as described above.

Another aspect of the present invention relates to a method of gene-silencing, comprising the steps of:

administering a therapeutically effective amount of an oligonucleotide to a mammal to silence a gene promoting unwanted cell proliferation, growth factor or growth factor receptor gene, a kinase gene, a gene encoding a G protein superfamily molecule, a gene encoding a transcription factor, a gene which mediates angiogenesis, a viral gene of a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene; wherein said oligonucleotide is a single-stranded oligonucleotide represented by formula V as described above, or said oligonucleotide is a double-stranded oligonucleotide comprising a first strand and a second strand represented by formula II as described above.

In certain embodiments, the present invention relates to the aforementioned method, wherein said oligonucleotide is a double-stranded oligonucleotide comprising a first strand and a second strand, wherein said first strand and said second are represented independently by formula II as described above.

Another aspect of the present invention relates to a method of gene-silencing, comprising the steps of:

administering a therapeutically effective amount of an oligonucleotide to a mammal to silence a PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium* ulcerans gene, a gene that is required for *Mycobacterium* ulcerans replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene; wherein said oligonucleotide is a single-stranded oligonucleotide represented by formula V as described above, or said oligonucleotide is a double-stranded oligonucleotide comprising a first strand and a second strand represented by formula II as described above.

In certain embodiments, the present invention relates to the aforementioned method, wherein, said mammal is a primate, equine, canine or feline.

In certain embodiments, the present invention relates to the aforementioned method, wherein, said mammal is a human.

In certain embodiments, the present invention relates to the aforementioned method, wherein said oligonucleotide is a double-stranded oligonucleotide comprising a first strand and a second strand, wherein said first strand and said second are represented independently by formula II as described above.

DEFINITIONS

For convenience, certain terms employed in the specification, examples, and appended claims are collected here.

The term "silence" means to at least partially suppress. For example, in certain instances, the gene is suppressed by at least about 25%, 35%, or 50% by administration of an oligonucleotide of the invention. In a preferred embodiment, the gene is suppressed by at least about 60%, 70%, or 80% by administration of an oligonucleotide of the invention. In a more preferred embodiment, the gene is suppressed by at least about 85%, 90%, or 95% by administration of an oligonucleotide of the invention. In a most preferred embodiment, the gene is suppressed by at least about 98% or 99% by administration of an oligonucleotide of the invention.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

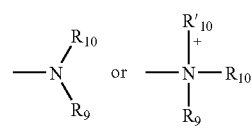

wherein $R_9$, $R_{10}$ and $R'_{10}$ each independently represent a group permitted by the rules of valence.

The term "acylamino" is art-recognized and refers to a moiety that can be represented by the general formula:

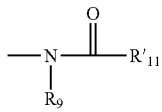

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

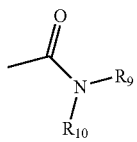

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

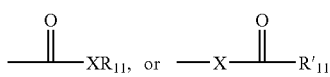

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

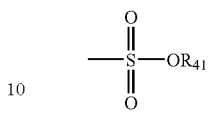

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

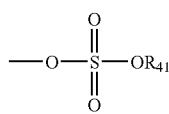

in which $R_{41}$ is as defined above.

The term "sulfonylamino" is art recognized and includes a moiety that can be represented by the general formula:

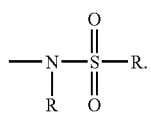

The term "sulfamoyl" is art-recognized and includes a moiety that can be represented by the general formula:

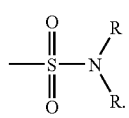

The term "sulfonyl", as used herein, refers to a moiety that can be represented by the general formula:

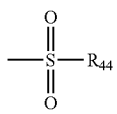

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

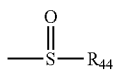

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated as alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT application WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See, e.g., U.S. Pat. No. 4,737,323.

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants, such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXEMPLIFICATION

The invention now being generally described, it will be more readily understood by reference to the following examples, which are included merely for purposes of illustration of certain aspects and embodiments of the present invention, and are not intended to limit the invention.

Example 1

Monomer Synthesis

Scheme 1[a]

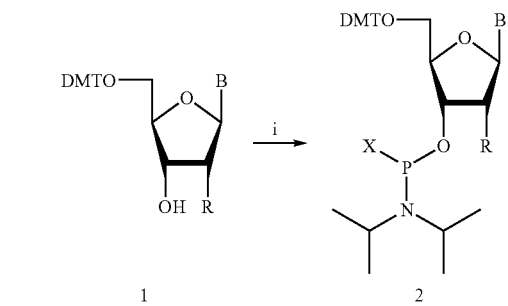

X = ispropyl, t-butyl, n-butyl, isobutyril, isopentyl, phenyl, aralkyl or any branched alkyl and aralkyl ——$(CH_2)_n$——Y and Y = H, OAc, COOMe, COOEt, NHCOCF$_3$, N(CH$_3$)(COCF$_3$) or NMe$_2$ and n = 1-20

R = ——OTBDMS, F, SMe,

——O[(CH$_2$)$_n$O]$_m$Me, where m = 1-20 and n = 1-20

——O[(CH$_2$)$_n$O]$_m$NMe$_2$, where m = 1-20 and n = 1-20

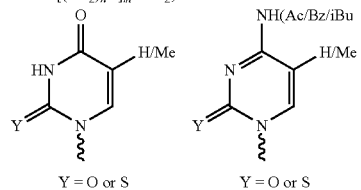

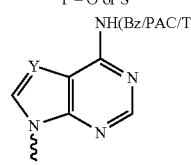

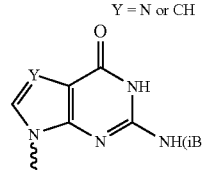

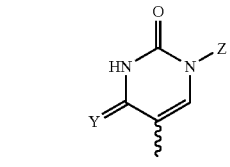

Z = H, ——$(CH_2)_n$——Y and Y = H, OAc, COOMe, COOEt, NHCOCF$_3$, N(CH$_3$)(COCF$_3$) or NMe$_2$ and n = 1-20

Y = N or CH

[a] (i) X——P(Cl)——N(iPr)$_2$, TEA/dichloromethane or X——P——[N(iPr)$_2$]$_2$, tetrazole/tetrazole-diisopropylammonium salt/MeCN; or X——(Cl$_2$), one eq. HN(iPr)$_2$ followed by one 1 eq. 1 in MeCN/dichloromethane.

Synthesis of methylphosphonamidite [2, R=OTBDMS, X=Me, B=Adenine (N-bz); Cytosine (N—Ac); 5-Methylcytosine (N-Bz); Uracil; 5-Methyluracil; Guanine (N-iBu); or Inosine, Scheme 1)

Method 1

Appropriately base protected 5'-O-DMT-2'-O-TBDS-nucleoside (adenosine, guanosine, cytidine, 5-methylcytidine, uridine, 5-methyluridine or inosine) purchased from ChemGenes Corporation, 33 Industrial Way, Wilmington, Mass. is reacted with 1.2 equivalent of chloro-N,N-diisopropylaminomethylphosphine (obtained from ChemGenes Corporation, 33 Industrial Way, Wilmington, Mass.) in anhydrous dichloromethane (or THF) containing 3.0 equivalent of diisopropylethylamine to obtain a diastereomeric mixture of the desired methylphosphonamidite 2 as reported by Sinha et al. (*Nucleic Acids Res.*, 1994, 22, 3119).

(N-Bz)-5'-O-DMT-2'-O-TBDMS-Adenosine-3'-O—(P-Methyl)phosphonamidite: To a solution of (N-Bz)-5'-O-DMT-2'-O-TBDMS-adenosine (5 g, 6.4 mmol) in anhydrous dichloromethane (50 mL) were added anhydrous diisopropyl amine (2.06 g, 2.8 mL, 16 mmol) and methyl-N,N'-diisopropylamino-chlorophosphine (2.3 g, 2.3 mL, 12.8 mmol) under argon atm. The reaction mixture was stirred at rt for 16 h. It was then diluted with dichloromethane (50 mL) and poured into ice-cold water (50 mL), shaken and separated. The aqueous layer was extracted with dichloromethane (3×25 mL). The combined organic layer was dried over anhydrous sodium sulfate and filtered. Upon removal of solvent under reduced pressure, 5.5 g of crude product was obtained. The crude product was subjected to flash column chromatography over silica gel. Hexane:EtOAc:Et$_3$N (74:25:1) mixture was used to elute the product. The product was obtained as a white foamy solid. (4.4 g, 74%). $^1$H NMR (400 MHz, CDCl$_3$): δ 8.68 (s, 1H), 7.98 (s, 1H), 7.7-7.8 (m, 4H), 7.54 (m, 4H), 7.2 (m, 2H), 7.05 (m, 2H), 6.94 (m, 2H), 6.78 (m, 4H), 6.2 (d, 1H), 6.08 (d, 1H, minor diastereomer), 5.45 (m, 1H), 5.16 (m, 1H, minor diastereomer), 4.58 (m, 2H), 3.78 (m, 1H), 3.64 (m, 1H), 3.32 (s, 6H), 2.4 (m, 2H), 1.4 (d, 2H), 1.05 (m, 7H), 0.9-1.0 (m, 8H), 0.8 (s, 9H), 0.2 (s, 3H). $^{31}$P NMR (161.82 MHz, CDCl$_3$): δ 122.01, 118.81. $^{13}$C NMR (100 MHz, CDCl$_3$): δ 159.23, 159.21, 152.18, 150.82, 145.55, 142.44, 136.31, 136.26, 136.14, 136.07, 134.79, 131.9, 130.67, 130.64, 128.85, 128.65, 128.12, 127.88, 127.19, 127.12, 124.58, 113.61, 88.96, 87.25, 85.28, 76.88, 76.73, 75.3, 64.35, 60.02, 54.78, 46.71, 44.43, 44.33, 25.93, 25.87, 20.52, 18.3, 18.15, 17.96, 17.84, 17.72, 14.17, 12.35.

(N-iBU)-5'-O-DMT-2'-O-TBDMS-Guanosine-3'-O—(P-Methyl)phosphonamidite: To a solution of (N-iBu)-5'-O-DMT-2'-O-TBDMS-guanosine (10 g, 12.98 mmol) in anhydrous dichloromethane (75 mL) were added anhydrous diisopropyl amine (5.03 g, 6.78 mL, 38.94 mmol) and methyl-N,N'-diisopropylamino-chlorophosphine (4.7 g, 4.7 mL, 25.9 mmol) under argon atm. The reaction mixture was stirred at rt for 5 h. It was then diluted with dichloromethane (100 mL) and poured into ice-cold water (50 mL), shaken and separated. The aqueous layer was extracted with dichloromethane (3×50 mL). The combined organic layer was dried over anhydrous sodium sulfate and filtered. Upon removal of solvent under reduced pressure, 11.1 g of crude product was obtained. The crude product was subjected to flash column chromatography over silica gel. Hexane:EtOAc:Et$_3$N (59:40:1) mixture was used to elute the product. The product was obtained as a white foamy solid. (9.0 g, 73%). $^1$H NMR (400 MHz, CDCl$_3$): δ 7.84 (s, 1H), 7.72 (d, 2H), 7.56 (m, 5H), 7.0-7.2 (m, 4H), 6.8 (m, 5H), 6.16 (d, 1H, minor diastereomer), 6.02 (d, 1H), 5.38 (m, 1H), 5.02 (m, 1H, minor diastereomer), 4.72 (m, 1H, minor diastereomer), 4.58 (m, 1H, minor diastereomer), 3.98 (s, 1H), 3.88 (m, 1H, minor diastereomer), 3.72 (m, 1H), 3.32 (d, 6H), 2.3 (s, 1H), 2.1 (s, 1H), 1.5 (m, 1H), 1.36 (d, 2H), 1.0 (m, 9H), 0.9 (s, 9H). $^{31}$P NMR (161.82 MHz, CDCl$_3$): δ 122.53, 115.88.

(N—Ac)-5'-O-DMT-2'-O-TBDMS-Cytidine-3'-O—(P-Methyl)phosphonamidite: The desired phosphonamidite (4.80 g, 66.3%) was prepared from (N—Ac)-5'-O-DMT-2'-O-TBDMS-Cytidine (6.0 g, 8.548 mmol) and methyl-N,N'-diisopropylamino-chlorophosphine (5.0 g, 27.526 mmol) in the presence of diisopropylethylamine (9 mL, 51.66 mmol) and purified as described above. $^{31}$P NMR (161.81 MHz, CDCl$_3$): δ 122.54, 121.63

5-Me-5'-O-DMT-2'-O-TBDMS-Uridine-3'-O—(P-Methyl) phosphonamidite: The desired phosphonamidite (1.90 g, 52.1%) was prepared from 5-Me-5'-O-DMT-2'-O-TBDMS-Uridine (3.0 g, 4.449 mmol) and methyl-N,N'-diisopropylamino-chlorophosphine (1.7 g, 9.354 mmol) in the presence of diisopropylethylamine (2.4 mL, 13.777 mmol) and purified as described above. $^{31}$P NMR (161.81 MHz, CDCl$_3$): δ 124.12, 117.38

Method 2

Appropriately base protected 5'-O-DMT-2'-O-TBDS-nucleoside (adenosine, guanosine, cytidine, 5-methylcytidine, uridine, 5-methyluridine or inosine) purchased from ChemGenes Corporation, 33 Industrial Way, Wilmington, Mass. is reacted with bis(diisopropylamino)methylphosphine and 1H-tetrazole in acetonitrile to obtain a diastereomeric mixture of the desired methylphosphonamidite 2 as reported in the literature (Lauritsen et al., *Bioorg. Med. Chem. Lett.*, 2003, 13, 253). The bis(diisopropylamino)methylphosphine reagent is obtained as reported Moriarty et al. (*J. Am. Chem. Soc.*, 1990, 112, 8575).

Method 3

Methyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside is added under constant stirring at ambient temperature. The diastereomeric mixture of the desired methylphosphonamidite after standard workup is purified by flash silica gel column chromatography to obtain pure compound 2 (Vaghefi et al., *Nucleic Acids Res.*, 1995, 23, 3600).

Example 2

Synthesis of isopropylphosphonamidite [2, R=H, OTBDMS or OMe, X=Isopropyl, B=Adenine (N-bz); Cytosine (N—Ac); 5-Methylcytosine (N-Bz); Uracil; 5-Methyluracil; Guanine (N-iBu); or Inosine, Scheme 1)

Isopropyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside is added under constant stirring at ambient temperature. The diastereomeric mixture of the desired isopropylphosphonamidite after standard workup is purified by flash silica gel column chromatography to obtain pure compound 2 (Vaghefi et al., *Nucleic Acids Res.*, 1995, 23, 3600).

5'-O-DMT-2'-deoxy-thymidine-3'-O—(P-isopropyl)phosphonamidite: To a solution of i-Pr$_2$NH (0.31 ml) in dry CH$_3$CN (4 mL) at −20° C. was added dichloroisopropylphosphine (11 uL) and stirred at the same temperature for 20 to 40 min. 5'-DMTr-2'-deoxy-T (500 mg) in dry dichloromethane (2-3 mL) and triethylamine (0.18 mL) were added and stirred at RT for 16 h under an argon atmosphere. The reaction mixture was concentrated into a crude which was applied to a column of silica gel eluted with hexanes-ethyl acetate (1:1) to give a pure compound (450 mg, 65%) as two isomers. $^{31}$P-NMR (CDCl$_3$, 400 MHz): δ 133.61, 132.17.

Example 3

Synthesis of tert-butylphosphonamidite [2, R=H, OTBDMS or OMe, X=tert-Butyl, B=Adenine (N-bz); Cytosine (N—Ac); 5-Methylcytosine (N-Bz); Uracil; 5-Methyluracil; Guanine (N-iBu); or Inosine, Scheme 1)

tert-Butyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside is added under constant stirring at ambient temperature. The diastereomeric mixture of the desired tert-butylphosphonamidite after standard workup is purified by flash silicagel column chromatography to obtain pure compound 2 (Vaghefi et al., *Nucleic Acids Res.*, 1995, 23, 3600). 5'-O-DMT-2'-deoxy-thymidine-3'-O—(P-tert-butyl)phosphonamidite: To a solution of i-Pr$_2$NH (6.17 ml) in dry CH$_3$CN (50 mL) at −20° C. was added tert-butyldichlorophosphine (3.0 g) and stirred at −20 to 0° C. for 20 to 40 min. 5'-DMTr-2'-deoxy-T (10 g) in dry dichloromethane (50 mL) and triethylamine (3.56 mL) were added and stirred at RT for 4-6 days under an argon atmosphere. The reaction mixture was concentrated into a crude which was applied to a column of silica gel eluted with hexanes-ethyl acetate (1:1) to give a pure compound (200 mg, 1.42%) as two isomers. One isomer NMR data: $^1$H-NMR (CDCl$_3$, 400 MHz): δ 8.15 (br, NH), 7.58 (s, 1H), 7.40-7.20 (m, 9H, ArH),6.80 (d, 4H), 6.50-6.40 (dd, 1H, H'-1), 5.40 (t, 1H), 4.23 (dd, 1H), 3.79 (s, 6H, 2 OCH$_3$), 3.50-3.38 (m, 2H, H'-5a, H'-5b), 2.80 (dd, 1H, H'-2a), 2.50-2.40 (m, 1H, H'-2b), 2.10 (s, 3H, 5-CH$_3$), 1.50-1.00 (m, 23H). $^{31}$P-NMR (CDCl$_3$, 400 MHz): δ 133.47.

Example 4

Synthesis of methylphosphonamidite of psuedouridine (2, R=H or OTBDMS and Z=H, Scheme 1)

5'-O-DMT-2'-O-TBDMS pseudouridine is obtained as reported in the literature (Hall and McLaughlin, *Nucleic Acids Res.*, 1992, 20, 1883). The desired psuedouridine methylphonamidite is prepared from 5'-O-DMT-2'-O-TBDMS pseudouridine and chloro-N,N-diisopropylaminomethylphosphine as described in Example 1, method 2.

Synthesis of isopropylphosphonamidite of psuedouridine (2, R=H or OTBDMS and Z=H, Scheme 1)

5'-O-DMT-2'-O-TBDMS pseudouridine is obtained as reported in the literature (Hall and McLaughlin, *Nucleic Acids Res.*, 1992, 20, 1883). The desired psuedouridine isopropylphonamidite 2 is prepared from 5'-O-DMT-2'-O-TBDMS pseudouridine and dichloroisopropylphosphine as described in Example 1, method 3.

Synthesis of methylphosphonamidite of psuedouridine (2, R=OMe and Z=H, Scheme 1)

5'-O-DMT-2'-O-Me pseudouridine is obtained as reported in the literature (Ross et al., *Nucleosides Nucleotides*, 1997, 16, 1547). The desired psuedouridine methylphonamidite 2 is prepared from 5'-O-DMT-2'-O-Me pseudouridine and chloro-N,N-diisopropylaminomethylphosphine as described in Example 1, method 2.

Synthesis of isopropylphosphonamidite of psuedouridine (2, R=OMe and Z=H, Scheme 1)

5'-O-DMT-2'-O-Me pseudouridine is obtained as reported in the literature (Ross et al., *Nucleosides Nucleotides*, 1997, 16, 1547). The desired psuedouridine isopropylphonamidite 2 is prepared from 5'-O-DMT-2'-O-Me pseudouridine and dichloroisopropylphosphine as described in Example 1, method 3.

Example 5

Synthesis of methylphosphonamidite of 2'-O-Me-2-thiouridine (2, Scheme 1)

5'-O-DMT-2'-O-Me-2-thiouridine is obtained as reported in the literature (Shoda et al., *Bioorg. Med. Chem. Lett.*, 2000, 10, 1795). The desired methylphoanmidite 2 is prepared from 5'-O-DMT-2'-O-Me-2-thiouridine and chloro-N,N-diisopropylaminomethylphosphine as described in Example 1, method 2.

Synthesis of isopropylphosphonamidite of 2'-O-Me-2-thiouridine (2, Scheme 1)

5'-O-DMT-2'-O-Me-2-thiouridine is obtained as reported in the literature (Shoda et al., *Bioorg. Med. Chem. Lett.*, 2000, 10, 1795). The desired isopropylphoanmidite 2 is prepared from 5'-O-DMT-2'-O-Me-2-thiouridine and dichloroisopropylphosphine as described in Example 1, method 3.

Synthesis of methylphosphonamidite of 2'-deoxy-2-thiothymidine (2, Scheme 1)

The desired methylphoanmidite 2 is prepared from 5'-O-DMT-2'-deoxy-2-thiothymidine (Connolly et al, *Nucleic Acids Res.*, 1989, 17, 4957) and chloro-N,N-diisopropylaminomethylphosphine as described in Example 1, method 2.

Synthesis of isopropylphosphonamidite of 2'-deoxy-2-thiothymidine (2, Scheme 1)

The desired isopropylphoanmidite 2 is prepared from 5'-O-DMT-2'-deoxy-2-thiothymidine (Connolly et al, *Nucleic Acids Res.*, 1989, 17, 4957) and dichloroisopropylphosphine as described in Example 1, method 3.

Example 6

Synthesis of methylphosphonamidite of 7-deazaadenosine (N$^6$-bz, 2, Scheme 1)

N$^6$-Benzoyl-5'-O-(dimethoxytrityl)-7-deaza-2'-deoxyadenosine (1) is purchased from Berry & Associates, Inc. 2434 Bishop Circle East Dexter, Mich., 48130 USA. Compound 1 is reacted with chloro-N,N-diisopropylaminomethylphosphine as described in Example 1, method 2 to obtain diastereomeric mixture of the desired methylphosphonamidite 2.

Synthesis of methylphosphonamidite of 7-deazainosine (2, Scheme 1)

5'-O-DMT-7-deazainosine (1) is synthesized as reported in the literature (Seela and Klaus, *Nucleic Acids Res.*, 1986, 14, 1825). Compound 1 is reacted with chloro-N,N-diisopropylaminomethylphosphine as described in Example 1, method 2 to obtain diastereomeric mixture of the desired methylphosphonamidite 2.

Synthesis of methylphosphonamidite of 7-deazaguanosine (N$^2$-iBu, 2, Scheme 1)

N$^2$-isoBu-5'-O-DMT-7-deazaguanosine (1) is synthesized as reported in the literature (Seela and Driller, *Nucleic Acids Res.*, 1985, 13, 911). Compound 1 is reacted with chloro-N, N-diisopropylaminomethylphosphine as described in Example 1, method 2 to obtain diastereomeric mixture of the desired methylphosphonamidite 2.

Synthesis of isopropylphosphonamidite of 7-deazaadenosine (N⁶-bz, 2, Scheme 1)

N⁶-Benzoyl-5'-O-(dimethoxytrityl)-7-deaza-2'-deoxyadenosine (1) is purchased from Berry & Associates, Inc. 2434 Bishop Circle East Dexter, Mich., 48130 USA. Compound 1 is reacted with dichloroisopropylphosphine as described in Example 1, method 3 to obtain diastereomeric mixture of the desired isopropylphosphonamidite 2.

Synthesis of isopropylphosphonamidite of 7-deazainosine (2, Scheme 1)

5'-O-DMT-7-deazainosine (1) is synthesized as reported in the literature (Seela and Klaus, *Nucleic Acids Res.*, 1986, 14, 1825). Compound 1 is reacted with dichloroisopropylphosphine as described in Example 1, method 3 to obtain diastereomeric mixture of the desired isopropylphosphonamidite 2.

Synthesis of isopropylphosphonamidite of 7-deazaguanosine (N²-iBu, 2, Scheme 1)

N²-isoBu-5'-O-DMT-7-deazaguanosine (1) is synthesized as reported in the literature (Seela and Driller, *Nucleic Acids Res.*, 1985, 13, 911). Compound 1 is reacted with dichloroisopropylphosphine as described in Example 1, method 3 to obtain diastereomeric mixture of the desired isopropylphosphonamidite 2.

Example 7

Separation of R and S Isomers of Alkylphosphonamidites

A portion of the diastereomeric mixture of each of the alkylphosphonamidites obtained from Examples 1-6 is subjected to normal-phase high-performance liquid chromatography to obtain respective R and S stereo isomers as described by Cormier and Plomley (*J. Chromatography*, A, 1994, 662, 401).

Example 8

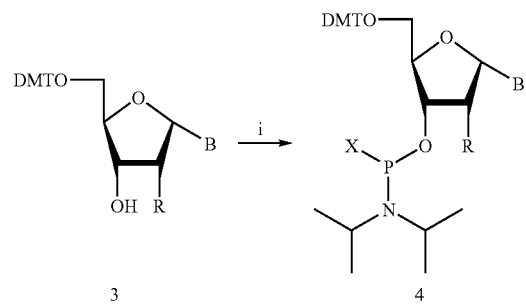

Scheme 2ᵃ

3                4

X = ispropyl, t-butyl, n-butyl, isobutyril, isopentyl, phenyl, aralkyl or any branched alkyl and aralkyl ——(CH₂)ₙ—Y and Y = H, OAc, COOMe, COOEt, NHCOCF₃, N(CH₃)(COCF₃) or NMe₂ and n = 1-20

R = ——OTBDMS, F, SMe,

——O[(CH₂)ₙO]ₘMe, where m = 1-20 and n = 1-20

——O[(CH₂)ₙO]ₘNMe₂, where m = 1-20 and n = 1-20

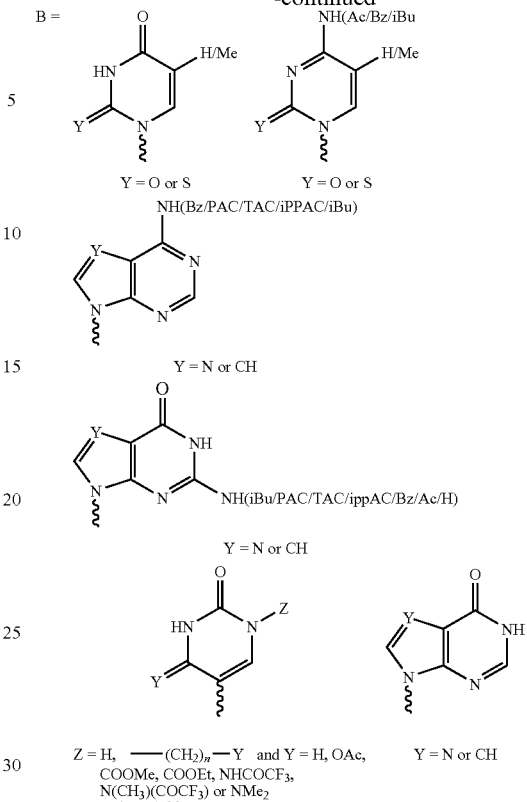

-continued

B =

Y = O or S    Y = O or S
NH(Bz/PAC/TAC/iPPAC/iBu)

Y = N or CH

NH(iBu/PAC/TAC/ippAC/Bz/Ac/H)

Y = N or CH

Z = H, ——(CH₂)ₙ—Y and Y = H, OAc, COOMe, COOEt, NHCOCF₃, N(CH₃)(COCF₃) or NMe₂ and n = 1-20

Y = N or CH

ᵃ (i) X——P(Cl)——N(iPr)₂, TEA/dichloromethane or X——P——[N(iPr)₂]₂, tetrazole/tetrazole-diisopropylammonium salt/MeCN; or X——P(Cl₂), one eq. HN(iPr)₂ followed by one 1 eq. 1 in MeCN/dichloromethane.

General synthetic procedure of methylphosphonamidite of α-anomeric B [4, A(N⁶-Bz), C(N-Bz), G(N²—Ac) and U; R=OTBDMS, X=Me, Scheme 2)

Method 1

5'-O-DMT-3'-O-TBDMS-6-N-benzoyl-α-adenosine, 5'-O-DMT-3'-O-TBDMS-4-N-benzoyl-α-cytidine, 5'-O-DMT-3'-O-TBDMS-2-N-acetyl-α-guanosine and 5'-O-DMT-3'-O-TBDMS-α-uridine are prepared as reported by Debart et al., (*Nucleic Acids Res.*, 1992, 20, 1193). The protected nucleoside 3 thus obtained is reacted with bis(diisopropylamino)methylphosphine and 1H-tetrazole in acetonitrile to obtain a diastereomeric mixture of the desired methylphosphonamidite 4 as reported in the literature (Lauritsen et al., *Bioorg. Med. Chem. Lett.*, 2003, 13, 253). The bis(diisopropylamino)methylphosphine reagent is obtained as reported Moriarty et al. (*J. Am. Chem. Soc.*, 1990, 112, 8575).

Method 2

5'-O-DMT-3'-O-TBDMS-6-N-benzoyl-α-adenosine, 5'-O-DMT-3'-O-TBDMS-4-N-benzoyl-α-cytidine, 5'-O-DMT-3'-O-TBDMS-2-N-acetyl-α-guanosine and 5'-O-DMT-3'-O-TBDMS-α-uridine are prepared as reported by Debart et al., (*Nucleic Acids Res.*, 1992, 20, 1193). The protected nucleoside 3 thus obtained is reacted with 1.2 equivalent of chloro-N,N-diisopropylaminomethylphosphine (obtained from ChemGenes Corporation, 33 Industrial Way, Wilmington, Mass.) in anhydrous dichloromethane (or THF) containing 3.0 equivalent of diisopropylethylamine obtain a diastereomeric mixture of the desired methylphosphonamidite 4 as reported by Sinha et al. (*Nucleic Acids Res.*, 1994, 22, 3119).

Method 3

Methyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside 3 is added under constant stirring at ambient temperature. The diastereomeric mixture of the desired methylphosphonamidite after standard workup is purified by flash silicagel column chromatography to obtain pure compound 4 (Vaghefi et al., Nucleic Acids Res., 1995, 23, 3600).

Example 9

General synthetic procedure of isopropylphosphonamidite of α-anomeric B [4, A($N^6$-Bz), C($N^4$-Bz), G($N^2$—Ac) and U; R=OTBDMS, X=Me, Scheme 2)

Isopropyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside 3 is added under constant stirring at ambient temperature. The diastereomeric mixture of the desired isopropylphosphonamidite after standard workup is purified by flash silicagel column chromatography to obtain pure compound 4 (Vaghefi et al., Nucleic Acids Res., 1995, 23, 3600).

Example 10

General synthetic procedure of tert-butylphosphonamidite of α-anomeric B [4, A($N^6$-Bz), C($N^4$-Bz), G($N^2$—Ac) and U; R=OTBDMS, X=Me, Scheme 2)

tert-Butyldichlorophosphine (purchased from Aldrich) is reacted with one equivalent of anhydrous diisopropylamine (purchased from Aldrich) in dichloromethane containing three equivalent of diisopropylethylamine. To the resulting reaction mixture one equivalent of the appropriately protected nucleoside 3 is added under constant stirring at ambient temperature. The diastereomeric mixture of the desired isopropylphosphonamidite after standard workup is purified by flash silicagel column chromatography to obtain pure compound 4 (Vaghefi et al., Nucleic Acids Res., 1995, 23, 3600).

Example 11

Separation of R and S Isomers of Alkylphosphonamidites

A portion of the diastereomeric mixture of each of the alkylphosphonamidites (4) obtained from Examples 8-10 is subjected to normal-phase high-performance liquid chromatography to obtain respective R and S stereo isomers as described by Cormier and Plomley (J. Chromatography, A, 1994, 662, 401).

Example 12

Oligonucleotide Synthesis and Purification

TABLE 17 siRNA duplexes with P-Alkylphosphonate backbone for biological assays.

| Number | Name | Sequence[a] |
|---|---|---|
| 11 | Luc duplex | 5'CUUACGCUGAGUACUUCGAdTdT3' (SEQ ID NO: 2)<br>3'dTdTGAAUGCGACUCAUGAAGCU5' (SEQ ID NO: 3) |
| 12 | Luc sense | 5'C*UUACGCUGAGUACUUCGAdTdT3' (SEQ ID NO: 4) |
| 13 | Luc sense | 5'C*UUACGCUGAGUACUUCGAdT*dT3' (SEQ ID NO: 5) |
| 14 | Luc sense | 5'C*UU*ACGCUGAGUACUUCGAdTdT3' (SEQ ID NO: 6) |
| 15 | Luc sense | 5'C*UU*ACGCUGAGU*ACUUCGAdTdT3' (SEQ ID NO: 7) |
| 16 | Luc sense | 5'C*UU*ACGCUGAGU*ACUUCGAdT*dT3' (SEQ ID NO: 8) |
| 17 | Luc sense | 5'C*U*U*ACGCUGAGU*ACUUCGAdTdT3' (SEQ ID NO: 9) |
| 18 | Luc sense | 5'C*U*U*ACGCUGAGU*ACUUCGA*dT*dT3' (SEQ ID NO: 10) |
| 19 | Luc sense | 5'C*U*U*ACGCUGAGU*ACUUCG*A*dT*dT3' (SEQ ID NO: 11) |
| 20 | Luc sense | 5'C*UU*AC*GC*UG*AG*UA*CU*UC*GA*dTdT3' (SEQ ID NO: 12) |
| 21 | Luc sense | 5'CU*UA*CG*CU*GA*GU*AC*UU*CG*A*dT*dT3' (SEQ ID NO: 13) |

TABLE 17-continued siRNA duplexes with P-Alkylphosphonate backbone for biological assays.

| Number | Name | Sequence[a] |
|---|---|---|
| 22 | Luc sense | 5'C*U*U*A*C*G*C*U*G*A*G*U*A*C*U*U*C*G*A*dT*dT³' (SEQ ID NO: 14) |
| 23 | Luc sense | 5'C#UUACGCUGAGUACUUCGAdTdT³' (SEQ ID NO: 15) |
| 24 | Luc sense | 5'C#UUACGCUGAGUACUUCGAdT#dT³' (SEQ ID NO: 16) |
| 25 | Luc sense | 5'C#UUACGCUGAGUACUUCGAdT*dT³' (SEQ ID NO: 17) |
| 26 | Luc sense | 5'CUU#ACGCUGAGUACUUCGAdTdT³' (SEQ ID NO: 18) |
| 27 | Luc sense | 5'C*UU#ACGCUGAGUACUUCGAdT*dT³' (SEQ ID NO: 19) |
| 28 | Luc sense | 5'CUUACGCUGAGU#ACUUCGAdTdT³' (SEQ ID NO: 20) |
| 29 | Luc sense | 5'CUU#ACGCUGAGU#ACUUCGAdT#dT³' (SEQ ID NO: 21) |
| 30 | Luc sense | 5'C*UUACGCUGAGUACUUCGAdT#dT³' (SEQ ID NO: 22) |
| 31 | Luc sense | 5'CUUACGCUGAGUACUUCGAdT#dT³' (SEQ ID NO: 23) |
| 32 | Luc sense | 5'CUUACGCUGAGUACUUCGAdT⁺dT³' (SEQ ID NO: 24) |
| 33 | Luc sense | 5'C*UUACGCUGAGUACUUCGAdTdT³' (SEQ ID NO: 25) |
| 34 | Luc sense | 5'CUUACGCUGAGU#ACUUCGAdT⁺dT³' (SEQ ID NO: 26) |
| 35 | Luc sense | 5'CUU#ACGCUGAGU#ACUUCGAdT⁺dT³' (SEQ ID NO: 27) |
| 36 | Luc antisense | 3'dT#dTGAAUGCGACUCAUGAAGCU⁵' (SEQ ID NO: 28) |
| 37 | Luc antisense | 3'dT#dTGAAUGCGACUCAUGAAGC*U⁵' (SEQ ID NO: 29) |
| 38 | Luc antisense | 3'dT⁺dTGAAUGCGACUCAUGAAGCU⁵' (SEQ ID NO: 30) |
| 39 | Luc antisense | 3'dT⁺dTGAAUGCGACUCAUGAAGC*U⁵' (SEQ ID NO: 31) |
| 40 | Luc antisense | 3'dT⁺dTGAAUGCGACUCAUGAAGC#U⁵' (SEQ ID NO: 32) |
| 41 | VEGF duplex | 5'GCGGAUCAAACCUCACCAAdTdT³' (SEQ ID NO: 33)<br>3'dTdTCGCCUAGUUUGGAGUGGUU⁵' (SEQ ID NO: 34) |
| 42 | VEGF sense | 5'G*CGGAUCAAACCUCACCAAdTdT³' (SEQ ID NO: 35) |
| 43 | VEGF sense | 5'G*CGGAUCAAACCUCACCAAdT*dT³' (SEQ ID NO: 36) |
| 44 | VEGF sense | 5'G*C*GGAUCAAACCUCACCAAdT*dT³' (SEQ ID NO: 37) |
| 45 | VEGF sense | 5'G*C*GGAUCAAACCUCACCAA*dT*dT³' (SEQ ID NO: 38) |
| 46 | VEGF sense | 5'G*CG*GA*UC*AA*AC*CU*CA*CC*AA*dTdT³' (SEQ ID NO: 39) |

TABLE 17-continued siRNA duplexes with P-Alkylphosphonate backbone for biological assays.

| Number | Name | Sequence[a] |
|---|---|---|
| 47 | VEGF sense | 5'GC*GG*AU*CA*AA*CC*UC*AC*CA*AdT*dT3' (SEQ ID NO: 40) |
| 48 | VEGF sense | 5'G*C*G*G*A*U*C*A*A*A*C*C*U*C*A*C*C*A*A*dT*dT3' (SEQ ID NO: 41) |
| 49 | VEGF sense | 5'GCGGAUCAAACCUCACCAAdT#dT3' (SEQ ID NO: 42) |
| 50 | VEGF sense | 5'G*CGGAUCAAACCUCACCAAdT#dT3' (SEQ ID NO: 43) |
| 51 | VEGF sense | 5'GCGGAUCAAACCUCACCAAdT+dT3' (SEQ ID NO: 44) |
| 52 | VEGF sense | 5'G*CGGAUCAAACCUCACCAAdT+dT3' (SEQ ID NO: 45) |
| 53 | VEGF antisense | 3'dT#dTCGCCUAGUUUGGAGUGGUU5' (SEQ ID NO: 46) |
| 54 | VEGF antisense | 3'dT#dTCGCCUAGUUUGGAGUGGU*U5' (SEQ ID NO: 47) |
| 55 | VEGF antisense | 3'dT+dTCGCCUAGUUUGGAGUGGUU5' (SEQ ID NO: 48) |
| 56 | VEGF antisense | 3'dT+dTCGCCUAGUUUGGAGUGGU*U5' (SEQ ID NO: 49) |
| 57 | VEGF antisense | 3'dT+dTCGCCUAGUUUGGAGUGGU#U5' (SEQ ID NO: 50) |
| 58 | PTEN[b] | 5'CAAAUCCAGAGGCUAGCAGdTdT3' (SEQ ID NO: 51) <br> 3'dTdTGUUUAGGUCUCCGAUCGUC5' (SEQ ID NO: 52) |
| 59 | PTEN sense | 5'C*AAAUCCAGAGGCUAGCAGdTdT3' (SEQ ID NO: 53) |
| 60 | PTEN sense | 5'C*AAAUCCAGAGGCUAGCAGdT*dT3' (SEQ ID NO: 54) |
| 61 | PTEN sense | 5'C*A*AUCCAGAGGCUAGCAGdT*dT3' (SEQ ID NO: 55) |
| 62 | PTEN sense | 5'C*AA*AU*CC*AG*AG*GC*UA*GC*AG*dTdT3' (SEQ ID NO: 56) |
| 63 | PTEN sense | 5'CA*AA*UC*CA*GA*GG*CU*AG*CA*GdT*dT3' (SEQ ID NO: 57) |
| 64 | PTEN sense | 5'C*A*A*A*U*C*C*A*G*A*G*G*C*U*A*G*C*A*G*dT*dT3' (SEQ ID NO: 58) |
| 65 | PTEN sense | 5'CAAAUCCAGAGGCUAGCAGdT#dT3' (SEQ ID NO: 59) |
| 66 | PTEN sense | 5'C#AAAUCCAGAGGCUAGCAGdT#dT3' (SEQ ID NO: 60) |
| 67 | PTEN sense | 5'C*AAAUCCAGAGGCUAGCAGdT#dT3' (SEQ ID NO: 61) |
| 68 | PTEN sense | 5'CAAAUCCAGAGGCUAGCAGdT+dT3' (SEQ ID NO: 62) |
| 69 | PTEN sense | 5'C#AAAUCCAGAGGCUAGCAGdT+dT3' (SEQ ID NO: 63) |
| 70 | PTEN sense | 5'C*AAAUCCAGAGGCUAGCAGdT+dT3' (SEQ ID NO: 64) |
| 71 | PTEN antisense | 3'dT#dTGUUUAGGUCUCCGAUCGUC5' (SEQ ID NO: 65) |

TABLE 17-continued siRNA duplexes with P-Alkylphosphonate backbone for biological assays.

| Number | Name | Sequence[a] |
|---|---|---|
| 72 | PTEN antisense | 3'dT#dTGUUUAGGUCUCCGAUCGU*C5' (SEQ ID NO: 66) |
| 73 | PTEN antisense | 3'dT+dTGUUUAGGUCUCCGAUCGUC5' (SEQ ID NO: 67) |
| 74 | PTEN antisense | 3'dT+dTGUUUAGGUCUCCGAUCGU*C5' (SEQ ID NO: 68) |

[a]The sense strand is written 5' to 3' on the top line. The antisense strand is written 3' to 5' below. The oligonucleotides are phosphodiester RNA except for two 3' deoxythymidines indicated by dT in the sequence. dt represent cholesterol conjugation at C5 of 2'-deoxyuridine and dc represent cholesterol conjugation at C5 of 2'-deoxycytidine. dt represent 5β-cholanic acid conjugation at C5 of 2'-deoxyuridine and dc represent 5β-cholanic acid conjugation at C5 of 2'-deoxycytidine. Scrambled sequences were generated by randomizing the sequence of the sense strand.
[b]The PTEN sequence is identical (with the exception of the 3' dTdT) on the antisense strand to that of an antisense oligonucleotide with pharmacological activity. [M. Butler, R. A. McKay, I. J. Popoff, W. A. Gaarde, D. Witchell, S. F. Murray, N. M. Dean, S. Bhanot, B. P. Monia, Diabetes. 2002 51, 1028]
*Indicates racemic or R or S methylphosphonate/methylthiophosphonate backbone
Indicates racemic or R or S isopropylphosphonate/isopropylthiophosphonate backbone
+Indicates racemic or R or S tert-butylphosphonate/tert-butylthiophosphonate backbone Synthesis of Oligonucleotides:

The designed RNA molecules are synthesized on a 394 ABI machine using the standard protocols for phosphate and phosphorothioate backbone with a slight changes in the capping step by using acetic anhydride and 4-(dimethylamino) (pyridine (DMAP) as the capping reagent. The alkylphosphonate backbone is introduced as described by Hogrefe et al. (*An improved method for the synthesis and deprotection of methylphosphonate oligonucleotides. Methods in Molecular Biology* (Totowa, N.J., United States) (1993), 20 (Protocols for Oligonucleotides and Analogs), 143-64.). A general protocol from for synthesizing alkylphosphonate oligonucleotides is described below:

1. Wash with acetonitrile
2. Detritylate
3. Wash well with acetonitrile to dry column
4. Couple using subroutine.
   a. Add monomer (phosphoanmidite 2 or 4) and activator (5-(ethylthio)-1H-tetrazole, ETT) (monomer to activator ratio, 1:4)
   b. Couple (same amount of time as standard amidites, or extended or double coupling if necessary)
   c. Oxidize immediately, with no prewash, using a low-water-content oxidant
   d. Wash until oxidant is rinsed away
5. Cap using acetic anhydride and DMAP
6. Wash well with acetonitrile
7. Begin cycle again Optimum reagents and conditions as recommended by Hogrefe et al. (*An improved method for the synthesis and deprotection of methylphosphonate oligonucleotides. Methods in Molecular Biology* (Totowa, N.J., United States) (1993), 20 (*Protocols for Oligonucleotides and Analogs*), 143-64.) are used to obtain phosphonate and thiophosphonate backbone modified oligonucleotides. Commercially available DNA and RNA phosphoramidites and supports are used unless otherwise specified. Commercial phosphoramidites with fast protecting groups (5'-O-dimethoxytrityl N6-phenoxyacetyl-2'-O-t-butyldimethylsilyladenosine-3'-O—N,N'-diisopropyl-cyanoethylphosphoramidite, 5'-O-dimethoxytrityl-N4-acetyl-2'-O-t-butyldimethylsilylcytidine-3'-O—N, N'-diisopropyl-2-cyanoethylphosphoramidite, 5'-O-dimethoxytrityl-N2-p-isopropylphenoxyacetyl-2'-O-t-butyldimethylsilylguanosine-3'-O—N,N'-diisopropyl-2-cyanoethylphosphoramidite, and 5'-O-dimethoxytrityl-2'-O-t-butyldimethylsilyluridine-3'-O—N,N'-diisopropyl-2-cyanoethylphosphoramidite are purchased either from Pierce Nucleic Acids Technologies, Milwaukee, Wis. or from Proligo LLC, Boulder, Colo. All 2'-O-Me amidites are received from Glen Research. All amidites are used at a concentration of 0.15 M in acetonitrile ($CH_3CN$) and a coupling time of 8-15 min. The activator is 5-(ethylthio)-1H-tetrazole (0.25M), for the PO-oxidation Iodine/Water/Pyridine is used and for PS-oxidation, 2% Beaucage reagent (Iyer et al., *J. Am. Chem. Soc.*, 1990, 112, 1253) in anhydrous acetonitrile is used. The sulphurization time is about 6 min.

Deprotection-I (Nucleobase Deprotection)

After completion of the synthesis, the support is dried thoroughly and is transferred into a screw-cap vial. The support is then mixed with a solution of absolute ethanol:acetonitrile:ammonium hydroxide (45:45:10, stored at 5° C. or freshly prepared, about 1 mL for 1 μM scale synthesis). The suspension is vortexed for 30 min, after 30 min 1 vol of ethylenediamine is added and vortex for 6 h. The solution is decanted and the support is washed twice with acetonitrile:water (1:1). Washings and the deprotection solution are combined and lyophilized to dryness.

Deprotection-II (Removal of 2' TBDMS Group)

The white residue obtains is resuspended in 400 μl of triethylamine, triethylamine trihydrofluoride (TEA.3HF) and NMP (4:3:7) and heats at 50° C. for overnight to remove the tert-butyldimethylsilyl (TBDMS) groups at the 2'position (Wincott et al., *Nucleic Acids Res.*, 1995, 23, 2677). The reaction is then quenched with 400 μl of isopropoxytrimethylsilane (i$PrOMe_3$Si, purchased from Aldrich) and further incubates on the heating block leaving the caps open for 10 min; (This causes the volatile isopropxytrimethylsilylfluoride adduct to vaporize). The residual quenching reagent is removed by drying in a speed vac. 1.5 ml of 3% triethylamine in diethyl ether is added and the oligonucleotide is pelleted out by centrifuging. The supernatant is pipetted out without disturbing the pellet and the pellet is dried in speed vac to obtain the crude oligonucleotide as a white fluffy material.

Quantitation of Crude Oligomer or Raw Analysis

Samples are dissolved in RNase free deionied water (1.0 mL) and quantitates as follows: Blanking is first performed with water alone (1 mL); 20 µL of sample and 980 µL of water are mixed well in a microfuge tube, transfers to cuvette and absorbance reading is obtained at 260 nm. The crude material is dried down and stored at −20° C.

Purification of Oligomers:

(a) Page Purification

PAGE purification of oligomer synthesized is performed as reported by Sambrook et al. (Molecular Cloning: a Laboratory Manual, Second Edition, Cold Spring Harbor Laboratory Press, Cold Spring Harbor, N.Y., 1989). A 12% denaturing gel is prepared for purification of unmodified and modified oligonucleotides. To a mixture of 120 mL Concentrate, 105 mL Diluents and 25 mL Buffer (National Diagnostics) is added 50 µL TEMED and 1.5 mL 10% APS. After pouring the gel, it is left for ½ h to polymerize. Oligonucleotide is suspended in 20 µL water and 80 µL formamide. Loads gel tracking dye on left lane followed by the sample slowly on to the gel. Run the gel on 1×TBE buffer at 36 W for 4-6 h. Once run is completed, transfer the gel on to preparative TLC plates and see under UV light. Cut the bands, soak and crush in RNase free water and leaves the vial containing purified oligonucletide in a shaker for overnight. Eluent is removed, wash residue with more RNase free water, combined washing and lyophilize to obtain the pure oligonucleotide.

Desalting of Purified Oligomer

The purified dry oligomer is desalted using Sephadex G-25 M (Amersham Biosciences). The cartridge is conditioned with 10 mL of RNase free deionised water thrice. Finally the purified oligomer is dissolved in 2.5 mL RNasefree water and passed through the cartridge with very slow drop wise elution. The salt free oligomer is eluted with 3.5 mL of RNase free water directly into a screw cap vial.

Analysis:

Capillary Gel Electrophoresis (CGE) and Electrospray LC/Ms

Approximately 0.10 OD of oligomer is first dried down, then redissolves in water (50 □L) and pipettes in specified vials for CGE and LC/MS analysis.

Example 13

In Vitro Cell Culture Activities of siRNA Containing Alkylphosphonate or Alkylthiophosphonate Backbone Dual Luciferase Gene Silencing Assays Sense and antisense strands were arrayed into PCR tubes or plates (VWR, West Chester, Pa.) in annealing buffer (100 mM KOAc, 30 mM HEPES, 2 mM MgOAc, pH 7.4) to give a final concentration of 20 µM duplex. Annealing was performed employing a thermal cycler (ABI PRISM 7000, Applied Biosystems, Foster City, Calif.) capable accommodating the PCR tubes or plates. The oligoribonucleotides were held at 90° C. for two minutes and 37° C. for one hour. Duplex formation was verified by native agarose gel electrophoresis of a random sample of the sense and antisense combinations.

HeLa SS6 cells were grown at 37° C. in Dulbecco's modified Eagle medium (DMEM) supplemented with 10% fetal bovine serum (FBS), 100 units/mL penicillin, and 100 µg/mL streptomycin (Invitrogen, Carlsbad, Calif.). HeLa Dual-luc cells (HeLa cells stably expressing both firefly and renilla luciferase) were grown at 37° C. in Eagle medium supplemented with 10% fetal bovine serum (FBS), 100 units/mL penicillin, and 100 µg/mL streptomycin, 0.5 µg/mL puromycin, 500 µg/mL zeocin (Invitrogen, Carlsbad, Calif.). Cells were passaged regularly to maintain exponential growth. Twenty-four hours prior to siRNA transfection, cells were seeded on opaque, white 96-well plates (Costar, Corning, N.Y.) at a concentration of 15,000 cells/well in antibiotic-free, phenol red-free DMEM (Invitrogen).

In vitro activity of siRNAs was determined using a high-throughput 96-well plate format luciferase silencing assay. Assays were performed in one of two possible formats. In the first format, HeLa SS6 cells were first transiently transfected with plasmids encoding firefly (target) and renilla (control) luciferase. DNA transfections were performed using Lipofectamine 2000 (Invitrogen) and the plasmids gWiz-Luc (Aldevron, Fargo, N. Dak.) (200 ng/well) and pRL-CMV (Promega, Madison, Wis.) (200 ng/well). After 2 h, the plasmid transfection medium is removed, and the firefly luciferase targeting siRNAs were added to the cells at various concentrations. In the second format, HeLa Dual-luc cells (stably expressing both firefly and renilla luciferase) are directly transfected with firefly luciferase targeting siRNAs. SiRNA transfections were performed using either TransIT-TKO (Mirus, Madison, Wis.) or Lipofectamine 2000 according to manufacturer protocols. After 24 h, cells were analyzed for both firefly and renilla luciferase expression using a plate luminometer (VICTOR$^2$, PerkinElmer, Boston, Mass.) and the Dual-Glo Luciferase Assay kit (Promega). Firefly/renilla luciferase expression ratios were used to determine percent gene silencing relative to mock-treated (no siRNA) controls.

TABLE 18

Methylphosphonate backbone and Luc activity

| Number | Sequence$^a$ (SEQ ID NOS 69-76) | Luc Activity |
|---|---|---|
| 101 | 5'CUUACGCUGAGUACUUCGAdTdT3'<br>3'dTdTGAAUGCGACUCAUGAAGCU5' | Active |
| 102 | 5'CUUACGCUGAGUACUUCGAdT*dT3'<br>3'dTdTGAAUGCGACUCAUGAAGCU5' | Active |
| 103 | 5'CUUACGCUGAGUACUUCGAdTdT3'<br>3'dT*dTGAAUGCGACUCAUGAAGCU5' | Active |
| 104 | 5'CUUACGCUGAGUACUUCGAdT*dT3'<br>3'dT*dTGAAUGCGACUCAUGAAGCU5' | Active |

* Methylphosphonate

Single Incorporation of Methylphosphonate Linkages at the 3'-End of Sense and Antisense Retain Luciferase Activity (Table 18).

Example 14

Serum Stability of siRNAs Containing Alkylphosphonate or Alkylthiophosphonate Backbone siRNA duplexes were prepared at a stock concentration of 1 µM in which either the sense (S) or antisense strand (AS) contains a trace amount of 5'-$^{32}$P labeled material (e.g. $^{32}$P—S/AS and S/$^{32}$P-AS). The presence of the end-labeled sense or antisense strand allows for monitoring of the individual strand within the context of the siRNA duplex. Therefore, two duplex preparations are made for each siRNA sequence tested. siRNA duplexes were incubated in 90% human serum at a final concentration of 100 nM duplex. Samples were removed and quenched in a stop mix at appropriate times. For a typical time course, 10 seconds, 15 minutes, 30 minutes, 1 hour, 2 hours and 4 hours time points are taken. Samples were analyzed by denaturing polyacrylamide gel electrophoresis along with a control sample (4 hour buffer-alone incubation) and a partial alkaline hydrolysis ladder of the labeled sense or antisense strand as a marker. The gel is imaged using a Fuji phosphorimager to detect the full length sense and antisense strands along with any degradation fragments that are generated by serum nucleases during incubation.

Serum stability of methylphosphonate backbone modification was tested and the result showed enhanced serum stability as compared to a unmodified siRNA duplex. A description of each modification, its location within the siRNA duplex, and the serum stability data follows.

Figure 13:
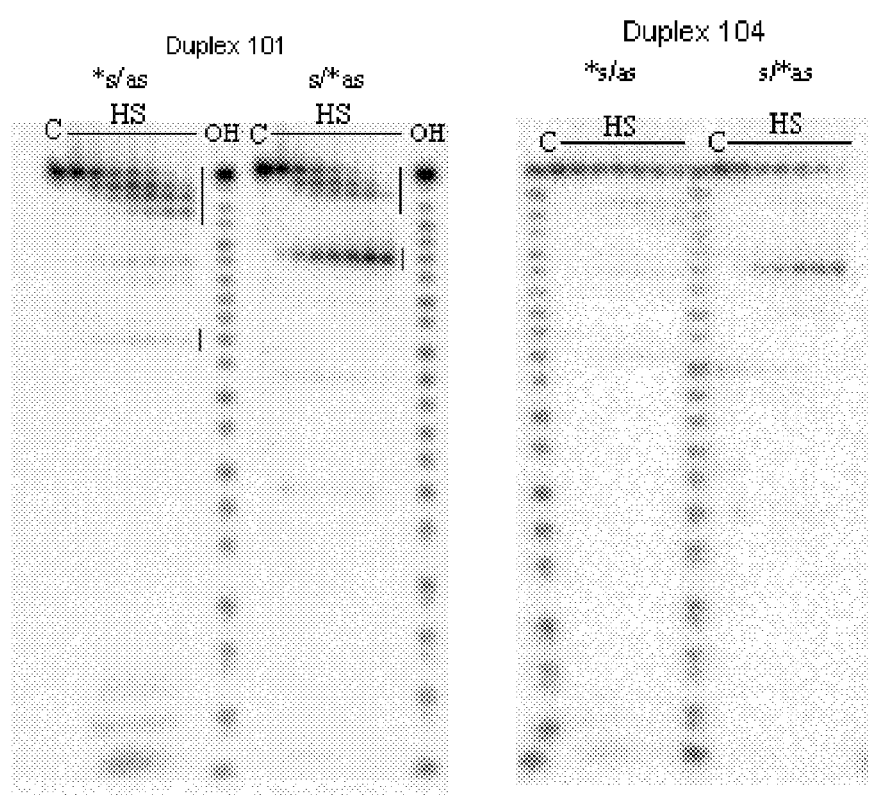
FIG. 13 depicts results from denaturing gel analysis of the human serum stability assay for duplex 101 and 104 (See Example 14).

The results from denaturing gel analysis of the human serum stability assay for duplex 101 and 104 (Table 18) are presented in FIG. 13. C is the 4 hour time point for siRNA duplex incubated in PBS buffer alone, OH⁻ is the partial alkaline hydrolysis marker, *s/as represents siRNA duplex containing 5' end-labeled sense RNA and s/*as represents duplex containing 5' end-labeled antisense RNA. Samples were incubated in 90% human serum and time points were assayed at 10 seconds, 5 min, 15 min, 30 min, 1 hour, 2 hours, and 4 hours. Black lines to the right of bands indicate exonucleolytic degradation fragments and the red lines highlight a few of the endonucleolytic degradation fragment. Methylphosphonate substitution at the 3' end inhibit exonuclease degradation of the 3' overhangs.

The parent duplex used to establish a serum stability baseline for evaluating the effects of chemical modifications on nuclease resistance is shown in FIG. 13. Duplex 101 (Table 18) was subjected to the serum stability assay to evaluate its inherent nuclease resistance and to define its degradation pattern (FIG. 13, duplex 101). This unmodified duplex is degraded by both 3'-5' exonucleases and endonucleases.

Cleavage of the 3' end of both the sense and antisense strands by 3'-5' exonucleases occurs within the first 5 minutes of incubation resulting in the loss of the 3' terminal dT residues (black line in FIG. 13, duplex 101). In addition to exonuclease degradation, both strands are cleaved by endonucleases. There is a major endonuclease site at position sixteen of the antisense strand (red line in FIG. 13, duplex 101) that appears as early as 10 seconds. Very little full length sense or antisense strand is remaining after 1 hour in human serum.

Specific phophodiester linkages of the siRNA duplex were replaced by methylphosphonate and their stability was evaluated in the human serum stability assay (FIG. 13, duplex 104). Substitution of the phosphodiester linkage at the 3' end of both the sense and antisense strands inhibits exonucleolytic degradation of the 3' overhangs (FIG. 13, duplex 104) as compared to the unmodified parent duplex 101. Full length starting material is present out to four hours for both the sense and antisense strands. The endonucleolytic cleavage pattern seen in the unmodified duplex is unchanged. In summary, a single methylphosphonate between the two 3' terminal nucleotides is sufficient to protect the 3' ends from exonuclease degradation.

Methods

Method 1
Binding Affinity of siRNA Containing Alkylphosphonate or Alkylthiophosphonate Backbone to Plasma Proteins.
Measurement of Binding Affinity:

To measure binding affinity of siRNAs to plasma protein, the 5' end of the sense strand of an siRNA duplex is labeled with $^{32}$P using T4 polynucleotide kinase using standard procedures. Each of the siRNA duplexes shown in Table I will be tested in this assay. The unincorporated label is removed using a G25 column and labeling is confirmed by polyacrylamide gel electrophoresis. A fixed concentration of labeled RNA (50 nM) and complementary strand (50 nM) is incubated with increasing concentration of plasma proteins at 25° C. for one hour in phosphate-buffered saline buffer containing 0.1 mM EDTA and 0.005% Tween 80. After incubation, the samples are loaded onto low binding, regenerated cellulose filter membranes with a molecular weight cut-off of 30,000 (Millipore). The samples are spun gently in a microfuge (NYCentrifuge 5415C; Eppendorf, Westbury, N.Y.) at 3000 rpm (735 g) for 3 to 6 minutes, allowing collection of ~20% of the loaded volume in the filtrate.

Radioactivity present in aliquots from the filtrate and the initial (unfiltered) solutions is measured using a scintillation counter (model LS6000IC, Beckman, Fullerton, Calif.). The counts obtained in the filtrate aliquots represent the free (unbound) RNA, and appropriate calculations are performed to obtain the concentration of free RNA. Further calculations yield the concentration of RNA bound to protein. See R. Zini, J. Barre, F. Bree, J. P. Tillement, B. Sebille, *J. Chromatogr.* 1981, 216, 191 and A. N. Kuznetsov, G. V. Gyul'khandanyan, B. Ebert, *Mol. Biol. (Moscow)* 1977, 11, 1057.

The extent of siRNA binding to plasma proteins is determined using an equilibrium filtration method. The fraction of bound RNA is plotted vs. the total protein concentration. The equilibrium constant, $K_d$, is determined from nonlinear regression analysis of the fraction of siRNA bound ($f_{bound}$) as a function of the free protein concentration ($f_{free}$). Thus, the data can be fit to a two-state model:

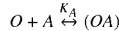

$$O + A \overset{K_A}{\leftrightarrow} (OA)$$

where O is the unbound siRNA, A is the unbound protein, OA is the siRNA-protein complex and $K_A$ is the equilibrium association constant.

Method 2
Inhibition of mRNA Expression in Balb-C Mouse Treated with siRNAs. Female BALB/c mice (6 weeks old, Harlan Sprague Dawley, Indianapolis, Ind.) are housed three to a cage under conditions meeting National Institue of Health regulations (19). siRNAs, including unconjugated and scrambled controls and vehicle containing no siRNA are administered in 0.9% NaCl, i. p. at indicated dose levels once daily for three days and tissues are harvested for analysis.

Total mRNA is extracted from mouse liver by rapid homogenization of the tissue in 4 M guanidinuim isothiocyanate followed by centrifugation over a cesium chloride gradient. RNAs (20-40 g) are resolved in 1.2% agarose gels containing 1.1% formaldehyde and transferred to nylon membranes. The blots are hybridized with a radiolabelled human cDNA probe. Probes hybridized to mRNA transcripts are visualized and quantified using a PhosPhorImager (Molecular Dynamics). After stripping the blots of radiolabelled probe, they are reprobed with G3PDH cDNA to confirm equal loading.

Method 3
siRNA Treatment of Human Tumor Cells in Nude Mice—Intraperitoneal Injection. Human lung carcinoma A549 cells are harvested and 5×10⁶ cells (200 μL) were injected subcutaneously into the inner thigh of nude mice. Palpable tumors develop in approximately one month. siRNAs that target the c-raf and the H-ras messages, including steroid/lipid-conjugated RNA and scrambled controls and vehicle containing no siRNA are administered to mice intraperitoneally at a dosage of 20 mg/kg body weight, every other day for approximately ten weeks. Mice are monitored for tumor growth during this time.

Method 4
siRNA Treatment of Human Breast Tumor Cells in Nude Mice. Human breast carcinoma MDA-MB-231 cells are harvested and 5×10$^5$ cells (200 μL) are injected subcutaneously into the mammary fat pads of athymic nude mice. Palpable tumors develop in approximately one month. siRNAs that target the c-raf and the H-ras messages, including steroid/lipid-conjugated siRNA and scrambled controls and vehicle containing no siRNA are administered to mice intraperitoneally at a dosages of 5, 10, and 25 mg/kg/day body weight, every day for approximately 20 days. Mice are monitored for tumor growth during this time.

Method 5
siRNA Treatment of Human Lung Tumor Cells in Nude Mice. Human lung carcinoma A549 cells are harvested and 5×10$^6$ cells (200 μL) are injected subcutaneously into the inner thigh of nude mice. Palpable tumors develop in approximately one month. siRNAs that target the c-raf and the H-ras messages, including cholesterol or cholanic acid—conjugated RNA and scrambled controls and vehicle containing no siRNA are administered to mice subcutaneously at the tumor site. Drug treatment begins one week following tumor cell inoculation and is given twice a week for four weeks. Mice are monitored for tumor growth for a total of nine weeks.

Method 6
Inhibition of Apo-B mRNA Expression in Hep G-2 cells and in Balb-C Mouse Treated with siRNAs. Inhibition of Aop-B mRNA expression by siRNA (Table I, siRNAs 141-146) will be evaluated in vitro and in vivo. Effect of siRNA treatment on message levels in HEP-G2 cells is analyzed following treatment. The procedure is described by Yao Z Q, Zhou Y X, Guo J, Feng Z H, Feng X M, Chen C X, Jiao J Z, and Wang S Q in "Inhibition of hepatitis B virus in vitro by antisense oligonucleotides." *Acta Virol.* 1996, 40(1), 35-9.

Female BALB/c mice (6 weeks old, Harlan Sprague Dawley, Indianapolis, Ind.) are housed three to a cage under conditions meeting National Institue of Health regulations (19). siRNAs, including unconjugated and scrambled controls and vehicle containing no siRNA are administered in 0.9% NaCl, i. p. at indicated dose levels once daily for three days and tissues are harvested for analysis.

Total mRNA is extracted from mouse liver by rapid homogenization of the tissue in 4 M guanidinuim isothiocyanate followed by centrifugation over a cesium chloride gradient. RNAs (20-40 μg) are resolved in 1.2% agarose gels containing 1.1% formaldehyde and transferred to nylon membranes. The blots are hybridized with a radiolabelled human Apo-B cDNA probe as described (20). Probes hybridized to mRNA transcripts are visualized and quantified using a PhosPhorImager (Molecular Dynamics). After stripping the blots of radiolabelled probe, they are reprobed with G3PDH cDNA to confirm equal loading.

Example 15

Synthesis of Naproxen-Bearing Tether

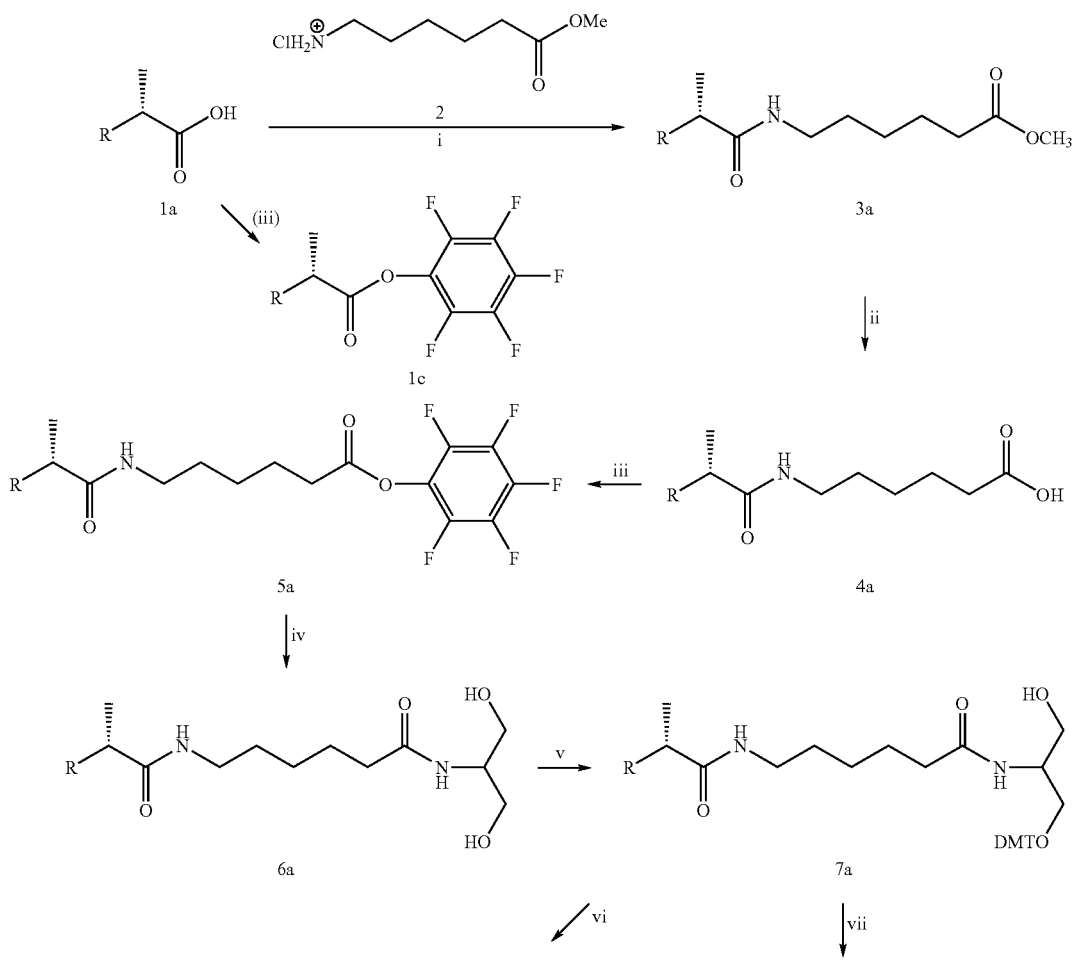

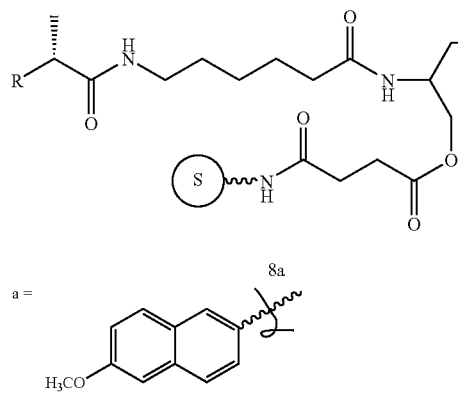

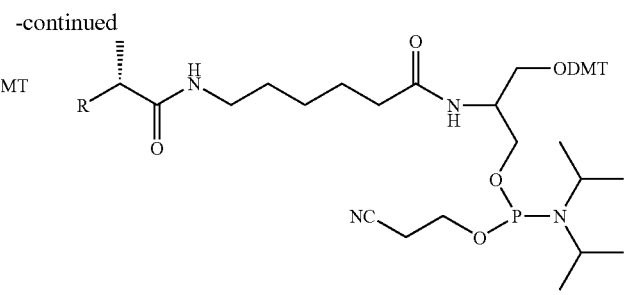

(i) DCC, DMAP, DIEA/Dichloromethane; (ii) LiOH/THF-H$_2$O; (iii) DCC, DMAP, Pentafluorophenol/Dichloromethane; (iv) Serinol, TEA/Dichloromethane; (v) DMT-Cl, DMAP/Py; (vi) (a) Succinic anhydride, DMAP/Dichloroethane and (b) DTNP, DMAP, Ph$_3$P, Aminoalkyl solid support and (vii) N,N-diisopropylamino b-cyanoethylphosphonamidic chloride {[(CH$_3$)$_2$CH]$_2$N—P(Cl)—OCH$_2$CH$_2$CN}, DIEA/Dichloromethane or 2-Cyanoethyl-N,N,N',N'-tetraisopropylphosphane, tetrazole (or tetrazolediisopropylammonium salt)/Acetonitrile.

N-Naproxyl-6-aminohexanoic acid methyl ester (3a)

The ester 3a was prepared according to reported procedure from the literature (*Org. Syn.*, 1984, 63, 183). Naproxen (1a 10.00 g, 43.427 mmol, purchased from Aldrich) and 4-(Dimethylamino)pyridine (DMAP, 0.53 g, 4.338 mmol, purchased from Aldrich) were dissolved in anhydrous N,N-dimethylformamide (DMF) and 1,3-diisopropylcarbodiimide (DICC, 6.8 mL, 43.914 mmol, purchased from Aldrich) was added into the solution and stirred at ambient temperature for 5 minute. 6-aminohexanoic acid methyl ester hydrochloride (2, 10.00 g, 57.408 mmol, purchased from Fluka) and diisopropylethylamine (DIEA, 10 mL, purchased from Aldrich) were added into the stirring solution after 5 minute of addition of DICC and stirred overnight at ambient temperature. DMF was removed from the reaction in vacuo, the product was extracted into ethyl acetate (EtOAc, 200 mL), washed successively with aqueous KHSO$_4$, water, sodium bicarbonate solution and water. The organic layer was dried over anhydrous sodium sulfate (Na$_2$SO$_4$) and filtered. A white solid was precipitated out from the EtOAc extract by adding hexane to afford the desired compound 3a, 11.20 g (72.14%). $^1$H NMR (400 MHz, [D$_6$]DMSO, 25° C.): δ 7.95-7.92 (t, J(H,H)=5.2 & 5.6 Hz, 1H), 7.76-7.68 (m, 3H), 7.43-7.40 (dd, J'(H,H)=1.6 and J"(H,H)=8.4 Hz, 1H), 7.25-7.24 (d, J(H,H)=2.0 Hz, 1H), 7.13-7.11 (dd, J'(H,H)=2.4 and J"(H,H)=8.8 Hz, 1H), 3.84 (s, 3H), 3.70-3.65 (q, J(H,H)=6.8 and 7.2 Hz, 1H), 3.54 (s, 3H), 3.00-2.97 (q, J(H,H)=6.8 Hz, 2H), 2.21-2.17 (t, 2H), 1.48-1.29 (m, 7H), 1.19-1.13 (m, 2H).

N-Naproxyl-6-aminohexanoic acid (4a)

Hydrolysis of the ester 3a was performed as reported earlier (Rajeev et al., 2002, 4, 4395). Compound 3a (10.80 g, 30.24 mmol) was suspended in tetrahydrofuran-water (THF-H$_2$O) mixture (4:1, 40 mL) and stirred with LiOH (1.65 g, 39.32 mmol) for 4 h at ambient temperature. THF was removed from the reaction in vacuo and free acid was precipitated out from water by adding concentrated KHSO$_4$ solution, thoroughly washed with water, filtered through a sintered filter, triturated with diethyl ether and dried over P$_2$O$_5$ under vacuum overnight to obtain the acid 4a as a white solid, 10.22 g (98.4%). $^1$H NMR (400 MHz, [D$_6$]DMSO, 25° C.): δ 11.96 (bs, 1H), 7.95-7.92 (t, J(H,H) 5.37 Hz, 1H), 7.77-7.68 (m, 3H), 7.43-7.41 (d, J(H,H)=8.3 Hz, 1H), 7.25-7.24 (d, J(H, H) 2.44 Hz, 1H), 7.13-7.11 (dd, J'(H,H)=1.95, 2.44 and J"(H, H)=8.79, 9.27 Hz, 1H), 3.84 (s, 3H), 3.71-3.65 (q, J(H,H)= 6.84, 7.33 Hz, 1H), 3.02-2.97 (m, 2H), 2.13-2.09 (t, J(H,H)= 7.33 Hz, 2H), 1.46-1.30 (m, 7H), 1.21-1.15 (m, 2H).

N-Naproxyl-6-aminohexanoic acid pentafluorophenyl ester (5a)

Compound 4a (5.00 g, 14.57 mmol), DMAP (0.18 g, 1.47 mmol) and pentafluorophenol (3.50 g, 19.02 mmol, purchased from Aldrich) were taken in dichloromethane (40 mL) and DCC (3.00 g, 14.54 mmol) was added into the solution. Reaction mixture was stirred at ambient temperature for 8 h. The reaction mixture was diluted to 100 mL by adding EtOAc and precipitated DCU was removed by filtration. Combined filtrate, evaporated solvent in vacuo, and the residue was subsequently filtered through a column of silica gel, eluent hexane/EtOAc 4:1 to obtain a mixture (7.90 g) of the desired ester 5a and excess pentafluorophenol from the reaction. The crude product thus obtained was directly used for proceeding experiments without further purification.

Naproxen-6-aminohexanoic acid-serinol conjugate (6a)

Pentafluorophenol ester 5a was stirred with serinol in the presence of TEA to obtain compound 6a (*J. Org. Chem.*, 1991, 56, 1713). Compound 5a (4.00 g, 7.86 mmol) and serinol (1.5 g, 16.46 mmol, purchased from Aldrich) were suspended in dichloromethane (30 mL) and triethylamine (TEA, 2.3 mL, purchased from Aldrich) was added into the suspension, stirred at ambient temperature for 2 h. A white precipitate was formed during the course of the reaction. After 2 h, the precipitate was filtered through a sintered filter, washed successively with excess of dichloromethane, water and diethyl ether to afford desired product 6a (2.82 g, 86.2%). $^1$H NMR (400 MHz, [D$_6$]DMSO, 25° C.): δ 7.95-7.92 (t, J(H, H)=5.49 Hz, 1H, exchangeable with D$_2$O), 7.77-7.68 (m, 3H), 7.43-7.39 (m, 2H, accounted for 1H after D$_2$O exchange), 7.26-7.25 (d, J(H,H)=2.14 Hz, 1H), 7.13-7.11

(dd, J'(H,H)=2.44 and J"(H,H)=8.85 Hz, 1H), 4.58-4.55 (t, J(H,H)=5.49 Hz, 2H, exchangeable with $D_2O$), 3.84 (s, 3H), 3.71-3.65 (m, 2H), 3.37-3.35 (t, became doublet after $D_2O$ exchange, 4H), 3.02-2.95 (m, 2H), 2.03-2.01 (t, J(H,H)=7.32, 7.63 Hz, 2H), 1.46-1.30 (m, 7H), 1.20-1.12 (m, 2H).

Naproxen-6-aminohexanoic acid-serinol mono DMT (7a)

Compound 6a was prepared by modifying reported literature procedure (Rajeev et al., *Org. Lett.*, 2003, 5, 3005). A solid mixture of compound 6a (2.50 g, 6.01 mmol) and DMAP (0.075 g, 0.61 mmol) was dried over $P_2O_5$ under vacuum overnight. The solid mixture was suspended in anhydrous pyridine (100 mL) under argon and heated to obtain a homogenous solution. The temperature of the mixture was brought to room temperature and stirred. 4,4'-Di-O-methyltrityl chloride (2.24 g, 6.61 mmol, purchased from Chem Genes Corporation) was separately dissolved in 20 mL of anhydrous dichloromethane and added drop-wise into the stirring pyridine solution over a period of 45 minute under argon. Reaction mixture was further stirred overnight. Solvents were removed form the reaction mixture and the product was extracted into EtOAc (150 mL) and washed successively with water, $NaHCO_3$ solution and water, dried over anhydrous $Na_2SO_4$ and evaporated to solid mass. Desired product was purified by flash silica gel column chromatography: (a) eluent: 1% methylalcohol (MeOH) in dichloromethane—1.60 g of undesired bis DMT derivative (26.1%) and (b) 5% MeOH in dichloromethane—2.50 g of desired product 7a (57.9%). $^1$H NMR (400 MHz, [$D_6$]DMSO, 25° C.): δ 7.94-7.91 (t, J(H,H)=5.49 Hz, 1H, exchangeable with $D_2O$), 7.7-7.68 (m, 3H), 7.60-7.58 (d, J(H,H)=8.55 Hz, 1H, exchangeable with $D_2O$), 7.43-7.10 (m, 12H), 6.86-6.84 (d, 4H), 4.62-4.59 (t, J(H,H)=5.18, 5.49 Hz, 1H, exchangeable with $D_2O$), 4.01-3.96 (m, 1H), 3.83 (s, 3H), 3.71-3.65 (m, 7H), 3.44-3.42 (t, J(H,H)=5.19, 5.49 Hz, 2H), 3.03-2.87 (m, 4H), 2.05-2.01 (t, J(H,H)=7.33, 7.63 Hz, 2H), 1.48-1.30 (m, 7H), 1.21-1.14 (m, 2H).

Naproxen-6-aminohexanoic acid-serinol CPG (8a)

The desired solid support 8a was prepared according to reported procedures (References for succinilation: Rajeev et al., *Org. Lett.*, 2003, 5, 3005 and for conjugation to CPG: Kumar et al., *Nucleosides Nucleotides*, 1996, 15, 879). A mixture of compound 7a (1.00 g, 1.39 mmol), succinic anhydride (0.17 g, 1.69 mmol, purchased from Aldrich) and DMAP (0.21 g, 1.72 mmol) were suspended in 7 mL of anhydrous ethylene dichloride for 24 h. Reaction mixture was diluted to 50 mL by adding dichloromethane and washed with dilute aqueous citric acid solution (20 mL), dried over anhydrous $Na_2SO_4$ and evaporated to dryness. The residue obtained was further dried over $P_2O_5$ under vacuum to afford an almost pure but crude monosuccinate as a white solid (1.10 g, 96.5%). The product obtained was directly used for subsequent reaction without further purification. $^1$H NMR (400 MHz, [$D_6$]DMSO, 25° C.): δ 7.94-7.91 (t, J(H,H)=5.19, 5.49 Hz, 1H, exchangeable with $D_2O$), 7.83-7.81 (d, J(H,H)=7.94 Hz, 1H, exchangeable with $D_2O$), 7.76-7.68 (m, 3H), 7.42-7.10 (m, 12H), 6.88-6.86 (d, 4H), 4.18-4.12 (m, 2H), 4.07-3.98 (m, 2H), 3.83 (s, 3H), 3.71-3.66 (m, 7H), 3.00-2.91 (m, 4H), 2.40 (s, 4H), 2.04-2.00 (t, J(H,H)=7.32 Hz, 2H), 1.44-1.22 (m, 7H), 1.19-1.15 (m, 2H).

2,2'-Dithiobis(5-nitropyridine) (0.38 g, 1.22 mmol, purchased from Adrich) was dissolved in a 1:1 mixture of acetonitrile and ethylene dichloride (5 mL) and added into a suspension of naproxen-6-aminohexanoic acid-serinol conjugate mono DMT mono succinate (1.00 g, 1.21 mmol) and DMAP (0.16 g, 1.31 mmol) in 2 mL of anhydrous acetonitrile. Triphenylphosphine ($Ph_3P$, 0.32 g, 1.22 mmol, purchased from Aldrich) was added into the reaction mixture and shaken for 3-4 minute. 5.5 g of long chain aminoalkyl controlled-pore-glass (CPG) with 500 Å size and a loading of 112.7 µM/g (purchased from Millipore), and excess of acetonitrile (to soak the CPG completely) were added into the reaction mixture and the suspension was shaken (agitated) for 45 minute at ambient temperature. CPG was filtered through a sintered funnel, washed extensively with acetonitrile, dichloromethane and diethyl ether and subsequently re-suspended in pyridine-dichloromethane and treated with acetic anhydride in the presence of DIEA to cap unreacted amino groups on the CPG. After 10 minute, CPG was filtered and extensively washed with dichloromethane, acetonitrile and diethyl ether followed by drying under vacuum to obtain the desired CPG 8a with a loading 54.12 µM/g. The loading was determined as reported in the literature (Prakash et al., *J. Org. Chem.*, 2002, 67, 357 and references cited therein).

Naproxen-6-aminohexanoic acid-serinol mono DMT phosphoramidite (9a)

The phosphoramidite was prepared as reported in the literature (Rajeev et al., *Org. Lett.*, 2003, 5, 3005 and references cited therein). Compound 7a (1.00 g, 1.39 mmol) and diisopropylammonium tetrazolide (0.12 g, 0.70 mmol) were dried over $P_2O_5$ vacuum overnight and subsequently suspended in anhydrous acetonitrile (5 mL) under argon atmosphere. 2-Cyanoethyl-N,N,N',N'-tetraisopropylphosphane (0.69 mL, 2.09 mmol) was added into the suspension and stirred at ambient temperature for 14 h. Solvent was removed form the reaction in vacuo and residue was suspended in EtOAc (40 mL) and washed with dilute $NaHCO_3$ solution followed by standard work. Desired amidite 9a was purified by flash silica gel column chromatography; eluent: EtOAc, yield 0.79 g (61.8%). $^{31}$P NMR (161.8 MHz, $CDCl_3$, 25° C.): δ 146.01, 145.69.

Naproxen pentafluoropehenol ester (1c)

Naproxen (1, 11.25 g, 48.86 mmol), pentafluorophenol (10.00 g, 54.33 mmol) and DMAP (0.60 g, 4.91 mmol) were dissolved in DMF (40 mL) and stirred at ambient temperature. 1,3-dicyclohexylcarbodiimide (DCC, 11.00 g, 53.31 mmol) was added into the solution and continued stirring overnight. 1,3-dicyclohexylurea (DCU) was precipitated out during the course of the reaction. The precipitated DCU was filtered off, washed with DMF, combined filtrate and removed DMF in vacuo. Oily residue obtained was filtered through a small column of silica gel, eluent 10% EtOAc in hexane to remove dissolved DCU to afford a mixture of the desired ester 1c and excess pentafluorophenol (20.30 g). The crude product thus obtained was directly used for proceeding experiments without further purification. $^1$H NMR (400 MHz, [$D_6$]DMSO, 25° C.): δ 7.85-7.81 (m, 3H), 7.48-7.46 (dd, J'(H,H) 1.53 and J"(H,H)=8.55 Hz, 1H), 7.32-7.31 (d, J(H,H)=2.44 Hz, 1H), 7.18-7.16 (dd, J'(H,H) 2.44 and J"(H,H)=8.85 Hz, 1H), 4.47-4.44 (q, J(H,H)=7.02 Hz), 3.86 (s, 3H), 1.63-1.61 (d, J(H,H)=7.34 Hz, 3H).

Example 16

Synthesis of Ibuprofen-Bearing Tether

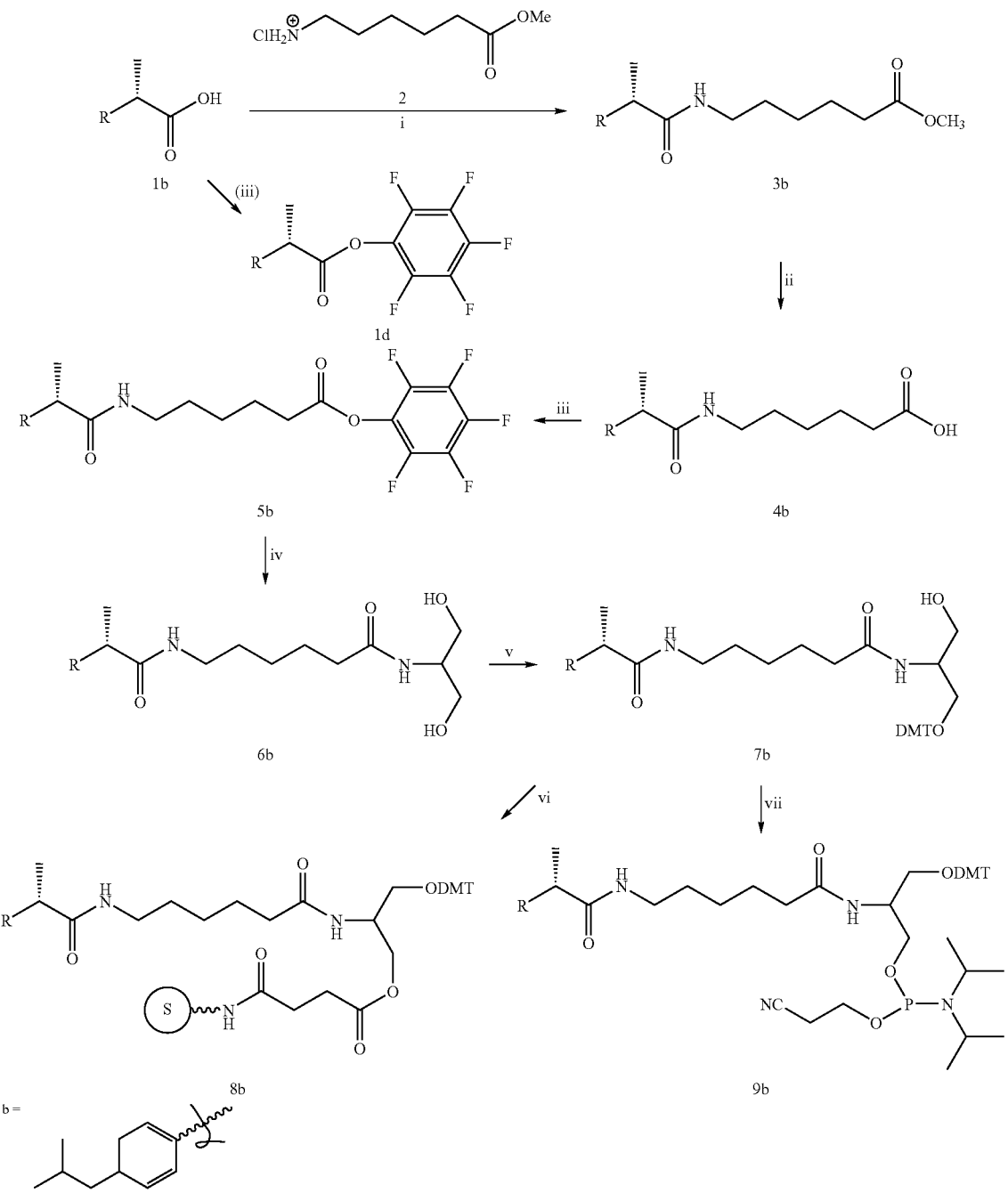

(i) DCC, DMAP, DIEA/Dichloromethane; (ii) LiOH/THF-H₂O; (iii) DCC, DMAP, Pentafluorophenol/Dichloromethane; (iv) Serinol, TEA/Dichloromethane; (v) DMT-Cl, DMAP/Py; (vi) (a) Succinic anhydride, DMAP/Dichloroethane and (b) DTNP, DMAP, Ph₃P, Aminoalkyl solid support and (vii) N,N-diisopropylamino b-cyanoethylphosphonamidic chloride {[(CH₃)₂CH]₂N—P(Cl)-OCH₂CH₂CN}, DIEA/Dichloromethane or 2-Cyanoethyl-N,N,N',N'-tetraisopropylphosphane, tetrazole (or tetrazolediisopropylammonium salt)/Acetonitrile.

N-Ibuprofyl-6-Aminohexanoic Acid Methyl Ester (3b)

Ibuprofen (1b, 5.0 g, 24.23 mmol, purchased from Acros Organic), methyl 6-aminohexanoic acid monohydrochloride (2, 6.60 g, 36.33 mmol, purchased from Fluka) and DMAP (0.30 g, 2.46 mmol) were suspended in dichloromethane (60 mL) in a 200 mL round bottom flask and DCC (5.00 g, 24.23 mmol) was added into the suspension, stirred for 3 minute. After 3 minute, 3.6 mL (25.83 mmol) of TEA was added into the reaction and continued stirring at ambient temperature for 18 h. Solvent and excess TEA were removed from the reaction in vacuo and residue obtained was triturated with diethyl ether, filtered through a sintered funnel to remove DCU. Combined filtrate and evaporated on a rotary evaporator. Residue was redissolved in EtOAc (100 mL) and successively washed with KHSO$_4$ solution, water, NaHCO$_3$ solution and water followed by drying over anhydrous Na$_2$SO$_4$ and evaporation of solvent in vacuo to obtain yellowish viscous residue of compound 3b (8.0 g). The crude product thus obtained was directly used for subsequent reaction without further purification. $^1$H NMR (400 MHz, [D$_6$]DMSO, 25° C.): δ 7.86-7.84 (bt, J(H,H)=5.39, 5.00 Hz, 1H, exchangeable with D$_2$O), 7.19-7.03 (m, 4H), 3.56 (s, 3H), 3.53-3.47 (q, J(H,H)=7.05 Hz, 1H), 3.00-2.95 (q, J(H,H)=6.64, 5.81 Hz, 2H), 2.39-2.37 (m, 2H, mixture of rotamers), 2.23-2.20 (t, J(H,H)=7.45, 7.05 Hz, 2H), 1.81-1.74 (m, 1H), 1.49-1.41 (m, 2H), 1.36-1.26 (m, 5H), 1.19-1.11 (m, 2H), 0.84-0.82 (m, 6H, mixture of rotamers).

N-Ibuprofyl-6-aminohexanoic acid (4b)

Compound 3b (8.00 g, 24.01 mmol) was stirred with LiOH (1.21 g, 28.84 mmol) in THF-H$_2$O (4:1, 40 mL) for 4 h. Solvents were removed from the reaction mixture in vacuo and the residue was washed with concentrated KHSO$_4$ solution. Unlike the corresponding naproxen analogue 4a, the free acid 4b did not precipitate out from the aqueous phase, so the aqueous phase was repeatedly extracted with EtOAc, combined extract, dried over Na$_2$SO$_4$ and evaporated in vacuo to obtain slightly yellowish viscous residue, 6.60 g (86.1%). The acid 4b thus obtained was directly used for subsequent experiments without further purification. $^1$H NMR (400 MHz, [D$_6$] DMSO, 25° C.): δ 11.96 (bs, 1H, exchangeable with D$_2$O), 7.87-7.84 (t, J(H,H)=5.39 Hz, 1H, exchangeable with D$_2$O), 7.19-7.04 (m, 4H), 4.04-3.99 (q, J(H,H)=7.05 Hz, 1H), 3.62-3.57 (q, J(H,H)=7.05 Hz, 0.1H, minor rotamer), 3.53-3.47 (q, J(H,H)=7.05 Hz, 1.9H), 3.00-2.95 (q, J(H,H)=6.22 Hz, 2H), 2.41-2.37 (m, 2H, mixture of rotamers), 2.14-2.10 (t, J(H,H)=7.47, 7.05 Hz, 2H), 1.81-1.74 (m, 1H), 1.46-1.40 (m, 2H), 1.36-1.26 (m, 5H), 1.20-1.12 (m, 2H), 0.85-0.82 (m, 6H, mixture of rotamers).

N-Ibuprofyl-6-aminohexanoic acid serinol conjugate (6b)

Compound 4b (6.60 g, 20.676 mmol), DMAP (0.26 g, 2.128 mmol) and pentafluorophenol (5.70 g, 30.97 mmol) were dissolved in dichloromethane (60 mL) and DCC (4.27 g, 20.70 mmol) was added into the stirring solution. The reaction mixture was allowed to stir for 8 h. Precipitated DCU was removed by filtration and the filtrate was evaporated to obtain a crude oil containing the desired ester 5b. The crude 5b thus obtained was stirred with serinol (3.5 g, 38.42 mmol) in dichloromethane in the presence of TEA (8 mL) for 2 h. A white precipitate was formed during the course of the reaction, which was filtered washed successively with dichloromethane, water and diethyl ether and dried over P$_2$O$_5$ to obtain 2.4 g of the product 6b. Extraction of the aqueous phase with EtOAc afforded another 1.05 g of the desired product 6b. Combined yield was 42.5%. $^1$H NMR (400 MHz, [D$_6$] DMSO, 25° C.): δ 7.87-7.84 (t, J(H,H)=5.86, 5.37 Hz, 1H, exchangeable with D$_2$O), 7.42-7.40 (d, J(H,H)=7.81 Hz, 1H, exchangeable with D$_2$O), 7.19-7.17 (d, J(H,H)=8.30 Hz, 2H), 7.06-7.04 (d, J(H,H) 8.30 Hz, 2H), 4.57 (bs, 2H, exchangeable with D$_2$O), 3.69-3.63 (m, 1H), 3.53-3.47 (q, J(H,H) 6.83 Hz, 1H), 3.36-3.34 (d, J(H,H) 5.37 Hz, 4H), 3.02-2.91 (m, 2H), 2.39-2.37 (d, J(H,H)=7.34 Hz, 2H), 2.04-2.00 (t, J(H,H) 7.33 Hz, 2H), 1.81-1.75 (m, 1H), 1.44-1.26 (m, 7H), 1.18-1.12 (m, 2H), 0.84-0.83 (d, J(H,H) 6.35 Hz, 6H).

N-Ibuprofyl-6-aminohexanoic acid serinol mono DMT (7b)

A solid mixture of compound 6b (3.00 g, 7.65 mmol), 4,4'-dimethoxytrityl chloride (2.85 g, 8.41 mmol) and DMAP (0.20 g, 1.64 mmol) was taken in a 200 mL RB and dried over P$_2$O$_5$ under vacuum overnight. Anhydrous pyridine (40 mL) was added into the mixture under argon and stirred for overnight. Pyridine was removed from the reaction and residue was suspended in EtOAc (100 mL) followed by standard workup. Desired mono DMT and bis DMT products were separated by flash silica gel column chromatography, eluent: 2-3% methanol in dichloromethane, 170 g (22.3%, bis DMT derivative) and eluent: 4% methanol in dichloromethane, 1.89 g (35.6%, desired mono DMT product 7b). $^1$H NMR (400 MHz, [D$_6$]DMSO, 25° C.): δ 7.83-7.80 (t, J(H,H)=5.37 Hz, 1H, exchangeable with D$_2$O), 7.58-7.55 (d, J(H,H)=8.79 Hz, 1H, exchangeable with D$_2$O), 7.34-7.32 (d, J(H,H)=7.33 Hz, 2H), 7.26-7.14 (m, 9H), 7.02-7.00 (d, J(H,H)=7.81 Hz, 2H), 6.83-6.81 (d, J(H,H)=8.79 Hz, 4H), 4.58-4.56 (t, J(H,H)=5.37, 4.88 Hz, 1H, exchangeable with D$_2$O), 3.95-3.93 (m, 1H), 3.68 (s, 6H), 3.48-3.45 (q, J(H,H)=7.34 Hz, 1H), 3.41-3.38 (t, J(H,H)=5.37 Hz, 2H), 2.96-2.84 (m, 4H), 2.34-2.33 (d, J(H,H)=7.33 Hz, 2H), 2.02-1.98 (t, J(H,H)=7.33, 7.81 Hz, 2H), 1.76-1.69 (m, 1H), 1.44-1.36 (m, 2H), 1.33-1.23 (m, 5H), 1.16-1.08 (m, 2H), 0.80-0.78 (d, J(H,H)=6.35 Hz, 6H). $^{13}$C NMR (100 MHz, [D$_6$]DMSO, 25° C.): δ 174.0, 172.8, 158.3, 145.4, 139.9, 139.7, 136.2, 130.1, 129.2, 128.2, 128.1, 127.3, 113.5, 85.5, 61.0, 55.4, 51.1, 45.1, 44.6, 35.7, 30.0, 29.1, 26.3, 25.4, 22.5, 18.8.

Ibuprofen-6-aminohexanoic acid-serinol CPG (8b)

The desired succinate (0.98 g, 85.7%) was synthesized from the corresponding precursor 7b (1.00 g, 1.44 mmol), DMAP (0.27 g, 2.21 mmol) and succinic anhydride (0.22 g, 2.20 mmol) as described for the corresponding naproxen derivative. The succinic acid derivative was purified by flash silica gel column chromatography, eluent: 5% methanol in dichloromethane. $^1$H NMR (400 MHz, [D$_6$]DMSO, 25° C.): δ 7.86-7.80 (m, 2H, exchangeable with D$_2$O), 7.34-7.32 (d, J(H,H)=7.33 Hz, 2H), 7.28-7.13 (m, 9H), 7.02-7.00 (d, J(H,H)=8.30 Hz, 2H), 6.85-6.83 (d, J(H,H)=8.79 Hz, 4H), 4.14-1.10 (bm, 1H), 4.02-3.98 (m, 1H), 3.68 (s, 6H), 3.50-3.44 (q, J(H,H)=7.33, 6.83 Hz, 2H), 2.96-2.87 (m, 2H), 2.35-2.33 (m, 6H), 2.51-2.45 (m, 7H, 2H+DMSO-d$_6$), 2.01-1.96 (t, J(H,H)=7.32 Hz, 2H), 1.77-1.69 (m, 1H), 1.42-1.22 (m, 7H), 1.15-1.07 (m, 2H), 0.80-0.78 (d, J(H,H)=6.35 Hz, 6H). $^{13}$C NMR (100 MHz, [D$_6$]DMSO, 25° C.): δ 174.9, 174.3, 173.2, 158.5, 145.3, 139.9, 139.8, 136.0, 130.2, 129.3, 128.4, 128.1, 127.4, 113.6, 85.8, 55.5, 46.1, 46.1, 45.3, 44.7, 35.6, 30.1, 29.0, 26.2, 25.4, 22.6, 18.8.
The desired CPG 8b (4.50 g) with a loading capacity of 85.62 μM/g was prepared from 0.92 g (1.16 mmol) of the ibuprofen succinate thus obtained, 2,2'-Dithiobis(5-nitropyridine) (0.37 g, 1.18 mmol), DMAP (0.15 g, 1.23 mmol), Ph$_3$P (0.31 g, 1.18 mmol) and long chain aminoalkyl controlled-pore-glass (CPG) with 500 Å size and a loading of 162.5 μM/g as described for the preparation of the corresponding naproxen analogue 8a.

Ibuprofen Pentafluorophenol Ester (1d)

Ibuprofen pentafluorophenol ester (1d) was prepared from ibuprofen (1b, 5.00 g, 24.23 mmol), pentafluorophenol (5.4 g, 29.02 mmol), DCC (5.00 g, 24.23 mmol) and DMAP (0.30 g, 2.46 mmol) as described for the synthesis of pentafluorophenol ester (1c) of naproxen (1a).

Example 17

Synthesis of Naproxen-Bearing Linker

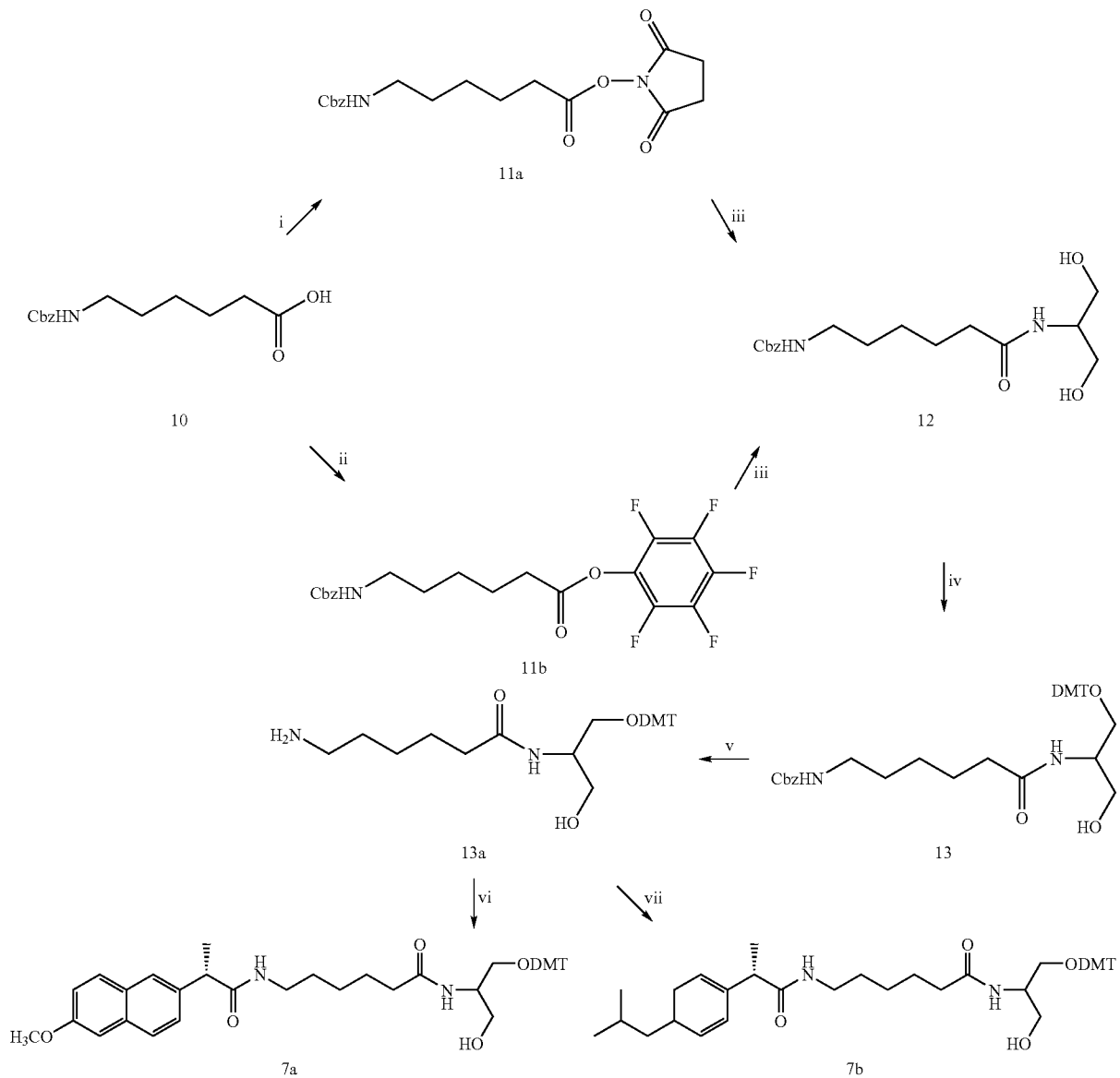

[a] (i) N-hydroxysuccinimide, DCC, DMAP/Dichloromethane-DMF; (ii) Pentafluorophenol, DCC, DMAP/Dichloromethane; (iii) Serinol, TEA/dichloromethane; (iv) DMT-Cl, DMAP/Py; (v) Pd—C (10%), ammonium formate; (vi) Naproxen-NHS ester (14), TEA/Dichloromethane; (vii) Ibuprofen-NHS ester (15), TEA/Dichloromethane.

N-Cbz-6-aminohexanoic acid pentafluorophenol ester 11b

N-Cbz-6-aminohexanoic acid (10, 30.31 g, 114.25 mmol, purchased from Novabiochem), pentafluorophenol (25.00 g, 135.83 mmol) and DMAP (1.54 g, 12.60 mmol) were taken in dichloromethane (100 mL) and to this DCC (26.00 g, 121.01 mmol) added slowly under stirring. During the course of addition, temperature of the reaction rose and dichloromethane started boiling out, so it was cooled down to room temperature and allowed to stir overnight. Reaction mixture was diluted to 200 mL by adding diethyl ether and subsequently filtered through a sintered funnel to remove DCU, washed residue with diethyl ether, combined washing and evaporated to dryness. The desired product 11b was purified by flash silica gel column chromatography, eluent: hexane/EtOAc 2:1, yield 43.54 g (88.4%). $^1$H NMR (400 MHz, [D$_6$]DMSO, 25° C.): δ 7.36-7.23 (m, 6H), 4.99 (s, 2H), 3.01-2.96 (q, J(H,H)=6.35 Hz, 2H), 2.78-2.52 (q, J(H,H)=7.33 Hz, 2H), 1.69-1.61 (m, 2H), 1.47-1.29 (m, 4H).

N-Cbz-6-aminohexanoic acid serinol (12)

Compound 11b (26.00 g, 60.31 mmol) and serinol (5.00 g, 54.88 mmol) were suspended in 200 mL of dichloromethane and stirred in the presence of TEA (17 mL, 121.97 mmol) at ambient temperature overnight. A thick white precipitate was formed during the course of the reaction. The reaction mixture was diluted to 200 mL by adding diethyl ether, triturated and filtered. The precipitate was thoroughly washed with diethyl ether and dried under vacuum over $P_2O_5$ to obtain 16.51 g (81.0%) of the desired compound 12 as a white solid. $^1$H NMR (400 MHz, [$D_6$]DMSO, 25° C.): δ 7.44-7.42 (d, J(H,H)=7.81 Hz, 1H, exchangeable with $D_2O$), 7.37-7.27 (m, 5H), 7.24-7.20 (t, J(H,H)=5.86, 5.37 Hz, 1H, exchangeable with $D_2O$), 4.99 (s, 2H), 4.58-4.55 (t, J(H,H)=5.37 Hz, 2H, exchangeable with $D_2O$), 3.70-3.65 (m, 1H), 3.37-3.34 (t, J(H,H)=5.86, 3.37 Hz, changed to doublet after $D_2O$ exchange, J(H,H, after $D_2O$ exchange) 5.37 Hz, 4H), 2.98-2.92 (q, J(H,H)=6.84, 6.35 Hz, 2H), 2.06-2.02 (t, J(H,H)= 7.33 Hz, 2H), 1.49-1.33 (m, 4H), 1.24-1.16 (m, 2H).

N-Cbz-6-aminohexanoic acid serinol mono DMT (13)

Compound 12 (14.10 g, 41.66 mmol) and DMAP (0.60 g, 4.91 mmol) were taken in a 200 mL RB and dried under vacuum over $P_2O_5$. The solid mixture then suspended in 50 mL of anhydrous pyridine under argon. 4,4-Dimethoxytrityl chloride (15.5 g, 44.27 mmol) was separately dissolved in 40 mL of anhydrous dichloromethane and added into the stirring pyridine solution under argon. The reaction mixture was allowed to stir at ambient temperature overnight. Solvents were removed from the reaction mixture and residue was extracted into EtOAC (200 mL), washed with $NaHCO_3$ solution followed by standard workup. The desired product 13 was purified by flash silica gel column chromatography, eluent: hexane/EtOAc 3:2, 8.62 g (28.0%, bis DMT derivative) and 3-4% MeOH in chloroform, 15.28 g (57.3%, desired mono DMT derivative 13). $^1$H NMR (400 MHz, [$D_6$]DMSO, 25° C.): δ 7.63-7.60 (d, J(H,H)=8.79 Hz, 1H, exchangeable with $D_2O$), 7.38-7.17 (m, 15H, accounted for 14H after $D_2O$ exchange), 6.87-6.84 (d, J(H,H)=8.79 Hz, 4H), 4.98 (s, 2H), 4.62-4.59 (t, J(H,H)=5.37 Hz, 1H, exchangeable with $D_2O$), 4.00-3.95 (m, 1H), 3.72 (s, 6H), 3.46-3.41 (t, J(H,H)=5.37 Hz, 2H), 3.00-2.87 (m, 4H), 2.08-2.04 (t, J(H,H)=7.33 Hz, 2H) 1.50-1.33 (m, 4H), 1.25-1.16 (m, 2H).

Synthesis of Compound 7a from Compound 13

DCC (14.80 g, 71.73 mmol) was added into a stirring mixture of naproxen (15.00 g, 65.14 mmol), DMAP (0.80 g, 6.55 mmol) and N-hydroxysuccinimide (10.00 g, 86.82 mmol) in 80 mL of DMF at ambient temperature and the stirring was continued overnight. Precipitated DCU was filtered off from the reaction, washed with DMF, combined the washings and evaporated to dryness in vacuo. Residue obtained was triturated with diethyl ether, filtered, washed the residue extensively with diethyl ether and dried to obtain a white solid naproxen N-hydroxy succinimide ester, 22.00 g (21.31 g theoretical value). $^1$H NMR (400 MHz, [$D_6$]DMSO, 25° C.): δ 7.83-7.78 (m, 3H), 7.46-7.43 (dd, J'(H,H)=1.95, 1.46 and J"(H,H)=8.79, 8.30 Hz, 1H), 7.32-7.31 (d, J(H,H)=2.44 Hz, 1H), 7.17-7.15 (dd, J'(H,H)=2.44 and J"(H,H)=8.79 Hz, 1H), 4.41-4.35 (q, J(H,H)=6.84, 7.33 Hz, 1H), 3.86 (s, 3H), 2.74 (s, 4H), 1.59-1.57 (d, J(H,H) 6.84 Hz, 3H).

Compound 13a

Compound 13 and ammonium formate are suspended in a 1:1 mixture of methanol-EtOAc and 10% by wt Pd—C (10%) is added into the suspension, the reaction mixture is slightly warmed using a heat gun and allowed stir at ambient temperature for 2 h. Removed Pd—C and insoluble ammonium formate by filtration, combined filtrate and evaporated. Residue was suspended in EtOAc and washes with aqueous $NaHCO_3$ solution to obtain compound 13a.

Synthesis of Compound 7a from Compound 13

Naproxen N-hydroxysuccinimide ester (21.0 g) was prepared from naproxen (1a, 15.00 g, 65.14 mmol) and N-hydroxysuccinimide (10.00 g, 86.82 mmol) using DCC (14.80 g, 71.73 mmol) as the coupling agent in the presence of DMAP (0.80 g, 6.55 mmol) as described in Example 15 for the synthesis of the corresponding pentafluorophenol ester ic. $^1$H NMR (400 MHz, [$D_6$]DMSO, 25° C.): δ 7.83-7.78 (m, 3H), 7.46-7.43 (dd, J'(H,H)=1.95, 1.46 and J"(H,H)=8.79, 8.30 Hz, 1H), 7.32-7.31 (d, J(H,H)=2.44 Hz, 1H), 7.17-7.15 (dd, J'(H,H)=2.44 and J"(H,H)=8.79 Hz, 1H), 4.41-4.35 (q, J(H,H)=6.84, 7.33 Hz, 1H), 3.86 (s, 3H), 2.74 (s, 4H), 1.59-1.57 (d, J(H,H)=6.84 Hz, 3H).
Naproxen N-hydroxysuccinimide ester is stirred with compound 13a to obtain compound 7a. See Example 15 for analytical data.

Synthesis of Compound 7B from Compound 13

DCC (6.60 g, 31.99 mmol) was added into a stirring mixture of ibuprofen (6.00 g, 29.09 mmol), DMAP (40 g, 3.27 mmol), and N-hydroxysuccinimide (4.40 g, 38.23 mmol) in 30 mL of DMF and allowed to stir overnight. DCU was filtered off as described for the synthesis of the corresponding naproxen derivative. Residue obtained was triturated with diethyl ether and filtered, the product dissolved in ether. Combined filtrate, reduced to small volume on the rotary evaporator. Hexane was added into the concentrated to solution to precipitate out the desired product, which was filtered, washed with hexane and dried to obtain the desired ester 7.48 g, (yield 84.8%). $^1$H NMR (400 MHz, [$D_6$]DMSO, 25° C.): δ 7.28-7.25 (d, J(H,H)=8.30 Hz, 2H), 7.16-7.13 (d, J(H,H)=8.30 Hz, 2H), 4.24-4.18 (q, J(H,H)=6.84, 7.32 Hz, 1H), 2.77 (s, 4H), 2.43-2.41 (d, J(H,H)=7.32 Hz, 2H), 1.84-1.77 (m, 1H), 1.49-1.47 (d, J(H,H)=7.32 Hz, 3H), 0.85-0.83 (d, J(H,H)=6.84 Hz, 6H).
Naproxen N-hydroxysuccinimide ester is stirred with compound 13a to obtain compound 7b. See Example 16 for analytical data.

Example 18

Synthesis of Naproxen Bound to a Solid Support

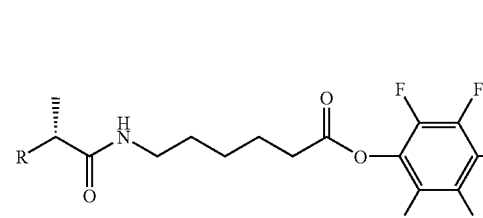
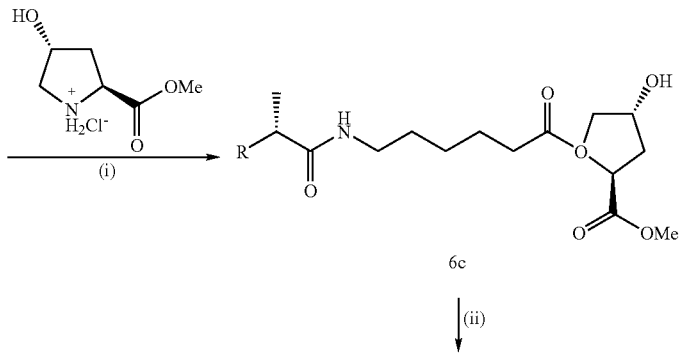

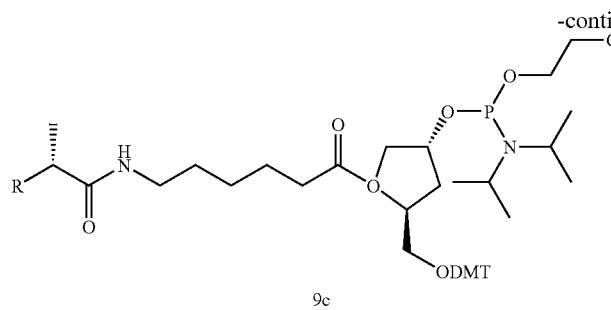

9c

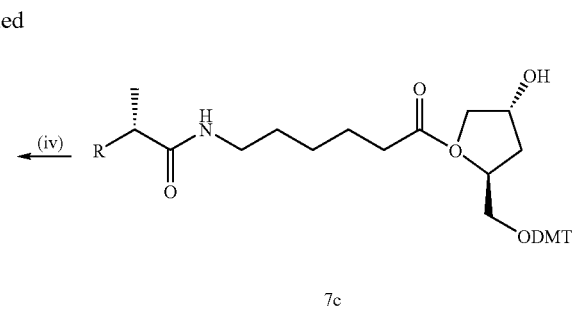

7c

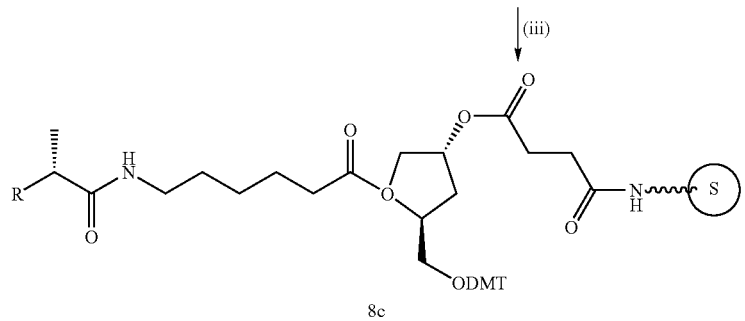

8c (i) TEA/Dichloromethane; (ii) (a) LiBH₄/MeOH and (b) DMT-Cl, DMAP/Py; (iii) (a) Succinic anhydride, DMAP/Dichloroethane and (b) DTNP, DMAP, Ph₃P, Aminoalkyl solid support and (iv) N,N-diisopropylamino b-cyanoethylphosphonamidic chloride {[(CH₃)₂CH]₂N—P(Cl)-OCH₂CH₂CN}, DIEA/Dichloromethane or 2-Cyanoethyl-N,N,N',N'-tetraisopropylphosphane, tetrazole (or tetrazolediisopropylammonium salt)/Acetonitrile.

Compound 6c

Compound 5a (2.90 g, 5.70 mmol) and commercially available trans-4-hydroxy-L-proline methyl ester hydrochloride (1.25 g, 6.88 mmol, obtained from CNH Technologies Inc.) were suspended in dichloromethane (30 mL) and excess TEA was added into the suspension and stirred at ambient temperature for 2 h. Solvent and excess TEA were removed from the reaction mixture in vacuo and the product was extracted into EtOAc (100 mL). The organic layer was successively washed with aqueous KHSO₄ solution, water, NaHCO₃ solution and water followed by standard workup. Residue obtained was purified by flash slice gel column chromatography, eluent 5% MeOH in dichloromethane, to afford compound 6c, 2.1 g (78.4%). $^1$H NMR (400 MHz, [D₆] DMSO, 25° C.): δ 7.94-7.92 (bt, 1H, exchangeable with D₂O), 7.77-7.68 (m, 3H), 7.43-7.41 (dd, J'(H,H)=1.66, 1.40 and J"(H,H)=8.30 Hz, 1H), 7.26-7.25 (d, J(H,H)=2.10 Hz, 1H), 7.14-7.11 (dd, J'(H,H)=2.49 and J"(H,H)=8.71 Hz, 1H), 5.16-5.15 (d, 0.85H, exchangeable with D₂O, major rotamer), 5.09-5.08 (d, 0.15H, exchangeable with D₂O, minor rotamer), 4.59-4.57 (m, 0.15H), 4.30-4.20 (m, 1.85H), 3.84 (s, 3H), 3.69-3.52 (m, 6H including H₂O from the solvent), 3.34-3.32 (bd, 2.5H, accounted for 1H after D₂O exchange), 3.02-2.97 (m, 2H), 2.15-2.04 (m, 3H), 1.89-1.82 (m, 1H), 1.44-1.30 (m, 7H), 1.15-1.14 (m, 2H). $^{13}$C NMR (100 MHz, [D₆]DMSO, 25° C.): δ 173.9, 173.0, 171.7, 157.3, 137.8, 133.4, 129.4, 128.7, 126.9, 126.7, 125.5, 118.9, 106.0, 69.1, 57.5, 55.5, 55.0, 52.1, 45.5, 38.7, 33.7, 29.0, 26.1, 24.1, 18.7.

Compound 7c

Compound 6c is treated with LliBH₄ in methanol to obtain the corresponding diol (Rajeev et al., *J. Org. Chem.*, 1997, 62, 5169). The diol thus obtained is stirred with DMT-Cl in anhydrous pyridine in the presence of DMAP to obtain compound 7c.

Solid Support 8c

The desired CPG 8c is prepared from compound 7c as described in Example 15 for the synthesis of compound 8a.

Phosphoramidite 9c

The desired phosphoramidite 9c is prepared from compound 7c as described in Example 15 for the synthesis of compound 9a Example 19

Synthesis of Naproxen Bound to a Solid Support

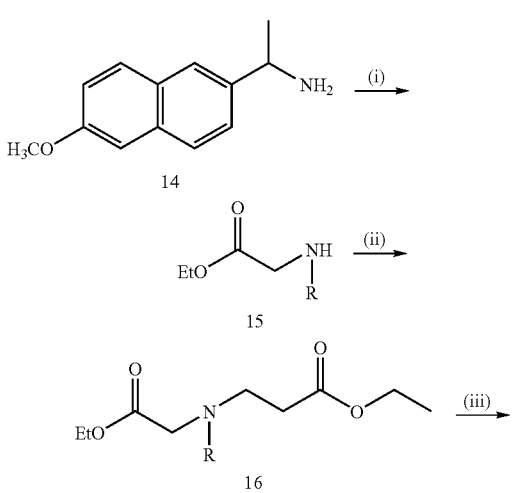

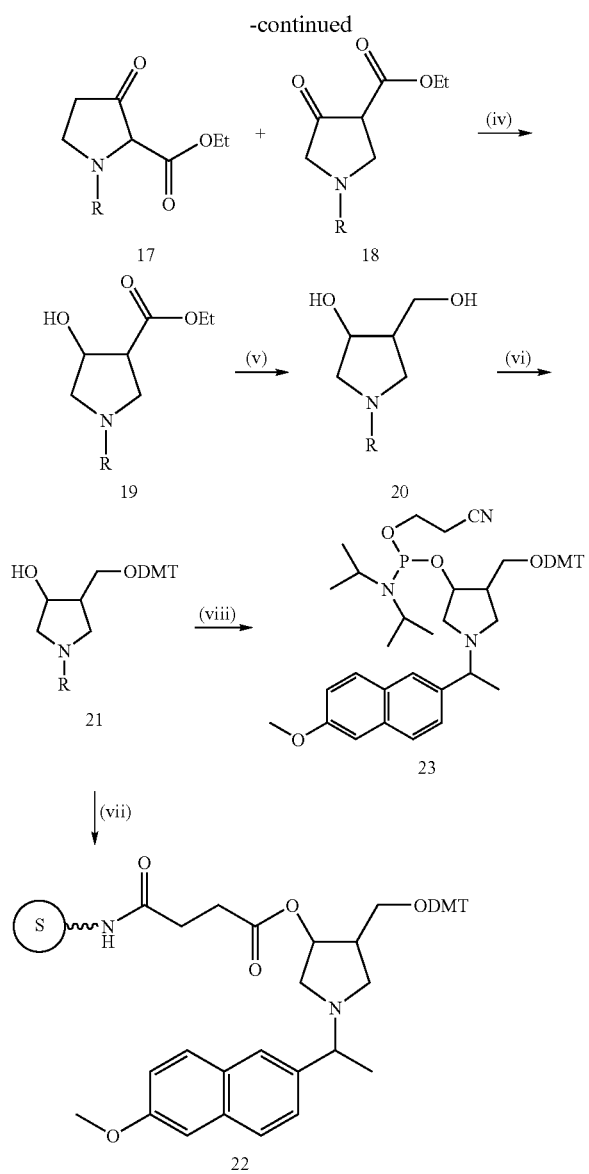

(i) Ethyl glyoxalate, NaBH(OAc)$_3$, HOAc/MeOH; (ii) Ethyl bromopropionate, DIEA/Dichloromethane; (iii) KO'Bu/Toluene: (iv) Baker's yeast/H$_2$O; (v) LiBH$_4$/MeOH; (vi) DMT-Cl, DMAP/Py; (vii) (a) Succinic anhydride, DMAP/Dichloroethane and (b) DTNP, DMAP, Ph$_3$P, Aminoalkyl solid support and (viii) N,N-diisopropylamino b-cyanoethylphosphonamidic chloride {[(CH$_3$)$_2$CH]$_2$N—P(Cl)-OCH$_2$CH$_2$CN}, DIEA/Dichloromethane or 2-Cyanoethyl-N,N,N',N'-tetraisopropylphosphane, tetrazole (or tetrazolediisopropylammonium salt)/Acetonitrile.

Compound 15

Compound 14 is prepared as reported in the literature. General procedure for synthesizing amine 15 (Ref: Abdel-Magid et al. *J. Org. Chem.* 1996, 61 (11), 3849-3862): A representative example of this reductive amination is shown with the reaction of amine 14 and ethyl glyoxalate: Ethylglyoxalate (45% solution in Toluene; 1 equiv.) and amine (1 equiv.) are mixed in anhydrous THF and then treated with sodium triacetoxyborohydride (1.5 equiv.). The mixture is stirred at ambient temperature for 24 h. The reaction mixture is quenched by the addition of saturated NaHCO$_3$ solution and the product is extracted into EtOAc. Amine 15 is obtained by the concentration of organic layer.

Compound 16

Synthesis of diester 16 (Ref: St-Denis et al. *Can. J. Chem.* 2000, 776): To a solution of freshly prepared amine 15 (1 equiv.) in toluene is added ethyl 3-bromopropionate (1.2 equiv) in toluene. The suspension is heated at 60° C. for 6 h and poured into aqueous sodium carbonate solution. The aqueous phase is extracted with chloroform and concentrated to afford diester 16.

Compound 17 and 18

Synthesis of ketoester 17 and 18 (Ref: Blake et al. J. Org. Chem. 1964, 5293)

To a suspension of potassium t-butoxide (1.5 equiv) in toluene at 0° C. under nitrogen is added 1 equiv. of diester 16 in toluene over a period of 30 min. The solution is stirred at 0° C. till the starting material disappears and glacial acetic acid is added, immediately followed by a solution of NaH$_2$PO$_4$.H$_2$O in ice-cold water. The resultant mixture is extracted with chloroform and the combined organic extracts are washed twice with pH 7.0 phosphate buffer, dried and evaporated to a residue. The residue is dissolved in toluene, cooled to 0° C., and extracted with portions of cold pH 9.5 carbonate buffer. The aqueous extract is converted to pH 3 with slow addition of phosphoric acid and extract with chloroform (3×100 mL). The combined organic layer is dried over anhydrous sodium sulfate and evaporated to afford ketoester 18. Toluene layer is dried over sodium sulfate and evaporated to dryness to yield ketoester 17.

Compound 19

Baker's yeast reduction of 18 to obtain compound 19 (Ref: St-Denis et al. Can. J. Chem. 2000, 776). To a solution of sucrose (2 equiv by wt.) in distilled water is added baker's yeast (1.5 equiv. by wt.). The suspension is heated at 32° C. in the rotary evaporator. The content of the flask is then poured into diester 18 (1 equiv. by wt.). Stirring is continued for a day after which additional sucrose in warm (40° C.) distilled water is added. After 2 days Celite is added to the mixture and is filtered through a sintered glass funnel. The filtrate is re-filtered through a pad of Kieselguhr. After washing, the aqueous layer is extracted with dichloromethane. The organic layer is combined and evaporated to yield ester alcohol 19.

Diol 20

Compound 19 (1 equiv.) is dissolved in anhydrous THF and is added to IM lithium borohydride (1 Equiv.) in anhydrous THF at 0° C. The reaction mixture is stirred at 0° C. till the disappearance of starting materials. Excess lithium borohydride is quenched by the addition of water. The reaction mixture is concentrated under reduced pressure. To the residue 3N hydrochloric acid is added and stirred for 3 h. The resultant aqueous layer is extracted with ethyl acetate. The combined organic layer is dried over sodium sulfate and concentrated to yield diol 20 which is purified by column chromatography.

Compound 21

Compound 21 is obtained from the diol 20 as described in Example 15 for the preparation of compound 7a from diol 6a.

Solid Support 22

Compound 22 is obtained from compound 21 as described in Example 15 for the preparation of compound 8a from compound 7a.

Phosphoramidite 23

Phosphoramidite 22 is obtained from compound 21 as described in Example 15 for the preparation of compound 9a from compound 7a.

Example 20

Synthesis of Naproxen Bound to a Solid Support

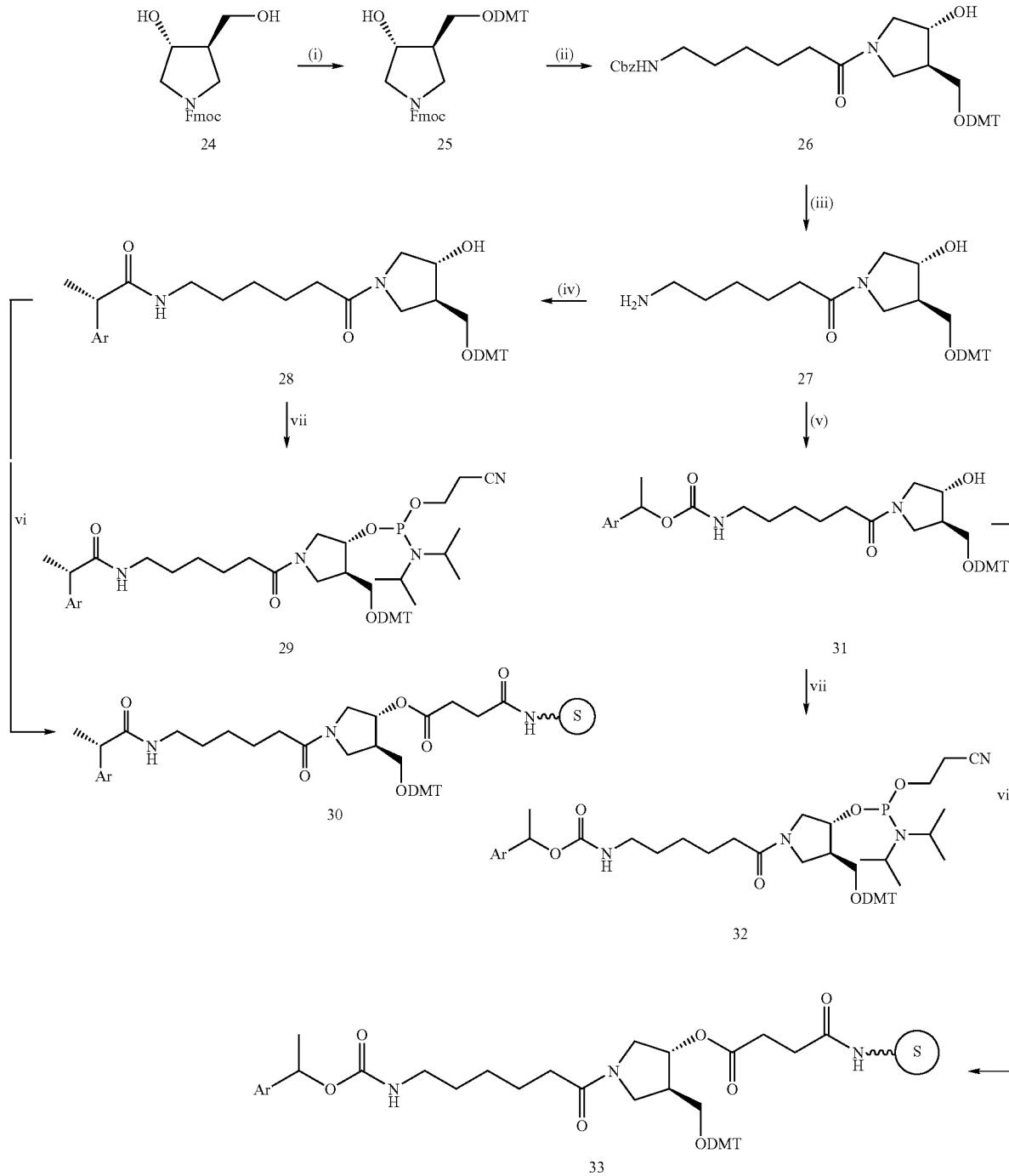

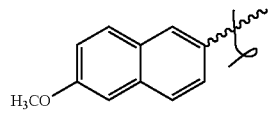

(i) DMT-Cl, DMAP/Py; (ii) (a) Piperidine/DMF (b) 11a, TEA/Dichloromethane (iii) H$_2$/Pd—C or Ammonium formate, Pd—C; (iv) Ic, TEA/Dichloromethane (v) DL-6-Methoxy-α-methyl-2-napthalenemethanol, CDI/THF (vi) (a) Succinic anhydride, DMAP/Dichloroethane and (b) DTNP, DMAP, Ph$_3$P, Aminoalkyl solid support and (vii) N,N-diisopropylamino b-cyanoethylphosphonamidic chloride {[(CH$_3$)$_2$CH]$_2$N—P(Cl)-OCH$_2$CH$_2$CN}, DIEA/Dichloromethane or 2-Cyanoethyl-N,N,N',N'-tetraisopropylphosphane, tetrazole (or tetrazolediisopropylammonium salt)/Acetonitrile.

Compound 25

Compound 24 is prepared as reported in the literature (Filichev and Pedersen, *Tetrahedron*, 2001, 57, 9163-68). The mono DMT compound 25 is prepared from compound 24 as described in Example 15 for the preparation of compound 7a from compound 6a.

Compound 26

Fmoc group is removed from compound 25 by treating with piperidine as reported in the literature (Atherton and Sheppard, *The Peptides*, 1987, 9, 1, Udenfriend and Meienhofer Eds., Academic Press, New York). After removing Fmoc, the free amine obtained is stirred with compound 11a (see Scheme 2) in the presence of TEA to obtain compound 26.

Compound 27

Catalytic hydrogenation of compound 26 yields compound 27.

Compound 28

Compound 27 is stirred with the ester 1c (Scheme 1) in the presence of TEA to obtain compound 28.

Compound 29

The phosphoramidite 29 is prepared from compound 28 as described in Example 15 for the preparation of phosphoramidite 9a from 7a.

Compound 30

The solid support 30 is obtained from 28 as described in Example 15 for the preparation of support 8a from 7a.

Compound 31

Compound 27 is treated with 1,1'-carbonyldiimidazole and commercially available DL-6-Methoxy-α-methyl-2-napthalenemethanol (Acros Organics) in THF as reported in the literature to obtain compound 31 (Hernandez and Hodges, *J. Org. Chem.*, 1997, 62, 3153).

Compound 32

The phosphoramidite 32 is prepared from compound 31 as described in Example 15 for the preparation of compound 9a from compound 7a.

Compound 33

The solid support 33 is obtained from compound 31 as described for the preparation of support 8a from compound 7a.

Example 21

Synthesis of Naproxen Bound to a Solid Support

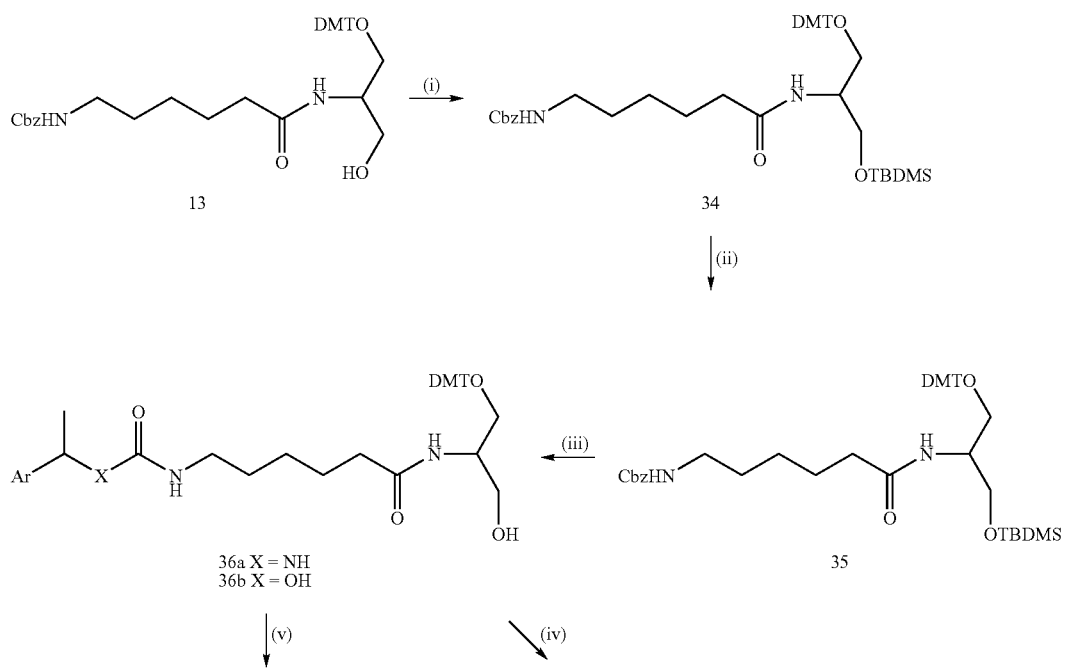

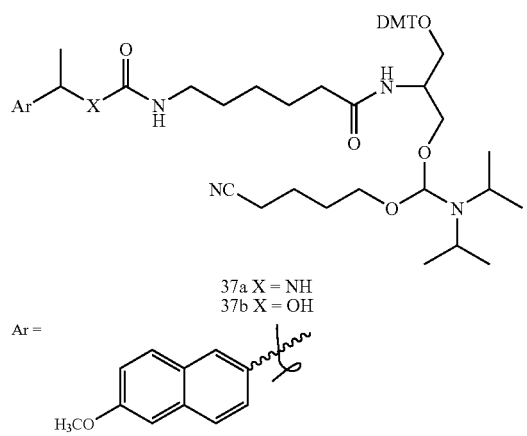
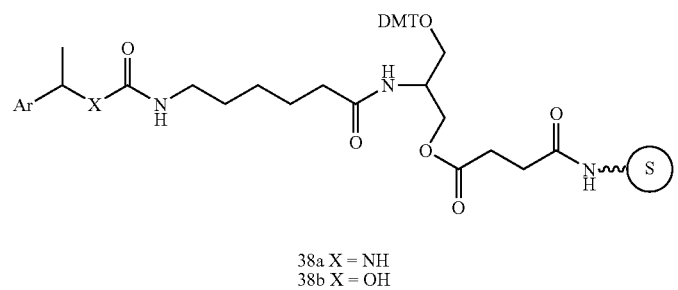

37a X = NH
37b X = OH

38a X = NH
38b X = OH

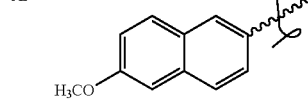

(i) TBDMS-Cl, Imidazole/Pyridine; (ii) H$_2$/Pd—C; (iii) for 36a, DL-6-methoxy-α-methyl-2-Naphthalenemethanamine, CDI/THF and for 36b, DL-6-Methoxy-α-methyl-2-napthalenemethanol, CDI/THF; (iv) (a) Succinic anhydride, DMAP/Dichloroethane and (b) DTNP, DMAP, Ph$_3$P, Aminoalkyl solid support and (v) N,N-diisopropylamino b-cyanoethylphosphonamidic chloride {[(CH$_3$)$_2$CH]$_2$N—P(Cl)-OCH$_2$CH$_2$CN}, DIEA/Dichloromethane or 2-Cyanoethyl-N,N,N',N'-tetraisopropylphosphane, tetrazole (or tetrazolediisopropylammonium salt)/Acetonitrile.

Compound 34

Compound 13 (12.91 g, 20.16 mmol) was stirred with TBDMS-Cl (4.60 g, 30.52 mmol) in pyridine in the presence of imidazole (6.30 g, 92.54 mmol) at ambient temperature under argon for 6 h. Pyridine was removed from the reaction mixture in vacuo and residue was extracted into EtOAc (100 mL) and washed with NaHCO$_3$ solution followed by standard workup. Residue was purified by flash silica gel column chromatography to obtain compound 34, eluent: 2-3% methanol in dichloromethane, yield: 15.10 g (99.3%). $^1$H NMR (400 MHz, [D$_6$]DMSO, 25° C.): δ 7.65-7.63 (d, J(H,H)=8.30 Hz, 1H, exchangeable with D$_2$O), 7.38-7.17 (m, 15H, accounted for 14H after D$_2$O exchange), 6.86-6.84 (d, J(H,H)=8.79 Hz), 4.01-3.96 (m, 1H), 3.71 (s, 6H), 3.58-3.54 (m, 2H), 3.04-2.88 (m, 4H), 2.08-2.04 (t, J(H,H)=7.33 Hz, 2H), 1.49-1.31 (m, 4H), 1.23-1.17 (m, 2H), 0.72 (s, 9H), −0.08 (s, 3H), −0.10 (s, 3H).

Compound 35

Compound 34 is stirred with ammonium formate and Pd—C to obtain compound 35 as described in Example 17 for the preparation of compound 13a from compound 13.

Compound 36a

Compound 35 is treated with 1,1'-carbonyldiimidazole and DL-6-methoxy-α-methyl-2-Naphthalenemethanamine as described in Example 20 for the preparation of compound 31 from compound 27. DL-6-methoxy-α-methyl-2-Naphthalenemethanamine is prepared according to literature procedure (Wolber and Ruechardt, *Chem. Ber.*, 1991, 124, 1667). After making the completely protected urea derivative, the product obtained is treated with TEA.3HF (Nystrom et al., *Tetrahedron Lett.*, 1985, 26, 5393) in the presence of excess of TEA in THF to obtain compound 36a.

Compound 36b

Compound 35 is treated with 1,1'-carbonyldiimidazole and commercially available DL-6-Methoxy-α-methyl-2-napthalenemethanol (Acros Organics) as described in Example 20 for the preparation of compound 31 from compound 27. After making the completely protected carbamate derivative, the product obtained is treated with TEA.3HF (Nystrom et al., *Tetrahedron Lett.*, 1985, 26, 5393) in the presence of excess of TEA in THF to obtain compound 36b.

Compound 37a

The phosphoramidite 37a is prepared from compound 36 as described in Example 15 for the preparation of phosphoramidite 9a from 7a.

Compound 38a

The solid support 38a is obtained from 36a as described in Example 15 for the preparation of support 8a from 7a.

Compound 37b

The phosphoramidite 37b is prepared from compound 36b as described in Example 15 for the preparation of compound 9a from compound 7a.

Compound 38b

The solid support 38b is obtained from compound 36b as described for the preparation of support 8a from compound 7a.

Example 22

Synthesis of Naproxen Bound to a Solid Support

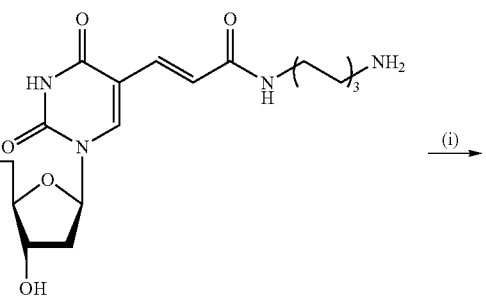

39

-continued

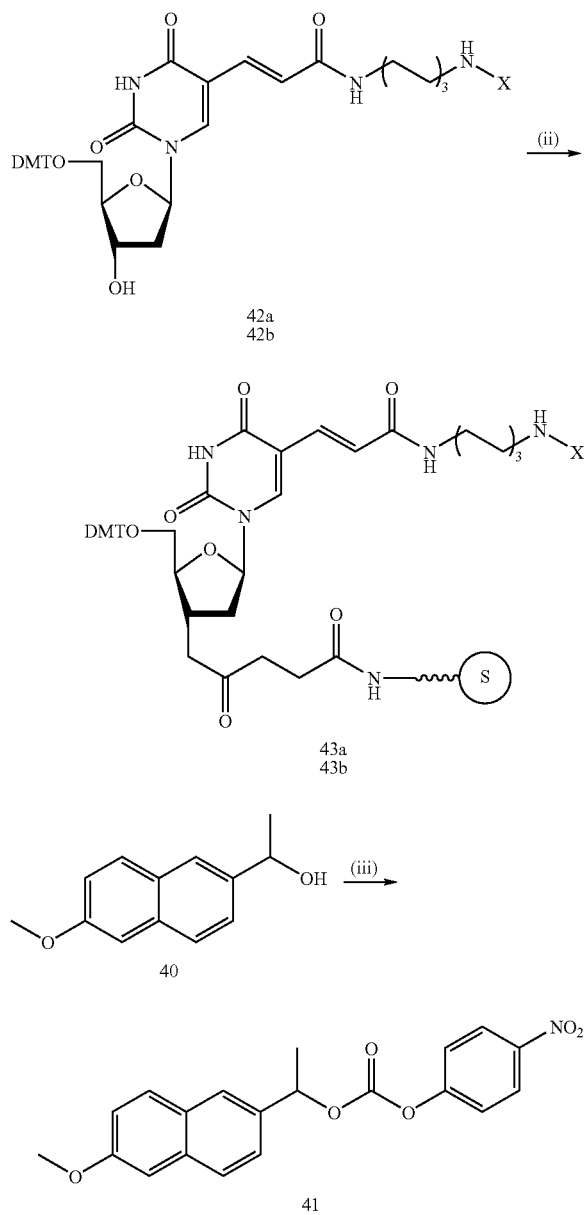

42a
42b 43a
43b

40

41

42a, 43a X =

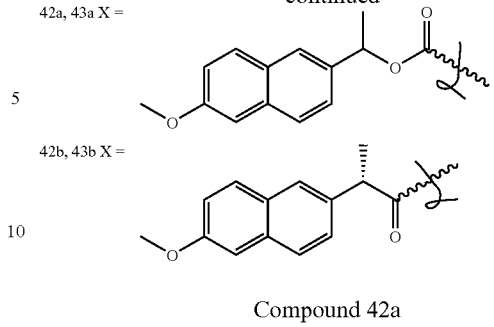

42b, 43b X =

Compound 42a

Compound 39 was purchased from Chem Genes Corporation. Compound 39 (1.50 g, 2.15 mmol) and compound 1c (1.30 g, 3.28 mmol, see Example 15 for the preparation of 1c) were stirred in dichloromethane (10 mL) in the presence of excess TEA for 4 h. The reaction mixture was diluted after to 80 mL by adding more dichloromethane and washed with NaHCO$_3$ solution, the organic layer was evaporated to dryness. Residue obtained was purified by flash silica gel column chromatography to afford compound 42a (0.85 g, 43.5%, eluent: 4% MeOH in dichloromethane). $^1$H NMR (400 MHz, [D$_6$]DMSO, 25° C.): δ 11.61 (s, 1H, exchangeable with D$_2$O), 8.00-7.91 (bm, 3H, partly exchangeable with D$_2$O), 7.76-7.68 (m, 3H), 7.43-7.01 (m, 15H), 6.87-6.83 (m, 4H), 6.17-6.14 (t, J(H,H)=6.41, 6.71 Hz, 1H), 5.28-5.27 (d, J(H,H)=4.88 Hz, 1H, exchangeable with D$_2$O), 4.23-4.19 (m, 1H), 3.89-3.82 (m, 4H), 3.71-3.65 (m, 8H), 3.32 (s, 3H), 3.32-2.90 (m, 6H), 2.49-2.31 (m, 1H), 2.29-2.13 (m, 1H), 1.38-1.18 (m, 9H).

Compound 43a

3'-O-succinate (0.67 g, 92.8%) of compound 42a (0.65 g, 0.71 mmol) was prepared as described in Example 15. $^1$H NMR (400 MHz, [D$_6$]DMSO, 25° C.): δ 12.19 (bs, 1H, exchangeable with D$_2$O), 11.64-11.60 (bm, 1H, exchangeable with D$_2$O), 8.03-7.75 (m, 3H), 7.76-7.67 (m, 3H), 7.42-7.01 (m, 15H), 6.87-6.76 (m, 4H), 6.16-6.12 (t, J(H,H)=6.71, 7.02 Hz, 1H), 5.17-5.15 (m, 1H), 4.08-3.99 (m, 2H), 3.84-3.82 (m, 3H), 3.71-3.65 (m, 9H), 3.30-3.19 (m, 2H), 3.11-2.98 (m, 6H), 2.65-2.40 (11H), 2.34-2.28 (m, 1H), 1.37-1.28 (m, 9H), 1.17-1.13 (m, 10H).

The 3'-O-succinate (0.51 g, 0.50 mmol) thus obtained was conjugated to CPG as described in example 15 for the preparation of compound 8a to obtain the desired CPG. Loading 12 μM/g, was determined as described in the literature (Prakash et al., J. Org. Chem., 2002, 67, 357 and references cited therein).

Example 23

In Vitro Luc Activity of siRNA

TABLE 19

In vitro Luc activity of siRNA with methylphosphonate backbone at terminal and internal positions

| Sequence (SEQ ID NOS 77-80) | Mass Calc. | Mass Found | Purity (%, CGE) | in vitro Luc Activity[c] |
|---|---|---|---|---|
| 101[a] 5' CUUACGCUG AGUACUUCGA dTdT 3' | 6606.0 | 6606.45 | 99.2 | +++ |
| 3' dTGAAUGCGACUCA UGAAGCU 5' | 6693.3 | 6693.0 | 89.01 | |
| 105[b] 5' C*UpdTACGCUGAGpdTACUUCGApdTdT 3' | 6616.20 | 6612.24 | 90.19 | +++ |
| 3' dTdTGAAUGCGACUCAUGAAGCU 5' | 6693.3 | 6693.0 | 89.00 | |

[a]Control Luc sequence;
[b]modified sense strand with methylphosphonate linkages (pdT = methylphosphonate linkage at the 3'-position of dT), a phosphorothioate linkage (here, * at the 3'-potition of cytidine); and
[c]both control and modified siRNA showed comparable in vitro gene silencing.

The synthesis details of the sequences in Table 19 are provided in Example 12. The details of the luciferase activity assay are provided in Example 13; the control duplex 101 is listed above in Table 18, entry 101.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A double-stranded iRNA agent comprising a first strand and a second strand, wherein said first strand and said second strand are represented independently by formula II:

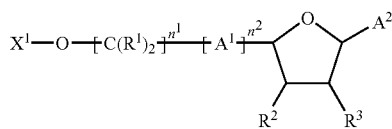

wherein $X^1$ is H, —P(O)(OM)$_2$, —P(O)(OM)-O—P(O)(OM)$_2$, —P(O)(Oalkyl)$_2$, —P(O)(Oalkyl)-O—P(O)(Oalkyl)$_2$, or -A$^6$-[A$^7$-(A$^5$)$_w$]$_y$;

M represents independently for each occurrence an alkali metal or a transition metal with an overall charge of +1;

$R^1$ and $R^5$ represent independently for each occurrence H, alkyl, or halogen;

$R^2$ and $R^3$ represent independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, —S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, —O(C(R$^{19}$)$_2$)$_k$ON((C$_1$-C$_6$)alkyl)$_2$, or —O-A$^6$-[A$^7$-(A$^5$)$_w$]$_y$;

$R^4$ represents independently for each occurrence H, OH, F, —Oalkyl, —Oallyl, —O(C(R$^{19}$)$_2$)$_k$OR$^{19}$, —O(C(R$^{19}$)$_2$)$_k$SR$^{19}$, —O(C(R$^{19}$)$_2$)$_k$N(R$^{19}$)$_2$, —O(C(R$^{19}$)$_2$)$_k$C(O)N(R$^{19}$)$_2$, —N(R$^{19}$)$_2$, —S(C$_1$-C$_6$)alkyl, —O(C(R$^{19}$)$_2$)$_k$O(C$_1$-C$_6$)alkyl, —O(C(R$^{19}$)$_2$)$_k$S(C$_1$-C$_6$)alkyl, —O(C(R$^{19}$)$_2$)$_k$O(C(R$^{19}$)$_2$)$_k$N((C$_1$-C$_6$)alkyl)$_2$, or —O(C(R$^{19}$)$_2$)$_k$ON((C$_1$-C$_6$)alkyl)$_2$;

$R^6$, $R^7$, and $R^9$ represent independently for each occurrence H, alkyl, aryl, or aralkyl;

$R^8$ represents independently for each occurrence alkyl, aryl, or aralkyl;

k represents independently for each occurrence 1, 2, 3, or 4;

$n^1$ is 1, 2, or 3;

$n^2$ is an integer in the range of about 15-28, inclusive;

w represents independently for each occurrence 1, 2, or 3 in accord with the rules of valence;
x represents independently for each occurrence 0, 1, 2, or 3;
y represents independently for each occurrence 1, 2, 3, 4, or 5 in accord with the rules of valence;
$A^1$ represents independently for each occurrence:

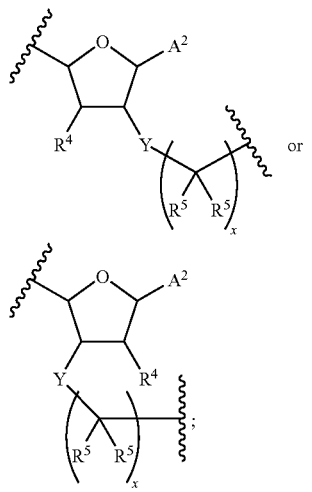

$A^2$ represents independently for each occurrence

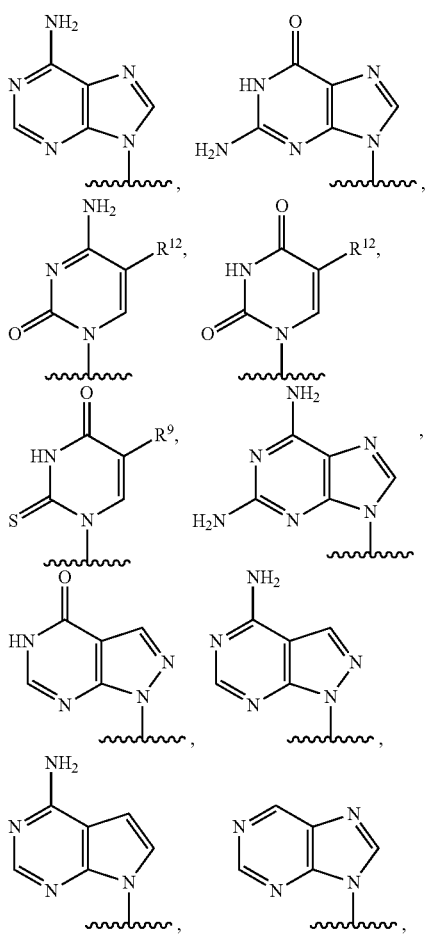

-continued

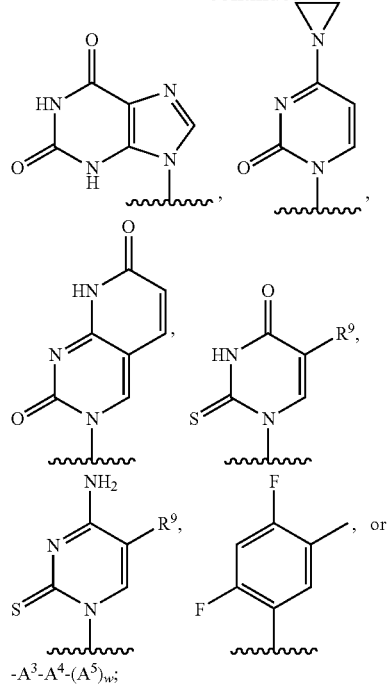

$-A^3-A^4-(A^5)_w;$ $A^3$ represents independently for each occurrence

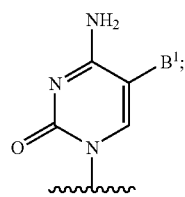

$A^4$ represents independently for each occurrence a bond, alkyl diradical, heteroalkyl diradical, alkenyl diradical, alkynyl diradical, alkylalkynyl diradical, aminoalkyl diradical, thioether, —C(O)—, —S(O)—, —S(O)$_2$—, $B^1C(R)_2B^2$, $B^1C(R)(B^2)_2$, $B^1C(B^2)_3$, $B^1N(R)(B^2)$, $B^1N(B^2)_2$, or has the formula:

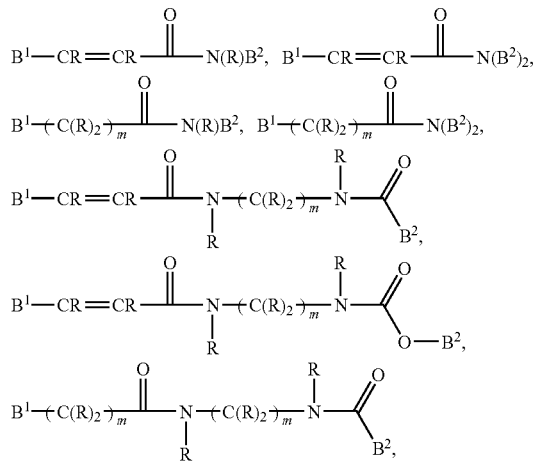

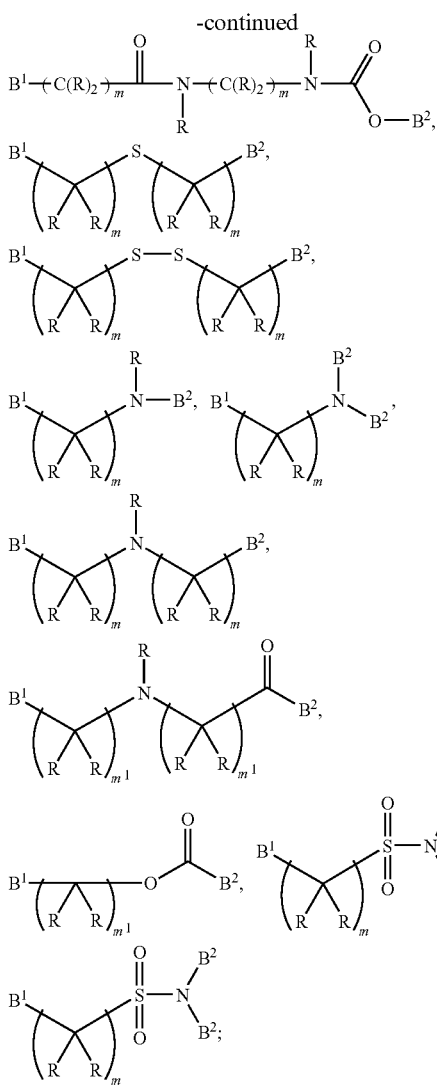

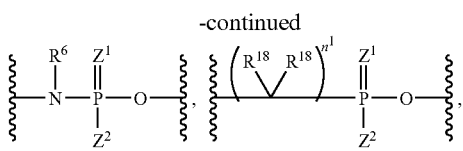

[C(R⁵)₂]ₜN(R⁶)O[C(R⁵)₂]ₜ—, —[C(R⁵)₂]ₜN(R⁶)N(R⁶)O[C(R⁵)₂]ₜ—, —[C(R⁵)₂]ₜN(R⁷)C(O)[C(R⁵)₂]ₜ—, —[C(R⁵)₂]ₜN(R)CO₂[C(R⁵)₂]ₜ—, —[C(R⁵)₂]ₜN(R⁷)C(S)[C(R⁵)₂]ₜ—, —[C(R⁵)₂]ₜN(R⁷)C(S)O[C(R⁵)₂]ₜ—, —[C(R⁵)₂]ₜOC(O)S[C(R⁵)₂]ₜ—, —[C(R⁵)₂]ₜSN(R⁷)CO₂[C(R⁵)₂]ₜ—, —[C(R⁵)₂]ₜ—OSi(R⁸)₂—O[C(R⁵)₂]ₜ—, —[C(R⁵)₂]ₜ—OSO₂N(R⁷)[C(R⁵)₂]ₜ—, —[C(R⁵)₂]ₜN(R⁷)SO₂N(R⁷)[C(R⁵)₂]ₜ—, —[C(R⁵)₂]ₜSO₂N(morpholino)-[C(R⁵)₂]ₜ—, —[C(R⁵)₂]ₜSO₂N(R⁷)[C(R⁵)₂]ₜ—, —[C(R¹)₂]ₜS[C(R⁵)₂]ₜ—, —[C(R⁵)₂]ₜ—OSO₂[C(R⁵)₂]ₜ—, —[C(R⁵)₂]ₜS[C(R⁵)₂]ᵥ—O[C(R⁵)₂]ₜ—, —[C(R⁵)₂]ₜO[C(R⁵)₂]ᵥO[C(R⁵)₂]ₜ—, —[C(R⁵)₂]ₜO[C(R⁵)₂]ₜ—, —[C(R⁵)₂]ₜN(R⁷)[C(R⁵)₂]ₜ—, —[C(R⁵)₂]ₜC=NO[C(R⁵)₂]ₜ—, —[C(R⁵)₂]ₜC(O)C(R⁵)=C(R⁵)[C(R⁵)₂]ₜ—, —[C(R⁵)₂]ₜC(R⁵)=C(R⁵)[C(R⁵)₂]ₜ—, or —[C(R⁵)₂]ₜX²C(O)X²[C(R⁵)₂]ₜ—;

$X^2$ represents independently for each occurrence a bond, O, or $N(R^6)$;

$Z^1$ represents independently for each occurrence O, S, or $N(R^8)$;

$Z^2$ represents independently for each occurrence alkyl, aryl, aralkyl, $B(R^9)_3$, —OM, —Oalkyl, —Oaryl, —Oaralkyl, —SM, —Salkyl, —Saryl, —Saralkyl, —[C(R⁵)₂]ₘN(R⁶)₂, —N(R¹⁰)R¹¹, —N(R¹⁹)(C(R¹⁹)₂)ₘN(R¹⁹)₂, —N(R⁷)C(O)R⁸, H, —OC(O)R⁸, —CO₂R⁸, F, Se, —SeR⁸, —(C(R¹⁹)₂)ₘOR¹⁹, —(C(R¹⁹)₂)ₘSR¹⁹, —N(R¹⁹)(C(R¹⁹)₂)ₘ—OR¹⁹, —N(R¹⁹)(C(R¹⁹)₂)ₘSR¹⁹, —N(R¹⁹)(C(R¹⁹)₂)ₘN(R¹⁹)C(O)alkyl, —(C(R¹⁹)₂)ₘN(R¹⁹)C(O)alkyl, or -A⁸-[A⁹-(A⁵)ᵥᵥ]ᵧ;

$R^{10}$ and $R^{11}$ are independently H, alkyl, or aryl; or $R^{10}$ and $R^{11}$ taken together form a 3-, 4-, 5-, 6-, or 7-member ring;

$R^{12}$ represents independently for each occurrence H, alkyl, or —NHCH₂CH=CH₂;

t represents independently for each occurrence 0, 1, 2, 3, or 4;

v represents independently for each occurrence 0, 1, 2, 3, 4, 5, 6, 7, or 8;

$A^5$ represents independently for each occurrence aryl, aralkyl, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring;

$A^6$ represents independently for each occurrence a bond, alkyl diradical, heteroalkyl diradical, alkenyl diradical, aminoalkyl, —C(O)—, —S(O)—, —S(O)₂—, or is represented by formula:

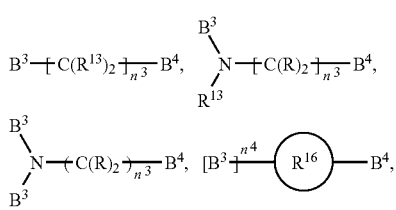

$B^1$ is a bond between $A^3$ and $A^4$;

$B^2$ is a bond between $A^4$ and $A^5$;

R represents independently for each occurrence hydrogen or alkyl;

m represents independently for each occurrence 1, 2, 3, 4, 5, 6, 7, or 8;

$m^1$ represents independently for each occurrence 0, 1, 2, 3, 4, 5, 6, 7, or 8;

Y represents independently for each occurrence an alkyl diradical, cycloalkyl diradical, heteroalkyl diradical, heterocycloalkyl diradical, alkenyl diradical, alkynyl diradical, aryl diradical, heteroaryl diradical, aralkyl diradical, heteroaralkyl diradical, —X²C(O)X²[C(R⁵)₂]ᵥX²—, —X²C(NR⁶)X²[C(R⁵)₂]ᵥX²—, —X²C(S)X²[C(R⁵)₂]ᵥX²—, —X²C(O)X²[C(R⁵)₂]ᵥX²C(O)X²—,

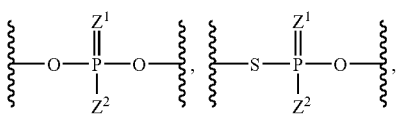

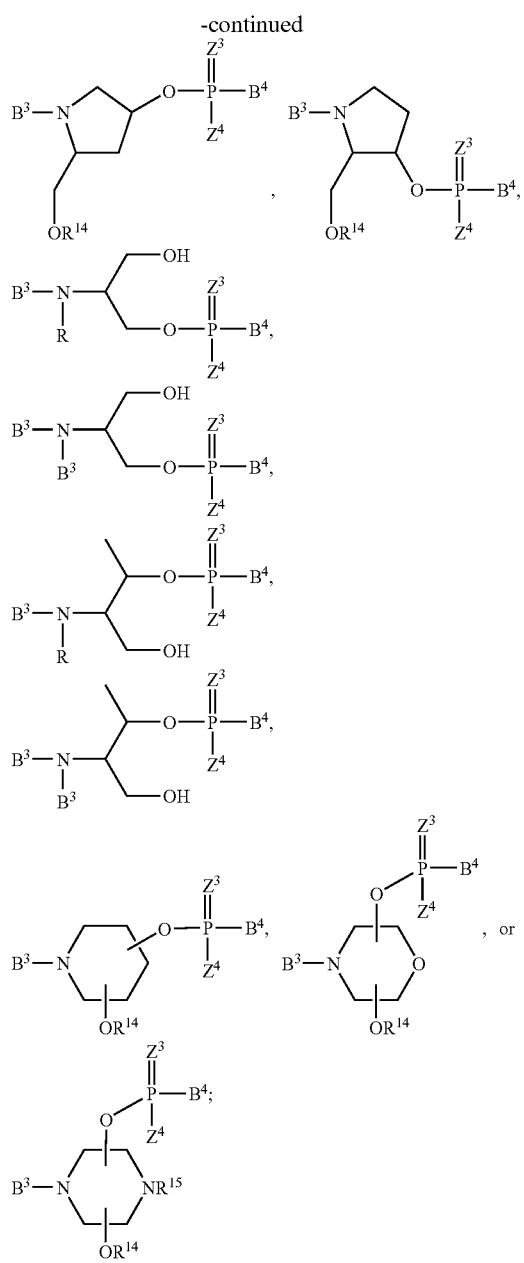

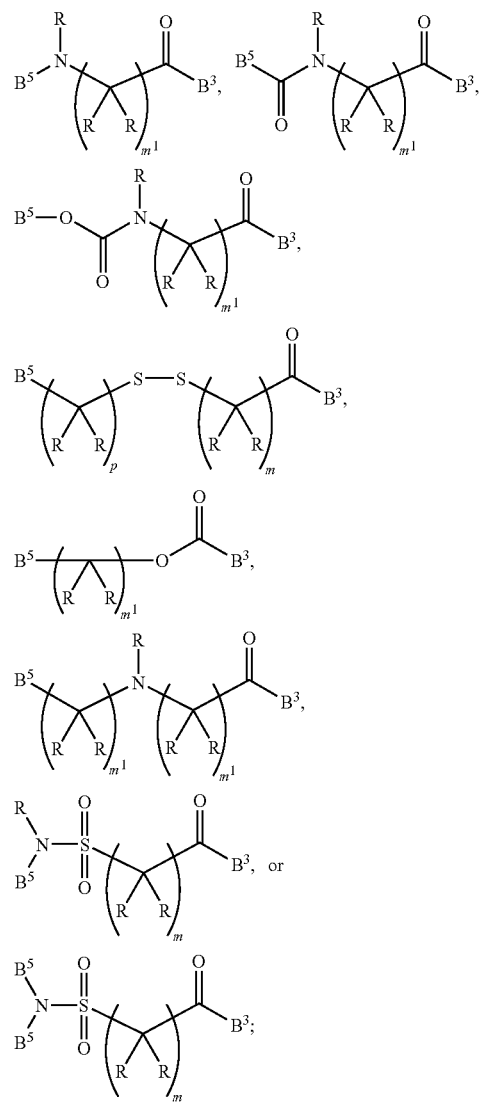

$Z^3$ represents independently for each occurrence O or S;
$Z^4$ represents independently for each occurrence —OM, —Oalkyl, —Oaryl, —Oaralkyl, —SM, —Salkyl, —Saryl, —Saralkyl, —N(R$^{10}$)R$^{11}$, —[C(R$^5$)$_2$]$_m$N(R$^6$)$_2$, —N(R$^{19}$)(C(R$^{19}$)$_2$)$_m$N(R$^{19}$)$_2$, —(C(R$^{19}$)$_2$)$_m$OR$^{19}$, —(C(R$^{19}$)$_2$)$_m$SR$^{19}$, —N(R$^{19}$)(C(R$^{19}$)$_2$)$_m$—OR$^{19}$, —N(R$^{19}$)(C(R$^{19}$)$_2$)$_m$SR$^{19}$, —N(R$^{19}$)(C(R$^{19}$)$_2$)$_m$N(R$^{19}$)C(O)alkyl, —(C(R$^{19}$)$_2$)$_m$N(R$^{19}$)C(O)alkyl, aryl, or alkyl;

$R^{13}$ represent independently for each occurrence H, alkyl, cycloalkyl, heteroalkyl, aryl, aralkyl, acyl, silyl, or B$^3$;

$R^{14}$ represents independently for each occurrence alkyl, aryl, aralkyl, acyl, or silyl;

$R^{15}$ represents independently for each occurrence hydrogen, alkyl, aryl, aralkyl, acyl, alkylsulfonyl, alkylsulfoxide, arylsulfonyl, arylsulfoxide, or silyl;

$R^{16}$ represents independently for each occurrence cycloalkyl, heterocycloalkyl, aryl, or heteroaryl;

$B^3$ is a bond between $A^6$ and $A^7$;

$B^4$ is a bond between $A^6$ and O;

$n^3$ represents independently for each occurrence an integer in the range of 1-15, inclusive;

$n^4$ represents independently for each occurrence 1, 2, 3, 4, or 5 in accord with the rules of valence;

$A^7$ represents independently for each occurrence a bond, alkyl diradical, heteroalkyl diradical, —C(O)—, —S(O)—, —S(O)$_2$—, B$^3$C(R)$_2$B$^5$, B$^3$C(R)(B$^5$)$_2$, B$^3$C(B$^5$)$_3$, B$^3$N(R)(B$^5$), B$^3$N(B$^5$)$_2$, or has the formula:

p represents independently for each occurrence 1, 2, 3, or 4;

$B^5$ is a bond between $A^5$ and $A^7$;

$A^8$ is a bond, alkyl diradical, heteroalkyl diradical, alkenyl diradical, aminoalkyl, or is represented by formula:

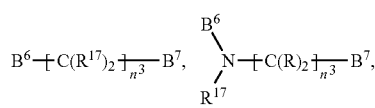

-continued

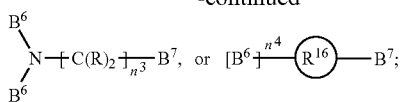

R$^{17}$ represent independently for each occurrence H, alkyl, cycloalkyl, heteroalkyl, aryl, aralkyl, acyl, silyl, or B$^6$;
R$^{18}$ represents independently for each occurrence H, halogen, alkyl, alkoxyl, —N(R$^6$)$_2$, —CN, —[C(R$^5$)$_2$]$_v$C(R$^5$)=C(R$^5$)$_2$;
R$^{19}$ represents independently for each occurrence H or alkyl;
B$^6$ is a bond between A$^8$ and A$^9$;
B$^7$ is a bond between A$^8$ and P;
A$^9$ is a bond, alkyl diradical, heteroalkyl diradical, —C(O)—, —S(O)—, —S(O)$_2$—, B$^6$C(R)$_2$B$^8$, B$^6$C(R)(B$^8$)$_2$, B$^6$C(B$^8$)$_3$, B$^6$N(R)(B$^8$), B$^6$N(B$^8$)$_2$, or has the formula:

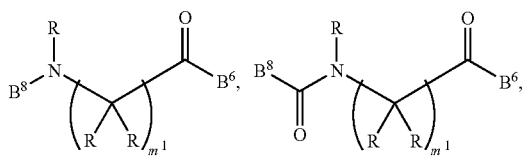

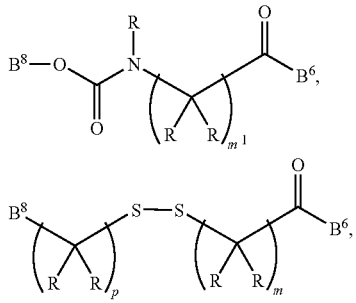

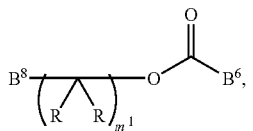

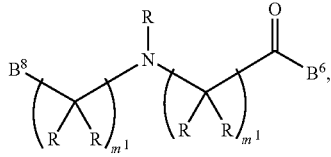

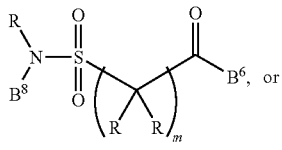

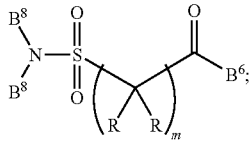

and
B$^8$ is a bond between A$^5$ and A$^9$;
provided that at least one occurrence of Y is a P-alkylphosphonate.

2. The compound of claim 1, wherein A$^5$ occurs at least once.

3. The compound of claim 2, wherein A$^5$ is represented by formula III:

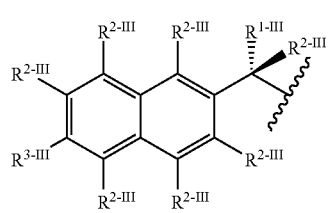

wherein
R$^{1\text{-}III}$, R$^{2\text{-}III}$, and R$^{3\text{-}III}$ represent independently for each occurrence H, halogen, amino, hydroxyl, alkyl, alkoxyl, amino alkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

4. The compound of claim 3, wherein R$^{1\text{-}III}$ is methyl, R$^{2\text{-}III}$ is H, and R$^{3\text{-}III}$ is methoxy.

5. The compound of claim 2, wherein A$^5$ is represented by formula IV:

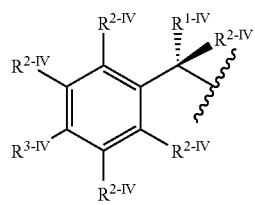

wherein
R$^{1\text{-}IV}$, R$^{2\text{-}IV}$, and R$^{3\text{-}IV}$ represent independently for each occurrence H, halogen, amino, hydroxyl, alkyl, alkoxyl, amino alkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

6. The compound of claim 5, wherein R$^{1\text{-}IV}$ is methyl, R$^{2\text{-}IV}$ is H, and R$^{3\text{-}IV}$ is isobutyl.

7. The compound of claim 5, wherein R$^3$ and R$^4$ represent independently for each occurrence —NH$_2$, —N(H)CH$_3$, or —N(CH$_3$)$_2$.

8. The compound of claim 1, wherein the double-stranded iRNA agent is a double-stranded siRNA.

9. The compound of claim 1, wherein the P-alkylphosphonate is selected from the group consisting of methylphosphonate, isopropylphosphonate, and tert-butylphosphonate.

10. A single-stranded iRNA agent represented by formula V:

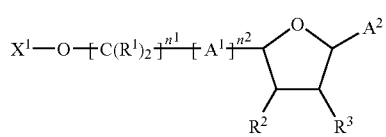

wherein
X$^1$ is H, —P(O)(OM)$_2$, —P(O)(OM)-O—P(O)(OM)$_2$, —P(O)(Oalkyl)$_2$, —P(O)(Oalkyl)-O—P(O)(Oalkyl)$_2$, or -A$^6$-[A$^7$-(A$^5$)$_w$]$_y$;

M represents independently for each occurrence an alkali metal or a transition metal with an overall charge of +1;

$R^1$ and $R^5$ represent independently for each occurrence H, alkyl, or halogen;

$R^2$ and $R^3$ represent independently for each occurrence H, OH, F, —Oalkyl, —Oallyl, —O(C($R^{19}$)$_2$)$_k$O$R^{19}$, —O(C($R^{19}$)$_2$)$_k$S$R^{19}$, —O(C($R^{19}$)$_2$)$_k$N($R^{19}$)$_2$, —O(C($R^{19}$)$_2$)$_k$C(O)N($R^{19}$)$_2$, —N($R^{19}$)$_2$, —S(C$_1$-C$_6$)alkyl, —O(C($R^{19}$)$_2$)$_k$O(C$_1$-C$_6$)alkyl, —O(C($R^{19}$)$_2$)$_k$S(C$_1$-C$_6$)alkyl, —O(C($R^{19}$)$_2$)$_k$O(C($R^{19}$)$_2$)$_k$N((C$_1$-C$_6$)alkyl)$_2$, —O(C($R^{19}$)$_2$)$_k$ON((C$_1$-C$_6$)alkyl)$_2$, or —O-$A^6$-[$A^7$-($A^5$)$_w$]$_y$;

$R^4$ represents independently for each occurrence H, OH, F, —Oalkyl, —Oallyl, —O(C($R^{19}$)$_2$)$_k$O$R^{19}$, —O(C($R^{19}$)$_2$)$_k$S$R^{19}$, —O(C($R^{19}$)$_2$)$_k$N($R^{19}$)$_2$, —O(C($R^{19}$)$_2$)$_k$C(O)N($R^{19}$)$_2$, —N($R^{19}$)$_2$, —S(C$_1$-C$_6$)alkyl, —O(C($R^{19}$)$_2$)$_k$O(C$_1$-C$_6$)alkyl, —O(C($R^{19}$)$_2$)$_k$S(C$_1$-C$_6$)alkyl, —O(C($R^{19}$)$_2$)$_k$O(C($R^{19}$)$_2$)$_k$N((C$_1$-C$_6$)alkyl)$_2$, or —O(C($R^{19}$)$_2$)$_k$ON((C$_1$-C$_6$)alkyl)$_2$;

$R^6$, $R^7$, and $R^9$ represent independently for each occurrence H, alkyl, aryl, or aralkyl;

$R^8$ represents independently for each occurrence alkyl, aryl, or aralkyl;

k represents independently for each occurrence 1, 2, 3, or 4;

$n^1$ is 1, 2, or 3;

$n^2$ is an integer in the range of about 15-28, inclusive;

w represents independently for each occurrence 1, 2, or 3 in accord with the rules of valence;

x represents independently for each occurrence 0, 1, 2, or 3;

y represents independently for each occurrence 1, 2, 3, 4, or 5 in accord with the rules of valence;

$A^1$ represents independently for each occurrence:

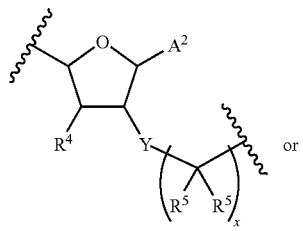

or

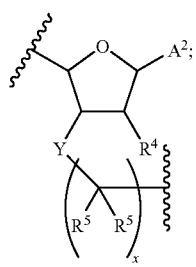

$A^2$ represents independently for each occurrence:

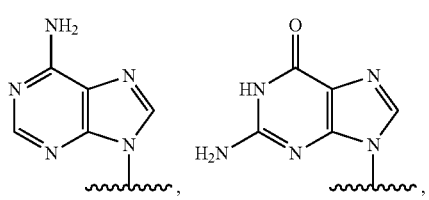

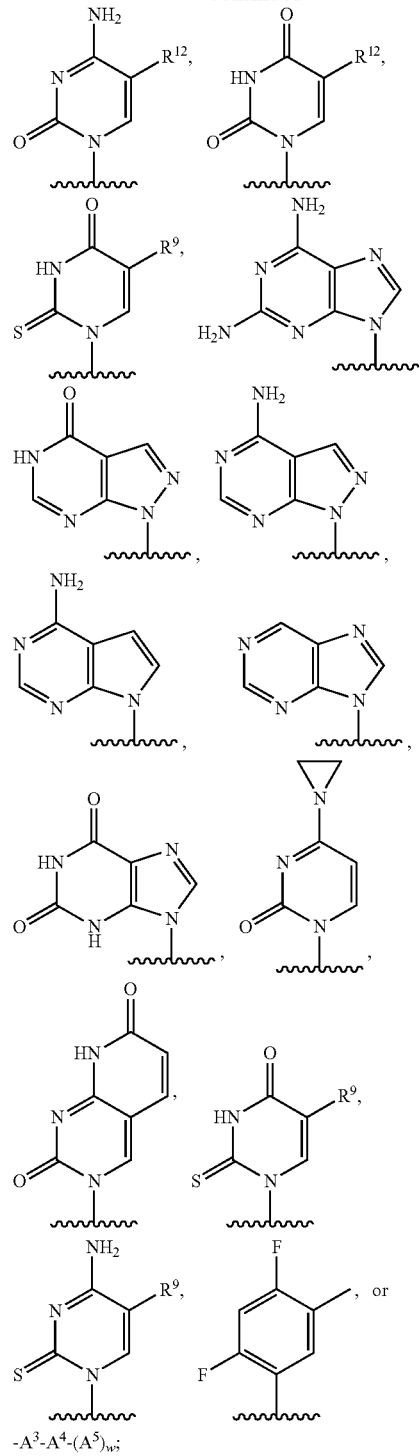

-$A^3$-$A^4$-($A^5$)$_w$;

$A^3$ represents independently for each occurrence

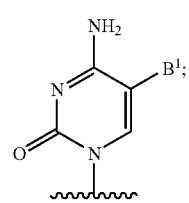

$A^4$ represents independently for each occurrence a bond, alkyl diradical, heteroalkyl diradical, alkenyl diradical, alkynyl diradical, alkylalkynyl diradical, aminoalkyl diradical, thioether, —C(O)—, —S(O)—, —S(O)$_2$—, $B^1C(R)_2B^2$, $B^1C(R)(B^2)_2$, $B^1C(B^2)_3$, $B^1N(R)(B^2)$, $B^1N(B^2)_2$, or has the formula:

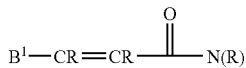

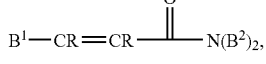

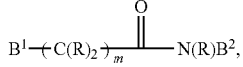

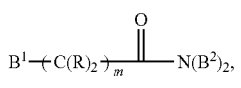

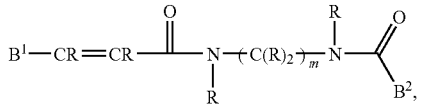

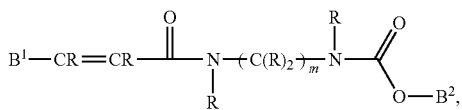

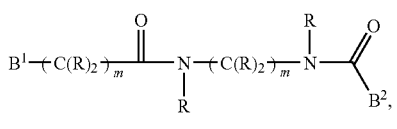

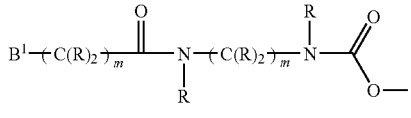

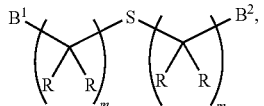

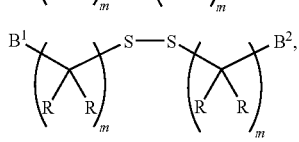

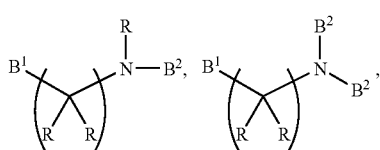

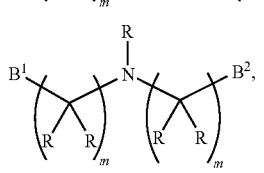

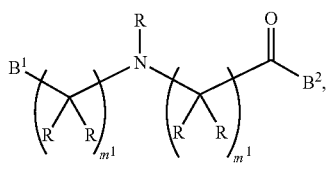

-continued

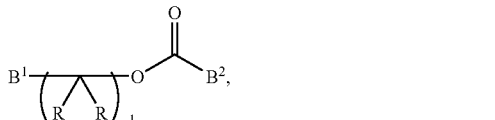

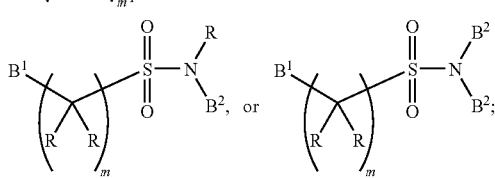

$B^1$ is a bond between $A^3$ and $A^4$;
$B^2$ is a bond between $A^4$ and $A^5$;
R represents independently for each occurrence hydrogen or alkyl;
m represents independently for each occurrence 1, 2, 3, 4, 5, 6, 7, or 8;
$m^1$ represents independently for each occurrence 0, 1, 2, 3, 4, 5, 6, 7, or 8;
Y represents independently for each occurrence an alkyl diradical, cycloalkyl diradical, heteroalkyl diradical, heterocycloalkyl diradical, alkenyl diradical, alkynyl diradical, aryl diradical, heteroaryl diradical, aralkyl diradical, heteroaralkyl diradical, —X$^2$C(O)X$^2$[C(R$^5$)$_2$]$_t$X$^2$—, —X$^2$C(NR$^6$)X$^2$[C(R$^5$)$_2$]$_v$X$^2$—, —X$^2$C(S)X$^2$[C(R$^5$)$_2$]$_v$X$^2$—, —X$^2$C(O)X$^2$-[C(R$^5$)$_2$]$_v$X$^2$C(O)X$^2$—,

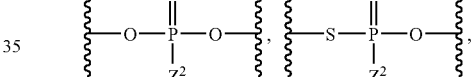

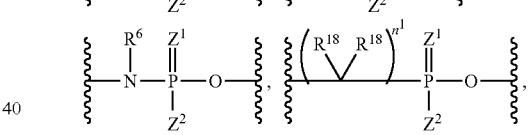

[C(R$^5$)$_2$]$_t$N(R$^6$)O[C(R$^5$)]$_t$—, —[C(R$^5$)$_2$]$_t$N(R$^6$)N(R$^6$)O[C(R$^5$)]$_t$—, —[C(R$^5$)$_2$]$_t$N(R$^7$)C(O)[C(R$^5$)$_2$]$_t$—, —[C(R$^5$)$_2$]$_t$N(R)CO$_2$[C(R$^5$)$_2$]$_t$—, —[C(R$^5$)$_2$]$_t$N(R$^7$)C(S)[C(R$^5$)$_2$]$_t$—, —[C(R$^5$)$_2$]$_t$N(R$^7$)C(S)O[C(R$^5$)$_2$]$_t$—, —[C(R$^5$)$_2$]$_t$—OC(O)S[C(R$^5$)$_2$]$_t$—, —[C(R$^5$)$_2$]$_t$SN(R$^7$)CO$_2$[C(R$^5$)$_2$]$_t$—, —[C(R$^5$)$_2$]$_t$OSi(R$^8$)$_2$—O[C(R$^5$)$_2$]$_t$—, —[C(R$^5$)$_2$]$_t$OSO$_2$N(R$^7$)[C(R$^5$)$_2$]$_t$—, —[C(R$^5$)$_2$]$_t$N(R$^7$)SO$_2$N(R$^7$)[C(R$^5$)$_2$]$_t$—, —[C(R$^5$)$_2$]$_t$SO$_2$N(morpholino)-[C(R$^5$)$_2$]$_t$—, —[C(R$^5$)$_2$]$_t$SO$_2$N(R$^7$)[C(R$^5$)$_2$]$_t$—, —[C(R$^1$)$_2$]$_t$S[C(R$^5$)$_2$]$_t$—, —[C(R$^5$)$_2$]$_t$—OSO$_2$[C(R$^5$)$_2$]$_t$—, —[C(R$^5$)$_2$]$_t$S[C(R$^5$)$_2$]$_y$—O[C(R$^5$)$_2$]$_t$—, —[C(R$^5$)$_2$]$_t$O[C(R$^5$)$_2$]$_y$—O[C(R$^5$)$_2$]$_t$—, —[C(R$^5$)$_2$]$_t$O[C(R$^5$)$_2$]$_t$—, —[C(R$^5$)$_2$]$_t$N(R$^7$)[C(R$^5$)$_2$]$_t$—, —[C(R$^5$)$_2$]$_t$C=NO[C(R$^5$)$_2$]$_t$—, —[C(R$^5$)$_2$]$_t$C(O)C(R$^5$)=C(R$^5$)[C(R$^5$)$_2$]$_t$—, —[C(R$^5$)$_2$]$_t$C(R$^5$)=C(R$^5$)[C(R$^5$)$_2$]$_t$—, or —[C(R$^5$)$_2$]$_t$X$^2$C(O)X$^2$[C(R$^5$)$_2$]$_t$—;
$X^2$ represents independently for each occurrence a bond, O, or N(R$^6$);
$Z^1$ represents independently for each occurrence O, S, or N(R$^8$);
$Z^2$ represents independently for each occurrence alkyl, aryl, aralkyl, B(R$^9$)$_3$, —OM, —Oalkyl, —Oaryl, —Oaralkyl, —SM, —Salkyl, —Saryl, —Saralkyl, —[C(R$^5$)$_2$]$_m$N(R$^6$)$_2$, —N(R$^{10}$)R$^{11}$, —N(R$^{19}$)(C(R$^{19}$)$_2$)$_m$N(R$^{19}$)$_2$, —N(R$^7$)C(O)R$^8$, H, —OC(O)R$^8$, —CO$_2$R$^8$, F, Se, —SeR$^8$, —(C(R$^{19}$)$_2$)$_m$—OR$^{19}$, —(C(R$^{19}$)$_2$)$_m$SR$^{19}$, —N(R$^{19}$)(C(R$^{19}$)$_2$)$_m$OR$^{19}$, —N(R$^{19}$)(C(R$^{19}$)$_2$)$_m$SR$^{19}$, —N(R$^{19}$)(C(R$^{19}$)$_2$)$_m$N(R$^{19}$)C(O)alkyl, —(C(R$^{19}$)$_2$)$_m$N(R$^{19}$)C(O)alkyl, or -A$^8$-[A$^9$-(A$^5$)$_w$]$_y$;

R$^{10}$ and R$^{11}$ are independently H, alkyl, or aryl; or R$^{10}$ and R$^{11}$ taken together form a 3-, 4-, 5-, 6-, or 7-member ring;

R$^{12}$ represents independently for each occurrence H, alkyl, or —NHCH$_2$CH=CH$_2$;

t represents independently for each occurrence 0, 1, 2, 3, or 4;

v represents independently for each occurrence 0, 1, 2, 3, 4, 5, 6, 7, or 8;

A$^5$ represents independently for each occurrence aryl, aralkyl, or the radical of a steroid, bile acid, lipid, folic acid, pyridoxal, B12, riboflavin, biotin, polycyclic compound, crown ether, intercalator, cleaver molecule, protein-binding agent, carbohydrate, or an optionally substituted saturated 5-membered ring;

A$^6$ represents independently for each occurrence a bond, alkyl diradical, heteroalkyl diradical, alkenyl diradical, aminoalkyl, —C(O)—, —S(O)—, —S(O)$_2$—, or is represented by formula:

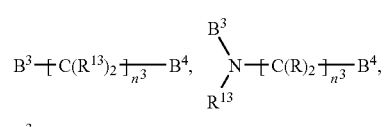
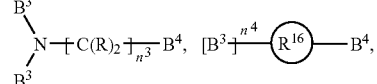
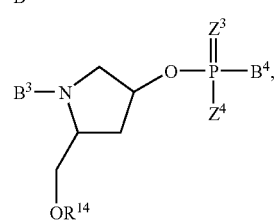
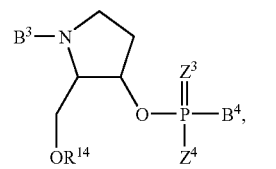
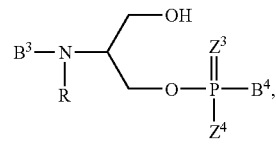
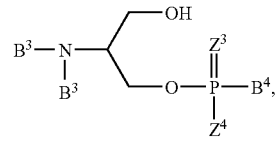
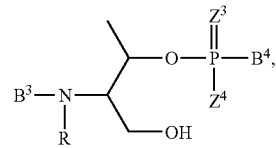

-continued

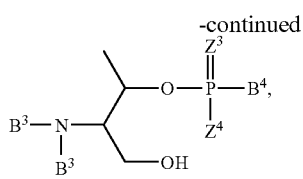
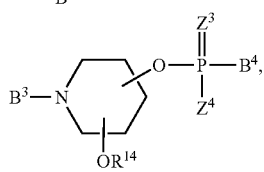
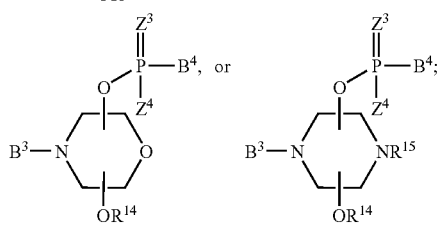

Z$^3$ represents independently for each occurrence O or S;

Z$^4$ represents independently for each occurrence —OM, —Oalkyl, —Oaryl, —Oaralkyl, —SM, —Salkyl, —Saryl, —-Saralkyl, —N(R$^{10}$)R$^{11}$, —[C(R$^5$)$_2$]$_m$N(R$^6$)$_2$, —N(R$^{19}$)(C(R$^{19}$)$_2$)$_m$N(R$^{19}$)$_2$, —(C(R$^{19}$)$_2$)$_m$OR$^{19}$, —(C(R$^{19}$)$_2$)$_m$SR$^{19}$, —N(R$^{19}$)(C(R$^{19}$)$_2$)$_m$—OR$^{19}$, —N(R$^{19}$)(C(R$^{19}$)$_2$)$_m$SR$^{19}$, —N(R$^{19}$)(C(R$^{19}$)$_2$)$_m$N(R$^{19}$)C(O)alkyl, —(C(R$^{19}$)$_2$)$_m$N(R$^{19}$)C(O)alkyl, aryl, or alkyl;

R$^{13}$ represent independently for each occurrence H, alkyl, cycloalkyl, heteroalkyl, aryl, aralkyl, acyl, silyl, or B$^3$;

R$^{14}$ represents independently for each occurrence alkyl, aryl, aralkyl, acyl, or silyl;

R$^{15}$ represents independently for each occurrence hydrogen, alkyl, aryl, aralkyl, acyl, alkylsulfonyl, alkylsulfoxide, arylsulfonyl, arylsulfoxide, or silyl;

R$^{16}$ represents independently for each occurrence cycloalkyl, heterocycloalkyl, aryl, or heteroaryl;

B$^3$ is a bond between A$^6$ and A$^7$;

B$^4$ is a bond between A$^6$ and O;

n$^3$ represents independently for each occurrence an integer in the range of 1-15, inclusive;

n$^4$ represents independently for each occurrence 1, 2, 3, 4, or 5 in accord with the rules of valence;

A$^7$ represents independently for each occurrence a bond, alkyl diradical, heteroalkyl diradical, —C(O)—, —S(O)—, —S(O)$_2$—, B$^3$C(R)$_2$B$^5$, B$^3$C(R)(B$^5$)$_2$, B$^3$C(B$^5$)$_3$, B$^3$N(R)(B$^5$), B$^3$N(B$^5$)$_2$, or has the formula:

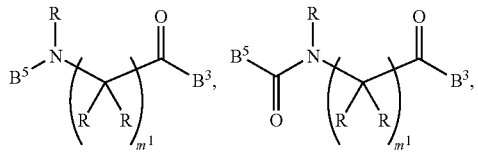
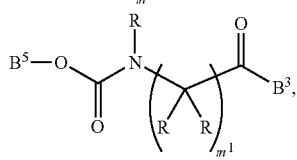

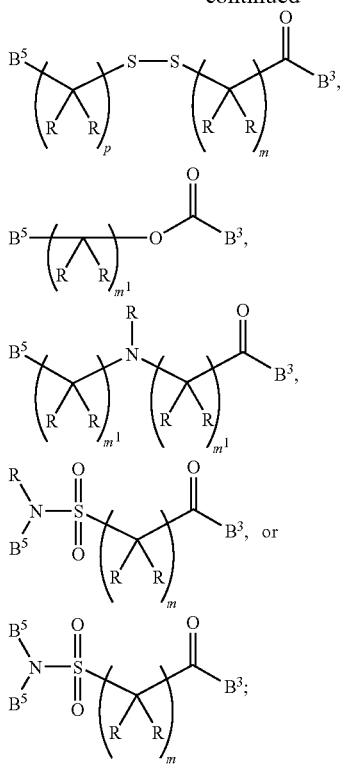

p represents independently for each occurrence 1, 2, 3, or 4;
$B^5$ is a bond between $A^5$ and $A^7$;
$A^8$ is a bond, alkyl diradical, heteroalkyl diradical, alkenyl diradical, aminoalkyl, or is represented by formula:

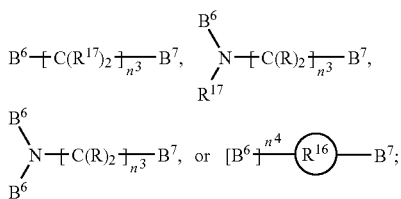

$R^{17}$ represent independently for each occurrence H, alkyl, cycloalkyl, heteroalkyl, aryl, aralkyl, acyl, silyl, or $B^6$;
$R^{18}$ represents independently for each occurrence H, halogen, alkyl, alkoxyl, —N($R^6$)$_2$, —CN, —[C($R^5$)$_2$]$_v$C($R^5$)=C($R^5$)$_2$;
$R^{19}$ represents independently for each occurrence H or alkyl;
$B^6$ is a bond between $A^8$ and $A^9$;
$B^7$ is a bond between $A^8$ and P;
$A^9$ is a bond, alkyl diradical, heteroalkyl diradical, —C(O)—, —S(O)—, —S(O)$_2$—, $B^6$C(R)$_2$B$^8$, $B^6$C(R)(B$^8$)$_2$, $B^6$C(B$^8$)$_3$, $B^6$N(R)(B$^8$), $B^6$N(B$^8$)$_2$, or has the formula:

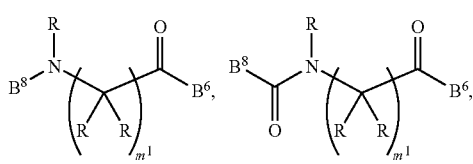

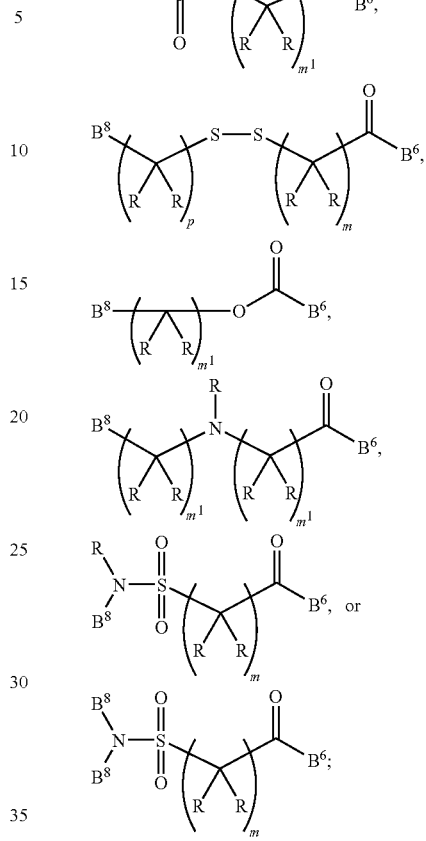

and
$B^8$ is a bond between $A^5$ and $A^9$;
provided that at least one occurrence of Y is a P-alkylphosphonate.

11. The compound of claim 10, wherein $A^5$ occurs at least once.

12. The compound of claim 11, wherein $A^5$ is represented by formula VI:

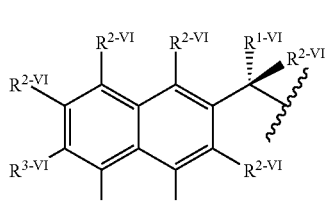

wherein
$R^{1\text{-}VI}$, $R^{2\text{-}VI}$, and $R^{3\text{-}VI}$ represent independently for each occurrence H, halogen, amino, hydroxyl, alkyl, alkoxyl, amino alkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

13. The compound of claim 12, wherein $R^{1\text{-}VI}$ is methyl, $R^{2\text{-}VI}$ is H, and $R^{3\text{-}VI}$ is methoxy.

14. The compound of claim 11, wherein $A^5$ is represented by formula VII:

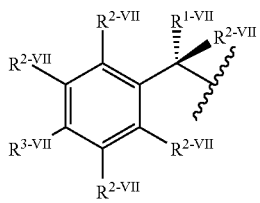

VII wherein $R^{I\text{-}VII}$, $R^{2\text{-}VII}$, and $R^{3\text{-}VII}$ represent independently for each occurrence H, halogen, amino, hydroxyl, alkyl, alkoxyl, amino alkyl, alkenyl, alkynyl, aryl, aralkyl, heteroaryl, heteroaralkyl, thiol, thioalkyl, silyl, nitro, nitrile, acyl, acylamino, —COR, or —CO$_2$R.

15. The compound of claim 14, wherein $R^{I\text{-}VII}$ is methyl, $R^{2\text{-}VII}$ is H, and $R^{3\text{-}VII}$ is isobutyl.

16. The compound of claim 14, wherein $R^3$ and $R^4$ represent independently for each occurrence —NH$_2$, —N(H)CH$_3$, or —N(CH$_3$)$_2$.

17. The compound of claim 10, wherein the single-stranded iRNA agent is a single-stranded siRNA.

18. The compound of claim 10, wherein the single-stranded iRNA agent is a microRNA.

19. The compound of claim 10, wherein the P-alkylphosphonate is selected from the group consisting of methylphosphonate, isopropylphosphonate, and tert-butylphosphonate.

20. A single-stranded iRNA agent comprising at least one P-alkylphosphonate backbone.

21. The single-stranded iRNA agent of claim 20, wherein the P-alkylphosphonate backbone is at the 3' end, the 5' end, the internucleotide, or a combination thereof.

22. The single-stranded iRNA agent of claim 20, wherein the P-alkylphosphonate backbone is at the 3' end.

23. The single-stranded iRNA agent of claim 20, wherein the P-alkylphosphonate backbone is at the 5' end.

24. The single-stranded iRNA agent of claim 20, wherein the P-alkylphosphonate backbone is at both the 3' end and the 5' end.

25. The single-stranded iRNA agent of claim 20, wherein the P-alkylphosphonate is selected from the group consisting of methylphosphonate, isopropylphosphonate, and tert-butylphosphonate.

26. The single-stranded iRNA agent of claim 20, wherein the single-stranded iRNA agent comprises at least one modified sugar moiety.

27. The single-stranded iRNA agent of claim 20, wherein the single-stranded iRNA agent is further conjugated to a ligand selected from the group consisting of an aromatic group, aralkyl group, steroid, bile acid, lipid, folic acid, pyridoxal, B12, riboflavin, biotin, polycyclic compound, crown ether, intercalator, cleaver molecule, protein-binding agent, and carbohydrate.

28. An siRNA comprising at least one P-alkylphosphonate backbone.

29. The siRNA of claim 28, wherein the P-alkylphosphonate backbone is at 3' end, the 5' end, the internucleotide, or a combination thereof.

30. The siRNA of claim 28, wherein the P-alkylphosphonate backbone is at the 3' end of the sense strand, the 3' end of the antisense strand, or the 3' end of both strands.

31. The siRNA of claim 28, wherein the P-alkylphosphonate backbone is at the 5' end of the sense strand, the 5' end of the antisense strand, or the 5' end of both strands.

32. The siRNA of claim 28, wherein the P-alkylphosphonate backbone is at the 3' end of either the sense or antisense stand, and at the 5' end of either the sense or antisense strand.

33. The siRNA of claim 28, wherein the P-alkylphosphonate is selected from the group consisting of methylphosphonate, isopropylphosphonate, and tert-butylphosphonate.

34. The siRNA of claim 28, wherein the siRNA comprises at least one modified sugar moiety.

35. The siRNA of claim 28, wherein siRNA is further conjugated to a ligand selected from the group consisting of an aromatic group, aralkyl group, steroid, bile acid, lipid, folic acid, pyridoxal, B12, riboflavin, biotin, polycyclic compound, crown ether, intercalator, cleaver molecule, protein-binding agent, and carbohydrate.

* * * * *

```
                        SEQUENCE LISTING

<160> NUMBER OF SEQ ID NOS: 80

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aagctggccc tggacatgga gat                                                23

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 2
cuuacgcuga guacuucgat t                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 3
ucgaaguacu cagcguaagt t                                                  21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone

<400> SEQUENCE: 4
cuuacgcuga guacuucgat t                                                  21
```

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 5
cuuacgcuga guacuucgat t                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone

<400> SEQUENCE: 6
cuuacgcuga guacuucgat t                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone

<400> SEQUENCE: 7
cuuacgcuga guacuucgat t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 8
cuuacgcuga guacuucgat t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone

<400> SEQUENCE: 9
cuuacgcuga guacuucgat t                                              21

<210> SEQ ID NO 10
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 10
cuuacgcuga guacuucgat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
```

```
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 11
cuuacgcuga guacuucgat t                                                   21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (5)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone

<400> SEQUENCE: 12
cuuacgcuga guacuucgat t                                                   21
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (10)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 13
cuuacgcuga guacuucgat t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
<221> NAME/KEY: misc_feature
<222> LOCATION: (5)
<223> OTHER INFORMATION: R or S methylphosphonate/methylthiophosphonate
      backbone
<220> FEATURE:
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (10)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
``` backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 14
cuuacgcuga guacuucgat t                                                  21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone

<400> SEQUENCE: 15
cuuacgcuga guacuucgat t                                                  21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 16
cuuacgcuga guacuucgat t                                                  21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:

Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 17
cuuacgcuga guacuucgat t                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (3)
<223> OTHER INFORMATION: R or S
      isopropylphosphonate/isopropylthiophosphonate backbone

<400> SEQUENCE: 18
cuuacgcuga guacuucgat t                                            21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 19
cuuacgcuga guacuucgat t                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:

```
<223> OTHER INFORMATION: Description of Artificial Sequence: Synthetic
      oligonucleotide
<220> FEATURE:
<221> NAME/KEY: misc_feature
<222> LOCATION: (12)
<223> OTHER INFORMATION: R or S
      isopropylphosphonate/isopropylthiophosphonate backbone

<400> SEQUENCE: 20
cuuacgcuga guacuucgat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (3)
<223> OTHER INFORMATION: R or S
      isopropylphosphonate/isopropylthiophosphonate backbone
<220> FEATURE:
<221> NAME/KEY: misc_feature
<222> LOCATION: (12)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 21
cuuacgcuga guacuucgat t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 22
cuuacgcuga guacuucgat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 23
cuuacgcuga guacuucgat t                                                    21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 24
cuuacgcuga guacuucgat t                                                    21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 25
cuuacgcuga guacuucgat t                                                    21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (12)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 26
```
cuuacgcuga guacuucgat t					21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (3)
<223> OTHER INFORMATION: R or S
      isopropylphosphonate/isopropylthiophosphonate backbone
<220> FEATURE:
<221> NAME/KEY: misc_feature
<222> LOCATION: (12)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 27
cuuacgcuga guacuucgat t					21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 28
ucgaaguacu cagcguaagt t					21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 29
ucgaaguacu cagcguaagt t					21

-continued

```
<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 30
ucgaaguacu cagcguaagt t                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 31
ucgaaguacu cagcguaagt t                                            21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 32
ucgaaguacu cagcguaagt t                                            21

<210> SEQ ID NO 33
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 33
gcggaucaaa ccucaccaat t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 34
uuggugaggu uugauccgct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone

<400> SEQUENCE: 35
gcggaucaaa ccucaccaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 36
gcggaucaaa ccucaccaat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
                               Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 37
gcggaucaaa ccucaccaat t                                                 21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 38
gcggaucaaa ccucaccaat t                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
```

```
                                 backbone
<220> FEATURE:
<221> NAME/KEY: misc_feature
<222> LOCATION: (5)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone

<400> SEQUENCE: 39
gcggaucaaa ccucaccaat t                                               21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (10)
```

```
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 40
gcggaucaaa ccucaccaat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
<221> NAME/KEY: misc_feature
<222> LOCATION: (5)
<223> OTHER INFORMATION: R or S methylphosphonate/methylthiophosphonate
      backbone
<220> FEATURE:
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
```

```
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (10)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
      backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 41
gcggaucaaa ccucaccaat t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
```

-continued

```
<221> NAME/KEY: misc_feature
<222> LOCATION: (20)
<223> OTHER INFORMATION: R or S
      isopropylphosphonate/isopropylthiophosphonate backbone

<400> SEQUENCE: 42
gcggaucaaa ccucaccaat t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 43
gcggaucaaa ccucaccaat t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 44
gcggaucaaa ccucaccaat t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 45
```
gcggaucaaa ccucaccaat t             21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 46
uuggugaggu uugauccgct t             21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 47
uuggugaggu uugauccgct t             21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 48
uuggugaggu uugauccgct t             21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic

```
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 49
uuggugaggu uugauccgct t                                          21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 50
uuggugaggu uugauccgct t                                          21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 51
caaauccaga ggcuagcagt t                                          21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 52
cugcuagccu cuggauuugt t                                          21

<210> SEQ ID NO 53
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone

<400> SEQUENCE: 53
caaauccaga ggcuagcagt t                                                    21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 54
caaauccaga ggcuagcagt t                                                    21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 55
caaauccaga ggcuagcagt t                                                    21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (5)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone

<400> SEQUENCE: 56
caaauccaga ggcuagcagt t                                               21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
```

```
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (10)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 57
caaauccaga ggcuagcagt t                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (2)
<223> OTHER INFORMATION: R or S methylphosphonate/methylthiophosphonate
      backbone
<220> FEATURE:
<221> NAME/KEY: misc_feature
<222> LOCATION: (3)
<223> OTHER INFORMATION: R or S methylphosphonate/methylthiophosphonate
      backbone
<220> FEATURE:
<221> NAME/KEY: misc_feature
<222> LOCATION: (4)
<223> OTHER INFORMATION: R or S methylphosphonate/methylthiophosphonate
      backbone
<220> FEATURE:
<221> NAME/KEY: misc_feature
<222> LOCATION: (5)
<223> OTHER INFORMATION: R or S methylphosphonate/methylthiophosphonate
      backbone
```

```
<220> FEATURE:
<221> NAME/KEY: misc_feature
<222> LOCATION: (6)
<223> OTHER INFORMATION: R or S methylphosphonate/methylthiophosphonate
      backbone
<220> FEATURE:
<221> NAME/KEY: misc_feature
<222> LOCATION: (7)
<223> OTHER INFORMATION: R or S methylphosphonate/methylthiophosphonate
      backbone
<220> FEATURE:
<221> NAME/KEY: misc_feature
<222> LOCATION: (8)
<223> OTHER INFORMATION: R or S methylphosphonate/methylthiophosphonate
      backbone
<220> FEATURE:
<221> NAME/KEY: misc_feature
<222> LOCATION: (9)
<223> OTHER INFORMATION: R or S methylphosphonate/methylthiophosphonate
      backbone
<220> FEATURE:
<221> NAME/KEY: misc_feature
<222> LOCATION: (10)
<223> OTHER INFORMATION: R or S methylphosphonate/methylthiophosphonate
      backbone
<220> FEATURE:
<221> NAME/KEY: misc_feature
<222> LOCATION: (11)
<223> OTHER INFORMATION: R or S methylphosphonate/methylthiophosphonate
      backbone
<220> FEATURE:
<221> NAME/KEY: misc_feature
<222> LOCATION: (12)
<223> OTHER INFORMATION: R or S methylphosphonate/methylthiophosphonate
      backbone
<220> FEATURE:
<221> NAME/KEY: misc_feature
<222> LOCATION: (13)
<223> OTHER INFORMATION: R or S methylphosphonate/methylthiophosphonate
      backbone
<220> FEATURE:
<221> NAME/KEY: misc_feature
<222> LOCATION: (14)
<223> OTHER INFORMATION: R or S methylphosphonate/methylthiophosphonate
      backbone
<220> FEATURE:
<221> NAME/KEY: misc_feature
<222> LOCATION: (15)
<223> OTHER INFORMATION: R or S methylphosphonate/methylthiophosphonate
      backbone
<220> FEATURE:
<221> NAME/KEY: misc_feature
<222> LOCATION: (16)
<223> OTHER INFORMATION: R or S methylphosphonate/methylthiophosphonate
      backbone
<220> FEATURE:
<221> NAME/KEY: misc_feature
<222> LOCATION: (17)
<223> OTHER INFORMATION: R or S methylphosphonate/methylthiophosphonate
      backbone
<220> FEATURE:
<221> NAME/KEY: misc_feature
<222> LOCATION: (18)
<223> OTHER INFORMATION: R or S methylphosphonate/methylthiophosphonate
      backbone
<220> FEATURE:
<221> NAME/KEY: misc_feature
<222> LOCATION: (19)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S methylphosphonate/methylthiophosphonate
      backbone

<400> SEQUENCE: 58
caaauccaga ggcuagcagt t                                            21
```

```
<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 59
caaauccaga ggcuagcagt t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 60
caaauccaga ggcuagcagt t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 61
caaauccaga ggcuagcagt t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
         Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 62
caaauccaga ggcuagcagt t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S
      isopropylphosphonate/isopropylthiophosphonate backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 63
caaauccaga ggcuagcagt t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 64
caaauccaga ggcuagcagt t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
```

```
<223> OTHER INFORMATION: R or S
      isopropylphosphonate/isopropylthiophosphonate backbone

<400> SEQUENCE: 65
cugcuagccu cuggauuugt t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      isopropylphosphonate/isopropylthiophosphonate backbone

<400> SEQUENCE: 66
cugcuagccu cuggauuugt t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 67
cugcuagccu cuggauuugt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone
<220> FEATURE:
<221> NAME/KEY: misc_feature
<222> LOCATION: (20)
<223> OTHER INFORMATION: R or S
      tert-butylphosphonate/tert-butylthiophosphonate backbone

<400> SEQUENCE: 68
cugcuagccu cuggauuugt t                                              21
```

```
<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 69
cuuacgcuga guacuucgat t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 70
ucgaaguacu cagcguaagt t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: Methylphosphonate backbone

<400> SEQUENCE: 71
cuuacgcuga guacuucgat t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 72
ucgaaguacu cagcguaagt t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
```

```
<400> SEQUENCE: 73
cuuacgcuga guacuucgat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: Methylphosphonate backbone

<400> SEQUENCE: 74
ucgaaguacu cagcguaagt t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: Methylphosphonate backbone

<400> SEQUENCE: 75
cuuacgcuga guacuucgat t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)
<223> OTHER INFORMATION: Methylphosphonate backbone

<400> SEQUENCE: 76
ucgaaguacu cagcguaagt t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 77
cuuacgcuga guacuucgat t                                              21
```

```
<210> SEQ ID NO 78
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 78
ucgaaguacu cagcguaagt                                                    20

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: R or S methylphosphonate/methylthiophosphonate
      backbone

<400> SEQUENCE: 79
cutacgcuga gtacuucgat t                                                  21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      oligonucleotide

<400> SEQUENCE: 80
ucgaaguacu cagcguaagt t                                                  21
```